(12) United States Patent
Descamps et al.

(10) Patent No.: US 12,129,308 B2
(45) Date of Patent: Oct. 29, 2024

(54) MMP13 BINDING IMMUNOGLOBULINS

(71) Applicants: Merck Patent GmbH, Darmstadt (DE); ABLYNX NV, Zwijnaarde (BE)

(72) Inventors: Francis Descamps, Roeselare (BE); Gerald Beste, Ghent (BE); Guy Hermans, Merelbeke (BE); Hans Guehring, Geissenheim (DE); Lars Toleikis, Kleinniedesheim (DE); Christoph Ladel, Darmstadt (DE)

(73) Assignees: MERCK PATENT GMBH, Darmstadt (DE); ABLYNX NV, Zwijnaarde (BE)

( * ) Notice: Subject to any disclaimer, the term of this patent is extended or adjusted under 35 U.S.C. 154(b) by 0 days.

(21) Appl. No.: 16/617,869

(22) PCT Filed: Jun. 4, 2018

(86) PCT No.: PCT/EP2018/064667
§ 371 (c)(1),
(2) Date: Nov. 27, 2019

(87) PCT Pub. No.: WO2018/220235
PCT Pub. Date: Dec. 6, 2018

(65) Prior Publication Data
US 2020/0190216 A1 Jun. 18, 2020

(30) Foreign Application Priority Data
Jun. 2, 2017 (EP) .................................... 17174402

(51) Int. Cl.
C07K 16/40 (2006.01)
A61K 38/00 (2006.01)
A61K 39/00 (2006.01)
A61K 39/395 (2006.01)
A61P 19/02 (2006.01)

(52) U.S. Cl.
CPC .............. *C07K 16/40* (2013.01); *A61P 19/02* (2018.01); *A61K 38/00* (2013.01); *A61K 39/3955* (2013.01); *A61K 2039/505* (2013.01); *A61K 2039/507* (2013.01); *C07K 2317/22* (2013.01); *C07K 2317/31* (2013.01); *C07K 2317/33* (2013.01); *C07K 2317/565* (2013.01); *C07K 2317/569* (2013.01); *C07K 2317/76* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 9,156,914 B2 | 10/2015 | Blanchetot et al. | |
| 2008/0311113 A1 | 12/2008 | Morris et al. | |
| 2009/0202474 A1 | 8/2009 | Chockalingam et al. | |
| 2012/0088722 A1 | 4/2012 | D'Angelo et al. | |
| 2012/0095193 A1 | 4/2012 | Burden et al. | |
| 2015/0050266 A9* | 2/2015 | Baumeister | G01N 33/6857 424/133.1 |
| 2015/0323528 A1 | 11/2015 | Chun et al. | |

FOREIGN PATENT DOCUMENTS

| | | |
|---|---|---|
| CN | 1826130 A | 8/2006 |
| CN | 102482700 A | 5/2012 |
| CN | 106573984 A | 4/2017 |
| EP | 2 186 894 A1 | 5/2010 |
| EP | 2 258 392 A1 | 12/2010 |
| JP | 2012-531902 A | 12/2012 |
| JP | 2014-533329 A | 12/2014 |
| JP | 2015-532417 A | 11/2015 |
| KR | 10-2004-0094413 A | 11/2004 |
| KR | 10-2012-0098587 A | 9/2012 |
| RU | 2455312 C2 | 7/2012 |
| WO | WO-98/29560 A1 | 7/1998 |
| WO | WO-2008/074840 A2 | 6/2008 |
| WO | WO-2008/074840 A3 | 6/2008 |
| WO | WO-2009/008414 A1 | 1/2009 |
| WO | WO-2011/002968 A2 | 1/2011 |
| WO | WO-2011/002968 A3 | 1/2011 |
| WO | WO-2013/109829 A1 | 7/2013 |
| WO | WO-2015/056808 A1 | 4/2015 |
| WO | WO-2017/080850 A1 | 5/2017 |
| WO | WO-2017/085172 A2 | 5/2017 |
| WO | WO-2018/073216 A1 | 4/2018 |

OTHER PUBLICATIONS

Appleby et al., "Biochemical Characterization and structure determination of a Potent, Selective Antibody Inhibitor of Human MMP9", Journal of Biological Chemistry, 2017, pp. 6810-6820, vol. 292, No. 16, 2017 The American Society for Biochemistry and Molecular Biology, Inc.

Demeestere et al., "Development and Validation of a Small Single-Domain Antibody That Effectively Inhibits Matrix Metalloproteinase 8", The American Society of Gene & Cell Therapy, May 2016, pp. 890-902, vol. 24, No. 5.

Harmsen et al., "Properties, Production, and Applications of Camelid Single-Domain Antibody Fragments", Applied Microbiology and Biotechnology, 2007, pp. 13-22, vol. 77, No. 1, Springer-Verlag 2007.

International Search Report and Written Opinion Issued in Corresponding International Application No. PCT/EP2018/064667 on Oct. 2, 2018, thirty-two (32) pages total.

(Continued)

*Primary Examiner* — Marianne P Allen
(74) *Attorney, Agent, or Firm* — Foley & Lardner LLP

(57) ABSTRACT

The present invention relates to immunoglobulins that specifically bind MMP13 and more in particular to polypeptides, nucleic acids encoding such polypeptides; to methods for preparing such polypeptides; to compositions and in particular to pharmaceutical compositions that comprise such polypeptides, for prophylactic, therapeutic or diagnostic purposes. In particular, the immunoglobulins of the present invention inhibit an activity of MMP13 and preferably are also stable.

16 Claims, 3 Drawing Sheets

Figure 1:
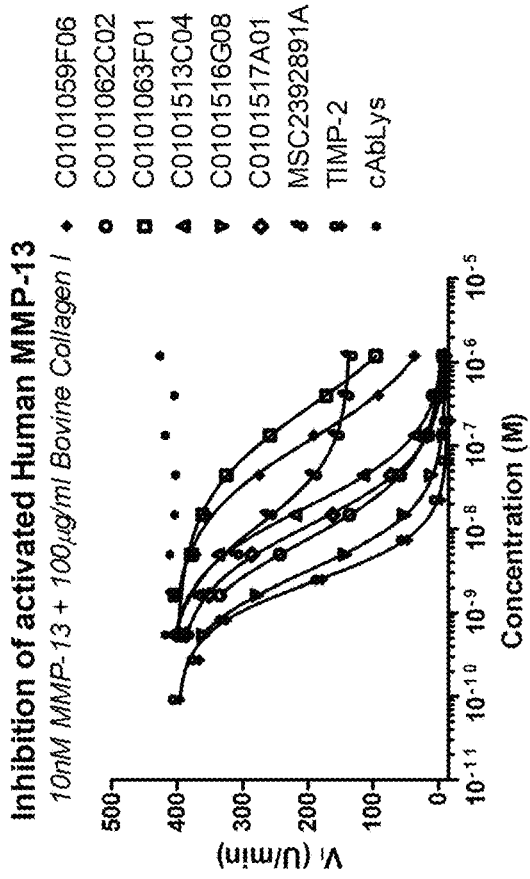
Figure 1:
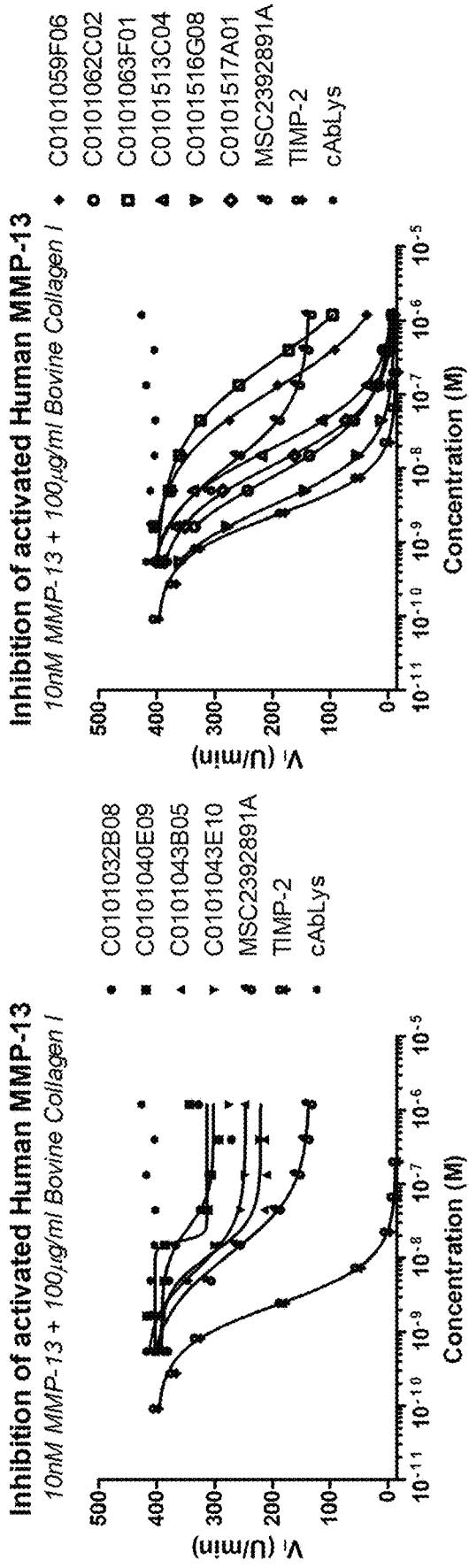

Specification includes a Sequence Listing.

(56) References Cited

OTHER PUBLICATIONS

Mohan et al., "Matrix Metalloproteinase Protein Inhibitors: Highlighting a new Beginning for Metalloproteinases in Medicine", Metalloproteinases in Medicine, 2016, pp. 1-16, vol. 3.

Nam et al., "Active-Site MMP-Selective Antibody Inhibitors Discovered from Convex Paratope Synthetic Libraries", PNAS, Dec. 27, 2016, pp. 14970-14975, vol. 113, No. 52.

Pivetta et al., "MMP-13 Stimulates Osteoclast Differentiation and Activation in Tumour Breast Bone Metastases", Breast Cancer Research, 2011, pp. R105 (1-15), vol. 13, No. 5.

Chiusaroli et al., "Targeting of ADAMTS5's Ancillary Domain with the Recombinant mAb CRB0017 Ameliorates Disease Progression in a Spontaneous Murine Model of Osteoarthritis", Osteoarthritis and Cartilage, 2013, pp. 1807-1810, vol. 21, No. 11, 2013 Osteoarthritis Research Society International, Elsevier Ltd.

International Search Report and Written Opinion issued in corresponding International Application No. PCT/EP2018/064668 dated Oct. 1, 2018, eighteen (18) pages.

Kontermann, "Strategies for extended serum half-life of protein therapeutics", Current Opinion in Biotechnology, 2011, pp. 868-876, vol. 22, No. 6, Elsevier Ltd.

Larkin et al., "Translational Development of an ADAMTS-5 Antibody for Osteoarthritis Disease Modification", Osteoarthritis and Cartilage, 2015, pp. 1254-1266, vol. 23, No. 8, 2015 The Authors, Elsevier ltd and Osteoarthritis Research Society International.

Naito et al., "Development of a Neutralizing Antibody Specific for the Active Form of Matrix Metalloproteinase-13", Biochemistry, 2012, pp. 8877-8884, vol. 51, No. 44, 2012 American Chemical Society, ACS Publications.

Santamaria et al: "Antibody-based exosite inhibitors of ADAMTS-5 (aggrecanase-2)", Biochemical Journal, Nov. 2015, pp. 391-401, vol. 471, No. 3, Portland Press Limited.

Siebuhr et al: "The ANTI-ADAMTS-5 Nanobody, M6495, Protects Against Cartilage Breakdown in Cartilage and Synovial Joint Tissue Explant Models", Apr. 1, 2018, page S187, XP055493294, Retrieved from the Internet: URL: https://www.oarsijournal.com/article/S1063-4584(18)30502-8/pdf [retrieved on Jul. 17, 2018] Abstract.

Troeberg et al., "Proteases Involved in Cartilage Matrix Degradation in Osteoarthritis", Biochimica et Biophysica Acta, 2012, pp. 133-145, vol. 1824, 2011 Elsevier B.V.

Chen et al., "Fusion protein linkers: Property, Design and Functionality", Author Manuscript of Advanced Drug Delivery Reviews, Oct. 15, 2013, pp. 1-35, vol. 64, No. 10, 2012 Elsevier B.V.

Colman P.M., "Effects of amino acid sequence changes on antibody-antigen interactions", Research in Immunology, 1994, pp. 33-36, vol. 145, Issue 1.

Dashivets T. et al., "Oxidation in the complementarity-determining regions differentially influences the properties of therapeutic antibodies", Mabs, 2016, pp. 1525-1535, vol. 8, No. 8, Taylor & Francis Group, LLC.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody", The Journal of Immunology, 2002, pp. 3076-3084, vol. 169, The American Association of Immunologists, Inc.

Kuznetsova E., "Brackets in the text of the legal document as a Linguistic and Cognitive Phenomenon", 2015, N3, pp. 37-43, Vestnik MGOU. Series, Russian Philology, English Abstract.

Maeda et al., "Engineering of Functional Chimeric Protein G-Vargula Luciferase", Analytical Biochemistry, 1997, pp. 147-152, vol. 249, Article No. AB972181, Academic Press.

Muller et al., "Spliceosomal Peptide P140 for Immunotherapy of Systemic Lupus Erythematosus", Arthritis & Rheumatism, Dec. 2008, pp. 3873-3883, vol. 58, No. 12, 2008, American College of Rheumatology.

Safdari Y. et al., "Antibody humanization methods—a review and update", Biotechnology and Genetic Engineering Reviews, 2013, pp. 175-186, vol. 29, No. 2, 2013 Taylor & Francis.

Torres M. et al., "The immunoglobulin constant region contributes to affinity and specificity", Trends in Immunology, 2008, pp. 91-97, vol. 29, No. 2, 2007 Elsevier Ltd.

Vajdos et al., "Comprehensive Functional Maps of the Antigen-binding Site of an Anti-ErbB2 Antibody Obtained with Shotgun Scanning Mutagenesis", Journal of Molecular Biology, 2002, pp. 415-428, vol. 320, 2002 Elsevier Science Ltd.

Banerjee et al., "Poly(ethylene glycol)-Prodrug Conjugates: Concept, Design, and Applications", Journal of Drug Delivery, May 7, 2012, pp. 1-17, vol. 2012, Article ID 103973, Hindawi Publishing Corporation.

Isin et al., "Use of Radiolabeled Compounds in Drug Metabolism and Pharmocokinetic Studies", Chemical Research in Toxicology, Feb. 28, 2012, pp. 532-542, vol. 25, 2012 American Chemical Society.

Kratz et al., "Clinical impact of serum proteins on drug delivery", Journal of Controlled Release, Jul. 20, 2012, pp. 429-445, vol. 161, 2011 Elsevier B.V.

Hoshi, Hiroko et al: "Effect of inhibiting MMP13 and ADAMTS5 by intra-articular injection of small interfering RNA in a surgically induced osteoarthritis model of mice", Cell and Tissue Research, Springer, DE, vol. 368, No. 2, Jan. 24, 2017 (Jan. 24, 2017), pp. 379-387, XP036216068.

Caljon et al: "Affinity Is an Important Determinant of the Anti-Trypanosome Activity of Nanobodies", PLoS Neglected Tropical Diseases, Nov. 15, 2012, pp. 1-8, e1902, vol. 6, Issue 11, XP055085029, ISSN: 193-2727, DOI: 10.1371/journal.pntd.0001902.

Dennis, "Welfare Issues of Genetically Modified Animals", ILAR Journal, Apr. 1, 2002, pp. 100-109, vol. 43, No. 2.

Edwards et al., "The Remarkable Flexibility of the Human Antibody Repertoire; Isolation of Over One Thousand Different Antibodies to a Single Protein, BlyS", Journal of Molecular Biology, Nov. 14, 2003, pp. 103-118, vol. 334, Elsevier Ltd.

Ghahroudi et al., "Selection and identification of single domain antibody fragments from camel heavy-chain antibodies", FEBS Letters, Sep. 15, 1997, pp. 521-526, vol. 414, No. 3, Federation of European Biochemical Societies.

Goel et al., "Plasticity within the Antigen-Combining Site May Manifest as Molecular Mimicry in the Humoral Immune Response", The Journal of Immunology, Dec. 15, 2004, pp. 7358-7367, vol. 173, No. 12, The American Association of Immunologists, Inc.

Janeway, Jr. et al., "Immunobiology, The Immune System in Health and Disease", Third Edition, 1997, pp. 3:1-3:11, Garland Publishing Inc.

Kanyavuz et al., "Breaking the law: unconventional strategies for antibody diversification", Nature Reviews | Immunology, Jun. 2019, pp. 355-368, vol. 19, No. 6, doi: 10.1038/S41577-019-0126-7.

Lloyd et al., "Modelling the human immune response: performance of a 10" human antibody repertoire against a broad panel of therapeutically relevant antigens", Protein Engineering, Design & Selection, Oct. 29, 2008, pp. 159-168, vol. 22, No. 3, Oxford University Press, doi: 10.1093/protein/gzn058.

Mitchell et al., "Comparative analysis of nanobody sequence and structure data", Proteins: Structure, Function, and Bioinformatics, Apr. 15, 2018 (Apr. 15, 2018), pp. 697-706, vol. 86, No. 7, XP055788282, US, ISSN: 0887-3585, DOI: 10.1002/prot.25497, Retrieved from the Internet: URL: https://api.wiley.com/onlinelibrary/tdm/v1/articles/10.1002%2Fprot.25497.

Roitt I. et al., "Immunology" Fifth Edition, Moscow, Mir, 2000, pp. 110-111 (English Translation).

Rudikoff et al., "Single amino acid substitution altering antigen-binding specificity", Proceedings of the National Academy of Sciences of the United States of America USA, Mar. 1982, pp. 1979-1983, vol. 79, No. 6.

Zhou et al., "Developing tTA Transgenic Rats for Inducible and Reversible Gene Expression", International Journal of Biological Sciences, Jan. 29, 2009, pp. 171-181, vol. 5, No. 2, Ivyspring International Publisher.

Bever et al., "VHH antibodies: Emerging reagents for the analysis of environmental chemicals", Anal Bioanal Chem, Author Manuscript, Sep. 1, 2017, pp. 1-34, vol. 408, No. 22.

(56) References Cited

OTHER PUBLICATIONS

Kishimoto et al., "Therapeutic applications of antigen binding domain VHH derived from heavy chain antibodies of Camelidae", Medchem News, Feb. 1, 2017, pp. 35-41, vol. 27, No. 1, English Abstract.
Office Action with a Search Report issued in a Canadian Application No. 3,064,469 dated Sep. 1, 2023.
Office Action dated Feb. 28, 2023 in corresponding Chinese patent application No. 201880049024.2.
Office Action issued in a Korean Application No. 10-2019-7038466, dated Nov. 23, 2023.
Office Action issued in a Korean Application No. 10-2019-7038633, dated Dec. 8, 2023.
Office Action with Search Report issued in a Chinese Application No. 201880049243.0, dated Nov. 16, 2023.

* cited by examiner

SEQUENCE LISTING

<160> NUMBER OF SEQ ID NOS: 201

<210> SEQ ID NO 1
<211> LENGTH: 114
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 1

Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Phe Ser Arg Tyr
                20                  25                  30

Ser Met Asn Trp Tyr Arg Gln Ala Pro Gly Lys Gln Arg Glu Phe Val
            35                  40                  45

Ala Gly Ile Ser Val Gly Arg Ile Thr Asn Tyr Ala Val Ser Val Arg
50                  55                  60

Gly Arg Phe Thr Ile Ser Arg Asp Asn Ala Glu Gly Thr Gly Tyr Leu
65                  70                  75                  80

Gln Met Asn Ser Leu Lys Pro Glu Asp Thr Ala Val Tyr Tyr Cys Asn
                85                  90                  95

Ala Gly Gly Leu Gln Gly Tyr Trp Gly Leu Gly Thr Gln Val Thr Val
                100                 105                 110

Ser Ser

<210> SEQ ID NO 2
<211> LENGTH: 114
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 2

Lys Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Phe Ser Arg Arg
                20                  25                  30

Ser Met Asn Trp Tyr Arg Gln Ala Pro Gly Lys Gln Arg Glu Phe Val
            35                  40                  45

Ala Gly Ile Ser Thr Gly Arg Ile Thr Asn Tyr Ala Val Ser Val Lys
50                  55                  60

Gly Arg Phe Thr Ile Ser Arg Asp Asn Ala Glu Gly Thr Gly Tyr Leu
65                  70                  75                  80

Gln Met Asn Ser Leu Lys Pro Glu Asp Thr Ala Val Tyr Tyr Cys Asn
                85                  90                  95

Ala Gly Gly Leu Gln Gly Tyr Trp Gly Leu Gly Thr Gln Val Thr Val
                100                 105                 110

Ser Ser

<210> SEQ ID NO 3
<211> LENGTH: 114
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 3

Glu Val Gln Leu Val Glu Ser Gly Arg Gly Ser Val Gln Ala Gly Gly
1               5                   10                  15

Ser Leu Arg Leu Ser Cys Ala Ala Ser Gly Ser Thr Phe Ser Arg Arg
            20                  25                  30

Ser Met Asn Trp Tyr Arg Gln Ala Pro Gly Lys Gln Arg Glu Phe Val
        35                  40                  45

Ala Gly Ile Ser Thr Gly Arg Ile Thr Asn Tyr Ala Val Ser Val Lys
    50                  55                  60

Gly Arg Phe Thr Ile Ser Arg Asp Asn Ala Glu Gly Thr Gly Tyr Leu
65              70                  75                  80

Gln Met Asn Ser Leu Lys Pro Glu Asp Thr Ala Val Tyr Tyr Cys Asn
            85                  90                  95

Ala Gly Gly Leu Gln Gly Tyr Trp Gly Leu Gly Thr Gln Val Thr Val
            100                 105                 110

Ser Ser

<210> SEQ ID NO 4
<211> LENGTH: 114
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 4

Glu Val Gln Leu Val Glu Ser Gly Gly Gly Ser Val Gln Thr Gly Gly
1               5                   10                  15

Ser Leu Arg Leu Ser Cys Ala Ala Ser Gly Ser Thr Phe Ser Arg Arg
            20                  25                  30

Ser Met Asn Trp Tyr Arg Gln Ala Pro Gly Lys Gln Arg Glu Phe Val
        35                  40                  45

Ala Gly Ile Ser Thr Gly Arg Ile Thr Asn Tyr Ala Val Ser Val Lys
    50                  55                  60

Gly Arg Phe Thr Ile Ser Arg Asp Asn Ala Glu Gly Thr Gly Tyr Leu
65              70                  75                  80

Gln Met Asn Ser Leu Lys Pro Glu Asp Thr Ala Val Tyr Tyr Cys Asn
            85                  90                  95

Ala Gly Gly Leu Gln Gly Tyr Trp Gly Leu Gly Thr Gln Val Thr Val
            100                 105                 110

Ser Ser

<210> SEQ ID NO 5
<211> LENGTH: 114
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 5

Glu Val Gln Leu Val Glu Ser Glu Gly Gly Ser Val Gln Ala Gly Gly
1               5                   10                  15

Ser Leu Arg Leu Ser Cys Ala Ala Ser Gly Ser Thr Phe Ser Arg Tyr
            20                  25                  30

Ser Met Asn Trp Tyr Arg Gln Ala Pro Gly Lys Gln Arg Glu Phe Val
        35                  40                  45

```
Ala Gly Ile Ser Val Gly Arg Ile Thr Asn Tyr Ala Val Ser Val Arg
    50                  55                  60

Gly Arg Phe Thr Ile Ser Arg Asp Asn Ala Glu Gly Thr Gly Tyr Leu
65                  70                  75                  80

Gln Met Asn Ser Leu Lys Pro Glu Asp Thr Ala Val Tyr Tyr Cys Asn
                85                  90                  95

Ala Gly Gly Leu Gln Gly Tyr Trp Gly Leu Gly Thr Gln Val Thr Val
                100                 105                 110

Ser Ser

<210> SEQ ID NO 6
<211> LENGTH: 114
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 6

Glu Val Gln Leu Val Glu Ser Arg Gly Gly Ser Val Gln Ala Gly Gly
1               5                   10                  15

Ser Leu Arg Leu Ser Cys Ala Ala Ser Gly Ser Thr Phe Ser Arg Tyr
                20                  25                  30

Ser Met Asn Trp Tyr Arg Gln Ala Pro Gly Lys Gln Arg Glu Phe Val
            35                  40                  45

Ala Gly Ile Ser Val Gly Arg Ile Thr Asn Tyr Ala Val Ser Val Lys
    50                  55                  60

Gly Arg Phe Thr Ile Ser Arg Asp Asn Ala Glu Gly Thr Gly Tyr Leu
65                  70                  75                  80

Gln Met Asn Ser Leu Lys Pro Glu Asp Thr Ala Val Tyr Tyr Cys Asn
                85                  90                  95

Ala Gly Gly Leu Gln Gly Tyr Trp Gly Leu Gly Thr Gln Val Thr Val
                100                 105                 110

Ser Ser

<210> SEQ ID NO 7
<211> LENGTH: 114
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 7

Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Phe Ser Arg Tyr
                20                  25                  30

Ser Met Asn Trp Tyr Arg Gln Ala Pro Gly Lys Gln Arg Glu Phe Val
            35                  40                  45

Ala Gly Ile Ser Val Gly Arg Ile Thr Asn Tyr Ala Val Ser Val Lys
    50                  55                  60

Gly Arg Phe Thr Ile Ser Arg Asp Asn Ala Glu Gly Thr Gly Phe Leu
65                  70                  75                  80

Gln Met Asn Gly Leu Lys Pro Glu Asp Thr Ala Val Tyr Tyr Cys Asn
                85                  90                  95

Ala Gly Gly Leu Gln Gly Tyr Trp Gly Leu Gly Thr Gln Val Thr Val
                100                 105                 110
```

Ser Ser

<210> SEQ ID NO 8
<211> LENGTH: 114
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 8

```
Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Phe Ser Arg Tyr
            20                  25                  30

Ser Met Asn Trp Tyr Arg Gln Ala Pro Arg Lys Gln Arg Glu Phe Val
        35                  40                  45

Ala Gly Ile Ser Thr Ala Arg Ile Thr His Tyr Ala Val Ser Val Lys
    50                  55                  60

Gly Arg Phe Thr Ile Ser Arg Asp Asn Ala Glu Gly Thr Gly Tyr Leu
65                  70                  75                  80

Gln Met Asn Ser Leu Lys Pro Glu Asp Thr Ala Val Tyr Tyr Cys Asn
                85                  90                  95

Ala Gly Gly Leu Gln Gly Ser Trp Gly Leu Gly Thr Leu Val Thr Val
            100                 105                 110

Ser Ser
```

<210> SEQ ID NO 9
<211> LENGTH: 123
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 9

```
Asp Val Gln Leu Val Glu Ser Gly Gly Gly Leu Val Gln Pro Gly Gly
1               5                   10                  15

Ser Leu Arg Leu Ser Cys Val Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Ala Val Asp Ala Ser Arg Gly Leu Pro Tyr Glu Tyr Tyr Tyr
            100                 105                 110

Trp Gly Gln Gly Thr Leu Val Thr Val Ser Ser
        115                 120
```

<210> SEQ ID NO 10
<211> LENGTH: 129
<212> TYPE: PRT
<213> ORGANISM: Artificial Sequence
<220> FEATURE:
<223> OTHER INFORMATION: Description of Artificial Sequence: Synthetic anti-MMP13 inhibitor

<400> SEQUENCE: 10

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Leu Ala Val Tyr Gly Pro Asn Arg Tyr Arg Tyr Gly Pro
            100                 105                 110

Val Gly Glu Tyr Asn Tyr Trp Gly Gln Gly Thr Leu Val Thr Val Ser
        115                 120                 125

Ser
```

<210> SEQ ID NO 11
<211> LENGTH: 121
<212> TYPE: PRT
<213> ORGANISM: Artificial Sequence
<220> FEATURE:
<223> OTHER INFORMATION: Description of Artificial Sequence: Synthetic
    anti-MMP13 inhibitor

<400> SEQUENCE: 11

```
Glu Val Gln Leu Val Glu Ser Gly Gly Ala Leu Val Arg Pro Gly Gly
1               5                   10                  15

Ser Leu Arg Leu Ser Cys Ala Ala Ser Gly Phe Ala Phe Ser Ala Ala
            20                  25                  30

Tyr Met Ser Trp Val Arg Gln Ala Pro Gly Arg Gly Leu Glu Trp Val
        35                  40                  45

Ser Ser Ile Ser Asp Asp Gly Ser Lys Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Asp Asp Thr Ala Val Tyr Tyr Cys
                85                  90                  95

Asn Thr Gly Tyr Gly Ala Thr Thr Thr Arg Pro Gly Arg Tyr Trp Gly
            100                 105                 110

Gln Gly Thr Gln Val Thr Val Ser Ser
        115                 120
```

<210> SEQ ID NO 12
<211> LENGTH: 128
<212> TYPE: PRT
<213> ORGANISM: Artificial Sequence
<220> FEATURE:
<223> OTHER INFORMATION: Description of Artificial Sequence: Synthetic
    anti-MMP13 inhibitor

<400> SEQUENCE: 12

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Leu Ala Tyr Tyr
            20                  25                  30

Ser Ile Gly Trp Phe Arg Gln Ala Pro Gly Lys Glu Arg Glu Gly Val
        35                  40                  45

Ser Cys Ile Ser Ser Gly Ile Asp Gly Ser Thr Tyr Tyr Ala Asp Ser
    50                  55                  60

Val Lys Gly Arg Phe Thr Ile Ser Arg Asp Asn Ala Lys Asn Thr Met
65                  70                  75                  80

Tyr Leu Gln Met Asn Asn Leu Lys Pro Glu Asp Thr Gly Val Tyr Tyr
                85                  90                  95

Cys Ala Ala Asp Pro Ser His Tyr Tyr Ser Glu Tyr Asp Cys Gly Tyr
                100                 105                 110

Tyr Gly Met Asp Tyr Trp Gly Lys Gly Thr Leu Val Thr Val Ser Ser
        115                 120                 125

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 13

Asp Val Gln Leu Val Glu Ser Gly Gly Gly Leu Val Gln Pro Gly Gly
1               5                   10                  15

Ser Leu Arg Leu Ser Cys Ala Gly Ser Gly Ser Ile Phe Arg Ile Asn
            20                  25                  30

Val Met Ala Trp Tyr Arg Gln Ala Pro Gly Lys Gln Arg Glu Leu Val
        35                  40                  45

Ala Ala Ile Thr Ser Gly Gly Thr Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Ala Asp Ile Gly Trp Pro Tyr Val Leu Asp Tyr Asp Phe Trp Gly Gln
                100                 105                 110

Gly Thr Leu Val Thr Val Ser Ser
        115                 120

<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 14

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Ile Asn
            20                  25                  30

Ala Met Gly Trp Tyr Arg Gln Ala Pro Gly Lys Gln Arg Glu Leu Val
        35                  40                  45

Ala Ala Ile Ile Ser Gly Gly Thr Thr Tyr Tyr Ala Asp Ser Val Lys
    50                  55                  60
```

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Ala Asp Ile Gly Trp Pro Tyr Val Leu Asp Tyr Asp Phe Trp Gly Gln
            100                 105                 110

Gly Thr Leu Val Thr Val Ser Ser
        115                 120

<210> SEQ ID NO 15
<211> LENGTH: 126
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 15

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Arg Tyr
            20                  25                  30

Val Met Gly Trp Phe Arg Gln Ala Pro Gly Lys Glu Arg Glu Phe Val
        35                  40                  45

Ala Ala Ile Asn Trp Ser Ser Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Arg Arg Val Tyr Tyr Asp Thr Tyr Pro Asn Leu Arg Gly
            100                 105                 110

Tyr Asp Tyr Trp Gly Gln Gly Thr Leu Val Thr Val Ser Ser
        115                 120                 125

<210> SEQ ID NO 16
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 16

Asp Val Gln Leu Val Glu Ser Gly Gly Gly Leu Val Gln Pro Gly Gly
1               5                   10                  15

Ser Leu Arg Leu Ser Cys Val Ala Ser Gly Leu Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Arg Gly Pro Gly Ser Val Gly Pro Ser Glu Glu Tyr Asn
            100                 105                 110

Tyr Trp Gly Gln Gly Thr Leu Val Thr Val Ser Ser
         115                 120

<210> SEQ ID NO 17
<211> LENGTH: 127
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 17

Asp Val Gln Leu Val Glu Ser Gly Gly Gly Leu Val Gln Pro Gly Gly
1               5                   10                  15

Ser Leu Arg Leu Ser Cys Val Ala Ser Gly Pro Thr Phe Ser Asp Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Arg Gly Gly Gly Tyr Arg Ala Ser Gly Gly Pro Leu Ser
            100                 105                 110

Glu Tyr Asn Tyr Trp Gly Gln Gly Thr Leu Val Thr Val Ser Ser
        115                 120                 125

<210> SEQ ID NO 18
<211> LENGTH: 126
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 18

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Gly Gly Gly Ser Thr Tyr Tyr Ser Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Leu Gly Ser Thr Gly Ser Gly Ser Thr Pro Val Pro Glu
            100                 105                 110

Tyr Arg Tyr Trp Gly Gln Gly Thr Leu Val Thr Val Ser Ser
        115                 120                 125

<210> SEQ ID NO 19
<211> LENGTH: 126
<212> TYPE: PRT
<213> ORGANISM: Artificial Sequence
<220> FEATURE:

<223> OTHER INFORMATION: Description of Artificial Sequence: Synthetic
      anti-MMP13 inhibitor

<400> SEQUENCE: 19

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ser Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Arg Gly Gly Val Ala Gly Thr Asp Gly Pro Leu Gly Asp
            100                 105                 110

Tyr Asn Tyr Trp Gly Gln Gly Thr Leu Val Thr Val Ser Ser
        115                 120                 125

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 20

Asp Val Gln Leu Val Glu Ser Gly Gly Gly Leu Val Gln Pro Gly Gly
1               5                   10                  15

Ser Leu Arg Leu Ser Cys Ala Gly Ser Gly Ser Ile Phe Ser Gly Asn
            20                  25                  30

Ala Met Gly Trp Tyr Arg Gln Ala Pro Gly Lys Gln Arg Glu Leu Val
        35                  40                  45

Ala Ala Ile Thr Ser Gly Gly Val Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ala Asp Ile Arg Tyr Pro Thr Gly Leu Val Gly Asp Tyr Trp Gly Gln
            100                 105                 110

Gly Thr Leu Val Thr Val Ser Ser
        115                 120

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ser Ala Ser Thr Gly Ile Phe Arg Ile Asn

```
                20                  25                  30
Thr Met Gly Trp His Arg Gln Ala Pro Gly Lys Gln Arg Asp Leu Val
            35                  40                  45

Ala Thr Phe Thr Ser Asp Asp Asn Thr Lys Tyr Ala Asp Ser Val Lys
 50                  55                  60

Gly Arg Phe Thr Ile Ser Arg Asp Asn Ala Glu Asn Thr Val Tyr Leu
65                  70                  75                  80

Gln Met Asn Asp Leu Lys Pro Glu Asp Thr Ala Val Tyr Tyr Cys His
                85                  90                  95

Ala Thr Thr Val Met Tyr Asp Ser Asn Ser Pro Asp Tyr Trp Gly Gln
            100                 105                 110

Gly Thr Gln Val Thr Val Ser Ser
            115                 120

<210> SEQ ID NO 22
<211> LENGTH: 128
<212> TYPE: PRT
<213> ORGANISM: Artificial Sequence
<220> FEATURE:
<223> OTHER INFORMATION: Description of Artificial Sequence: Synthetic
      anti-MMP13 inhibitor

<400> SEQUENCE: 22

Glu Val Gln Leu Val Glu Ser Glu Gly Gly Thr Val Glu Pro Gly Glu
1               5                   10                  15

Ser Leu Arg Leu Ala Cys Ala Ala Pro Gly Pro Gly Ile Arg Thr Asn
            20                  25                  30

Phe Met Ala Trp Tyr Arg Gln Ala Pro Glu Lys Glu Arg Glu Met Val
        35                  40                  45

Ala Ser Ile Ser Arg Asp Gly Ser Thr His Tyr Ala Asp Ser Val Lys
    50                  55                  60

Gly Arg Phe Thr Ile Ser Ser Asp Asn Ala Thr Ser Thr Phe Tyr Leu
65                  70                  75                  80

Gln Met Asn Ser Leu Gln Val Glu Asp Thr Ala Val Tyr Tyr Cys Ala
                85                  90                  95

Thr Asp Pro His Ile Leu His Asn Asp Arg Ala Gly Ala Phe Leu Val
            100                 105                 110

Glu Asp Tyr Asp His Trp Gly Gln Gly Thr Gln Val Thr Val Ser Ser
        115                 120                 125

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 23

Gly Ser Thr Phe Ser Arg Tyr Ser Met Asn
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 24
```

```
Gly Ser Thr Phe Ser Arg Arg Ser Met Asn
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 25

Gly Ser Ile Phe Ser Ile Asn Ala Met Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 26

Gly Arg Thr Phe Ser Ser Tyr Ala Met Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 27

Gly Phe Ala Phe Ser Ala Ala Tyr Met Ser
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 28

Gly Phe Thr Leu Ala Tyr Tyr Ser Ile Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 29

Gly Ser Ile Phe Arg Ile Asn Val Met Ala
1               5                   10

<210> SEQ ID NO 30
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      CD1 sequence of anti-MMP13 ISVD

<400> SEQUENCE: 30

Gly Ser Ile Phe Arg Ile Asn Ala Met Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 31

Gly Arg Thr Phe Ser Arg Tyr Val Met Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 32

Gly Leu Thr Phe Ser Ser Tyr Ala Met Gly
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 33

Gly Pro Thr Phe Ser Asp Tyr Ala Met Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 34

Gly Ser Ile Phe Ser Gly Asn Ala Met Gly
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 35

Thr Gly Ile Phe Arg Ile Asn Thr Met Gly
1               5                   10
```

```
<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      CD1 sequence of anti-MMP13 ISVD

<400> SEQUENCE: 36

Gly Pro Gly Ile Arg Thr Asn Phe Met Ala
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 37

Gly Ile Ser Val Gly Arg Ile Thr Asn
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 38

Gly Ile Ser Thr Gly Arg Ile Thr Asn
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 39

Gly Ile Ser Thr Ala Arg Ile Thr His
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 40

Ala Ile Ser Ser Gly Gly Ser Thr Tyr
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD
```

```
<400> SEQUENCE: 41

Ala Ile Ser Trp Ser Gly Gly Ser Thr Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 42

Ser Ile Ser Asp Asp Gly Ser Lys Thr Tyr
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 43

Cys Ile Ser Ser Gly Ile Asp Gly Ser Thr Tyr
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 44

Ala Ile Thr Ser Gly Gly Thr Thr Asn
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 45

Ala Ile Ile Ser Gly Gly Thr Thr Tyr
1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 46

Ala Ile Asn Trp Ser Ser Gly Ser Thr Tyr
1               5                   10

<210> SEQ ID NO 47
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 47

Ala Ile Ser Trp Ser Gly Gly Arg Thr Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 48

Ala Ile Ser Trp Gly Gly Gly Ser Thr Tyr
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 49

Ala Ile Thr Ser Gly Gly Val Thr Asn
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 50

Thr Phe Thr Ser Asp Asp Asn Thr Lys
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      CD2 sequence of anti-MMP13 ISVD

<400> SEQUENCE: 51

Ser Ile Ser Arg Asp Gly Ser Thr His
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 52

Gly Gly Leu Gln Gly Tyr
1               5
```

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 53

Gly Gly Leu Gln Gly Ser
1               5

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 54

Ala Val Asp Ala Ser Arg Gly Leu Pro Tyr Glu Leu Tyr Tyr Tyr
1               5                   10                  15

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 55

Ala Leu Ala Val Tyr Gly Pro Asn Arg Tyr Arg Tyr Gly Pro Val Gly
1               5                   10                  15

Glu Tyr Asn Tyr
            20

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 56

Gly Tyr Gly Ala Thr Thr Thr Arg Pro Gly Arg Tyr
1               5                   10

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 57

Asp Pro Ser His Tyr Tyr Ser Glu Tyr Asp Cys Gly Tyr Tyr Gly Met
1               5                   10                  15

Asp Tyr

<210> SEQ ID NO 58
<211> LENGTH: 12

```
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 58

Asp Ile Gly Trp Pro Tyr Val Leu Asp Tyr Asp Phe
1               5                   10

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 59

Asp Arg Arg Val Tyr Tyr Asp Thr Tyr Pro Asn Leu Arg Gly Tyr Asp
1               5                   10                  15

Tyr

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 60

Ala Arg Gly Pro Gly Ser Val Gly Pro Ser Glu Glu Tyr Asn Tyr
1               5                   10                  15

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 61

Ala Arg Gly Gly Gly Tyr Arg Ala Ser Gly Gly Pro Leu Ser Glu Tyr
1               5                   10                  15

Asn Tyr

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 62

Ala Leu Gly Ser Thr Gly Ser Gly Ser Thr Pro Val Pro Glu Tyr Arg
1               5                   10                  15

Tyr

<210> SEQ ID NO 63
<211> LENGTH: 17
<212> TYPE: PRT
<213> ORGANISM: Artificial Sequence
<220> FEATURE:
```

-continued

<223> OTHER INFORMATION: Description of Artificial Sequence: Synthetic
      CD3 sequence of anti-MMP13 ISVD

<400> SEQUENCE: 63

Ala Arg Gly Gly Val Ala Gly Thr Asp Gly Pro Leu Gly Asp Tyr Asn
1               5                   10                  15
Tyr

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 64

Asp Ile Arg Tyr Pro Thr Gly Leu Val Gly Asp Tyr
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 65

Thr Thr Val Met Tyr Asp Ser Asn Ser Pro Asp Tyr
1               5                   10

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 66

Asp Pro His Ile Leu His Asn Asp Arg Ala Gly Ala Phe Leu Val Glu
1               5                   10                  15
Asp Tyr Asp His
            20

<210> SEQ ID NO 67
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 67

Glu Val Gln Leu Val Glu Ser Gly Gly Gly Ser Val Gln Ala Gly Gly
1               5                   10                  15
Ser Leu Arg Leu Ser Cys Ala Ala Ser
            20                  25

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic Framework FR1 of anti-MMP13 Nanobody

<400> SEQUENCE: 68

Lys Val Gln Leu Val Glu Ser Gly Gly Gly Ser Val Gln Ala Gly Gly
1               5                   10                  15

Ser Leu Arg Leu Ser Cys Ala Ala Ser
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 69

Glu Val Gln Leu Val Glu Ser Gly Arg Gly Ser Val Gln Ala Gly Gly
1               5                   10                  15

Ser Leu Arg Leu Ser Cys Ala Ala Ser
            20                  25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 70

Glu Val Gln Leu Val Glu Ser Gly Gly Gly Ser Val Gln Thr Gly Gly
1               5                   10                  15

Ser Leu Arg Leu Ser Cys Ala Ala Ser
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 71

Glu Val Gln Leu Val Glu Ser Glu Gly Gly Ser Val Gln Ala Gly Gly
1               5                   10                  15

Ser Leu Arg Leu Ser Cys Ala Ala Ser
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 72

Glu Val Gln Leu Val Glu Ser Arg Gly Gly Ser Val Gln Ala Gly Gly
1               5                   10                  15

Ser Leu Arg Leu Ser Cys Ala Ala Ser
            20                  25

```
<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 73

Asp Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 74

Asp Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 75

Glu Val Gln Leu Val Glu Ser Gly Gly Ala Leu Val Arg Pro Gly Gly
1               5                   10                  15

Ser Leu Arg Leu Ser Cys Ala Ala Ser
            20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 77

Asp Val Gln Leu Val Glu Ser Gly Gly Gly Leu Val Gln Pro Gly Gly
```

Ser Leu Arg Leu Ser Cys Ala Gly Ser
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      Framework FR1 of anti-MMP13 Nanobody

<400> SEQUENCE: 79

Glu Val Gln Leu Val Glu Ser Glu Gly Gly Thr Val Glu Pro Gly Glu
1               5                   10                  15

Ser Leu Arg Leu Ala Cys Ala Ala Pro
            20                  25

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-MMP13 Nanobody

<400> SEQUENCE: 80

Trp Tyr Arg Gln Ala Pro Gly Lys Gln Arg Glu Phe Val Ala
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-MMP13 Nanobody

<400> SEQUENCE: 81

Trp Tyr Arg Gln Ala Pro Arg Lys Gln Arg Glu Phe Val Ala
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-MMP13 Nanobody

<400> SEQUENCE: 82

Trp Tyr Arg Gln Ala Pro Gly Lys Gln Arg Glu Leu Val Ala

```
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-MMP13 Nanobody

<400> SEQUENCE: 83

Trp Phe Arg Gln Ala Pro Gly Lys Glu Arg Glu Phe Val Ala
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-MMP13 Nanobody

<400> SEQUENCE: 84

Trp Val Arg Gln Ala Pro Gly Arg Gly Leu Glu Trp Val Ser
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-MMP13 Nanobody

<400> SEQUENCE: 85

Trp Phe Arg Gln Ala Pro Gly Lys Glu Arg Glu Gly Val Ser
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-MMP13 Nanobody

<400> SEQUENCE: 86

Trp His Arg Gln Ala Pro Gly Lys Gln Arg Asp Leu Val Ala
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-MMP13 Nanobody

<400> SEQUENCE: 87

Trp Tyr Arg Gln Ala Pro Glu Lys Glu Arg Glu Met Val Ala
1               5                   10

<210> SEQ ID NO 88
<211> LENGTH: 39
<212> TYPE: PRT
<213> ORGANISM: Artificial Sequence
<220> FEATURE:
<223> OTHER INFORMATION: Description of Artificial Sequence: Synthetic
```

Framework FR3 of anti-MMP13 Nanobody

<400> SEQUENCE: 88

Tyr Ala Val Ser Val Arg Gly Arg Phe Thr Ile Ser Arg Asp Asn Ala
1               5                   10                  15
Glu Gly Thr Gly Tyr Leu Gln Met Asn Ser Leu Lys Pro Glu Asp Thr
            20                  25                  30
Ala Val Tyr Tyr Cys Asn Ala
        35

<210> SEQ ID NO 89
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-MMP13 Nanobody

<400> SEQUENCE: 89

Tyr Ala Val Ser Val Lys Gly Arg Phe Thr Ile Ser Arg Asp Asn Ala
1               5                   10                  15
Glu Gly Thr Gly Tyr Leu Gln Met Asn Ser Leu Lys Pro Glu Asp Thr
            20                  25                  30
Ala Val Tyr Tyr Cys Asn Ala
        35

<210> SEQ ID NO 90
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-MMP13 Nanobody

<400> SEQUENCE: 90

Tyr Ala Val Ser Val Lys Gly Arg Phe Thr Ile Ser Arg Asp Asn Ala
1               5                   10                  15
Glu Gly Thr Gly Phe Leu Gln Met Asn Gly Leu Lys Pro Glu Asp Thr
            20                  25                  30
Ala Val Tyr Tyr Cys Asn Ala
        35

<210> SEQ ID NO 91
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-MMP13 Nanobody

<400> SEQUENCE: 91

Tyr Ala Asp Ser Val Lys Gly Arg Phe Thr Ile Ser Arg Asp Asn Ser
1               5                   10                  15
Lys Asn Thr Val Tyr Leu Gln Met Asn Ser Leu Arg Pro Glu Asp Thr
            20                  25                  30
Ala Val Tyr Tyr Cys Asn Ala
        35

<210> SEQ ID NO 92
<211> LENGTH: 39
<212> TYPE: PRT
<213> ORGANISM: Artificial Sequence
<220> FEATURE:

<223> OTHER INFORMATION: Description of Artificial Sequence: Synthetic
    Framework FR3 of anti-MMP13 Nanobody

<400> SEQUENCE: 92

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Thr Ala
        35

<210> SEQ ID NO 93
<211> LENGTH: 39
<212> TYPE: PRT
<213> ORGANISM: Artificial Sequence
<220> FEATURE:
<223> OTHER INFORMATION: Description of Artificial Sequence: Synthetic
    Framework FR3 of anti-MMP13 Nanobody

<400> SEQUENCE: 93

Tyr Ala Asp Ser Val Lys Gly Arg Phe Thr Ile Ser Arg Asp Asn Ala
1               5                   10                  15

Lys Asn Thr Val Tyr Leu Gln Met Asn Asn Leu Lys Pro Asp Asp Thr
            20                  25                  30

Ala Val Tyr Tyr Cys Asn Thr
        35

<210> SEQ ID NO 94
<211> LENGTH: 39
<212> TYPE: PRT
<213> ORGANISM: Artificial Sequence
<220> FEATURE:
<223> OTHER INFORMATION: Description of Artificial Sequence: Synthetic
    Framework FR3 of anti-MMP13 Nanobody

<400> SEQUENCE: 94

Tyr Ala Asp Ser Val Lys Gly Arg Phe Thr Ile Ser Arg Asp Asn Ala
1               5                   10                  15

Lys Asn Thr Met Tyr Leu Gln Met Asn Asn Leu Lys Pro Glu Asp Thr
            20                  25                  30

Gly Val Tyr Tyr Cys Ala Ala
        35

<210> SEQ ID NO 95
<211> LENGTH: 39
<212> TYPE: PRT
<213> ORGANISM: Artificial Sequence
<220> FEATURE:
<223> OTHER INFORMATION: Description of Artificial Sequence: Synthetic
    Framework FR3 of anti-MMP13 Nanobody

<400> SEQUENCE: 95

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Tyr Ala
        35

<210> SEQ ID NO 96
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-MMP13 Nanobody

<400> SEQUENCE: 96

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Ala Ala
        35

<210> SEQ ID NO 97
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-MMP13 Nanobody

<400> SEQUENCE: 97

Tyr Ser Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Thr Ala
        35

<210> SEQ ID NO 98
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-MMP13 Nanobody

<400> SEQUENCE: 98

Tyr Ala Asp Ser Val Lys Gly Arg Phe Thr Ile Ser Arg Asp Asn Ala
1               5                   10                  15

Glu Asn Thr Val Tyr Leu Gln Met Asn Asp Leu Lys Pro Glu Asp Thr
            20                  25                  30

Ala Val Tyr Tyr Cys His Ala
        35

<210> SEQ ID NO 99
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-MMP13 Nanobody

<400> SEQUENCE: 99

Tyr Ala Asp Ser Val Lys Gly Arg Phe Thr Ile Ser Ser Asp Asn Ala
1               5                   10                  15

Thr Ser Thr Phe Tyr Leu Gln Met Asn Ser Leu Gln Val Glu Asp Thr
            20                  25                  30

Ala Val Tyr Tyr Cys Ala Thr
        35

<210> SEQ ID NO 100
<211> LENGTH: 11
<212> TYPE: PRT

```
<213> ORGANISM: Artificial Sequence
<220> FEATURE:
<223> OTHER INFORMATION: Description of Artificial Sequence: Synthetic
      Framework FR4 of anti-MMP13 Nanobody

<400> SEQUENCE: 100

Trp Gly Leu Gly Thr Gln Val Thr Val Ser Ser
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      Framework FR4 of anti-MMP13 Nanobody

<400> SEQUENCE: 101

Trp Gly Leu Gly Thr Leu Val Thr Val Ser Ser
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      Framework FR4 of anti-MMP13 Nanobody

<400> SEQUENCE: 102

Trp Gly Gln Gly Thr Leu Val Thr Val Ser Ser
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      Framework FR4 of anti-MMP13 Nanobody

<400> SEQUENCE: 103

Trp Gly Gln Gly Thr Gln Val Thr Val Ser Ser
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      Framework FR4 of anti-MMP13 Nanobody

<400> SEQUENCE: 104

Trp Gly Lys Gly Thr Leu Val Thr Val Ser Ser
1               5                   10

<210> SEQ ID NO 105
<211> LENGTH: 2415
<212> TYPE: PRT
<213> ORGANISM: Homo sapiens
<220> FEATURE:
<223> OTHER INFORMATION: Human aggrecan

<400> SEQUENCE: 105

Met Thr Thr Leu Leu Trp Val Phe Val Thr Leu Arg Val Ile Thr Ala
1               5                   10                  15
```

-continued

Ala Val Thr Val Glu Thr Ser Asp His Asp Asn Ser Leu Ser Val Ser
                20                  25                  30

Ile Pro Gln Pro Ser Pro Leu Arg Val Leu Leu Gly Thr Ser Leu Thr
            35                  40                  45

Ile Pro Cys Tyr Phe Ile Asp Pro Met His Pro Val Thr Thr Ala Pro
        50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Glu Gly Arg Val Arg Val
                85                  90                  95

Asn Ser Ala Tyr Gln Asp Lys Val Ser Leu Pro Asn Tyr Pro Ala Ile
            100                 105                 110

Pro Ser Asp Ala Thr Leu Glu Val Gln Ser Leu Arg Ser Asn Asp Ser
        115                 120                 125

Gly Val Tyr Arg Cys Glu Val Met His Gly Ile Glu Asp Ser Glu Ala
130                 135                 140

Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly His Val Tyr Leu
        275                 280                 285

Ala Trp Gln Ala Gly Met Asp Met Cys Ser Ala Gly Trp Leu Ala Asp
290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly
                325                 330                 335

Tyr Pro Asp Pro Ser Ser Arg Tyr Asp Ala Ile Cys Tyr Thr Gly Glu
            340                 345                 350

Asp Phe Val Asp Ile Pro Glu Asn Phe Phe Gly Val Gly Gly Glu Glu
        355                 360                 365

Asp Ile Thr Val Gln Thr Val Thr Trp Pro Asp Met Glu Leu Pro Leu
370                 375                 380

Pro Arg Asn Ile Thr Glu Gly Glu Ala Arg Gly Ser Val Ile Leu Thr
385                 390                 395                 400

Val Lys Pro Ile Phe Glu Val Ser Pro Ser Pro Leu Glu Pro Glu Glu
                405                 410                 415

Pro Phe Thr Phe Ala Pro Glu Ile Gly Ala Thr Ala Phe Ala Glu Val
            420                 425                 430

Glu Asn Glu Thr Gly Glu Ala Thr Arg Pro Trp Gly Phe Pro Thr Pro

```
            435                 440                 445
Gly Leu Gly Pro Ala Thr Ala Phe Thr Ser Glu Asp Leu Val Val Gln
450                 455                 460

Val Thr Ala Val Pro Gly Gln Pro His Leu Pro Gly Gly Val Val Phe
465                 470                 475                 480

His Tyr Arg Pro Gly Pro Thr Arg Tyr Ser Leu Thr Phe Glu Glu Ala
                    485                 490                 495

Gln Gln Ala Cys Pro Gly Thr Gly Ala Val Ile Ala Ser Pro Glu Gln
                500                 505                 510

Leu Gln Ala Ala Tyr Glu Ala Gly Tyr Glu Gln Cys Asp Ala Gly Trp
            515                 520                 525

Leu Arg Asp Gln Thr Val Arg Tyr Pro Ile Val Ser Pro Arg Thr Pro
530                 535                 540

Cys Val Gly Asp Lys Asp Ser Ser Pro Gly Val Arg Thr Tyr Gly Val
545                 550                 555                 560

Arg Pro Ser Thr Glu Thr Tyr Asp Val Tyr Cys Phe Val Asp Arg Leu
                565                 570                 575

Glu Gly Glu Val Phe Phe Ala Thr Arg Leu Glu Gln Phe Thr Phe Gln
                580                 585                 590

Glu Ala Leu Glu Phe Cys Glu Ser His Asn Ala Thr Ala Thr Thr Gly
            595                 600                 605

Gln Leu Tyr Ala Ala Trp Ser Arg Gly Leu Asp Lys Cys Tyr Ala Gly
610                 615                 620

Trp Leu Ala Asp Gly Ser Leu Arg Tyr Pro Ile Val Thr Pro Arg Pro
625                 630                 635                 640

Ala Cys Gly Gly Asp Lys Pro Gly Val Arg Thr Val Tyr Leu Tyr Pro
                645                 650                 655

Asn Gln Thr Gly Leu Pro Asp Pro Leu Ser Arg His His Ala Phe Cys
                660                 665                 670

Phe Arg Gly Ile Ser Ala Val Pro Ser Pro Gly Glu Glu Glu Gly Gly
            675                 680                 685

Thr Pro Thr Ser Pro Ser Gly Val Glu Glu Trp Ile Val Thr Gln Val
690                 695                 700

Val Pro Gly Val Ala Ala Val Pro Val Glu Glu Thr Thr Ala Val
705                 710                 715                 720

Pro Ser Gly Glu Thr Thr Ala Ile Leu Glu Phe Thr Thr Glu Pro Glu
                725                 730                 735

Asn Gln Thr Glu Trp Glu Pro Ala Tyr Thr Pro Val Gly Thr Ser Pro
                740                 745                 750

Leu Pro Gly Ile Leu Pro Thr Trp Pro Pro Thr Gly Ala Glu Thr Glu
            755                 760                 765

Glu Ser Thr Glu Gly Pro Ser Ala Thr Glu Val Pro Ser Ala Ser Glu
            770                 775                 780

Glu Pro Ser Pro Ser Glu Val Pro Phe Pro Ser Glu Glu Pro Ser Pro
785                 790                 795                 800

Ser Glu Glu Pro Phe Pro Ser Val Arg Pro Phe Pro Ser Val Glu Leu
                805                 810                 815

Phe Pro Ser Glu Glu Pro Phe Pro Ser Lys Glu Pro Ser Pro Ser Glu
                820                 825                 830

Glu Pro Ser Ala Ser Glu Glu Pro Tyr Thr Pro Ser Pro Pro Glu Pro
            835                 840                 845

Ser Trp Thr Glu Leu Pro Ser Ser Gly Glu Glu Ser Gly Ala Pro Asp
850                 855                 860
```

```
Val Ser Gly Asp Phe Thr Gly Ser Gly Asp Val Ser Gly His Leu Asp
865                 870                 875                 880

Phe Ser Gly Gln Leu Ser Gly Asp Arg Ala Ser Gly Leu Pro Ser Gly
                885                 890                 895

Asp Leu Asp Ser Ser Gly Leu Thr Ser Thr Val Gly Ser Gly Leu Thr
            900                 905                 910

Val Glu Ser Gly Leu Pro Ser Gly Asp Glu Arg Ile Glu Trp Pro
        915                 920                 925

Ser Thr Pro Thr Val Gly Glu Leu Pro Ser Gly Ala Glu Ile Leu Glu
    930                 935                 940

Gly Ser Ala Ser Gly Val Gly Asp Leu Ser Gly Leu Pro Ser Gly Glu
945                 950                 955                 960

Val Leu Glu Thr Ser Ala Ser Gly Val Gly Asp Leu Ser Gly Leu Pro
            965                 970                 975

Ser Gly Glu Val Leu Glu Thr Thr Ala Pro Gly Val Glu Asp Ile Ser
            980                 985                 990

Gly Leu Pro Ser Gly Glu Val Leu Glu Thr Thr Ala Pro Gly Val Glu
            995                 1000                1005

Asp Ile Ser Gly Leu Pro Ser Gly Glu Val Leu Glu Thr Thr Ala
    1010                1015                1020

Pro Gly Val Glu Asp Ile Ser Gly Leu Pro Ser Gly Glu Val Leu
    1025                1030                1035

Glu Thr Thr Ala Pro Gly Val Glu Asp Ile Ser Gly Leu Pro Ser
    1040                1045                1050

Gly Glu Val Leu Glu Thr Thr Ala Pro Gly Val Glu Asp Ile Ser
    1055                1060                1065

Gly Leu Pro Ser Gly Glu Val Leu Glu Thr Ala Ala Pro Gly Val
    1070                1075                1080

Glu Asp Ile Ser Gly Leu Pro Ser Gly Glu Val Leu Glu Thr Ala
    1085                1090                1095

Ala Pro Gly Val Glu Asp Ile Ser Gly Leu Pro Ser Gly Glu Val
    1100                1105                1110

Leu Glu Thr Ala Ala Pro Gly Val Glu Asp Ile Ser Gly Leu Pro
    1115                1120                1125

Ser Gly Glu Val Leu Glu Thr Ala Ala Pro Gly Val Glu Asp Ile
    1130                1135                1140

Ser Gly Leu Pro Ser Gly Glu Val Leu Glu Thr Ala Ala Pro Gly
    1145                1150                1155

Val Glu Asp Ile Ser Gly Leu Pro Ser Gly Glu Val Leu Glu Thr
    1160                1165                1170

Ala Ala Pro Gly Val Glu Asp Ile Ser Gly Leu Pro Ser Gly Glu
    1175                1180                1185

Val Leu Glu Thr Ala Ala Pro Gly Val Glu Asp Ile Ser Gly Leu
    1190                1195                1200

Pro Ser Gly Glu Val Leu Glu Thr Ala Ala Pro Gly Val Glu Asp
    1205                1210                1215

Ile Ser Gly Leu Pro Ser Gly Glu Val Leu Glu Thr Ala Ala Pro
    1220                1225                1230

Gly Val Glu Asp Ile Ser Gly Leu Pro Ser Gly Glu Val Leu Glu
    1235                1240                1245

Thr Ala Ala Pro Gly Val Glu Asp Ile Ser Gly Leu Pro Ser Gly
    1250                1255                1260
```

```
Glu Val Leu Glu Thr Ala Ala Pro Gly Val Glu Asp Ile Ser Gly
1265                1270                1275

Leu Pro Ser Gly Glu Val Leu Glu Thr Thr Ala Pro Gly Val Glu
1280                1285                1290

Glu Ile Ser Gly Leu Pro Ser Gly Glu Val Leu Glu Thr Thr Ala
1295                1300                1305

Pro Gly Val Asp Glu Ile Ser Gly Leu Pro Ser Gly Glu Val Leu
1310                1315                1320

Glu Thr Thr Ala Pro Gly Val Glu Glu Ile Ser Gly Leu Pro Ser
1325                1330                1335

Gly Glu Val Leu Glu Thr Ser Thr Ser Ala Val Gly Asp Leu Ser
1340                1345                1350

Gly Leu Pro Ser Gly Gly Glu Val Leu Glu Ile Ser Val Ser Gly
1355                1360                1365

Val Glu Asp Ile Ser Gly Leu Pro Ser Gly Glu Val Val Glu Thr
1370                1375                1380

Ser Ala Ser Gly Ile Glu Asp Val Ser Glu Leu Pro Ser Gly Glu
1385                1390                1395

Gly Leu Glu Thr Ser Ala Ser Gly Val Glu Asp Leu Ser Arg Leu
1400                1405                1410

Pro Ser Gly Glu Glu Val Leu Glu Ile Ser Ala Ser Gly Phe Gly
1415                1420                1425

Asp Leu Ser Gly Val Pro Ser Gly Gly Glu Gly Leu Glu Thr Ser
1430                1435                1440

Ala Ser Glu Val Gly Thr Asp Leu Ser Gly Leu Pro Ser Gly Arg
1445                1450                1455

Glu Gly Leu Glu Thr Ser Ala Ser Gly Ala Glu Asp Leu Ser Gly
1460                1465                1470

Leu Pro Ser Gly Lys Glu Asp Leu Val Gly Ser Ala Ser Gly Asp
1475                1480                1485

Leu Asp Leu Gly Lys Leu Pro Ser Gly Thr Leu Gly Ser Gly Gln
1490                1495                1500

Ala Pro Glu Thr Ser Gly Leu Pro Ser Gly Phe Ser Gly Glu Tyr
1505                1510                1515

Ser Gly Val Asp Leu Gly Ser Gly Pro Pro Ser Gly Leu Pro Asp
1520                1525                1530

Phe Ser Gly Leu Pro Ser Gly Phe Pro Thr Val Ser Leu Val Asp
1535                1540                1545

Ser Thr Leu Val Glu Val Val Thr Ala Ser Thr Ala Ser Glu Leu
1550                1555                1560

Glu Gly Arg Gly Thr Ile Gly Ile Ser Gly Ala Gly Glu Ile Ser
1565                1570                1575

Gly Leu Pro Ser Ser Glu Leu Asp Ile Ser Gly Arg Ala Ser Gly
1580                1585                1590

Leu Pro Ser Gly Thr Glu Leu Ser Gly Gln Ala Ser Gly Ser Pro
1595                1600                1605

Asp Val Ser Gly Glu Ile Pro Gly Leu Phe Gly Val Ser Gly Gln
1610                1615                1620

Pro Ser Gly Phe Pro Asp Thr Ser Gly Glu Thr Ser Gly Val Thr
1625                1630                1635

Glu Leu Ser Gly Leu Ser Ser Gly Gln Pro Gly Val Ser Gly Glu
1640                1645                1650

Ala Ser Gly Val Leu Tyr Gly Thr Ser Gln Pro Phe Gly Ile Thr
```

-continued

```
            1655                1660                1665
Asp Leu Ser Gly Glu Thr Ser Gly Val Pro Asp Leu Ser Gly Gln
            1670                1675                1680
Pro Ser Gly Leu Pro Gly Phe Ser Gly Ala Thr Ser Gly Val Pro
            1685                1690                1695
Asp Leu Val Ser Gly Thr Thr Ser Gly Ser Gly Glu Ser Ser Gly
            1700                1705                1710
Ile Thr Phe Val Asp Thr Ser Leu Val Glu Val Ala Pro Thr Thr
            1715                1720                1725
Phe Lys Glu Glu Glu Gly Leu Gly Ser Val Glu Leu Ser Gly Leu
            1730                1735                1740
Pro Ser Gly Glu Ala Asp Leu Ser Gly Lys Ser Gly Met Val Asp
            1745                1750                1755
Val Ser Gly Gln Phe Ser Gly Thr Val Asp Ser Ser Gly Phe Thr
            1760                1765                1770
Ser Gln Thr Pro Glu Phe Ser Gly Leu Pro Ser Gly Ile Ala Glu
            1775                1780                1785
Val Ser Gly Glu Ser Ser Arg Ala Glu Ile Gly Ser Ser Leu Pro
            1790                1795                1800
Ser Gly Ala Tyr Tyr Gly Ser Gly Thr Pro Ser Ser Phe Pro Thr
            1805                1810                1815
Val Ser Leu Val Asp Arg Thr Leu Val Glu Ser Val Thr Gln Ala
            1820                1825                1830
Pro Thr Ala Gln Glu Ala Gly Glu Gly Pro Ser Gly Ile Leu Glu
            1835                1840                1845
Leu Ser Gly Ala His Ser Gly Ala Pro Asp Met Ser Gly Glu His
            1850                1855                1860
Ser Gly Phe Leu Asp Leu Ser Gly Leu Gln Ser Gly Leu Ile Glu
            1865                1870                1875
Pro Ser Gly Glu Pro Pro Gly Thr Pro Tyr Phe Ser Gly Asp Phe
            1880                1885                1890
Ala Ser Thr Thr Asn Val Ser Gly Glu Ser Ser Val Ala Met Gly
            1895                1900                1905
Thr Ser Gly Glu Ala Ser Gly Leu Pro Glu Val Thr Leu Ile Thr
            1910                1915                1920
Ser Glu Phe Val Glu Gly Val Thr Glu Pro Thr Ile Ser Gln Glu
            1925                1930                1935
Leu Gly Gln Arg Pro Pro Val Thr His Thr Pro Gln Leu Phe Glu
            1940                1945                1950
Ser Ser Gly Lys Val Ser Thr Ala Gly Asp Ile Ser Gly Ala Thr
            1955                1960                1965
Pro Val Leu Pro Gly Ser Gly Val Glu Val Ser Ser Val Pro Glu
            1970                1975                1980
Ser Ser Ser Glu Thr Ser Ala Tyr Pro Glu Ala Gly Phe Gly Ala
            1985                1990                1995
Ser Ala Ala Pro Glu Ala Ser Arg Glu Asp Ser Gly Ser Pro Asp
            2000                2005                2010
Leu Ser Glu Thr Thr Ser Ala Phe His Glu Ala Asn Leu Glu Arg
            2015                2020                2025
Ser Ser Gly Leu Gly Val Ser Gly Ser Thr Leu Thr Phe Gln Glu
            2030                2035                2040
Gly Glu Ala Ser Ala Ala Pro Glu Val Ser Gly Glu Ser Thr Thr
            2045                2050                2055
```

Thr Ser Asp Val Gly Thr Glu Ala Pro Gly Leu Pro Ser Ala Thr
2060            2065              2070

Pro Thr Ala Ser Gly Asp Arg Thr Glu Ile Ser Gly Asp Leu Ser
2075            2080              2085

Gly His Thr Ser Gln Leu Gly Val Val Ile Ser Thr Ser Ile Pro
2090            2095              2100

Glu Ser Glu Trp Thr Gln Gln Thr Gln Arg Pro Ala Glu Thr His
2105            2110              2115

Leu Glu Ile Glu Ser Ser Ser Leu Leu Tyr Ser Gly Glu Glu Thr
2120            2125              2130

His Thr Val Glu Thr Ala Thr Ser Pro Thr Asp Ala Ser Ile Pro
2135            2140              2145

Ala Ser Pro Glu Trp Lys Arg Glu Ser Glu Ser Thr Ala Ala Ala
2150            2155              2160

Pro Ala Arg Ser Cys Ala Glu Glu Pro Cys Gly Ala Gly Thr Cys
2165            2170              2175

Lys Glu Thr Glu Gly His Val Ile Cys Leu Cys Pro Pro Gly Tyr
2180            2185              2190

Thr Gly Glu His Cys Asn Ile Asp Gln Glu Val Cys Glu Glu Gly
2195            2200              2205

Trp Asn Lys Tyr Gln Gly His Cys Tyr Arg His Phe Pro Asp Arg
2210            2215              2220

Glu Thr Trp Val Asp Ala Glu Arg Arg Cys Arg Glu Gln Gln Ser
2225            2230              2235

His Leu Ser Ser Ile Val Thr Pro Glu Glu Gln Glu Phe Val Asn
2240            2245              2250

Asn Asn Ala Gln Asp Tyr Gln Trp Ile Gly Leu Asn Asp Arg Thr
2255            2260              2265

Ile Glu Gly Asp Phe Arg Trp Ser Asp Gly His Pro Met Gln Phe
2270            2275              2280

Glu Asn Trp Arg Pro Asn Gln Pro Asp Asn Phe Phe Ala Ala Gly
2285            2290              2295

Glu Asp Cys Val Val Met Ile Trp His Glu Lys Gly Glu Trp Asn
2300            2305              2310

Asp Val Pro Cys Asn Tyr His Leu Pro Phe Thr Cys Lys Lys Gly
2315            2320              2325

Thr Val Ala Cys Gly Glu Pro Pro Val Val Glu His Ala Arg Thr
2330            2335              2340

Phe Gly Gln Lys Lys Asp Arg Tyr Glu Ile Asn Ser Leu Val Arg
2345            2350              2355

Tyr Gln Cys Thr Glu Gly Phe Val Gln Arg His Met Pro Thr Ile
2360            2365              2370

Arg Cys Gln Pro Ser Gly His Trp Glu Glu Pro Arg Ile Thr Cys
2375            2380              2385

Thr Asp Ala Thr Thr Tyr Lys Arg Arg Leu Gln Lys Arg Ser Ser
2390            2395              2400

Arg His Pro Arg Arg Ser Arg Pro Ser Thr Ala His
2405            2410              2415

<210> SEQ ID NO 106
<211> LENGTH: 20
<212> TYPE: PRT
<213> ORGANISM: Artificial Sequence
<220> FEATURE:

-continued

<223> OTHER INFORMATION: Description of Artificial Sequence: Synthetic
      CD3 sequence of anti-MMP13 ISVD

<400> SEQUENCE: 106

Ala Leu Ala Val Tyr Gly Pro Ser Arg Tyr Arg Tyr Gly Pro Val Gly
1               5                   10                  15

Glu Tyr Gln Tyr
            20

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      CD3 sequence of anti-MMP13 ISVD

<400> SEQUENCE: 107

Asp Pro Ser His Tyr Tyr Ser Glu Tyr Glu Cys Gly Tyr Tyr Gly Met
1               5                   10                  15

Asp Tyr

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      Framework FR2 of anti-MMP13 Nanobody

<400> SEQUENCE: 108

Trp Val Arg Gln Ala Pro Gly Lys Gly Leu Glu Trp Val Ser
1               5                   10

<210> SEQ ID NO 109
<211> LENGTH: 123
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 inhibitors

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
                20                  25                  30

Ala Met Gly Trp Tyr Arg Gln Ala Pro Gly Lys Gln Arg Glu Leu Val
            35                  40                  45

Ala Ala Ile Ser Ser Gly Gly Ser Thr Tyr Tyr Ala Asp Ser Val Lys
        50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Ala Val Asp Ala Ser Arg Gly Leu Pro Tyr Glu Leu Tyr Tyr Tyr
            100                 105                 110

Trp Gly Gln Gly Thr Leu Val Thr Val Ser Ser
        115                 120

<210> SEQ ID NO 110
<211> LENGTH: 129

```
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 inhibitors

<400> SEQUENCE: 110
```

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Leu Ala Val Tyr Gly Pro Ser Arg Tyr Arg Tyr Gly Pro
            100                 105                 110

Val Gly Glu Tyr Gln Tyr Trp Gly Gln Gly Thr Leu Val Thr Val Ser
        115                 120                 125

Ser

```
<210> SEQ ID NO 111
<211> LENGTH: 121
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 inhibitors

<400> SEQUENCE: 111
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ala Ala
            20                  25                  30

Tyr Met Ser Trp Val Arg Gln Ala Pro Gly Lys Gly Leu Glu Trp Val
        35                  40                  45

Ser Ser Ile Ser Asp Asp Gly Ser Lys Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Asn Thr Gly Tyr Gly Ala Thr Thr Thr Arg Pro Gly Arg Tyr Trp Gly
            100                 105                 110

Gln Gly Thr Leu Val Thr Val Ser Ser
        115                 120

```
<210> SEQ ID NO 112
<211> LENGTH: 128
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 inhibitors

<400> SEQUENCE: 112
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ala Tyr Tyr
            20                  25                  30

Ser Ile Gly Trp Phe Arg Gln Ala Pro Gly Lys Glu Arg Glu Gly Val
        35                  40                  45

Ser Cys Ile Ser Ser Gly Ile Asp Gly Ser Thr Tyr Tyr Ala Asp Ser
50                      55                  60

Val Lys Gly Arg Phe Thr Ile Ser Arg Asp Asn Ser Lys Asn Thr Leu
65                  70                  75                  80

Tyr Leu Gln Met Asn Ser Leu Arg Pro Glu Asp Thr Ala Val Tyr Tyr
                85                  90                  95

Cys Ala Ala Asp Pro Ser His Tyr Tyr Ser Glu Tyr Glu Cys Gly Tyr
                100                 105                 110

Tyr Gly Met Asp Tyr Trp Gly Gln Gly Thr Leu Val Thr Val Ser Ser
        115                 120                 125
```

<210> SEQ ID NO 113
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-MMP13 Nanobody

<400> SEQUENCE: 113

```
Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Asn Thr
            35
```

<210> SEQ ID NO 114
<211> LENGTH: 39
<212> TYPE: PRT
<213> ORGANISM: Artificial Sequence
<220> FEATURE:
<223> OTHER INFORMATION: Description of Artificial Sequence: Synthetic
      Framework FR3 of anti-MMP13 Nanobody

<400> SEQUENCE: 114

```
Tyr Ala Asp Ser Val Lys Gly Arg Phe Thr Ile Ser Arg Asp Asn Ser
1               5                   10                  15

Lys Asn Thr Leu Tyr Leu Gln Met Asn Ser Leu Arg Pro Glu Asp Thr
            20                  25                  30

Ala Val Tyr Tyr Cys Ala Ala
            35
```

<210> SEQ ID NO 115
<211> LENGTH: 471
<212> TYPE: PRT
<213> ORGANISM: Homo sapiens
<220> FEATURE:
<223> OTHER INFORMATION: MMP13

<400> SEQUENCE: 115

```
Met His Pro Gly Val Leu Ala Ala Phe Leu Phe Leu Ser Trp Thr His
1               5                   10                  15

Cys Arg Ala Leu Pro Leu Pro Ser Gly Gly Asp Glu Asp Asp Leu Ser
```

```
                  20                  25                  30
Glu Glu Asp Leu Gln Phe Ala Glu Arg Tyr Leu Arg Ser Tyr Tyr His
              35                  40                  45
Pro Thr Asn Leu Ala Gly Ile Leu Lys Glu Asn Ala Ala Ser Ser Met
  50                  55                  60
Thr Glu Arg Leu Arg Glu Met Gln Ser Phe Phe Gly Leu Glu Val Thr
 65                  70                  75                  80
Gly Lys Leu Asp Asp Asn Thr Leu Asp Val Met Lys Lys Pro Arg Cys
                  85                  90                  95
Gly Val Pro Asp Val Gly Glu Tyr Asn Val Phe Pro Arg Thr Leu Lys
              100                 105                 110
Trp Ser Lys Met Asn Leu Thr Tyr Arg Ile Val Asn Tyr Thr Pro Asp
          115                 120                 125
Met Thr His Ser Glu Val Glu Lys Ala Phe Lys Lys Ala Phe Lys Val
      130                 135                 140
Trp Ser Asp Val Thr Pro Leu Asn Phe Thr Arg Leu His Asp Gly Ile
145                 150                 155                 160
Ala Asp Ile Met Ile Ser Phe Gly Ile Lys Glu His Gly Asp Phe Tyr
                  165                 170                 175
Pro Phe Asp Gly Pro Ser Gly Leu Leu Ala His Ala Phe Pro Pro Gly
              180                 185                 190
Pro Asn Tyr Gly Gly Asp Ala His Phe Asp Asp Glu Thr Trp Thr
          195                 200                 205
Ser Ser Ser Lys Gly Tyr Asn Leu Phe Leu Val Ala Ala His Glu Phe
      210                 215                 220
Gly His Ser Leu Gly Leu Asp His Ser Lys Asp Pro Gly Ala Leu Met
225                 230                 235                 240
Phe Pro Ile Tyr Thr Tyr Thr Gly Lys Ser His Phe Met Leu Pro Asp
                  245                 250                 255
Asp Asp Val Gln Gly Ile Gln Ser Leu Tyr Gly Pro Gly Asp Glu Asp
              260                 265                 270
Pro Asn Pro Lys His Pro Lys Thr Pro Asp Lys Cys Asp Pro Ser Leu
          275                 280                 285
Ser Leu Asp Ala Ile Thr Ser Leu Arg Gly Glu Thr Met Ile Phe Lys
      290                 295                 300
Asp Arg Phe Phe Trp Arg Leu His Pro Gln Gln Val Asp Ala Glu Leu
305                 310                 315                 320
Phe Leu Thr Lys Ser Phe Trp Pro Glu Leu Pro Asn Arg Ile Asp Ala
                  325                 330                 335
Ala Tyr Glu His Pro Ser His Asp Leu Ile Phe Ile Phe Arg Gly Arg
              340                 345                 350
Lys Phe Trp Ala Leu Asn Gly Tyr Asp Ile Leu Glu Gly Tyr Pro Lys
          355                 360                 365
Lys Ile Ser Glu Leu Gly Leu Pro Lys Glu Val Lys Lys Ile Ser Ala
      370                 375                 380
Ala Val His Phe Glu Asp Thr Gly Lys Thr Leu Leu Phe Ser Gly Asn
385                 390                 395                 400
Gln Val Trp Arg Tyr Asp Asp Thr Asn His Ile Met Asp Lys Asp Tyr
                  405                 410                 415
Pro Arg Leu Ile Glu Glu Asp Phe Pro Gly Ile Gly Asp Lys Val Asp
              420                 425                 430
Ala Val Tyr Glu Lys Asn Gly Tyr Ile Tyr Phe Phe Asn Gly Pro Ile
          435                 440                 445
```

```
Gln Phe Glu Tyr Ser Ile Trp Ser Asn Arg Ile Val Arg Val Met Pro
    450                 455                 460

Ala Asn Ser Ile Leu Trp Cys
465                 470

<210> SEQ ID NO 116
<211> LENGTH: 471
<212> TYPE: PRT
<213> ORGANISM: Pan troglodytes
<220> FEATURE:
<223> OTHER INFORMATION: MMP13

<400> SEQUENCE: 116

Met His Pro Gly Val Leu Ala Ala Phe Leu Phe Leu Ser Trp Ala His
1               5                   10                  15

Cys Arg Ala Leu Pro Leu Pro Ser Gly Gly Asp Glu Asp Asp Leu Ser
            20                  25                  30

Glu Glu Asp Leu Gln Phe Ala Glu Arg Tyr Leu Arg Ser Tyr Tyr His
        35                  40                  45

Pro Thr Asn Leu Ala Gly Ile Leu Lys Glu Asn Ala Ala Ser Ser Met
    50                  55                  60

Thr Glu Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95

Gly Val Pro Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
        115                 120                 125

Met Thr His Ser Glu Val Glu Lys Ala Phe Lys Lys Ala Phe Lys Val
    130                 135                 140

Trp Ser Asp Val Thr Pro Leu Asn Phe Thr Arg Leu His Asp Gly Ile
145                 150                 155                 160

Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Glu Thr Trp Thr
        195                 200                 205

Ser Ser Ser Lys Gly Tyr Asn Leu Phe Leu Val Ala Ala His Glu Phe
    210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
            260                 265                 270

Pro Asn Pro Lys His Pro Lys Thr Pro Asp Lys Cys Asp Pro Ser Leu
        275                 280                 285

Ser Leu Asp Ala Ile Thr Ser Leu Arg Gly Glu Thr Met Ile Phe Lys
    290                 295                 300

Asp Arg Phe Phe Trp Arg Leu His Pro Gln Gln Val Asp Ala Glu Leu
305                 310                 315                 320

Phe Leu Thr Lys Ser Phe Trp Pro Glu Leu Pro Asn Arg Ile Asp Ala
                325                 330                 335
```

```
Ala Tyr Glu His Pro Ser His Asp Leu Ile Phe Ile Phe Arg Gly Arg
                340                 345                 350

Lys Phe Trp Ala Leu Asn Gly Tyr Asp Ile Leu Glu Gly Tyr Pro Lys
            355                 360                 365

Lys Ile Ser Glu Leu Gly Leu Pro Lys Glu Val Lys Lys Ile Ser Ala
        370                 375                 380

Thr Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
                405                 410                 415

Pro Arg Leu Ile Glu Glu Glu Phe Pro Gly Ile Gly Asp Lys Val Asp
            420                 425                 430

Ala Val Tyr Glu Lys Asn Gly Tyr Ile Tyr Phe Phe Asn Gly Pro Ile
        435                 440                 445

Gln Phe Glu Tyr Ser Ile Trp Ser Asn Arg Ile Val Arg Val Met Pro
    450                 455                 460

Ala Asn Ser Ile Leu Trp Cys
465                 470

<210> SEQ ID NO 117
<211> LENGTH: 471
<212> TYPE: PRT
<213> ORGANISM: Macaca mulatta
<220> FEATURE:
<223> OTHER INFORMATION: MMP13

<400> SEQUENCE: 117

Met His Pro Gly Val Leu Ala Ala Phe Leu Phe Leu Ser Trp Thr His
1               5                   10                  15

Cys Arg Ala Leu Pro Leu Pro Ser Gly Gly Asp Glu Asp Asp Leu Ser
            20                  25                  30

Glu Glu Asp Leu Gln Phe Ala Glu Arg Tyr Leu Arg Ser Tyr Tyr Tyr
        35                  40                  45

Pro Thr Asn Leu Ala Gly Ile Leu Lys Glu Asn Ala Ala Ser Ser Met
    50                  55                  60

Thr Asp Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95

Gly Val Pro Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
        115                 120                 125

Met Thr His Ser Glu Val Glu Lys Ala Phe Lys Lys Ala Phe Lys Val
    130                 135                 140

Trp Ser Asp Val Thr Pro Leu Asn Phe Thr Arg Leu His Asp Gly Ile
145                 150                 155                 160

Ala Asp Ile Met Ile Ser Phe Gly Thr Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Asp Glu Thr Trp Thr
        195                 200                 205

Ser Ser Ser Lys Gly Tyr Asn Leu Phe Leu Val Ala Ala His Glu Phe
    210                 215                 220
```

```
Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
            245                 250                 255

Asp Asp Val Gln Gly Ile Gln Ser Leu Tyr Gly Pro Gly Asp Glu Asp
        260                 265                 270

Pro Asn Pro Lys His Pro Lys Thr Pro Asp Lys Cys Asp Pro Ser Leu
    275                 280                 285

Ser Leu Asp Ala Ile Thr Ser Leu Arg Gly Glu Thr Met Ile Phe Lys
290                 295                 300

Asp Arg Phe Phe Trp Arg Leu His Pro Gln Val Asp Ala Glu Leu
305                 310                 315                 320

Phe Leu Thr Lys Ser Phe Trp Pro Glu Leu Pro Asn Arg Ile Asp Ala
                325                 330                 335

Ala Tyr Glu His Pro Ser His Asp Leu Ile Phe Ile Phe Arg Gly Arg
                340                 345                 350

Lys Phe Trp Ala Leu Asn Gly Tyr Asp Ile Leu Glu Gly Tyr Pro Lys
            355                 360                 365

Lys Ile Ser Glu Leu Gly Phe Pro Lys Glu Val Lys Lys Ile Ser Ala
370                 375                 380

Ala Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
                405                 410                 415

Pro Arg Leu Ile Glu Glu Asp Phe Pro Gly Ile Gly Asp Lys Val Asp
            420                 425                 430

Ala Val Tyr Glu Lys Asn Gly Tyr Ile Tyr Phe Phe Asn Gly Pro Ile
            435                 440                 445

Gln Phe Glu Tyr Ser Ile Trp Ser Asn Arg Ile Val Arg Val Met Pro
450                 455                 460

Ala Asn Ser Ile Leu Trp Cys
465                 470

<210> SEQ ID NO 118
<211> LENGTH: 496
<212> TYPE: PRT
<213> ORGANISM: Canis lupus
<220> FEATURE:
<223> OTHER INFORMATION: MMP13

<400> SEQUENCE: 118

Met Ser His His Cys Arg Ser Ile Lys Val Lys Val Leu Val Trp Glu
1               5                   10                  15

Arg Gln Gln Ala Pro Gly Thr Thr Thr Lys Met Leu Pro Gly Ile Leu
            20                  25                  30

Ala Ala Phe Leu Cys Leu Ser Trp Thr Gln Cys Trp Ser Leu Pro Leu
                35                  40                  45

Pro Ser Asp Gly Asp Asp Leu Ser Glu Glu Asp Phe Gln Leu Ala
    50                  55                  60

Glu Arg Tyr Leu Lys Ser Tyr Tyr Pro Leu Asn Pro Ala Gly Ile
65                  70                  75                  80

Leu Lys Lys Ser Ala Ala Gly Ser Val Ala Asp Arg Leu Arg Glu Met
                85                  90                  95

Gln Ser Phe Phe Gly Leu Glu Val Thr Gly Lys Leu Asp Asp Asn Thr
                100                 105                 110
```

Leu Asp Ile Met Lys Lys Pro Arg Cys Gly Val Pro Asp Val Gly Glu
            115                 120                 125

Tyr Asn Val Phe Pro Arg Thr Leu Lys Trp Ser Lys Thr Asn Leu Thr
        130                 135                 140

Tyr Arg Ile Val Asn Tyr Thr Pro Asp Leu Thr His Ser Glu Val Glu
145                 150                 155                 160

Lys Ala Phe Lys Lys Ala Phe Lys Val Trp Ser Asp Val Thr Pro Leu
                165                 170                 175

Asn Phe Thr Arg Leu His Asp Gly Thr Ala Asp Ile Met Ile Ser Phe
            180                 185                 190

Gly Thr Lys Glu His Gly Asp Phe Tyr Pro Phe Asp Gly Pro Ser Gly
        195                 200                 205

Leu Leu Ala His Ala Phe Pro Pro Gly Pro Asn Tyr Gly Gly Asp Ala
210                 215                 220

His Phe Asp Asp Asp Glu Thr Trp Thr Ser Ser Lys Gly Tyr Asn
225                 230                 235                 240

Leu Phe Leu Val Ala Ala His Glu Phe Gly His Ser Leu Gly Leu Asp
                245                 250                 255

His Ser Lys Asp Pro Gly Ala Leu Met Phe Pro Ile Tyr Thr Tyr Thr
            260                 265                 270

Gly Lys Ser His Phe Met Leu Pro Asp Asp Asp Val Gln Gly Ile Gln
        275                 280                 285

Ser Leu Tyr Gly Pro Gly Asp Glu Asp Pro Asn Pro Arg His Pro Lys
290                 295                 300

Thr Pro Asp Lys Cys Asp Pro Ser Leu Ser Leu Asp Ala Ile Thr Ser
305                 310                 315                 320

Leu Arg Gly Glu Thr Met Ile Phe Lys Asp Arg Phe Phe Trp Arg Leu
                325                 330                 335

His Pro Gln Gln Val Asp Ala Glu Leu Phe Leu Thr Lys Ser Phe Trp
            340                 345                 350

Pro Glu Leu Pro Asn Arg Ile Asp Ala Ala Tyr Glu His Pro Ser Arg
        355                 360                 365

Asp Leu Ile Phe Ile Phe Arg Gly Arg Lys Tyr Trp Ala Leu Asn Gly
370                 375                 380

Tyr Asp Ile Leu Glu Gly Tyr Pro Gln Lys Ile Ser Glu Leu Gly Phe
385                 390                 395                 400

Pro Lys Glu Val Lys Lys Ile Ser Ala Ala Val His Phe Glu Asp Thr
                405                 410                 415

Gly Lys Thr Leu Phe Phe Ser Gly Asn Gln Val Trp Ser Tyr Asp Asp
            420                 425                 430

Thr Asn Gln Ile Met Asp Lys Asp Tyr Pro Arg Leu Ile Glu Glu Asp
        435                 440                 445

Phe Pro Gly Ile Gly Asp Lys Val Asp Ala Val Tyr Glu Lys Asn Gly
450                 455                 460

Tyr Ile Tyr Phe Phe Asn Gly Pro Ile Gln Phe Glu Tyr Asn Ile Trp
465                 470                 475                 480

Ser Lys Arg Ile Val Arg Val Met Pro Ala Asn Ser Leu Leu Trp Cys
                485                 490                 495

<210> SEQ ID NO 119
<211> LENGTH: 471
<212> TYPE: PRT
<213> ORGANISM: Bos taurus
<220> FEATURE:

-continued

<223> OTHER INFORMATION: MMP13

<400> SEQUENCE: 119

```
Met His Pro Arg Val Leu Ala Gly Phe Leu Phe Ser Trp Thr Ala
 1               5                  10                  15

Cys Trp Ser Leu Pro Leu Pro Ser Asp Gly Asp Ser Glu Asp Leu Ser
             20                  25                  30

Glu Glu Asp Phe Gln Phe Ala Glu Ser Tyr Leu Lys Ser Tyr Tyr Tyr
             35                  40                  45

Pro Gln Asn Pro Ala Gly Ile Leu Lys Lys Thr Ala Ala Ser Ser Val
         50                  55                  60

Ile Asp Arg Leu Arg Glu Met Gln Ser Phe Phe Gly Leu Glu Val Thr
 65                  70                  75                  80

Gly Arg Leu Asp Asp Asn Thr Leu Asp Ile Met Lys Lys Pro Arg Cys
                 85                  90                  95

Gly Val Pro Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
        115                 120                 125

Leu Thr His Ser Glu Val Glu Lys Ala Phe Arg Lys Ala Phe Lys Val
    130                 135                 140

Trp Ser Asp Val Thr Pro Leu Asn Phe Thr Arg Ile His Asn Gly Thr
145                 150                 155                 160

Ala Asp Ile Met Ile Ser Phe Gly Thr Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Glu Thr Trp Thr
        195                 200                 205

Ser Ser Ser Lys Gly Tyr Asn Leu Phe Leu Val Ala Ala His Glu Phe
    210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
            260                 265                 270

Pro Tyr Ser Lys His Pro Lys Thr Pro Asp Lys Cys Asp Pro Ser Leu
        275                 280                 285

Ser Leu Asp Ala Ile Thr Ser Leu Arg Gly Glu Thr Leu Ile Phe Lys
    290                 295                 300

Asp Arg Phe Phe Trp Arg Leu His Pro Gln Gln Val Glu Ala Glu Leu
305                 310                 315                 320

Phe Leu Thr Lys Ser Phe Gly Pro Glu Leu Pro Asn Arg Ile Asp Ala
                325                 330                 335

Ala Tyr Glu His Pro Ser His Asp Leu Ile Phe Ile Phe Arg Gly Arg
            340                 345                 350

Lys Phe Trp Ala Leu Ser Gly Tyr Asp Ile Leu Glu Asp Tyr Pro Lys
        355                 360                 365

Lys Ile Ser Glu Leu Gly Phe Pro Lys His Val Lys Lys Ile Ser Ala
    370                 375                 380

Ala Leu His Phe Glu Asp Ser Gly Lys Thr Leu Phe Phe Ser Glu Asn
385                 390                 395                 400
```

```
Gln Val Trp Ser Tyr Asp Asp Thr Asn His Val Met Asp Lys Asp Tyr
                405                 410                 415
Pro Arg Leu Ile Glu Glu Val Phe Pro Gly Ile Gly Asp Lys Val Asp
            420                 425                 430
Ala Val Tyr Gln Lys Asn Gly Tyr Ile Tyr Phe Phe Asn Gly Pro Ile
        435                 440                 445
Gln Phe Glu Tyr Ser Ile Trp Ser Asn Arg Ile Val Arg Val Met Thr
    450                 455                 460
Thr Asn Ser Leu Leu Trp Cys
465                 470

<210> SEQ ID NO 120
<211> LENGTH: 472
<212> TYPE: PRT
<213> ORGANISM: Mus musculus
<220> FEATURE:
<223> OTHER INFORMATION: MMP13

<400> SEQUENCE: 120

Met His Ser Ala Ile Leu Ala Thr Phe Phe Leu Leu Ser Trp Thr Pro
1               5                   10                  15
Cys Trp Ser Leu Pro Leu Pro Tyr Gly Asp Asp Asp Asp Asp Asp Leu
            20                  25                  30
Ser Glu Glu Asp Leu Val Phe Ala Glu His Tyr Leu Lys Ser Tyr Tyr
        35                  40                  45
His Pro Ala Thr Leu Ala Gly Ile Leu Lys Lys Ser Thr Val Thr Ser
    50                  55                  60
Thr Val Asp Arg Leu Arg Glu Met Gln Ser Phe Gly Leu Glu Val
65                  70                  75                  80
Thr Gly Lys Leu Asp Asp Pro Thr Leu Asp Ile Met Arg Lys Pro Arg
                85                  90                  95
Cys Gly Val Pro Asp Val Gly Glu Tyr Asn Val Phe Pro Arg Thr Leu
            100                 105                 110
Lys Trp Ser Gln Thr Asn Leu Thr Tyr Arg Ile Val Asn Tyr Thr Pro
        115                 120                 125
Asp Met Ser His Ser Glu Val Glu Lys Ala Phe Arg Lys Ala Phe Lys
    130                 135                 140
Val Trp Ser Asp Val Thr Pro Leu Asn Phe Thr Arg Ile Tyr Asp Gly
145                 150                 155                 160
Thr Ala Asp Ile Met Ile Ser Phe Gly Thr Lys Glu His Gly Asp Phe
                165                 170                 175
Tyr Pro Phe Asp Gly Pro Ser Gly Leu Leu Ala His Ala Phe Pro Pro
            180                 185                 190
Gly Pro Asn Tyr Gly Gly Asp Ala His Phe Asp Asp Asp Glu Thr Trp
        195                 200                 205
Thr Ser Ser Ser Lys Gly Tyr Asn Leu Phe Ile Val Ala Ala His Glu
    210                 215                 220
Leu Gly His Ser Leu Gly Leu Asp His Ser Lys Asp Pro Gly Ala Leu
225                 230                 235                 240
Met Phe Pro Ile Tyr Thr Tyr Thr Gly Lys Ser His Phe Met Leu Pro
                245                 250                 255
Asp Asp Asp Val Gln Gly Ile Gln Phe Leu Tyr Gly Pro Gly Asp Glu
            260                 265                 270
Asp Pro Asn Pro Lys His Pro Lys Thr Pro Glu Lys Cys Asp Pro Ala
        275                 280                 285
```

-continued

```
Leu Ser Leu Asp Ala Ile Thr Ser Leu Arg Gly Glu Thr Met Ile Phe
            290                 295                 300

Lys Asp Arg Phe Phe Trp Arg Leu His Pro Gln Gln Val Glu Ala Glu
305                 310                 315                 320

Leu Phe Leu Thr Lys Ser Phe Trp Pro Glu Leu Pro Asn His Val Asp
                325                 330                 335

Ala Ala Tyr Glu His Pro Ser Arg Asp Leu Met Phe Ile Phe Arg Gly
            340                 345                 350

Arg Lys Phe Trp Ala Leu Asn Gly Tyr Asp Ile Leu Glu Gly Tyr Pro
                355                 360                 365

Arg Lys Ile Ser Asp Leu Gly Phe Pro Lys Glu Val Lys Arg Leu Ser
            370                 375                 380

Ala Ala Val His Phe Glu Asn Thr Gly Lys Thr Leu Phe Phe Ser Glu
385                 390                 395                 400

Asn His Val Trp Ser Tyr Asp Val Asn Gln Thr Met Asp Lys Asp
                405                 410                 415

Tyr Pro Arg Leu Ile Glu Glu Phe Pro Gly Ile Gly Asn Lys Val
            420                 425                 430

Asp Ala Val Tyr Glu Lys Asn Gly Tyr Ile Tyr Phe Phe Asn Gly Pro
                435                 440                 445

Ile Gln Phe Glu Tyr Ser Ile Trp Ser Asn Arg Ile Val Arg Val Met
450                 455                 460

Pro Thr Asn Ser Ile Leu Trp Cys
465                 470

<210> SEQ ID NO 121
<211> LENGTH: 472
<212> TYPE: PRT
<213> ORGANISM: Rattus norvegicus
<220> FEATURE:
<223> OTHER INFORMATION: MMP13

<400> SEQUENCE: 121

Met His Ser Ala Ile Leu Ala Thr Phe Phe Leu Leu Ser Trp Thr His
1               5                   10                  15

Cys Trp Ser Leu Pro Leu Pro Tyr Gly Asp Asp Asp Asp Asp Leu
            20                  25                  30

Ser Glu Glu Asp Leu Glu Phe Ala Glu His Tyr Leu Lys Ser Tyr Tyr
                35                  40                  45

His Pro Val Thr Leu Ala Gly Ile Leu Lys Lys Ser Thr Val Thr Ser
            50                  55                  60

Thr Val Asp Arg Leu Arg Glu Met Gln Ser Phe Gly Leu Asp Val
65                  70                  75                  80

Thr Gly Lys Leu Asp Asp Pro Thr Leu Asp Ile Met Arg Lys Pro Arg
                85                  90                  95

Cys Gly Val Pro Asp Val Gly Glu Tyr Asn Val Phe Pro Arg Thr Leu
            100                 105                 110

Lys Trp Ser Gln Thr Asn Leu Thr Tyr Arg Ile Val Asn Tyr Thr Pro
                115                 120                 125

Asp Ile Ser His Ser Glu Val Glu Lys Ala Phe Arg Lys Ala Phe Lys
130                 135                 140

Val Trp Ser Asp Val Thr Pro Leu Asn Phe Thr Arg Ile His Asp Gly
145                 150                 155                 160

Thr Ala Asp Ile Met Ile Ser Phe Gly Thr Lys Glu His Gly Asp Phe
                165                 170                 175
```

Tyr Pro Phe Asp Gly Pro Ser Gly Leu Leu Ala His Ala Phe Pro Pro
            180                 185                 190

Gly Pro Asn Leu Gly Gly Asp Ala His Phe Asp Asp Glu Thr Trp
        195                 200                 205

Thr Ser Ser Ser Lys Gly Tyr Asn Leu Phe Ile Val Ala Ala His Glu
210                 215                 220

Leu Gly His Ser Leu Gly Leu Asp His Ser Lys Asp Pro Gly Ala Leu
225                 230                 235                 240

Met Phe Pro Ile Tyr Thr Tyr Thr Gly Lys Ser His Phe Met Leu Pro
                245                 250                 255

Asp Asp Asp Val Gln Gly Ile Gln Ser Leu Tyr Gly Pro Gly Asp Glu
                260                 265                 270

Asp Pro Asn Pro Lys His Pro Lys Thr Pro Glu Lys Cys Asp Pro Ala
            275                 280                 285

Leu Ser Leu Asp Ala Ile Thr Ser Leu Arg Gly Glu Thr Met Ile Phe
290                 295                 300

Lys Asp Arg Phe Phe Trp Arg Leu His Pro Gln Gln Val Glu Pro Glu
305                 310                 315                 320

Leu Phe Leu Thr Lys Ser Phe Trp Pro Glu Leu Pro Asn His Val Asp
                325                 330                 335

Ala Ala Tyr Glu His Pro Ser Arg Asp Leu Met Phe Ile Phe Arg Gly
                340                 345                 350

Arg Lys Phe Trp Ala Leu Asn Gly Tyr Asp Ile Met Glu Gly Tyr Pro
            355                 360                 365

Arg Lys Ile Ser Asp Leu Gly Phe Pro Lys Glu Val Lys Arg Leu Ser
370                 375                 380

Ala Ala Val His Phe Glu Asp Thr Gly Lys Thr Leu Phe Phe Ser Gly
385                 390                 395                 400

Asn His Val Trp Ser Tyr Asp Asp Ala Asn Gln Thr Met Asp Lys Asp
                405                 410                 415

Tyr Pro Arg Leu Ile Glu Glu Glu Phe Pro Gly Ile Gly Asp Lys Val
                420                 425                 430

Asp Ala Val Tyr Glu Lys Asn Gly Tyr Ile Tyr Phe Phe Asn Gly Pro
            435                 440                 445

Ile Gln Phe Glu Tyr Ser Ile Trp Ser Asn Arg Ile Val Arg Val Met
450                 455                 460

Pro Thr Asn Ser Leu Leu Trp Cys
465                 470

<210> SEQ ID NO 122
<211> LENGTH: 471
<212> TYPE: PRT
<213> ORGANISM: Gallus gallus
<220> FEATURE:
<223> OTHER INFORMATION: MMP13

<400> SEQUENCE: 122

Met Gln Pro Arg Leu Ser Ala Val Phe Phe Leu Leu Gly Leu Ser
1               5                   10                  15

Phe Cys Leu Thr Val Pro Ile Pro Leu Asp Asp Ser His Glu Phe Thr
            20                  25                  30

Glu Glu Asp Leu Arg Phe Ala Glu Arg Tyr Leu Arg Thr His Tyr Asp
        35                  40                  45

Leu Arg Pro Asn Pro Thr Gly Ile Met Lys Lys Ser Ala Asn Thr Met
50                  55                  60

-continued

```
Ala Ser Lys Leu Arg Glu Met Gln Ala Phe Phe Gly Leu Glu Val Thr
 65                  70                  75                  80

Gly Lys Leu Asp Glu Glu Thr Tyr Glu Leu Met Gln Lys Pro Arg Cys
                 85                  90                  95

Gly Val Pro Asp Val Gly Glu Tyr Asn Phe Phe Pro Arg Lys Leu Lys
            100                 105                 110

Trp Ser Asn Thr Asn Leu Thr Tyr Arg Ile Met Ser Tyr Thr Ser Asp
        115                 120                 125

Leu Arg Arg Ala Glu Val Glu Arg Ala Phe Lys Arg Ala Phe Lys Val
    130                 135                 140

Trp Ser Asp Val Thr Pro Leu Asn Phe Thr Arg Ile Arg Ser Gly Thr
145                 150                 155                 160

Ala Asp Ile Met Ile Ser Phe Gly Thr Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asp Tyr Gly Gly Asp Ala His Phe Asp Asp Glu Thr Trp Ser
        195                 200                 205

Asp Asp Ser Arg Gly Tyr Asn Leu Phe Leu Val Ala Ala His Glu Phe
    210                 215                 220

Gly His Ser Leu Gly Leu Glu His Ser Arg Asp Pro Gly Ala Leu Met
225                 230                 235                 240

Phe Pro Ile Tyr Thr Tyr Thr Gly Lys Ser Gly Phe Val Leu Pro Asp
                245                 250                 255

Asp Asp Val Gln Gly Ile Gln Glu Leu Tyr Gly Ala Gly Asp Arg Asp
            260                 265                 270

Pro Asn Pro Lys His Pro Lys Thr Pro Glu Lys Cys Ala Ala Asp Leu
        275                 280                 285

Ser Ile Asp Ala Ile Thr Lys Leu Arg Gly Glu Met Leu Val Phe Lys
    290                 295                 300

Asp Arg Phe Phe Trp Arg Leu His Pro Gln Met Val Glu Ala Glu Leu
305                 310                 315                 320

Val Leu Ile Lys Ser Phe Trp Pro Glu Leu Pro Asn Lys Ile Asp Ala
                325                 330                 335

Ala Tyr Glu Asn Pro Ile Lys Asp Leu Val Phe Met Phe Lys Gly Lys
            340                 345                 350

Lys Val Trp Ala Met Asn Gly Tyr Asp Ile Val Glu Gly Phe Pro Lys
        355                 360                 365

Lys Ile Tyr Glu Met Gly Phe Pro Lys Glu Met Lys Arg Ile Asp Ala
    370                 375                 380

Val Val His Ile Asp Asp Thr Gly Lys Thr Leu Phe Phe Thr Gly Asn
385                 390                 395                 400

Lys Tyr Trp Ser Tyr Asp Glu Glu Thr Glu Val Met Asp Thr Gly Tyr
                405                 410                 415

Pro Lys Phe Ile Glu Asp Glu Phe Ala Gly Ile Gly Asp Arg Val Asp
            420                 425                 430

Ala Val Tyr His Arg Asn Gly Tyr Leu Tyr Phe Phe Asn Gly Pro Leu
        435                 440                 445

Gln Phe Glu Tyr Ser Ile Trp Ser Lys Arg Ile Val Arg Ile Leu His
    450                 455                 460

Thr Asn Ser Leu Phe Trp Cys
465                 470
```

```
<210> SEQ ID NO 123
<211> LENGTH: 23
<212> TYPE: PRT
<213> ORGANISM: Artificial Sequence
<220> FEATURE:
<223> OTHER INFORMATION: Description of Artificial Sequence: Synthetic
      MYC-HIS tag

<400> SEQUENCE: 123

Ala Ala Ala Glu Gln Lys Leu Ile Ser Glu Glu Asp Leu Asn Gly Ala
1               5                   10                  15

Ala His His His His His His
            20

<210> SEQ ID NO 124
<211> LENGTH: 34
<212> TYPE: PRT
<213> ORGANISM: Artificial Sequence
<220> FEATURE:
<223> OTHER INFORMATION: Description of Artificial Sequence: Synthetic
      FLAG3-HIS6 tag

<400> SEQUENCE: 124

Ala Ala Ala Asp Tyr Lys Asp His Asp Gly Asp Tyr Lys Asp His Asp
1               5                   10                  15

Ile Asp Tyr Lys Asp Asp Asp Lys Gly Ala Ala His His His His
            20                  25                  30

His His

<210> SEQ ID NO 125
<211> LENGTH: 3
<212> TYPE: PRT
<213> ORGANISM: Artificial Sequence
<220> FEATURE:
<223> OTHER INFORMATION: Description of Artificial Sequence: Synthetic
      Linker sequence with three alanines: AAA

<400> SEQUENCE: 125

Ala Ala Ala
1

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 126

Gly Gly Gly Gly Ser
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 127

Ser Gly Gly Ser Gly Gly Ser
1               5

<210> SEQ ID NO 128
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 128

Gly Gly Gly Gly Gly Gly Gly Ser
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 129

Gly Gly Gly Gly Ser Gly Gly Gly Ser
1               5

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 130

Gly Gly Gly Gly Ser Gly Gly Gly Gly Ser
1               5                   10

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 131

Gly Gly Gly Gly Ser Gly Gly Gly Gly Ser Gly Gly Gly Gly Ser
1               5                   10                  15

<210> SEQ ID NO 132
<211> LENGTH: 18
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 132

Gly Gly Gly Gly Ser Gly Gly Gly Gly Ser Gly Gly Gly Gly Gly
1               5                   10                  15

Gly Ser

<210> SEQ ID NO 133
<211> LENGTH: 20
<212> TYPE: PRT
<213> ORGANISM: Artificial Sequence
<220> FEATURE:
<223> OTHER INFORMATION: Description of Artificial Sequence: Synthetic
      Linker sequence
```

```
<400> SEQUENCE: 133

Gly Gly Gly Gly Ser Gly Gly Gly Gly Ser Gly Gly Gly Gly Ser Gly
1               5                   10                  15

Gly Gly Gly Ser
            20

<210> SEQ ID NO 134
<211> LENGTH: 25
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 134

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 135
<211> LENGTH: 30
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 135

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 136
<211> LENGTH: 35
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 136

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 137
<211> LENGTH: 40
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 137

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30
```

```
Gly Gly Ser Gly Gly Gly Gly Ser
        35                  40

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 138

Glu Pro Lys Ser Cys Asp Lys Thr His Thr Cys Pro Pro Cys Pro
1               5                   10                  15

<210> SEQ ID NO 139
<211> LENGTH: 24
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 139

Gly Gly Gly Gly Ser Gly Gly Gly Ser Glu Pro Lys Ser Cys Asp Lys
1               5                   10                  15

Thr His Thr Cys Pro Pro Cys Pro
                20

<210> SEQ ID NO 140
<211> LENGTH: 12
<212> TYPE: PRT
<213> ORGANISM: Lama glama
<220> FEATURE:
<223> OTHER INFORMATION: Linker sequence from Llama upper long hinge
      region

<400> SEQUENCE: 140

Glu Pro Lys Thr Pro Lys Pro Gln Pro Ala Ala Ala
1               5                   10

<210> SEQ ID NO 141
<211> LENGTH: 62
<212> TYPE: PRT
<213> ORGANISM: Artificial Sequence
<220> FEATURE:
<223> OTHER INFORMATION: Description of Artificial Sequence: Synthetic
      G3 hinge linker sequence

<400> SEQUENCE: 141

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
                20                  25                  30

Glu Pro Lys Ser Cys Asp Thr Pro Pro Pro Cys Pro Arg Cys Pro Glu
            35                  40                  45

Pro Lys Ser Cys Asp Thr Pro Pro Pro Cys Pro Arg Cys Pro
    50                  55                  60

<210> SEQ ID NO 142
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences
```

<400> SEQUENCE: 142

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 143
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 144
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 144

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Ser Gln Gly Thr Leu Val Thr
             100                 105                 110

Val Ser Ser Ala
         115

<210> SEQ ID NO 145
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 145

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
             20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Ser Gln Gly Thr Leu Val Thr
             100                 105                 110

Val Ser Ser Ala
         115

<210> SEQ ID NO 146
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 146

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 147
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 147

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 148
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 148

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 149
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 149

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
            115

<210> SEQ ID NO 150
<211> LENGTH: 117
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 150

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
            115

<210> SEQ ID NO 151
<211> LENGTH: 118
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences -continued

<400> SEQUENCE: 151

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala
        115

<210> SEQ ID NO 152
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 152

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 153
<211> LENGTH: 117
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 153

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val

```
                35                  40                  45
Ser Ser Ile Ser Gly Ser Gly Ser Asp Thr Leu Tyr Ala Asp Ser Val
         50                  55                  60
Lys Gly Arg Phe Thr Ile Ser Arg Asp Asn Ala Lys Thr Thr Leu Tyr
 65                  70                  75                  80
Leu Gln Met Asn Ser Leu Arg Pro Glu Asp Thr Ala Leu Tyr Tyr Cys
                 85                  90                  95
Thr Ile Gly Gly Ser Leu Ser Arg Ser Ser Gln Gly Thr Leu Val Thr
            100                 105                 110
Val Ser Ser Gly Gly
            115

<210> SEQ ID NO 154
<211> LENGTH: 118
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 154

Glu Val Gln Leu Val Glu Ser Gly Gly Gly Val Val Gln Pro Gly Asn
 1               5                  10                  15
Ser Leu Arg Leu Ser Cys Ala Ala Ser Gly Phe Thr Phe Ser Ser Phe
             20                  25                  30
Gly Met Ser Trp Val Arg Gln Ala Pro Gly Lys Gly Leu Glu Trp Val
         35                  40                  45
Ser Ser Ile Ser Gly Ser Gly Ser Asp Thr Leu Tyr Ala Asp Ser Val
     50                  55                  60
Lys Gly Arg Phe Thr Ile Ser Arg Asp Asn Ala Lys Thr Thr Leu Tyr
 65                  70                  75                  80
Leu Gln Met Asn Ser Leu Arg Pro Glu Asp Thr Ala Leu Tyr Tyr Cys
                 85                  90                  95
Thr Ile Gly Gly Ser Leu Ser Arg Ser Ser Gln Gly Thr Leu Val Thr
            100                 105                 110
Val Ser Ser Gly Gly
            115

<210> SEQ ID NO 155
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 155

Glu Val Gln Leu Val Glu Ser Gly Gly Gly Val Val Gln Pro Gly Gly
 1               5                  10                  15
Ser Leu Arg Leu Ser Cys Ala Ala Ser Gly Phe Thr Phe Arg Ser Phe
             20                  25                  30
Gly Met Ser Trp Val Arg Gln Ala Pro Gly Lys Gly Pro Glu Trp Val
         35                  40                  45
Ser Ser Ile Ser Gly Ser Gly Ser Asp Thr Leu Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Pro Glu Asp Thr Ala Leu Tyr Tyr Cys
```

```
                    85                  90                  95
Thr Ile Gly Gly Ser Leu Ser Arg Ser Ser Gln Gly Thr Leu Val Thr
            100                 105                 110

Val Ser Ser
        115

<210> SEQ ID NO 156
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 156

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 157

Ser Phe Gly Met Ser
1               5

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      Serum albumin binding ISVD sequences

<400> SEQUENCE: 158

Ser Ile Ser Gly Ser Gly Ser Asp Thr Leu Tyr Ala Asp Ser Val Lys
1               5                   10                  15

Gly

<210> SEQ ID NO 159
<211> LENGTH: 6
<212> TYPE: PRT
<213> ORGANISM: Artificial Sequence
<220> FEATURE:
```

<223> OTHER INFORMATION: Description of Artificial Sequence: Synthetic
      Serum albumin binding ISVD sequences

<400> SEQUENCE: 159

Gly Gly Ser Leu Ser Arg
1               5

<210> SEQ ID NO 160
<211> LENGTH: 278
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 constructs

<400> SEQUENCE: 160

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Leu Ala Val Tyr Gly Pro Asn Arg Tyr Arg Tyr Gly Pro
            100                 105                 110

Val Gly Glu Tyr Asn Tyr Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Gly
145                 150                 155                 160

Gly Gly Gly Ser Glu Val Gln Leu Val Glu Ser Gly Gly Gly Ser Val
                165                 170                 175

Gln Ala Gly Gly Ser Leu Arg Leu Ser Cys Ala Ala Ser Gly Ser Thr
            180                 185                 190

Phe Ser Arg Tyr Ser Met Asn Trp Tyr Arg Gln Ala Pro Gly Lys Gln
        195                 200                 205

Arg Glu Phe Val Ala Gly Ile Ser Val Gly Arg Ile Thr Asn Tyr Ala
    210                 215                 220

Val Ser Val Arg Gly Arg Phe Thr Ile Ser Arg Asp Asn Ala Glu Gly
225                 230                 235                 240

Thr Gly Tyr Leu Gln Met Asn Ser Leu Lys Pro Glu Asp Thr Ala Val
                245                 250                 255

Tyr Tyr Cys Asn Ala Gly Gly Leu Gln Gly Tyr Trp Gly Leu Gly Thr
            260                 265                 270

Leu Val Thr Val Ser Ser
        275
```

<210> SEQ ID NO 161
<211> LENGTH: 269
<212> TYPE: PRT
<213> ORGANISM: Artificial Sequence
<220> FEATURE:

-continued

<223> OTHER INFORMATION: Description of Artificial Sequence: Synthetic
      Amino acid sequences of anti-MMP13 constructs

<400> SEQUENCE: 161

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Ser Ile Phe Arg Ile Asn
            20                  25                  30

Val Met Ala Trp Tyr Arg Gln Ala Pro Gly Lys Gln Arg Glu Leu Val
        35                  40                  45

Ala Ala Ile Thr Ser Gly Gly Thr Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Ala Asp Ile Gly Trp Pro Tyr Val Leu Asp Tyr Asp Phe Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Ser Val Gln Ala Gly Gly Ser Leu Arg Leu Ser
                165                 170                 175

Cys Ala Ala Ser Gly Ser Thr Phe Ser Arg Tyr Ser Met Asn Trp Tyr
            180                 185                 190

Arg Gln Ala Pro Gly Lys Gln Arg Glu Phe Val Ala Gly Ile Ser Val
        195                 200                 205

Gly Arg Ile Thr Asn Tyr Ala Val Ser Val Arg Gly Arg Phe Thr Ile
    210                 215                 220

Ser Arg Asp Asn Ala Glu Gly Thr Gly Tyr Leu Gln Met Asn Ser Leu
225                 230                 235                 240

Lys Pro Glu Asp Thr Ala Val Tyr Tyr Cys Asn Ala Gly Gly Leu Gln
                245                 250                 255

Gly Tyr Trp Gly Leu Gly Thr Leu Val Thr Val Ser Ser
            260                 265
```

<210> SEQ ID NO 162
<211> LENGTH: 270
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 constructs

<400> SEQUENCE: 162

```
Glu Val Gln Leu Val Glu Ser Gly Gly Ala Leu Val Arg Pro Gly Gly
1               5                   10                  15

Ser Leu Arg Leu Ser Cys Ala Ala Ser Gly Phe Ala Phe Ser Ala Ala
            20                  25                  30

Tyr Met Ser Trp Val Arg Gln Ala Pro Gly Arg Gly Leu Glu Trp Val
        35                  40                  45

Ser Ser Ile Ser Asp Asp Gly Ser Lys Thr Tyr Tyr Ala Asp Ser Val
    50                  55                  60
```

```
Lys Gly Arg Phe Thr Ile Ser Arg Asp Asn Ala Lys Asn Thr Val Tyr
 65                  70                  75                  80

Leu Gln Met Asn Asn Leu Lys Pro Asp Asp Thr Ala Val Tyr Tyr Cys
                 85                  90                  95

Asn Thr Gly Tyr Gly Ala Thr Thr Thr Arg Pro Gly Arg Tyr Trp Gly
            100                 105                 110

Gln Gly Thr Leu Val Thr Val Ser Ser Gly Gly Gly Ser Gly Gly Gly
            115                 120                 125

Gly Gly Ser Gly Gly Gly Ser Gly Gly Gly Ser Gly Gly Gly
130                 135                 140

Gly Ser Gly Gly Gly Ser Gly Gly Gly Ser Glu Val Gln Leu
145                 150                 155                 160

Val Glu Ser Gly Gly Ser Val Gln Ala Gly Gly Ser Leu Arg Leu
            165                 170                 175

Ser Cys Ala Ala Ser Gly Ser Thr Phe Ser Arg Tyr Ser Met Asn Trp
            180                 185                 190

Tyr Arg Gln Ala Pro Gly Lys Gln Arg Glu Phe Val Ala Gly Ile Ser
            195                 200                 205

Val Gly Arg Ile Thr Asn Tyr Ala Val Ser Val Arg Gly Arg Phe Thr
210                 215                 220

Ile Ser Arg Asp Asn Ala Glu Gly Thr Gly Tyr Leu Gln Met Asn Ser
225                 230                 235                 240

Leu Lys Pro Glu Asp Thr Ala Val Tyr Tyr Cys Asn Ala Gly Leu
                245                 250                 255

Gln Gly Tyr Trp Gly Leu Gly Thr Leu Val Thr Val Ser Ser
            260                 265                 270

<210> SEQ ID NO 163
<211> LENGTH: 278
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 constructs

<400> SEQUENCE: 163

Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Phe Ser Arg Tyr
                20                  25                  30

Ser Met Asn Trp Tyr Arg Gln Ala Pro Gly Lys Gln Arg Glu Phe Val
            35                  40                  45

Ala Gly Ile Ser Val Gly Arg Ile Thr Asn Tyr Ala Val Ser Val Arg
 50                 55                  60

Gly Arg Phe Thr Ile Ser Arg Asp Asn Ala Glu Gly Thr Gly Tyr Leu
 65                 70                  75                  80

Gln Met Asn Ser Leu Lys Pro Glu Asp Thr Ala Val Tyr Tyr Cys Asn
                85                  90                  95

Ala Gly Gly Leu Gln Gly Tyr Trp Gly Leu Gly Thr Leu Val Thr Val
            100                 105                 110

Ser Ser Gly Gly Gly Gly Ser Gly Gly Gly Ser Gly Gly Gly Gly
            115                 120                 125

Ser Gly Gly Gly Gly Ser Gly Gly Gly Ser Gly Gly Gly Ser
        130                 135                 140

Gly Gly Gly Gly Ser Glu Val Gln Leu Val Glu Ser Gly Gly Gly Leu
145                 150                 155                 160
```

```
Val Gln Pro Gly Gly Ser Leu Arg Leu Ser Cys Ala Ala Ser Gly Arg
                165                 170                 175

Thr Phe Ser Ser Tyr Ala Met Gly Trp Phe Arg Gln Ala Pro Gly Lys
            180                 185                 190

Glu Arg Glu Phe Val Ala Ala Ile Ser Trp Ser Gly Gly Ser Thr Tyr
        195                 200                 205

Tyr Ala Asp Ser Val Lys Gly Arg Phe Thr Ile Ser Arg Asp Asn Ser
    210                 215                 220

Lys Asn Thr Val Tyr Leu Gln Met Asn Ser Leu Arg Pro Glu Asp Thr
225                 230                 235                 240

Ala Val Tyr Tyr Cys Thr Ala Ala Leu Ala Val Tyr Gly Pro Asn Arg
                245                 250                 255

Tyr Arg Tyr Gly Pro Val Gly Glu Tyr Asn Tyr Trp Gly Gln Gly Thr
            260                 265                 270

Leu Val Thr Val Ser Ser
            275

<210> SEQ ID NO 164
<211> LENGTH: 269
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 constructs

<400> SEQUENCE: 164

Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Phe Ser Arg Tyr
            20                  25                  30

Ser Met Asn Trp Tyr Arg Gln Ala Pro Gly Lys Gln Arg Glu Phe Val
        35                  40                  45

Ala Gly Ile Ser Val Gly Arg Ile Thr Asn Tyr Ala Val Ser Val Arg
    50                  55                  60

Gly Arg Phe Thr Ile Ser Arg Asp Asn Ala Glu Gly Thr Gly Tyr Leu
65                  70                  75                  80

Gln Met Asn Ser Leu Lys Pro Glu Asp Thr Ala Val Tyr Tyr Cys Asn
                85                  90                  95

Ala Gly Gly Leu Gln Gly Tyr Trp Gly Leu Gly Thr Leu Val Thr Val
            100                 105                 110

Ser Ser Gly Gly Gly Gly Ser Gly Gly Gly Ser Gly Gly Gly Gly
        115                 120                 125

Ser Gly Gly Gly Ser Gly Gly Gly Gly Ser Gly Gly Gly Gly Ser
    130                 135                 140

Gly Gly Gly Gly Ser Glu Val Gln Leu Val Glu Ser Gly Gly Gly Leu
145                 150                 155                 160

Val Gln Pro Gly Gly Ser Leu Arg Leu Ser Cys Ala Gly Ser Gly Ser
                165                 170                 175

Ile Phe Arg Ile Asn Val Met Ala Trp Tyr Arg Gln Ala Pro Gly Lys
            180                 185                 190

Gln Arg Glu Leu Val Ala Ala Ile Thr Ser Gly Gly Thr Thr Asn Tyr
        195                 200                 205

Ala Asp Ser Val Lys Gly Arg Phe Thr Ile Ser Arg Asp Asn Ser Lys
    210                 215                 220

Asn Thr Val Tyr Leu Gln Met Asn Ser Leu Arg Pro Glu Asp Thr Ala
```

Val Tyr Tyr Cys Tyr Ala Asp Ile Gly Trp Pro Tyr Val Leu Asp Tyr
            245                 250                 255

Asp Phe Trp Gly Gln Gly Thr Leu Val Thr Val Ser Ser
            260                 265

<210> SEQ ID NO 165
<211> LENGTH: 270
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 constructs

<400> SEQUENCE: 165

Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Phe Ser Arg Tyr
            20                  25                  30

Ser Met Asn Trp Tyr Arg Gln Ala Pro Gly Lys Gln Arg Glu Phe Val
        35                  40                  45

Ala Gly Ile Ser Val Gly Arg Ile Thr Asn Tyr Ala Val Ser Val Arg
    50                  55                  60

Gly Arg Phe Thr Ile Ser Arg Asp Asn Ala Glu Gly Thr Gly Tyr Leu
65                  70                  75                  80

Gln Met Asn Ser Leu Lys Pro Glu Asp Thr Ala Val Tyr Tyr Cys Asn
                85                  90                  95

Ala Gly Gly Leu Gln Gly Tyr Trp Gly Leu Gly Thr Leu Val Thr Val
            100                 105                 110

Ser Ser Gly Gly Gly Gly Ser Gly Gly Gly Ser Gly Gly Gly Gly
            115                 120                 125

Ser Gly Gly Gly Gly Ser Gly Gly Gly Gly Ser Gly Gly Gly Gly Ser
130                 135                 140

Gly Gly Gly Gly Ser Glu Val Gln Leu Val Glu Ser Gly Gly Ala Leu
145                 150                 155                 160

Val Arg Pro Gly Gly Ser Leu Arg Leu Ser Cys Ala Ala Ser Gly Phe
            165                 170                 175

Ala Phe Ser Ala Ala Tyr Met Ser Trp Val Arg Gln Ala Pro Gly Arg
            180                 185                 190

Gly Leu Glu Trp Val Ser Ser Ile Ser Asp Asp Gly Ser Lys Thr Tyr
            195                 200                 205

Tyr Ala Asp Ser Val Lys Gly Arg Phe Thr Ile Ser Arg Asp Asn Ala
        210                 215                 220

Lys Asn Thr Val Tyr Leu Gln Met Asn Asn Leu Lys Pro Asp Asp Thr
225                 230                 235                 240

Ala Val Tyr Tyr Cys Asn Thr Gly Tyr Gly Ala Thr Thr Arg Pro
            245                 250                 255

Gly Arg Tyr Trp Gly Gln Gly Thr Leu Val Thr Val Ser Ser
            260                 265                 270

<210> SEQ ID NO 166
<211> LENGTH: 121
<212> TYPE: PRT
<213> ORGANISM: Artificial Sequence
<220> FEATURE:
<223> OTHER INFORMATION: Description of Artificial Sequence: Synthetic
      ISVD specifically binding Aggrecan

```
<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Ile Ile Asn
            20                  25                  30

Val Val Arg Trp Tyr Arg Arg Ala Pro Gly Lys Gln Arg Glu Leu Val
        35                  40                  45

Ala Thr Ile Ser Ser Gly Gly Asn Ala Asn Tyr Val Asp Ser Val Arg
    50                  55                  60

Gly Arg Phe Thr Ile Ser Arg Asp Asn Ser Lys Asn Thr Val Tyr Leu
65              70                  75                  80

Gln Met Asn Ser Leu Arg Pro Glu Asp Thr Ala Val Tyr Tyr Cys Asn
                85                  90                  95

Val Pro Thr Thr His Tyr Gly Gly Val Tyr Tyr Gly Pro Tyr Trp Gly
            100                 105                 110

Gln Gly Thr Leu Val Thr Val Ser Ser
        115                 120

<210> SEQ ID NO 167
<211> LENGTH: 122
<212> TYPE: PRT
<213> ORGANISM: Artificial Sequence
<220> FEATURE:
<223> OTHER INFORMATION: Description of Artificial Sequence: Synthetic
      ISVD specifically binding Aggrecan

<400> SEQUENCE: 167

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Thr Phe Ile Ile Asn
            20                  25                  30

Val Val Arg Trp Tyr Arg Arg Ala Pro Gly Lys Gln Arg Glu Leu Val
        35                  40                  45

Ala Thr Ile Ser Ser Gly Gly Asn Ala Asn Tyr Val Asp Ser Val Arg
    50                  55                  60

Gly Arg Phe Thr Ile Ser Arg Asp Asn Ser Lys Asn Thr Val Tyr Leu
65              70                  75                  80

Gln Met Asn Ser Leu Arg Pro Glu Asp Thr Ala Leu Tyr Tyr Cys Asn
                85                  90                  95

Val Pro Thr Thr His Tyr Gly Gly Val Tyr Tyr Gly Pro Tyr Trp Gly
            100                 105                 110

Gln Gly Thr Leu Val Thr Val Ser Ser Ala
        115                 120

<210> SEQ ID NO 168
<211> LENGTH: 125
<212> TYPE: PRT
<213> ORGANISM: Artificial Sequence
<220> FEATURE:
<223> OTHER INFORMATION: Description of Artificial Sequence: Synthetic
      ISVD specifically binding Aggrecan

<400> SEQUENCE: 168

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Ser Tyr
            20                  25                  30

Thr Met Gly Trp Phe Arg Gln Ala Pro Gly Lys Glu Arg Glu Phe Val
```

```
                35                  40                  45
Ala Ala Ile Ser Trp Ser Gly Gly Arg Thr Tyr Tyr Ala Asp Ser Val
         50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Tyr Arg Arg Arg Arg Ala Ser Ser Asn Arg Gly Leu Trp Asp
            100                 105                 110

Tyr Trp Gly Gln Gly Thr Leu Val Thr Val Ser Ser Ala
        115                 120                 125

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of Aggrecan-binding ISVD

<400> SEQUENCE: 169

Gly Ser Thr Phe Ile Ile Asn Val Val Arg
 1               5                  10

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR2 of Aggrecan-binding ISVD

<400> SEQUENCE: 170

Thr Ile Ser Ser Gly Gly Asn Ala Asn
 1               5

<210> SEQ ID NO 171
<211> LENGTH: 13
<212> TYPE: PRT
<213> ORGANISM: Artificial Sequence
<220> FEATURE:
<223> OTHER INFORMATION: Description of Artificial Sequence: Synthetic
      CDR3 of Aggrecan-binding ISVD

<400> SEQUENCE: 171

Pro Thr Thr His Tyr Gly Gly Val Tyr Tyr Gly Pro Tyr
 1               5                  10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of Aggrecan-binding ISVD

<400> SEQUENCE: 172

Gly Arg Thr Phe Ser Ser Tyr Thr Met Gly
 1               5                  10

<210> SEQ ID NO 173
<211> LENGTH: 10
<212> TYPE: PRT
<213> ORGANISM: Artificial Sequence
<220> FEATURE:
```

-continued

<223> OTHER INFORMATION: Description of Artificial Sequence: Synthetic
     CDR2 of Aggrecan-binding ISVD

<400> SEQUENCE: 173

Ala Ile Ser Trp Ser Gly Gly Arg Thr Tyr
1               5                   10

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of Aggrecan-binding ISVD

<400> SEQUENCE: 174

Tyr Arg Arg Arg Arg Ala Ser Ser Asn Arg Gly Leu Trp Asp Tyr
1               5                   10                  15

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic
      Myc-tag

<400> SEQUENCE: 175

Ala Ala Ala Glu Gln Lys Leu Ile Ser Glu Glu Asp Leu Asn Gly Ala
1               5                   10                  15

Ala

<210> SEQ ID NO 176
<211> LENGTH: 277
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ala Ala
            20                  25                  30

Tyr Met Ser Trp Val Arg Gln Ala Pro Gly Lys Gly Leu Glu Trp Val
        35                  40                  45

Ser Ser Ile Ser Asp Asp Gly Ser Lys Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Asn Thr Gly Tyr Gly Ala Thr Thr Thr Arg Pro Gly Arg Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Glu Val Gln Leu
145                 150                 155                 160

-continued

```
Val Glu Ser Gly Gly Gly Leu Val Gln Pro Gly Gly Ser Leu Arg Leu
            165                 170                 175

Ser Cys Ala Ala Ser Gly Ser Thr Phe Ile Ile Asn Val Val Arg Trp
            180                 185                 190

Tyr Arg Arg Ala Pro Gly Lys Gln Arg Glu Leu Val Ala Thr Ile Ser
            195                 200                 205

Ser Gly Gly Asn Ala Asn Tyr Val Asp Ser Val Arg Gly Arg Phe Thr
            210                 215                 220

Ile Ser Arg Asp Asn Ser Lys Asn Thr Val Tyr Leu Gln Met Asn Ser
225                 230                 235                 240

Leu Arg Pro Glu Asp Thr Ala Val Tyr Tyr Cys Asn Val Pro Thr Thr
            245                 250                 255

His Tyr Gly Gly Val Tyr Tyr Gly Pro Tyr Trp Gly Gln Gly Thr Leu
            260                 265                 270

Val Thr Val Ser Ser
            275

<210> SEQ ID NO 177
<211> LENGTH: 433
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 177

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ala Ala
            20                  25                  30

Tyr Met Ser Trp Val Arg Gln Ala Pro Gly Lys Gly Leu Glu Trp Val
            35                  40                  45

Ser Ser Ile Ser Asp Asp Gly Ser Lys Thr Tyr Tyr Ala Asp Ser Val
            50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Asn Thr Gly Tyr Gly Ala Thr Thr Arg Pro Gly Arg Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Gly Ser Gly Gly Gly Gly Ser Gly Gly Gly
            130                 135                 140

Gly Ser Gly Gly Gly Ser Gly Gly Gly Ser Glu Val Gln Leu
145                 150                 155                 160

Val Glu Ser Gly Gly Gly Leu Val Gln Pro Gly Gly Ser Leu Arg Leu
            165                 170                 175

Ser Cys Ala Ala Ser Gly Ser Thr Phe Ile Ile Asn Val Val Arg Trp
            180                 185                 190

Tyr Arg Arg Ala Pro Gly Lys Gln Arg Glu Leu Val Ala Thr Ile Ser
            195                 200                 205

Ser Gly Gly Asn Ala Asn Tyr Val Asp Ser Val Arg Gly Arg Phe Thr
            210                 215                 220

Ile Ser Arg Asp Asn Ser Lys Asn Thr Val Tyr Leu Gln Met Asn Ser
225                 230                 235                 240
```

```
Leu Arg Pro Glu Asp Thr Ala Val Tyr Tyr Cys Asn Val Pro Thr Thr
                245                 250                 255

His Tyr Gly Gly Val Tyr Tyr Gly Pro Tyr Trp Gly Gln Gly Thr Leu
            260                 265                 270

Val Thr Val Ser Ser Gly Gly Gly Gly Ser Gly Gly Gly Gly Ser Gly
        275                 280                 285

Gly Gly Gly Ser Gly Gly Gly Ser Gly Gly Gly Ser Gly Gly
290                 295                 300

Gly Gly Ser Gly Gly Gly Ser Glu Val Gln Leu Val Glu Ser Gly
305                 310                 315                 320

Gly Gly Leu Val Gln Pro Gly Gly Ser Leu Arg Leu Ser Cys Ala Ala
                325                 330                 335

Ser Gly Ser Thr Phe Ile Ile Asn Val Val Arg Trp Tyr Arg Arg Ala
            340                 345                 350

Pro Gly Lys Gln Arg Glu Leu Val Ala Thr Ile Ser Ser Gly Gly Asn
                355                 360                 365

Ala Asn Tyr Val Asp Ser Val Arg Gly Arg Phe Thr Ile Ser Arg Asp
        370                 375                 380

Asn Ser Lys Asn Thr Val Tyr Leu Gln Met Asn Ser Leu Arg Pro Glu
385                 390                 395                 400

Asp Thr Ala Val Tyr Tyr Cys Asn Val Pro Thr Thr His Tyr Gly Gly
                405                 410                 415

Val Tyr Tyr Gly Pro Tyr Trp Gly Gln Gly Thr Leu Val Thr Val Ser
                420                 425                 430

Ser

<210> SEQ ID NO 178
<211> LENGTH: 280
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ala Ala
            20                  25                  30

Tyr Met Ser Trp Val Arg Gln Ala Pro Gly Lys Gly Leu Glu Trp Val
        35                  40                  45

Ser Ser Ile Ser Asp Asp Gly Ser Lys Thr Tyr Tyr Ala Asp Ser Val
    50                  55                  60

Lys Gly Arg Phe Thr Ile Ser Arg Asp Asn Lys Asn Thr Val Tyr
65                  70                  75                  80

Leu Gln Met Asn Ser Leu Arg Pro Glu Asp Thr Ala Val Tyr Tyr Cys
                85                  90                  95

Asn Thr Gly Tyr Gly Ala Thr Thr Thr Arg Pro Gly Arg Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Ser Gly Gly Gly
130                 135                 140

Gly Ser Gly Gly Gly Gly Ser Gly Gly Gly Gly Ser Glu Val Gln Leu
145                 150                 155                 160
```

```
Val Glu Ser Gly Gly Gly Leu Val Gln Pro Gly Gly Ser Leu Arg Leu
            165                 170                 175

Ser Cys Ala Ala Ser Gly Arg Thr Phe Ser Ser Tyr Thr Met Gly Trp
            180                 185                 190

Phe Arg Gln Ala Pro Gly Lys Glu Arg Glu Phe Val Ala Ala Ile Ser
            195                 200                 205

Trp Ser Gly Gly Arg Thr Tyr Tyr Ala Asp Ser Val Lys Gly Arg Phe
            210                 215                 220

Thr Ile Ser Arg Asp Asn Ser Lys Asn Thr Val Tyr Leu Gln Met Asn
225                 230                 235                 240

Ser Leu Arg Pro Glu Asp Thr Ala Val Tyr Tyr Cys Ala Ala Tyr Arg
            245                 250                 255

Arg Arg Arg Ala Ser Ser Asn Arg Gly Leu Trp Asp Tyr Trp Gly Gln
            260                 265                 270

Gly Thr Leu Val Thr Val Ser Ser
            275                 280

<210> SEQ ID NO 179
<211> LENGTH: 284
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ala Tyr Tyr
            20                  25                  30

Ser Ile Gly Trp Phe Arg Gln Ala Pro Gly Lys Glu Arg Glu Gly Val
            35                  40                  45

Ser Cys Ile Ser Ser Gly Ile Asp Gly Ser Thr Tyr Tyr Ala Asp Ser
        50                  55                  60

Val Lys Gly Arg Phe Thr Ile Ser Arg Asp Asn Ala Lys Asn Thr Met
65                  70                  75                  80

Tyr Leu Gln Met Asn Asn Leu Lys Pro Glu Asp Thr Gly Val Tyr Tyr
                85                  90                  95

Cys Ala Ala Asp Pro Ser His Tyr Tyr Ser Glu Tyr Asp Cys Gly Tyr
            100                 105                 110

Tyr Gly Met Asp Tyr Trp Gly Lys Gly Thr Leu Val Thr Val Ser Ser
            115                 120                 125

Gly Gly Gly Gly Ser Gly Gly Gly Ser Gly Gly Gly Gly Ser Gly Gly
            130                 135                 140

Gly Gly Ser Gly Gly Gly Ser Gly Gly Gly Ser Gly Gly
145                 150                 155                 160

Gly Gly Ser Glu Val Gln Leu Val Glu Ser Gly Gly Gly Leu Val Gln
            165                 170                 175

Pro Gly Gly Ser Leu Arg Leu Ser Cys Ala Ala Ser Gly Ser Thr Phe
            180                 185                 190

Ile Ile Asn Val Val Arg Trp Tyr Arg Arg Ala Pro Gly Lys Gln Arg
            195                 200                 205

Glu Leu Val Ala Thr Ile Ser Ser Gly Gly Asn Ala Asn Tyr Val Asp
            210                 215                 220

Ser Val Arg Gly Arg Phe Thr Ile Ser Arg Asp Asn Ser Lys Asn Thr
```

Val Tyr Leu Gln Met Asn Ser Leu Arg Pro Glu Asp Thr Ala Val Tyr
            225                 230                 235                 240

Tyr Cys Asn Val Pro Thr Thr His Tyr Gly Gly Val Tyr Tyr Gly Pro
            245                 250                 255
        260                 265                 270

Tyr Trp Gly Gln Gly Thr Leu Val Thr Val Ser Ser
        275                 280

<210> SEQ ID NO 180
<211> LENGTH: 440
<212> TYPE: PRT
<213> ORGANISM: Artificial Sequence
<220> FEATURE:
<223> OTHER INFORMATION: Description of Artificial Sequence: Synthetic
    Multivalent constructs comprising several ISVDs

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ala Tyr Tyr
            20                  25                  30

Ser Ile Gly Trp Phe Arg Gln Ala Pro Gly Lys Glu Arg Glu Gly Val
        35                  40                  45

Ser Cys Ile Ser Ser Gly Ile Asp Gly Ser Thr Tyr Tyr Ala Asp Ser
    50                  55                  60

Val Lys Gly Arg Phe Thr Ile Ser Arg Asp Asn Ala Lys Asn Thr Met
65                  70                  75                  80

Tyr Leu Gln Met Asn Asn Leu Lys Pro Glu Asp Thr Gly Val Tyr Tyr
                85                  90                  95

Cys Ala Ala Asp Pro Ser His Tyr Tyr Ser Glu Tyr Asp Cys Gly Tyr
            100                 105                 110

Tyr Gly Met Asp Tyr Trp Gly Lys Gly Thr Leu Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Gly Ser Gly Gly Gly Gly Ser Gly Gly
145                 150                 155                 160

Gly Gly Ser Glu Val Gln Leu Val Glu Ser Gly Gly Gly Leu Val Gln
                165                 170                 175

Pro Gly Gly Ser Leu Arg Leu Ser Cys Ala Ala Ser Gly Ser Thr Phe
            180                 185                 190

Ile Ile Asn Val Val Arg Trp Tyr Arg Arg Ala Pro Gly Lys Gln Arg
        195                 200                 205

Glu Leu Val Ala Thr Ile Ser Ser Gly Gly Asn Ala Asn Tyr Val Asp
    210                 215                 220

Ser Val Arg Gly Arg Phe Thr Ile Ser Arg Asp Asn Ser Lys Asn Thr
225                 230                 235                 240

Val Tyr Leu Gln Met Asn Ser Leu Arg Pro Glu Asp Thr Ala Val Tyr
                245                 250                 255

Tyr Cys Asn Val Pro Thr Thr His Tyr Gly Gly Val Tyr Tyr Gly Pro
            260                 265                 270

Tyr Trp Gly Gln Gly Thr Leu Val Thr Val Ser Ser Gly Gly Gly Gly
        275                 280                 285

Ser Gly Gly Gly Gly Ser Gly Gly Gly Gly Ser Gly Gly Gly Gly Ser
    290                 295                 300

Gly Gly Gly Ser Gly Gly Gly Ser Gly Gly Gly Ser Glu
305                 310                 315                 320

Val Gln Leu Val Glu Ser Gly Gly Leu Val Gln Pro Gly Gly Ser
            325                 330                 335

Leu Arg Leu Ser Cys Ala Ala Ser Gly Ser Thr Phe Ile Ile Asn Val
        340                 345                 350

Val Arg Trp Tyr Arg Arg Ala Pro Gly Lys Gln Arg Glu Leu Val Ala
    355                 360                 365

Thr Ile Ser Ser Gly Gly Asn Ala Asn Tyr Val Asp Ser Val Arg Gly
370                 375                 380

Arg Phe Thr Ile Ser Arg Asp Asn Ser Lys Asn Thr Val Tyr Leu Gln
385                 390                 395                 400

Met Asn Ser Leu Arg Pro Glu Asp Thr Ala Val Tyr Tyr Cys Asn Val
            405                 410                 415

Pro Thr Thr His Tyr Gly Gly Val Tyr Tyr Gly Pro Tyr Trp Gly Gln
        420                 425                 430

Gly Thr Leu Val Thr Val Ser Ser
        435                 440

<210> SEQ ID NO 181
<211> LENGTH: 287
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 181

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Leu Ala Tyr Tyr
            20                  25                  30

Ser Ile Gly Trp Phe Arg Gln Ala Pro Gly Lys Glu Arg Glu Gly Val
        35                  40                  45

Ser Cys Ile Ser Ser Gly Ile Asp Gly Ser Thr Tyr Tyr Ala Asp Ser
    50                  55                  60

Val Lys Gly Arg Phe Thr Ile Ser Arg Asp Asn Ala Lys Asn Thr Met
65                  70                  75                  80

Tyr Leu Gln Met Asn Asn Leu Lys Pro Glu Asp Thr Gly Val Tyr Tyr
                85                  90                  95

Cys Ala Ala Asp Pro Ser His Tyr Tyr Ser Glu Tyr Asp Cys Gly Tyr
            100                 105                 110

Tyr Gly Met Asp Tyr Trp Gly Lys Gly Thr Leu Val Thr Val Ser Ser
        115                 120                 125

Gly Gly Gly Gly Ser Gly Gly Gly Ser Gly Gly Gly Ser Gly
    130                 135                 140

Gly Gly Ser Gly Gly Gly Ser Gly Gly Gly Ser Gly Gly
145                 150                 155                 160

Gly Gly Ser Glu Val Gln Leu Val Glu Ser Gly Gly Leu Val Gln
                165                 170                 175

Pro Gly Gly Ser Leu Arg Leu Ser Cys Ala Ala Ser Gly Arg Thr Phe
            180                 185                 190

Ser Ser Tyr Thr Met Gly Trp Phe Arg Gln Ala Pro Gly Lys Glu Arg
        195                 200                 205

Glu Phe Val Ala Ala Ile Ser Trp Ser Gly Gly Arg Thr Tyr Tyr Ala
    210                 215                 220

Asp Ser Val Lys Gly Arg Phe Thr Ile Ser Arg Asp Asn Ser Lys Asn
225                 230                 235                 240

Thr Val Tyr Leu Gln Met Asn Ser Leu Arg Pro Glu Asp Thr Ala Val
            245                 250                 255

Tyr Tyr Cys Ala Ala Tyr Arg Arg Arg Ala Ser Ser Asn Arg Gly
        260                 265                 270

Leu Trp Asp Tyr Trp Gly Gln Gly Thr Leu Val Thr Val Ser Ser
        275                 280                 285

<210> SEQ ID NO 182
<211> LENGTH: 438
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 182

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Leu Ala Val Tyr Gly Pro Ser Arg Tyr Arg Tyr Gly Pro
            100                 105                 110

Val Gly Glu Tyr Gln Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Ser Gly
145                 150                 155                 160

Gly Gly Gly Ser Glu Val Gln Leu Val Glu Ser Gly Gly Gly Leu Val
                165                 170                 175

Gln Pro Gly Gly Ser Leu Arg Leu Ser Cys Ala Ala Ser Gly Ser Thr
            180                 185                 190

Phe Ser Arg Tyr Ser Met Asn Trp Tyr Arg Gln Ala Pro Gly Lys Gln
        195                 200                 205

Arg Glu Phe Val Ala Gly Ile Ser Val Gly Arg Ile Thr Asn Tyr Ala
    210                 215                 220

Val Ser Val Lys Gly Arg Phe Thr Ile Ser Arg Asp Asn Ser Lys Asn
225                 230                 235                 240

Thr Gly Tyr Leu Gln Met Asn Ser Leu Arg Pro Glu Asp Thr Ala Val
                245                 250                 255

Tyr Tyr Cys Asn Ala Gly Gly Leu Gln Gly Tyr Trp Gly Gln Gly Thr
            260                 265                 270

Leu Val Thr Val Ser Ser Gly Gly Gly Gly Ser Gly Gly Gly Gly Ser
        275                 280                 285

Gly Gly Gly Gly Ser Gly Gly Gly Gly Ser Gly Gly Gly Gly Ser Gly

```
            290                 295                 300
Gly Gly Gly Ser Gly Gly Gly Ser Glu Val Gln Leu Val Glu Ser
305                 310                 315                 320

Gly Gly Gly Leu Val Gln Pro Gly Gly Ser Leu Arg Leu Ser Cys Ala
                325                 330                 335

Ala Ser Gly Arg Thr Phe Ser Ser Tyr Thr Met Gly Trp Phe Arg Gln
                340                 345                 350

Ala Pro Gly Lys Glu Arg Glu Phe Val Ala Ala Ile Ser Trp Ser Gly
                355                 360                 365

Gly Arg Thr Tyr Tyr Ala Asp Ser Val Lys Gly Arg Phe Thr Ile Ser
            370                 375                 380

Arg Asp Asn Ser Lys Asn Thr Val Tyr Leu Gln Met Asn Ser Leu Arg
385                 390                 395                 400

Pro Glu Asp Thr Ala Val Tyr Tyr Cys Ala Ala Tyr Arg Arg Arg
                405                 410                 415

Ala Ser Ser Asn Arg Gly Leu Trp Asp Tyr Trp Gly Gln Gly Thr Leu
                420                 425                 430

Val Thr Val Ser Ser Ala
        435

<210> SEQ ID NO 183
<211> LENGTH: 434
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Leu Ala Val Tyr Gly Pro Ser Arg Tyr Arg Tyr Gly Pro
            100                 105                 110

Val Gly Glu Tyr Gln Tyr Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Gly
145                 150                 155                 160

Gly Gly Gly Ser Glu Val Gln Leu Val Glu Ser Gly Gly Gly Ser Val
                165                 170                 175

Gln Pro Gly Gly Ser Leu Arg Leu Ser Cys Ala Ala Ser Gly Ser Thr
            180                 185                 190

Phe Ser Arg Tyr Ser Met Asn Trp Tyr Arg Gln Ala Pro Gly Lys Gln
        195                 200                 205
```

```
Arg Glu Phe Val Ala Gly Ile Ser Val Gly Arg Ile Thr Asn Tyr Ala
    210                 215                 220

Val Ser Val Arg Gly Arg Phe Thr Ile Ser Arg Asp Asn Ser Glu Gly
225                 230                 235                 240

Thr Gly Tyr Leu Gln Met Asn Ser Leu Arg Pro Glu Asp Thr Ala Val
                245                 250                 255

Tyr Tyr Cys Asn Ala Gly Leu Gln Gly Tyr Trp Gly Leu Gly Thr
                260                 265                 270

Leu Val Thr Val Ser Ser Gly Gly Gly Ser Gly Gly Gly Ser
            275                 280                 285

Gly Gly Gly Gly Ser Gly Gly Gly Ser Gly Gly Gly Ser Gly
290                 295                 300

Gly Gly Gly Ser Gly Gly Gly Ser Glu Val Gln Leu Val Glu Ser
305                 310                 315                 320

Gly Gly Gly Leu Val Gln Pro Gly Gly Ser Leu Arg Leu Ser Cys Ala
                325                 330                 335

Ala Ser Gly Ser Thr Phe Ile Ile Asn Val Val Arg Trp Tyr Arg Arg
            340                 345                 350

Ala Pro Gly Lys Gln Arg Glu Leu Val Ala Thr Ile Ser Ser Gly Gly
            355                 360                 365

Asn Ala Asn Tyr Val Asp Ser Val Arg Gly Arg Phe Thr Ile Ser Arg
370                 375                 380

Asp Asn Ser Lys Asn Thr Val Tyr Leu Gln Met Asn Ser Leu Arg Pro
385                 390                 395                 400

Glu Asp Thr Ala Val Tyr Tyr Cys Asn Val Pro Thr Thr His Tyr Gly
                405                 410                 415

Gly Val Tyr Tyr Gly Pro Tyr Trp Gly Gln Gly Thr Leu Val Thr Val
            420                 425                 430

Ser Ser

<210> SEQ ID NO 184
<211> LENGTH: 590
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Leu Ala Val Tyr Gly Pro Ser Arg Tyr Arg Tyr Gly Pro
                100                 105                 110

Val Gly Glu Tyr Gln Tyr Trp Gly Gln Gly Thr Leu Val Thr Val Ser
            115                 120                 125
```

```
Ser Gly Gly Gly Gly Ser Gly Gly Gly Ser Gly Gly Gly Ser
    130                 135                 140
Gly Gly Gly Gly Ser Gly Gly Gly Ser Gly Gly Gly Ser Gly
145                 150                 155                 160
Gly Gly Gly Ser Glu Val Gln Leu Val Glu Ser Gly Gly Ser Val
                165                 170                 175
Gln Pro Gly Gly Ser Leu Arg Leu Ser Cys Ala Ala Ser Gly Ser Thr
            180                 185                 190
Phe Ser Arg Tyr Ser Met Asn Trp Tyr Arg Gln Ala Pro Gly Lys Gln
        195                 200                 205
Arg Glu Phe Val Ala Gly Ile Ser Val Gly Arg Ile Thr Asn Tyr Ala
    210                 215                 220
Val Ser Val Arg Gly Arg Phe Thr Ile Ser Arg Asp Asn Ser Glu Gly
225                 230                 235                 240
Thr Gly Tyr Leu Gln Met Asn Ser Leu Arg Pro Glu Asp Thr Ala Val
                245                 250                 255
Tyr Tyr Cys Asn Ala Gly Leu Gln Gly Tyr Trp Gly Leu Gly Thr
            260                 265                 270
Leu Val Thr Val Ser Ser Gly Gly Gly Ser Gly Gly Gly Gly Ser
        275                 280                 285
Gly Gly Gly Gly Ser Gly Gly Gly Ser Gly Gly Gly Ser Gly
    290                 295                 300
Gly Gly Gly Ser Gly Gly Gly Gly Ser Glu Val Gln Leu Val Glu Ser
305                 310                 315                 320
Gly Gly Gly Leu Val Gln Pro Gly Gly Ser Leu Arg Leu Ser Cys Ala
                325                 330                 335
Ala Ser Gly Ser Thr Phe Ile Ile Asn Val Val Arg Trp Tyr Arg Arg
            340                 345                 350
Ala Pro Gly Lys Gln Arg Glu Leu Val Ala Thr Ile Ser Ser Gly Gly
        355                 360                 365
Asn Ala Asn Tyr Val Asp Ser Val Arg Gly Arg Phe Thr Ile Ser Arg
    370                 375                 380
Asp Asn Ser Lys Asn Thr Val Tyr Leu Gln Met Asn Ser Leu Arg Pro
385                 390                 395                 400
Glu Asp Thr Ala Val Tyr Tyr Cys Asn Val Pro Thr Thr His Tyr Gly
                405                 410                 415
Gly Val Tyr Tyr Gly Pro Tyr Trp Gly Gln Gly Thr Leu Val Thr Val
            420                 425                 430
Ser Ser Gly Gly Gly Gly Ser Gly Gly Gly Gly Ser Gly Gly Gly Gly
        435                 440                 445
Ser Gly Gly Gly Gly Ser Gly Gly Gly Gly Ser Gly Gly Gly Ser
    450                 455                 460
Gly Gly Gly Gly Ser Glu Val Gln Leu Val Glu Ser Gly Gly Leu
465                 470                 475                 480
Val Gln Pro Gly Gly Ser Leu Arg Leu Ser Cys Ala Ala Ser Gly Ser
                485                 490                 495
Thr Phe Ile Ile Asn Val Val Arg Trp Tyr Arg Arg Ala Pro Gly Lys
            500                 505                 510
Gln Arg Glu Leu Val Ala Thr Ile Ser Ser Gly Gly Asn Ala Asn Tyr
        515                 520                 525
Val Asp Ser Val Arg Gly Arg Phe Thr Ile Ser Arg Asp Asn Ser Lys
    530                 535                 540
Asn Thr Val Tyr Leu Gln Met Asn Ser Leu Arg Pro Glu Asp Thr Ala
```

```
                      545                 550                 555                 560
              Val Tyr Tyr Cys Asn Val Pro Thr Thr His Tyr Gly Gly Val Tyr Tyr
                              565                 570                 575
              Gly Pro Tyr Trp Gly Gln Gly Thr Leu Val Thr Val Ser Ser
                              580                 585                 590

<210> SEQ ID NO 185
<211> LENGTH: 437
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Thr Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Leu Ala Val Tyr Gly Pro Ser Arg Tyr Arg Tyr Gly Pro
            100                 105                 110

Val Gly Glu Tyr Gln Tyr Trp Gly Gln Gly Thr Leu Val Thr Val Ser
        115                 120                 125

Ser Gly Gly Gly Gly Ser Gly Gly Gly Ser Gly Gly Gly Gly Ser
130                 135                 140

Gly Gly Gly Gly Ser Gly Gly Gly Ser Gly Gly Gly Gly Ser Gly
145                 150                 155                 160

Gly Gly Gly Ser Glu Val Gln Leu Val Glu Ser Gly Gly Ser Val
                165                 170                 175

Gln Pro Gly Gly Ser Leu Arg Leu Ser Cys Ala Ala Ser Gly Ser Thr
            180                 185                 190

Phe Ser Arg Tyr Ser Met Asn Trp Tyr Arg Gln Ala Pro Gly Lys Gln
        195                 200                 205

Arg Glu Phe Val Ala Gly Ile Ser Val Gly Arg Ile Thr Asn Tyr Ala
    210                 215                 220

Val Ser Val Arg Gly Arg Phe Thr Ile Ser Arg Asp Asn Ser Glu Gly
225                 230                 235                 240

Thr Gly Tyr Leu Gln Met Asn Ser Leu Arg Pro Glu Asp Thr Ala Val
                245                 250                 255

Tyr Tyr Cys Asn Ala Gly Gly Leu Gln Gly Tyr Trp Gly Leu Gly Thr
            260                 265                 270

Leu Val Thr Val Ser Ser Gly Gly Gly Ser Gly Gly Gly Gly Ser
        275                 280                 285

Gly Gly Gly Gly Ser Gly Gly Gly Ser Gly Gly Gly Gly Ser Gly
    290                 295                 300

Gly Gly Ser Gly Gly Gly Ser Glu Val Gln Leu Val Glu Ser
305                 310                 315                 320
```

```
Gly Gly Gly Leu Val Gln Pro Gly Gly Ser Leu Arg Leu Ser Cys Ala
                    325                 330                 335

Ala Ser Gly Arg Thr Phe Ser Ser Tyr Thr Met Gly Trp Phe Arg Gln
            340                 345                 350

Ala Pro Gly Lys Glu Arg Glu Phe Val Ala Ala Ile Ser Trp Ser Gly
            355                 360                 365

Gly Arg Thr Tyr Tyr Ala Asp Ser Val Lys Gly Arg Phe Thr Ile Ser
        370                 375                 380

Arg Asp Asn Ser Lys Asn Thr Val Tyr Leu Gln Met Asn Ser Leu Arg
385                 390                 395                 400

Pro Glu Asp Thr Ala Val Tyr Tyr Cys Ala Ala Tyr Arg Arg Arg Arg
            405                 410                 415

Ala Ser Ser Asn Arg Gly Leu Trp Asp Tyr Trp Gly Gln Gly Thr Leu
            420                 425                 430

Val Thr Val Ser Ser
            435

<210> SEQ ID NO 186
<211> LENGTH: 278
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Thr Ala Ala Leu Ala Val Tyr Gly Pro Ser Arg Tyr Arg Tyr Gly Pro
            100                 105                 110

Val Gly Glu Tyr Gln Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Ser Glu Val Gln Leu Val Glu Ser Gly Gly Gly Leu Val
            165                 170                 175

Gln Pro Gly Gly Ser Leu Arg Leu Ser Cys Ala Ala Ser Gly Ser Thr
            180                 185                 190

Phe Ser Arg Tyr Ser Met Asn Trp Tyr Arg Gln Ala Pro Gly Lys Gln
        195                 200                 205

Arg Glu Phe Val Ala Gly Ile Ser Val Gly Arg Ile Thr Asn Tyr Ala
    210                 215                 220

Val Ser Val Lys Gly Arg Phe Thr Ile Ser Arg Asp Asn Ser Lys Asn
225                 230                 235                 240
```

```
Thr Val Tyr Leu Gln Met Asn Ser Leu Arg Pro Glu Asp Thr Ala Val
                245                 250                 255

Tyr Tyr Cys Asn Ala Gly Gly Leu Gln Gly Tyr Trp Gly Gln Gly Thr
            260                 265                 270

Leu Val Thr Val Ser Ser
        275

<210> SEQ ID NO 187
<211> LENGTH: 278
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Ala Leu Ala Val Tyr Gly Pro Ser Arg Tyr Arg Tyr Gly Pro
            100                 105                 110

Val Gly Glu Tyr Gln Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Ser Glu Val Gln Leu Val Glu Ser Gly Gly Gly Leu Val
            165                 170                 175

Gln Pro Gly Gly Ser Leu Arg Leu Ser Cys Ala Ala Ser Gly Ser Thr
        180                 185                 190

Phe Ser Arg Tyr Ser Met Asn Trp Tyr Arg Gln Ala Pro Gly Lys Gln
    195                 200                 205

Arg Glu Phe Val Ala Gly Ile Ser Val Gly Arg Ile Thr Asn Tyr Ala
    210                 215                 220

Val Ser Val Lys Gly Arg Phe Thr Ile Ser Arg Asp Asn Ser Lys Asn
225                 230                 235                 240

Thr Gly Tyr Leu Gln Met Asn Ser Leu Arg Pro Glu Asp Thr Ala Val
                245                 250                 255

Tyr Tyr Cys Asn Ala Gly Gly Leu Gln Gly Tyr Trp Gly Gln Gly Thr
            260                 265                 270

Leu Val Thr Val Ser Ser
        275

<210> SEQ ID NO 188
<211> LENGTH: 283
<212> TYPE: PRT
```

```
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 188
```

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Ala Val Asp Ala Ser Arg Gly Leu Pro Tyr Glu Leu Tyr Tyr Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Ser Gly Gly Gly Gly Ser Glu Val
145                 150                 155                 160

Gln Leu Val Glu Ser Gly Gly Leu Val Gln Pro Gly Gly Ser Leu
                165                 170                 175

Arg Leu Ser Cys Ala Ala Ser Gly Arg Thr Phe Ser Ser Tyr Thr Met
            180                 185                 190

Gly Trp Phe Arg Gln Ala Pro Gly Lys Glu Arg Glu Phe Val Ala Ala
        195                 200                 205

Ile Ser Trp Ser Gly Gly Arg Thr Tyr Tyr Ala Asp Ser Val Lys Gly
    210                 215                 220

Arg Phe Thr Ile Ser Arg Asp Asn Ser Lys Asn Thr Val Tyr Leu Gln
225                 230                 235                 240

Met Asn Ser Leu Arg Pro Glu Asp Thr Ala Val Tyr Tyr Cys Ala Ala
                245                 250                 255

Tyr Arg Arg Arg Ala Ser Ser Asn Arg Gly Leu Trp Asp Tyr Trp
            260                 265                 270

Gly Gln Gly Thr Leu Val Thr Val Ser Ser Ala
        275                 280

```
<210> SEQ ID NO 189
<211> LENGTH: 279
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 189
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val

```
                35                  40                  45
Ala Ala Ile Ser Ser Gly Gly Ser Thr Tyr Tyr Ala Asp Ser Val Lys
         50                  55                  60
Gly Arg Phe Thr Ile Ser Arg Asp Asn Ser Lys Asn Thr Val Tyr Leu
 65                  70                  75                  80
Gln Met Asn Ser Leu Arg Pro Glu Asp Thr Ala Val Tyr Tyr Cys Asn
                 85                  90                  95
Ala Ala Val Asp Ala Ser Arg Gly Leu Pro Tyr Glu Leu Tyr Tyr Tyr
                100                 105                 110
Trp Gly Gln Gly Thr Leu Val Thr Val Ser Ser Gly Gly Gly Gly Ser
                115                 120                 125
Gly Gly Gly Gly Ser Gly Gly Gly Ser Gly Gly Gly Gly Ser Gly
        130                 135                 140
Gly Gly Gly Ser Gly Gly Gly Ser Gly Gly Gly Ser Glu Val
145                 150                 155                 160
Gln Leu Val Glu Ser Gly Gly Gly Leu Val Gln Pro Gly Gly Ser Leu
                165                 170                 175
Arg Leu Ser Cys Ala Ala Ser Gly Ser Thr Phe Ile Ile Asn Val Val
                180                 185                 190
Arg Trp Tyr Arg Arg Ala Pro Gly Lys Gln Arg Glu Leu Val Ala Thr
                195                 200                 205
Ile Ser Ser Gly Gly Asn Ala Asn Tyr Val Asp Ser Val Arg Gly Arg
                210                 215                 220
Phe Thr Ile Ser Arg Asp Asn Ser Lys Asn Thr Val Tyr Leu Gln Met
225                 230                 235                 240
Asn Ser Leu Arg Pro Glu Asp Thr Ala Val Tyr Tyr Cys Asn Val Pro
                245                 250                 255
Thr Thr His Tyr Gly Gly Val Tyr Tyr Gly Pro Tyr Trp Gly Gln Gly
                260                 265                 270
Thr Leu Val Thr Val Ser Ser
        275

<210> SEQ ID NO 190
<211> LENGTH: 435
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 190

Glu Val Gln Leu Val Glu Ser Gly Gly Gly Leu Val Gln Pro Gly Gly
 1               5                  10                  15
Ser Leu Arg Leu Ser Cys Ala Ala Ser Gly Ser Ile Phe Ser Ile Asn
                 20                  25                  30
Ala Met Gly Trp Tyr Arg Gln Ala Pro Gly Lys Gln Arg Glu Leu Val
         35                  40                  45
Ala Ala Ile Ser Ser Gly Gly Ser Thr Tyr Tyr Ala Asp Ser Val Lys
         50                  55                  60
Gly Arg Phe Thr Ile Ser Arg Asp Asn Ser Lys Asn Thr Val Tyr Leu
 65                  70                  75                  80
Gln Met Asn Ser Leu Arg Pro Glu Asp Thr Ala Val Tyr Tyr Cys Asn
                 85                  90                  95
Ala Ala Val Asp Ala Ser Arg Gly Leu Pro Tyr Glu Leu Tyr Tyr Tyr
                100                 105                 110
```

```
Trp Gly Gln Gly Thr Leu Val Thr Val Ser Ser Gly Gly Gly Ser
            115                 120                 125

Gly Gly Gly Gly Ser Gly Gly Gly Ser Gly Gly Gly Gly Ser Gly
130                 135                 140

Gly Gly Gly Ser Gly Gly Gly Ser Gly Gly Gly Ser Glu Val
145                 150                 155                 160

Gln Leu Val Glu Ser Gly Gly Leu Val Gln Pro Gly Gly Ser Leu
                165                 170                 175

Arg Leu Ser Cys Ala Ala Ser Gly Ser Thr Phe Ile Ile Asn Val Val
            180                 185                 190

Arg Trp Tyr Arg Arg Ala Pro Gly Lys Gln Arg Glu Leu Val Ala Thr
        195                 200                 205

Ile Ser Ser Gly Gly Asn Ala Asn Tyr Val Asp Ser Val Arg Gly Arg
    210                 215                 220

Phe Thr Ile Ser Arg Asp Asn Ser Lys Asn Thr Val Tyr Leu Gln Met
225                 230                 235                 240

Asn Ser Leu Arg Pro Glu Asp Thr Ala Val Tyr Tyr Cys Asn Val Pro
                245                 250                 255

Thr Thr His Tyr Gly Gly Val Tyr Tyr Gly Pro Tyr Trp Gly Gln Gly
            260                 265                 270

Thr Leu Val Thr Val Ser Ser Gly Gly Gly Ser Gly Gly Gly Gly
        275                 280                 285

Ser Gly Gly Gly Gly Ser Gly Gly Gly Gly Ser Gly Gly Gly Ser
    290                 295                 300

Gly Gly Gly Ser Gly Gly Gly Ser Glu Val Gln Leu Val Glu
305                 310                 315                 320

Ser Gly Gly Gly Leu Val Gln Pro Gly Gly Ser Leu Arg Leu Ser Cys
                325                 330                 335

Ala Ala Ser Gly Ser Thr Phe Ile Ile Asn Val Val Arg Trp Tyr Arg
            340                 345                 350

Arg Ala Pro Gly Lys Gln Arg Glu Leu Val Ala Thr Ile Ser Ser Gly
        355                 360                 365

Gly Asn Ala Asn Tyr Val Asp Ser Val Arg Gly Arg Phe Thr Ile Ser
    370                 375                 380

Arg Asp Asn Ser Lys Asn Thr Val Tyr Leu Gln Met Asn Ser Leu Arg
385                 390                 395                 400

Pro Glu Asp Thr Ala Val Tyr Tyr Cys Asn Val Pro Thr Thr His Tyr
                405                 410                 415

Gly Gly Val Tyr Tyr Gly Pro Tyr Trp Gly Gln Gly Thr Leu Val Thr
            420                 425                 430

Val Ser Ser
        435

<210> SEQ ID NO 191
<211> LENGTH: 282
<212> TYPE: PRT
<213> ORGANISM: Artificial Sequence
<220> FEATURE:
<223> OTHER INFORMATION: Description of Artificial Sequence: Synthetic
      Multivalent constructs comprising several ISVDs

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30
```

```
Ala Met Gly Trp Tyr Arg Gln Ala Pro Gly Lys Gln Arg Glu Leu Val
        35                  40                  45

Ala Ala Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Ala Val Asp Ala Ser Arg Gly Leu Pro Tyr Glu Leu Tyr Tyr Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Gly Gly Gly Gly Ser Gly
            130                 135                 140

Gly Gly Gly Ser Gly Gly Gly Ser Gly Gly Gly Ser Glu Val
145                 150                 155                 160

Gln Leu Val Glu Ser Gly Gly Leu Val Gln Pro Gly Gly Ser Leu
                165                 170                 175

Arg Leu Ser Cys Ala Ala Ser Gly Arg Thr Phe Ser Ser Tyr Thr Met
            180                 185                 190

Gly Trp Phe Arg Gln Ala Pro Gly Lys Glu Arg Glu Phe Val Ala Ala
            195                 200                 205

Ile Ser Trp Ser Gly Gly Arg Thr Tyr Tyr Ala Asp Ser Val Lys Gly
            210                 215                 220

Arg Phe Thr Ile Ser Arg Asp Asn Ser Lys Asn Thr Val Tyr Leu Gln
225                 230                 235                 240

Met Asn Ser Leu Arg Pro Glu Asp Thr Ala Val Tyr Tyr Cys Ala Ala
                245                 250                 255

Tyr Arg Arg Arg Arg Ala Ser Ser Asn Arg Gly Leu Trp Asp Tyr Trp
            260                 265                 270

Gly Gln Gly Thr Leu Val Thr Val Ser Ser
            275                 280

<210> SEQ ID NO 192
<211> LENGTH: 434
<212> TYPE: PRT
<213> ORGANISM: Artificial Sequence
<220> FEATURE:
<223> OTHER INFORMATION: Description of Artificial Sequence: Synthetic
      MMP13-CAP

<400> SEQUENCE: 192

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ala Phe Ser Ala Ala
                20                  25                  30

Tyr Met Ser Trp Val Arg Gln Ala Pro Gly Lys Gly Leu Glu Trp Val
            35                  40                  45

Ser Ser Ile Ser Asp Asp Gly Ser Lys Thr Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Asn Thr Gly Tyr Gly Ala Thr Thr Thr Arg Pro Gly Arg Tyr Trp Gly
```

-continued

```
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Glu Val Gln Leu
145                 150                 155                 160

Val Glu Ser Gly Gly Gly Val Val Gln Pro Gly Gly Ser Leu Arg Leu
                165                 170                 175
Ser Cys Ala Ala Ser Gly Ser Thr Phe Ile Ile Asn Val Val Arg Trp
            180                 185                 190
Tyr Arg Arg Ala Pro Gly Lys Gln Arg Glu Leu Val Ala Thr Ile Ser
        195                 200                 205

Ser Gly Gly Asn Ala Asn Tyr Val Asp Ser Val Arg Gly Arg Phe Thr
    210                 215                 220

Ile Ser Arg Asp Asn Ser Lys Asn Thr Val Tyr Leu Gln Met Asn Ser
225                 230                 235                 240
Leu Arg Pro Glu Asp Thr Ala Leu Tyr Tyr Cys Asn Val Pro Thr Thr
                245                 250                 255
His Tyr Gly Gly Val Tyr Tyr Gly Pro Tyr Trp Gly Gln Gly Thr Leu
            260                 265                 270

Val Thr Val Ser Ser Gly Gly Gly Gly Ser Gly Gly Gly Gly Ser Gly
        275                 280                 285

Gly Gly Gly Ser Gly Gly Gly Gly Ser Gly Gly Gly Gly Ser Gly Gly
    290                 295                 300

Gly Gly Ser Gly Gly Gly Gly Ser Glu Val Gln Leu Val Glu Ser Gly
305                 310                 315                 320
Gly Gly Val Val Gln Pro Gly Gly Ser Leu Arg Leu Ser Cys Ala Ala
                325                 330                 335
Ser Gly Ser Thr Phe Ile Ile Asn Val Val Arg Trp Tyr Arg Arg Ala
            340                 345                 350
Pro Gly Lys Gln Arg Glu Leu Val Ala Thr Ile Ser Ser Gly Gly Asn
        355                 360                 365

Ala Asn Tyr Val Asp Ser Val Arg Gly Arg Phe Thr Ile Ser Arg Asp
    370                 375                 380

Asn Ser Lys Asn Thr Val Tyr Leu Gln Met Asn Ser Leu Arg Pro Glu
385                 390                 395                 400

Asp Thr Ala Leu Tyr Tyr Cys Asn Val Pro Thr Thr His Tyr Gly Gly
                405                 410                 415
Val Tyr Tyr Gly Pro Tyr Trp Gly Gln Gly Thr Leu Val Thr Val Ser
            420                 425                 430

Ser Ala
```

<210> SEQ ID NO 193
<211> LENGTH: 116
<212> TYPE: PRT
<213> ORGANISM: Artificial Sequence
<220> FEATURE:
<223> OTHER INFORMATION: Description of Artificial Sequence: Synthetic
Serum albumin binding ISVD sequence

<400> SEQUENCE: 193

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
```

```
                    20                  25                  30

Gly Met Ser Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
                100                 105                 110

Val Lys Ser Ala
        115

<210> SEQ ID NO 194
<211> LENGTH: 155
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 inhibitors linked to
      FLAG-His tag.

<400> SEQUENCE: 194

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Ser Ala Ala
                20                  25                  30

Tyr Met Ser Trp Val Arg Gln Ala Pro Gly Lys Gly Leu Glu Trp Val
                35                  40                  45

Ser Ser Ile Ser Asp Asp Gly Ser Lys Thr Tyr Tyr Ala Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
                85                  90                  95

Asn Thr Gly Tyr Gly Ala Thr Thr Thr Arg Pro Gly Arg Tyr Trp Gly
                100                 105                 110

Gln Gly Thr Leu Val Thr Val Ser Ser Ala Ala Ala Asp Tyr Lys Asp
                115                 120                 125

His Asp Gly Asp Tyr Lys Asp His Asp Ile Asp Tyr Lys Asp Asp Asp
                130                 135                 140

Asp Lys Gly Ala Ala His His His His His
145                 150                 155

<210> SEQ ID NO 195
<211> LENGTH: 162
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 inhibitors linked to
      FLAG-His tag.

<400> SEQUENCE: 195

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ala Tyr Tyr
                20                  25                  30
```

```
Ser Ile Gly Trp Phe Arg Gln Ala Pro Gly Lys Glu Arg Glu Gly Val
        35                  40                  45

Ser Cys Ile Ser Ser Gly Ile Asp Gly Ser Thr Tyr Tyr Ala Asp Ser
 50                  55                  60

Val Lys Gly Arg Phe Thr Ile Ser Arg Asp Asn Ala Lys Asn Thr Met
 65                  70                  75                  80

Tyr Leu Gln Met Asn Asn Leu Lys Pro Glu Asp Thr Gly Val Tyr Tyr
                 85                  90                  95

Cys Ala Ala Asp Pro Ser His Tyr Tyr Ser Glu Tyr Asp Cys Gly Tyr
                100                 105                 110

Tyr Gly Met Asp Tyr Trp Gly Lys Gly Thr Leu Val Thr Val Ser Ser
        115                 120                 125

Gly Ala Ala Asp Tyr Lys Asp His Asp Gly Asp Tyr Lys Asp His Asp
    130                 135                 140

Ile Asp Tyr Lys Asp Asp Asp Lys Gly Ala Ala His His His His
145                 150                 155                 160

His His
```

```
<210> SEQ ID NO 196
<211> LENGTH: 312
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 inhibitors linked to
      FLAG-His tag.

<400> SEQUENCE: 196
```

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ser Ser Tyr
             20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
             85                  90                  95

Thr Ala Leu Ala Val Tyr Gly Pro Asn Arg Tyr Arg Tyr Gly Pro
            100                 105                 110

Val Gly Glu Tyr Asn Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Ser Glu Val Gln Leu Val Glu Ser Gly Gly Gly Ser Val
                165                 170                 175

Gln Ala Gly Gly Ser Leu Arg Leu Ser Cys Ala Ala Ser Gly Ser Thr
            180                 185                 190

Phe Ser Arg Tyr Ser Met Asn Trp Tyr Arg Gln Ala Pro Gly Lys Gln
        195                 200                 205

Arg Glu Phe Val Ala Gly Ile Ser Val Gly Arg Ile Thr Asn Tyr Ala
```

```
            210                 215                 220
Val Ser Val Arg Gly Arg Phe Thr Ile Ser Arg Asp Asn Ala Glu Gly
225                 230                 235                 240

Thr Gly Tyr Leu Gln Met Asn Ser Leu Lys Pro Glu Asp Thr Ala Val
                245                 250                 255

Tyr Tyr Cys Asn Ala Gly Gly Leu Gln Gly Tyr Trp Gly Leu Gly Thr
            260                 265                 270

Leu Val Thr Val Ser Ser Gly Ala Ala Asp Tyr Lys Asp His Asp Gly
                275                 280                 285

Asp Tyr Lys Asp His Asp Ile Asp Tyr Lys Asp Asp Asp Lys Gly
            290                 295                 300

Ala Ala His His His His His His
305                 310

<210> SEQ ID NO 197
<211> LENGTH: 157
<212> TYPE: PRT
<213> ORGANISM: Artificial Sequence
<220> FEATURE:
<223> OTHER INFORMATION: Description of Artificial Sequence: Synthetic
      Amino acid sequences of anti-MMP13 inhibitors linked to
      FLAG-His tag.

<400> SEQUENCE: 197

Glu Val Gln Leu Val Glu Ser Gly Gly Gly Leu Val Gln Pro Gly Gly
1               5                  10                  15

Ser Leu Arg Leu Ser Cys Ala Ala Ser Gly Ser Ile Phe Ser Ile Asn
                20                  25                  30

Ala Met Gly Trp Tyr Arg Gln Ala Pro Gly Lys Gln Arg Glu Leu Val
            35                  40                  45

Ala Ala Ile Ser Ser Gly Gly Ser Thr Tyr Tyr Ala Asp Ser Val Lys
        50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Ala Val Asp Ala Ser Arg Gly Leu Pro Tyr Glu Leu Tyr Tyr Tyr
            100                 105                 110

Trp Gly Gln Gly Thr Leu Val Thr Val Ser Ser Ala Ala Ala Asp Tyr
        115                 120                 125

Lys Asp His Asp Gly Asp Tyr Lys Asp His Asp Ile Asp Tyr Lys Asp
    130                 135                 140

Asp Asp Asp Lys Gly Ala Ala His His His His His His
145                 150                 155

<210> SEQ ID NO 198
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: E, G, A, P, T, R, M, W, or Y
<220> FEATURE:
<221> NAME/KEY: MOD_RES
<222> LOCATION: (16)..(16)
<223> OTHER INFORMATION: A, R, N, D, E, Q, Z, G, I, L, K, F, P, S, W, Y,
      or V
```

```
<220> FEATURE:
<221> NAME/KEY: MOD_RES
<222> LOCATION: (17)..(17)
<223> OTHER INFORMATION: A, R, N, C, E, Q, Z, G, H, I, L, K, M, S, T, W,
      Y, or V
<220> FEATURE:
<221> NAME/KEY: MOD_RES
<222> LOCATION: (18)..(18)
<223> OTHER INFORMATION: A, R, N, D, C, E, Q, Z, G, H, I, L, K, M, F, P,
      S, T, W, or V

<400> SEQUENCE: 198

Asp Pro Ser His Tyr Tyr Ser Glu Tyr Xaa Cys Gly Tyr Tyr Gly Xaa
1               5                   10                  15

Xaa Xaa

<210> SEQ ID NO 199
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Leu Ala Val Tyr Gly Pro Gln Arg Tyr Arg Tyr Gly Pro Val Gly
1               5                   10                  15

Glu Tyr Val Tyr
            20

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Gly Gly Ser Ser Gly Gly Ser Ser Gly Gly Gly Ser Ser
1               5                   10                  15

<210> SEQ ID NO 201
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 201

His His His His His His
1               5
```

MMP13 BINDING IMMUNOGLOBULINS

RELATED APPLICATIONS

The present application claims priority under 35 U.S.C. § 371 to International Patent Application No. PCT/EP2018/064667, filed Jun. 4, 2018, which claims priority to European Patent Application No. 17174402.2, filed on Jun. 2, 2017. The contents of these applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 20, 2021, is named 103926-0500_SL.txt and is 225,978 bytes in size.

1 FIELD OF THE INVENTION

The present invention relates to immunoglobulins that bind MMP13 and more in particular to polypeptides, that comprise or essentially consist of one or more such immunoglobulins (also referred to herein as "immunoglobulin(s) of the invention", and "polypeptides of the invention", respectively). The invention also relates to constructs comprising such immunoglobulins or polypeptides as well as nucleic acids encoding such immunoglobulins or polypeptides (also referred to herein as "nucleic acid(s) of the invention"; to methods for preparing such immunoglobulins, polypeptides and constructs; to host cells expressing or capable of expressing such immunoglobulins or polypeptides; to compositions, and in particular to pharmaceutical compositions, that comprise such immunoglobulins, polypeptides, constructs, nucleic acids and/or host cells; and to uses of immunoglobulins, polypeptides, constructs, nucleic acids, host cells and/or compositions, in particular for prophylactic and/or therapeutic purposes, such as the prophylactic and/or therapeutic purposes mentioned herein. Other aspects, embodiments, advantages and applications of the invention will become clear from the further description herein.

2 BACKGROUND OF THE INVENTION

Osteoarthritis (OA) is one of the most common causes of disability worldwide. It affects 30 million Americans and is the most common joint disorder. It is projected to affect more than 20 percent of the U.S. population by 2025. The disease is non-systemic and is usually restricted to few joints. However, the disease can occur in all joints, most often the knees, hips, hands and spine. OA is characterized by progressive erosion of articular cartilage (cartilage that covers the bones) resulting in chronic pain and disability. Eventually, the disease leads to total destruction of the articular cartilage, sclerosis of underlying bone, osteophyte formation etc., all leading to loss of movement and pain. Pain is the most prominent symptom of OA and most often the reason patients seek medical help. There is no cure for OA; disease management is limited to treatments that are palliative at best and do little to address the underlying cause of disease progression.

Disease modifying anti-osteoarthritic drugs (DMOADs), which can be defined as drugs that inhibit structural disease progression and ideally also improve symptoms and/or function are intensely sought after. DMOADs are likely to be prescribed for long periods in this chronic illness of an aging population, therefore demanding excellent safety data in a target population with multiple comorbidities and the potential for drug-drug interactions.

Osteoarthritis can be defined as a diverse group of conditions characterised by a combination of joint symptoms, signs stemming from defects in the articular cartilage and changes in adjacent tissues including bone, tendons and muscle. The most abundant components of articular cartilage are proteoglycans and Collagen (foremost Collagen II).The main proteoglycan in cartilage is Aggrecan. Although disease initiation may be multi-factorial, the cartilage destruction appears to be a result of uncontrolled proteolytic extracellular matrix destruction (ECM).

As mentioned above, a major component of the cartilage extracellular matrix is Aggrecan (Kiani et al. 2002 Cell Research 12:19-32). This molecule is important in the proper functioning of the articular cartilage because it provides a hydrated gel structure that endows the cartilage with load-bearing properties. Aggrecan is a large, multimodular molecule (2317 amino acids) expressed by chondrocytes. Its core protein is composed of three globular domains (G1, G2 and G3) and a large extended region between G2 and G3 for glycosaminoglycan chain attachment. This extended region comprises two domains, one substituted with keratan sulfate chains (KS domain) and one with chondroitin sulfate chains (CS domain). The CS domain has 100-150 glycosaminoglycan (GAG) chains attached to it. Aggrecan forms large complexes with Hyaluronan in which 50-100 Aggrecan molecules interact via the G1 domain and Link Protein with one Hyaluronan molecule. Upon uptake of water (due to the GAG content) these complexes form a reversibly deformable gel that resists compression. The structure, fluid retention and function of joint cartilage is linked to the matrix content of Aggrecan, and the amount of chondroitin sulfate bound to the intact core protein.

Type II Collagen (Collagen II, Col II) makes up 50% of the articular cartilage. Collagen fibrils form a network allowing the cartilage to entrap the proteoglycan as well as providing strength to the tissue. Collagen is a structural protein that is composed of a right handed bundle of three parallel-left handed polyproline II-type (PPII) helices. Because of the tight packing of PPII helices within the triple helix, every third residue, which is an amino acid, is Gly (Glycine). Because glycine is the smallest amino acid with no side chain, it plays a unique role in fibrous structural proteins. In Collagen, Gly is required at every third position because the assembly of the triple helix puts this residue at the interior (axis) of the helix, where there is no space for a larger side group than glycine's single hydrogen atom.

OA is characterized by 1) degradation of Aggrecan, progressively releasing domains G3 and G2 (resulting in 'deflation' of the cartilage) and eventually release of the G1 domain and 2) degradation of Collagen, irreversibly destroying the cartilage structure.

There is compelling evidence to demonstrate that matrix metalloproteinases (MMPs) have a major role in tissue destruction associated with OA. MMPs are a family of zinc-dependent endopeptidases involved in the degradation of extracellular matrix and tissue remodeling. There are some 28 MMP family members, which can be classified into various subgroups including collagenases, gelatinases, stromelysins, membrane-type MMPs, matrilysins, enamelysins and others. The collagenases, comprising MMP1, MMP8, MMP13 and MMP18, are capable of degrading triple-helical fibrillar Collagens into distinctive ¾ and ¼ fragments. In addition, MMP14 has also been shown to cleave fibrillar Collagen, and there is evidence that also MMP2 is capable of collagenolysis. MMPs have long been considered as attractive therapeutic targets for treatment of OA. However, broad-spectrum MMP inhibitors developed for treatment of arthritis have failed in clinical trials due to painful, joint-stiffening side effects termed musculoskeletal syndrome (MSS). It is believed that MSS is caused by non-selective inhibition of multiple MMPs.

Nam et al. (2017 Proc Natl Acad Sci USA 113:14970-14975) describe Nanobodies which are apparent specifically directed against the active site of MMP14.

Therapeutic interventions in OA have also been hindered by the difficulty of targeting drugs to articular cartilage. Because articular cartilage is an avascular and alymphatic tissue, traditional routes of drug delivery (oral, intravenous, intramuscular) ultimately rely on transsynovial transfer of drugs from the synovial capillaries to cartilage by passive diffusion. Thus, in the absence of a mechanism for selectively targeting a drug to the cartilage, one needs to expose the body systemically to high drug concentrations to achieve a sustained, intra-articular therapeutic dose. As a consequence of high systemic exposure, most of the traditional therapies for OA have been plagued by serious toxicities.

In addition, most of the newly developed DMOADs have a short residence time in the joint, even when administered intra-articularly (Edwards 2011 Vet. J. 190:15-21; Larsen et al. 2008 J Pham Sci 97:4622-4654). Intra-articular (IA) delivery of therapeutic proteins has been limited by their rapid clearance from the joint space and lack of retention within cartilage. Synovial residence time of a drug in the joint is often less than 24 h. Due to the rapid clearance of most IA injected drugs, frequent injections would be needed to maintain an effective concentration (Owen et al. 1994 Br. J. Clin Pharmacol. 38:349-355). However, frequent IA-injections are undesired due to the pain and discomfort they may cause challenging patient compliance, as well as the risk of introducing joint infections.

There remains a need for effective DMOADs.

3 SUMMARY OF THE INVENTION

The present invention aims to provide polypeptides against OA with improved prophylactic, therapeutic and/or pharmacological properties, in addition to other advantageous properties (such as, for example, improved ease of preparation, good stability, and/or reduced costs of goods), compared to the prior art amino acid sequences and antibodies. In particular, the present invention aims to provide immunoglobulin single variable domains (ISVDs) and polypeptides comprising the same for inhibiting MMPs and especially inhibiting MMP13.

The inventors hypothesized that the best region to inhibit the enzymatic activity of MMP13 would be raising ISVDs against the catalytic pocket. However, this turned out to be a major challenge. In particular, MMP13 is secreted as an inactive pro-form (proMMP13), in which the pro-domain masks the catalytic pocket, because of which the pocket is not accessible for raising an immune response. On the other hand, activated MMP13 has a short half-life, which is mainly due to autoproteolysis. Furthermore, even after the inventors overcame the two previous problems, it turned out that the high sequence conservation of the catalytic domain between various species foregoes a robust immune response.

In the end, the inventors were able to meet these challenges by the original development of new tools and unconventional screening methods.

From different screening campaigns ISVDs were isolated and further engineered with diverse and favorable features, including stability, affinity and inhibitory activity. The comparator drug was outperformed by the monovalent ISVDs of the invention binding MMP13. Biparatopic polypeptides, comprising an ISVD which was less expedient in inhibiting the activity of MMP13, were even more potent.

Accordingly, the present invention relates to a polypeptide comprising at least 1 immunoglobulin single variable domain (ISVD) binding a matrix metalloproteinase (MMP) and preferably binding the matrix metalloproteinase MMP13. The invention also includes a polypeptide comprising two or more ISVDs which each individually specifically bind MMP13, wherein a) at least a "first" ISVD specifically binds a first antigenic determinant, epitope, part, domain, subunit or conformation of MMP13; and wherein, b) at least a "second" ISVD specifically binds a second antigenic determinant, epitope, part, domain, subunit or conformation of MMP13, different from the first antigenic determinant epitope, part, domain, subunit or conformation, respectively.

Also provided is a polypeptide of the invention comprising a comprising a single variable domain (ISVD) that binds a matrix metalloproteinase (MMP) and a further single variable domain (ISVD) that binds a cartilage proteoglycan and preferably Aggrecan.

A further aspect relates to a polypeptide according to the invention for use as a medicament. Yet another aspect relates to a method of treating prevention of diseases or disorders in an individual, for instance in which MMP13 activity is involved, the method comprising administering the polypeptide according to the invention to said individual in an amount effective to treat or prevent a symptom of said disease or disorder.

Other aspects, advantages, applications and uses of the polypeptides and compositions will become clear from the further disclosure herein. Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

4 FIGURE LEGENDS

FIG. 1: Dose response curves of profile 1 Nanobodies (left graph) and profile 2 Nanobodies (right graph) in the fluorogenic Collagen assay.

Figure 2:
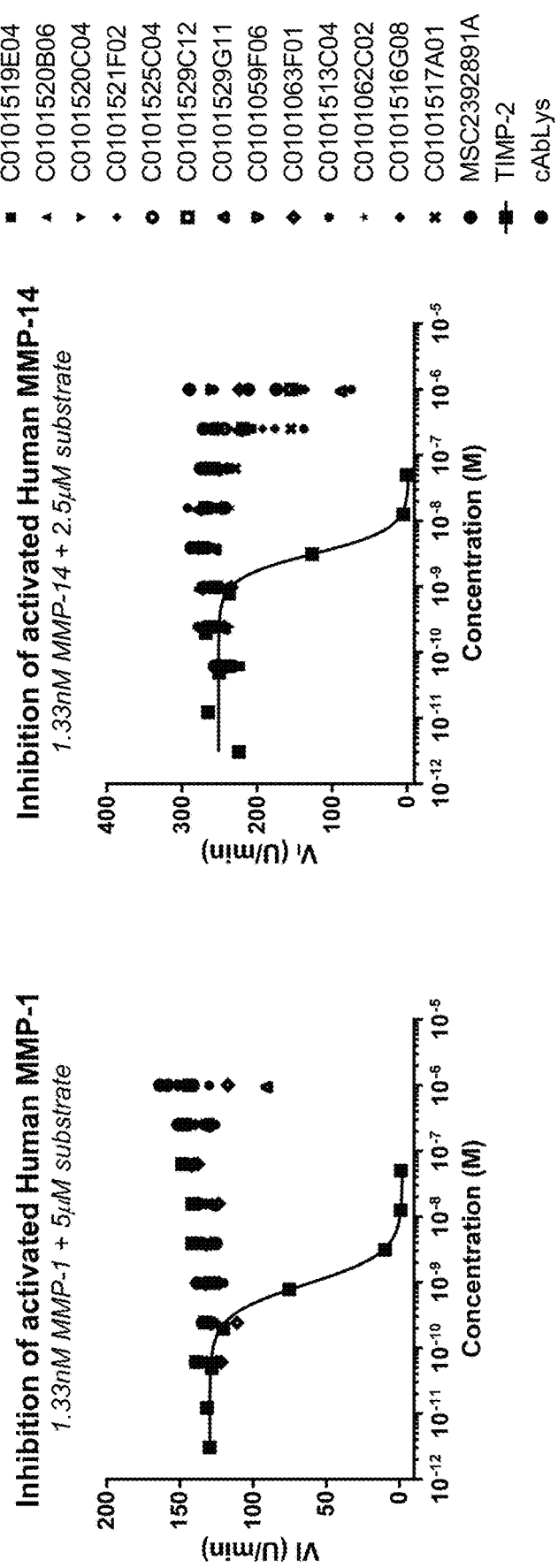

FIG. 2: Selectivity of MMP13 lead Nanobodies.

Figure 3:
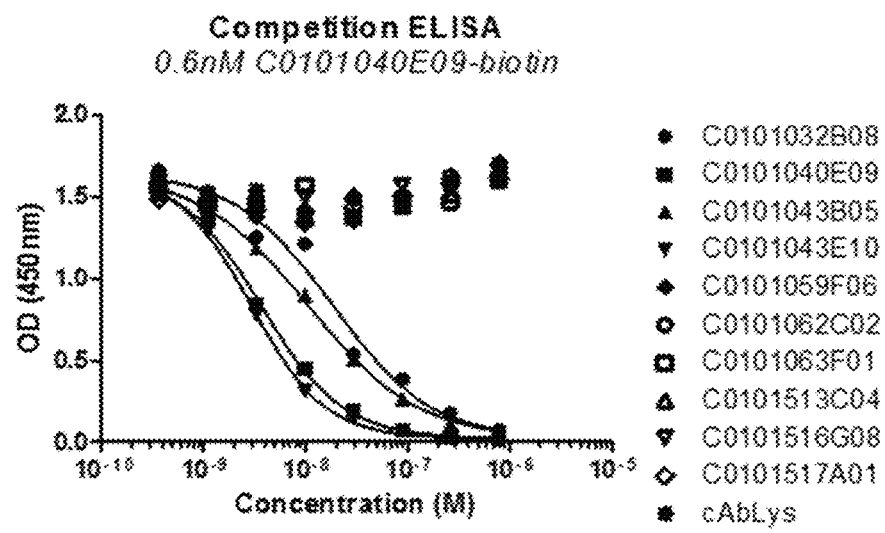

FIG. 3: Competition ELISA with 0.6 nM biotinylated 40E09 against a panel of profile 1 and profile 2 Nanobodies on human full-length MMP13, coated via mouse anti-human MMP13 mAb (R&D Systems #MAB511). MMP13 was activated via incubation with APMA for 90 min at 37° C.

Figure 4:
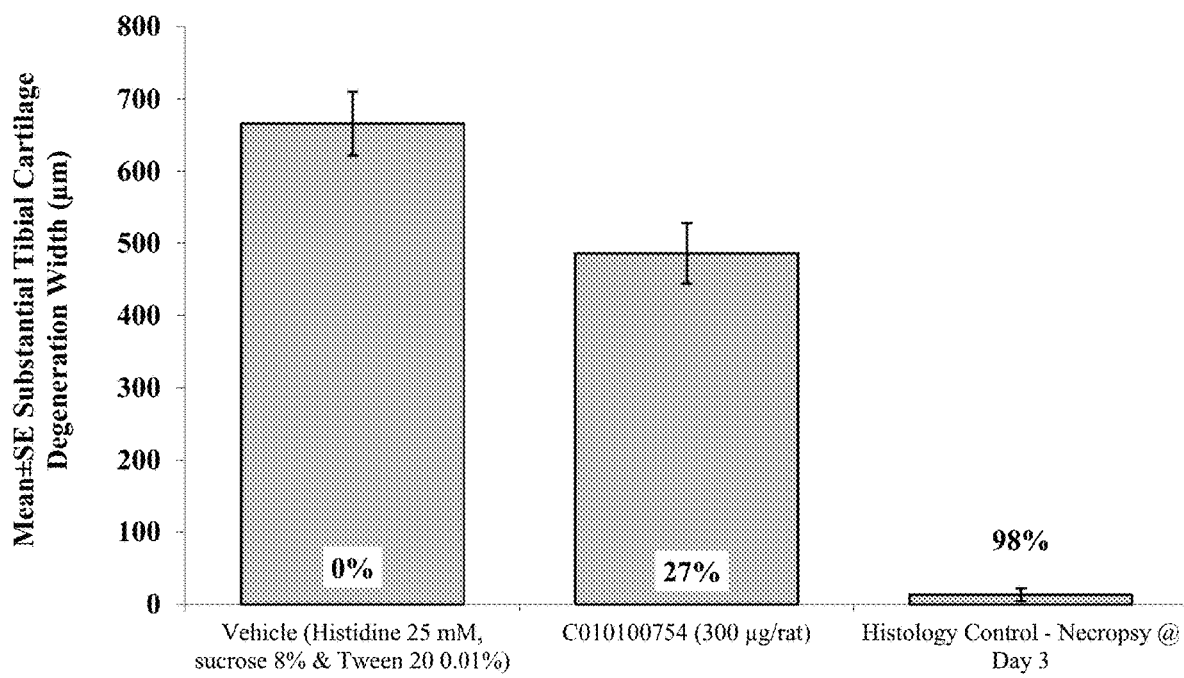

FIG. 4: Inhibition of cartilage degradation by Nanobodies in a rat MMT model.

5 DETAILED DESCRIPTION

There remains a need for safe and efficacious OA medicaments. These medicaments should comply with various and frequently opposing requirements, especially when a broadly applicable format is intended. As such, the format should preferably be useful in a broad range of patients. The format should preferably be safe and not induce infections due to frequent IA administration. In addition, the format should preferably be patient friendly. For instance, the format should have an extended half-life in the joints, such that the format is not removed instantaneously upon administration.

However, extending the half-life should preferably not introduce off-target activity and side effects or limit efficacy.

The present invention realizes at least one of these requirements.

Based on unconventional screening, characterization and combinatory strategies, the present inventors surprisingly observed that immunoglobulin single variable domains (ISVDs) performed exceptionally well in in vitro and in vivo experiments.

Moreover, the present inventors were able to re-engineer the ISVDs to outperform the comparator drug. In a biparatopic modus, this performance was not only retained but even ameliorated.

On the other hand, the ISVDs of the invention were also demonstrated to be significantly more efficacious than the comparator molecules.

The present invention provides polypeptides antagonizing MMPs in particular MMP13 with improved prophylactic, therapeutic and/or pharmacological properties, including a safer profile, compared to the comparator molecules.

Accordingly, the present invention relates to ISVDs and polypeptides that are directed against/and or that may specifically bind (as defined herein) to MMPs, preferably said MMP is chosen from the group consisting of MMP13 (collagenase), MMP8 (collagenase), MMP1 (collagenase), MMP19 (matrix metalloproteinase RASI) and MMP20 (enamelysin), preferably said MMP is MMP13, and modulate an activity thereof, in particular a polypeptide comprising at least one immunoglobulin single variable domain (ISVD) specifically binding MMP13, wherein binding to MMP13 modulates an activity of MMP13.

Definitions

Unless indicated or defined otherwise, all terms used have their usual meaning in the art, which will be clear to the skilled person. Reference is for example made to the standard handbooks, such as Sambrook et al. (Molecular Cloning: A Laboratory Manual ($2^{nd}$ Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering (2nd edition) University of California Press, Berkeley, CA, 1981); Roitt et al. (Immunology ($6^{th}$ Ed.) Mosby/Elsevier, Edinburgh, 2001), Roitt et al. (Roitt's Essential Immunology ($10^{th}$ Ed.) Blackwell Publishing, UK, 2001), and Janeway et al. (Immunobiology ($6^{th}$ Ed.) Garland Science Publishing/ Churchill Livingstone, New York, 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: S106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 15%, more preferably within 10%, and most preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid sequences are interpreted to mean a single amino acid or an unbranched sequence of two or more amino acids, depending of the context. Nucleotide sequences are interpreted to mean an unbranched sequence of 3 or more nucleotides.

Amino acids are those L-amino acids commonly found in naturally occurring proteins. Amino acid residues will be indicated according to the standard three-letter or one-letter amino acid code. Reference is for instance made to Table A-2 on page 48 of WO 08/020079. Those amino acid sequences containing D-amino acids are not intended to be embraced by this definition. Any amino acid sequence that contains post-translationally modified amino acids may be described as the amino acid sequence that is initially translated using the symbols shown in this Table A-2 with the modified positions; e.g., hydroxylations or glycosylations, but these modifications shall not be shown explicitly in the amino acid sequence. Any peptide or protein that can be expressed as a sequence modified linkages, cross links and end caps, non-peptidyl bonds, etc., is embraced by this definition.

The terms "protein", "peptide", "protein/peptide", and "polypeptide" are used interchangeably throughout the disclosure and each has the same meaning for purposes of this disclosure. Each term refers to an organic compound made of a linear chain of two or more amino acids. The compound may have ten or more amino acids; twenty-five or more amino acids; fifty or more amino acids; one hundred or more amino acids, two hundred or more amino acids, and even three hundred or more amino acids. The skilled artisan will appreciate that polypeptides generally comprise fewer amino acids than proteins, although there is no art-recognized cut-off point of the number of amino acids that distinguish a polypeptides and a protein; that polypeptides may be made by chemical synthesis or recombinant methods; and that proteins are generally made in vitro or in vivo by recombinant methods as known in the art. By convention, the amide bond in the primary structure of polypeptides is in the order that the amino acids are written, in which the amine end (N-terminus) of a polypeptide is always on the left, while the acid end (C-terminus) is on the right.

A nucleic acid or amino acid sequence is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid sequence is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain ("ISVD"), this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence). Also, when a construct of the invention is said to comprise a polypeptide or ISVD, this may mean that said construct at least encompasses said polypeptide or ISVD, respectively, but more usually this means that said construct encompasses groups, residues (e.g. amino acid residues), moieties and/or binding units in addition to said polypeptide or ISVD, irrespective of how said polypeptide or ISVD is connected to said groups, residues (e.g. amino acid residues), moieties and/or binding units and irrespective of how sad construct has been generated or obtained.

By "essentially consist of" is meant that the immunoglobulin single variable domain used in the method of the invention either is exactly the same as the immunoglobulin single variable domain of the invention or corresponds to the immunoglobulin single variable domain of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from, e.g. WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al. ("Principles of Protein Structure", Springer-Verlag, 1978), on the analyses of structure forming potentials developed by Chou and Fasman (Biochemistry 13: 211, 1974; Adv. Enzymol., 47: 45-149, 1978), and on the analysis of hydrophobicity patterns in proteins developed by Eisenberg et al. (Proc. Natl. Acad Sci. USA 81: 140-144, 1984), Kyte and Doolittle (J. Molec. Biol. 157: 105-132, 1981), and Goldman et al. (Ann. Rev. Biophys. Chem. 15: 321-353, 1986), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) and Decanniere et al. (Structure, 7 (4): 361, 1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid(s) difference" refers to an insertion, deletion or substitution of a single amino acid residue on a position of the first sequence, compared to the second sequence; it being understood that two amino acid sequences can contain one, two or more such amino acid differences. More particularly, in the ISVDs and/or polypeptides of the present invention, the term "amino acid(s) difference" refers to an insertion, deletion or substitution of a single amino acid residue on a position of the CDR sequence specified in b), d) or f), compared to the CDR sequence of respectively a), c) or e); it being understood that the CDR sequence of b), d) and f) can contain one, two, three, four or maximal five such amino acid differences compared to the CDR sequence of respectively a), c) or e).

The "amino acid(s) difference" can be any one, two, three, four or maximal five substitutions, deletions or insertions, or any combination thereof, that either improve the properties of the MMP13 binder of the invention, such as the polypeptide of the invention or that at least do not detract too much from the desired properties or from the balance or combination of desired properties of the MMP13 binder of the invention, such as the polypeptide of the invention. In this respect, the resulting MMP13 binder of the invention, such as the polypeptide of the invention should at least bind MMP13 with the same, about the same, or a higher affinity compared to the polypeptide comprising the one or more CDR sequences without the one, two, three, four or maximal five substitutions, deletions or insertions. The affinity can be measured by any suitable method known in the art, but is preferably measured by a method as described in the examples section.

In this respect, the amino acid sequence of the CDRs according to b), d) and/or f) may be an amino acid sequence that is derived from an amino acid sequence according to a), c) and/or e) respectively by means of affinity maturation using one or more techniques of affinity maturation known per se or as described in the Examples. For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art (cf. Examples).

As used herein "represented by" in the context of any SEQ ID NO is equivalent to "comprises or consists of" said SEQ ID NO and preferably equivalent to "consists of" said SEQ ID NO.

A "Nanobody family", "$V_{HH}$ family" or "family" as used in the present specification refers to a group of Nanobodies and/or $V_{HH}$ sequences that have identical lengths (i.e. they have the same number of amino acids within their sequence) and of which the amino acid sequence between position 8 and position 106 (according to Kabat numbering) has an amino acid sequence identity of 89% or more.

The terms "epitope" and "antigenic determinant", which can be used interchangeably, refer to the part of a macromolecule, such as a polypeptide or protein that is recognized by antigen-binding molecules, such as immunoglobulins, conventional antibodies, immunoglobulin single variable domains and/or polypeptides of the invention, and more particularly by the antigen-binding site of said molecules.

Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

An amino acid sequence (such as an immunoglobulin single variable domain, an antibody, a polypeptide of the invention, or generally an antigen binding protein or polypeptide or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-MMP13).

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or M$^{-1}$). In the present specification, the stability of the interaction between two molecules will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the change of free energy ($\Delta G$) of binding by the well-known relation $\Delta G=RTln(K_D)$ (equivalently $\Delta G=-RTln(K_A)$), where R equals the gas constant, T equals the absolute temperature and ln denotes the natural logarithm.

The $K_D$ for biological interactions which are considered meaningful (e.g. specific) are typically in the range of $10^{-12}$ M (0.001 nM) to $10^{-5}$ M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units M$^{-1}$s$^{-1}$. The on-rate may vary between $10^2$ M$^{-1}$s$^{-1}$ to about $10^7$ M$^{-1}$s$^{-1}$, approaching the diffusion-limited association rate constant for bimolecular interactions. The off-rate is related to the half-life of a given molecular interaction by the relation $t_{1/2}=ln(2)/k_{off}$. The off-rate may vary between $10^{-6}$ s$^{-1}$ (near irreversible complex with a $t_{1/2}$ of multiple days) to 1 s$^{-1}$ ($t_{1/2}=0.69$ s).

Specific binding of an antigen-binding protein, such as an ISVD, to an antigen or antigenic determinant can be determined in any suitable manner known per se, including, for example, saturation binding assays and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules can be measured via different techniques known per se, such as the well-known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE® instruments (Pharmacia Biosensor AB, Uppsala, Sweden). Kinetic Exclusion Assay (KINEXA®) (Drake et al. 2004, Analytical Biochemistry 328: 35-43) measures binding events in solution without labeling of the binding partners and is based upon kinetically excluding the dissociation of a complex. In-solution affinity analysis can also be performed using the GYROLAB® immunoassay system, which provides a platform for automated bioanalysis and rapid sample turnaround (Fraley et al. 2013, Bioanalysis 5: 1765-74).

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition site for the other molecule. In such situation the measured affinity may be affected by the avidity of the interaction by the two molecules. In particular, the accurate measurement of $K_D$ may be quite labor-intensive and as consequence, often apparent $K_D$ values are determined to assess the binding strength of two molecules. It should be noted that as long as all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

The term "specificity" refers to the number of different types of antigens or antigenic determinants to which a particular antigen-binding molecule or antigen-binding protein (such as an ISVD or polypeptide of the invention) molecule can bind, for instance as described in paragraph n) on pages 53-56 of WO 08/020079. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as a polypeptide or ISVD of the invention) and the pertinent antigen. Typically, antigen-binding proteins (such as the ISVDs and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ liter/mol) is generally considered to indicate non-specific binding. Preferably, a monovalent ISVD of the invention will bind to the desired antigen with an affinity less than 500 nM, preferably less than 200 nM, more preferably less than 10 nM, such as less than 500 pM, such as e.g., between 10 and 5 pM or less.

An immunoglobulin single variable domain and/or polypeptide is said to be "specific for" a (first) target or antigen compared to another (second) target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times or more better than the affinity with which the immunoglobulin single variable domain and/or polypeptide binds to the second target or antigen. For example, the immunoglobulin single variable domain and/or polypeptide may bind to the first target or antigen with a $K_D$ value that is at least 10 times less, such as at least 100 times less, and preferably at least 1000 times less or even less than that, than the $K_D$ with which said immunoglobulin single variable domain and/or polypeptide binds to the second target or antigen. Preferably, when an immunoglobulin single variable domain and/or polypeptide is "specific for" a first target or antigen compared to a second target or antigen, it is directed against (as defined herein) said first target or antigen, but not directed against said second target or antigen.

Specific binding of an antigen-binding protein to an antigen or antigenic determinant can be determined in any suitable manner known per se, including, for example, saturation binding assays, Scatchard analysis and/or competitive binding assays, such as radioimmunoassays (RIA), enzyme immunoassays (EIA) and sandwich competition assays, and the different variants thereof known in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

Another preferred approach that may be used to assess affinity is the 2-step ELISA (Enzyme-Linked Immunosorbent Assay) procedure of Friguet et al. 1985 (J. Immunol. Methods 77: 305-19). This method establishes a solution phase binding equilibrium measurement and avoids possible artifacts relating to adsorption of one of the molecules on a support such as plastic. As will be clear to the skilled person, and for instance as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

In an aspect the invention relates to an MMP13 binder such as an ISVD and polypeptide of the invention, wherein said MMP13 binder does not bind MMP1 or MMP14 (membrane type).

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{D ref})$. Note that if $c_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the difference in strength or stability of a molecular interaction can be assessed by comparing the $IC_{50}$ and this measurement is judged as equivalent to $K_D$ or to apparent $K_D$ throughout this text.

The half maximal inhibitory concentration ($IC_{50}$) can also be a measure of the effectiveness of a compound in inhibiting a biological or biochemical function, e.g. a pharmacological effect. This quantitative measure indicates how much of the polypeptide or ISVD (e.g. a Nanobody) is needed to inhibit a given biological process (or component of a process, i.e. an enzyme, cell, cell receptor, chemotaxis, anaplasia, metastasis, invasiveness, etc.) by half. In other words, it is the half maximal (50%) inhibitory concentration (IC) of a substance (50% IC, or $IC_{50}$). $IC_{50}$ values can be calculated for a given antagonist such as the polypeptide or ISVD (e.g. a Nanobody) of the invention by determining the concentration needed to inhibit half of the maximum biological response of the agonist. The $K_D$ of a drug can be determined by constructing a dose-response curve and examining the effect of different concentrations of antagonist such as the polypeptide or ISVD (e.g. a Nanobody) of the invention on reversing agonist activity.

The term half maximal effective concentration ($EC_{50}$) refers to the concentration of a compound which induces a response halfway between the baseline and maximum after a specified exposure time. In the present context it is used as a measure of a polypeptide or an ISVD (e.g. a Nanobody) its potency. The $EC_{50}$ of a graded dose response curve represents the concentration of a compound where 50% of its maximal effect is observed. Concentration is preferably expressed in molar units.

In biological systems, small changes in ligand concentration typically result in rapid changes in response, following a sigmoidal function. The inflection point at which the increase in response with increasing ligand concentration begins to slow is the $EC_{50}$. This can be determined mathematically by derivation of the best-fit line. Relying on a graph for estimation is convenient in most cases. In case the $EC_{50}$ is provided in the examples section, the experiments were designed to reflect the KD as accurately as possible. In other words, the $EC_{50}$ values may then be considered as KD values. The term "average KD" relates to the average KD value obtained in at least 1, but preferably more than 1, such as at least 2 experiments. The term "average" refers to the mathematical term "average" (sums of data divided by the number of items in the data).

It is also related to $IC_{50}$ which is a measure of a compound its inhibition (50% inhibition). For competition binding assays and functional antagonist assays $IC_{50}$ is the most common summary measure of the dose-response curve. For agonist/stimulator assays the most common summary measure is the $EC_{50}$.

The inhibition constant, Ki, is an indication of how potent an inhibitor is; it is the concentration required to produce half maximum inhibition. Unlike $IC_{50}$, which may potentially change depending on the experimental conditions (but see above), the Ki is an absolute value and is often referred to as the inhibition constant of a drug. The inhibition constant $K_i$ can be calculated by using the Cheng-Prusoff equation:

$$K_i = \frac{IC50}{\frac{[L]}{K_D} + 1}$$

in which [L] is the fixed concentration of the ligand.

The term "potency" of a polypeptide of the invention, as used herein, is a function of the amount of polypeptide of the invention required for its specific effect to occur. It is measured simply as the inverse of the $IC_{50}$ for that polypeptide. It refers to the capacity of said polypeptide of the invention to modulate and/or partially or fully inhibit an activity of MMP13. More particularly, it may refer to the capacity of said polypeptide to reduce or even totally inhibit an MMP13 activity as defined herein. As such, it may refer to the capacity of said polypeptide to inhibit proteolysis, such as protease activity endopeptidase activities, and/or binding a substrate, such as, for instance, Aggrecan, Collagen II, Collagen I, Collagen III, Collagen IV, Collagen IX, Collagen X, Collagen XIV and gelatin. The potency may be measured by any suitable assay known in the art or described herein.

The "efficacy" of the polypeptide of the invention measures the maximum strength of the effect itself, at saturating polypeptide concentrations. Efficacy indicates the maximum response achievable from the polypeptide of the invention. It refers to the ability of a polypeptide to produce the desired (therapeutic) effect.

In an aspect the invention relates to a polypeptide as described herein, wherein said polypeptide binds to MMP13 with a $K_D$ between $1E^{-07}$ M and $1E^{-13}$ M, such as between $1E^{-08}$ M and $1E^{-12}$ M, preferably at most $1E^{-07}$ M, preferably lower than $1E^{-08}$ M or $1E^{-09}$ M, or even lower than $1E^{-10}$M, such as $5E^{-11}$ M, $4E^{-11}$ M, $3E^{-11}$ M, $2E^{-11}$ M, $1.7E^{-11}$ M, $1E^{-11}$ M, or even $5E^{-12}$ M, $4E^{-12}$ M, $3E^{-12}$ M, $1E^{-12}$ M, for instance as determined by KinExA.

In an aspect the invention relates to a polypeptide as described herein, wherein said polypeptide inhibits an activity of MMP13 with an $IC_{50}$ between $1E^{-07}$ M and $1E^{-12}$ M, such as between $1E^{-08}$ M and $1E^{-11}$ M, for instance as determined by competition ELISA, competition TIMP-2 ELISA, fluorogenic peptide assay, fluorogenic collagen assay or collagenolytic assay, such as for instance as detailed in the Examples section.

In an aspect the invention relates to a polypeptide as described herein, wherein said polypeptide inhibits an activity of MMP13 with an $IC_{50}$ of at most $1E^{-07}$ M, preferably $1E^{-08}$ M, $5E^{-09}$ M, or $4E^{-9}$ M, $3E^{-9}$ M, $2E^{-9}$ M, such as $1E^{-9}$ M.

In an aspect the invention relates to a polypeptide as described herein, wherein said polypeptide binds to MMP13 with an $EC_{50}$ between $1E^{-07}$ M and $1E^{-12}$ M, such as between $1E^{-08}$ M and $1E^{11}$ M, for instance as determined by ELISA, competition TIMP-2 ELISA, fluorogenic peptide assay, fluorogenic collagen assay or collagenolytic assay.

In an aspect the invention relates to a polypeptide as described herein, wherein said polypeptide binds to MMP13 with an off-rate of less than $5E^{-04}$ ($s^{-1}$), for instance as determined by SPR.

An amino acid sequence, such as an ISVD or polypeptide, is said to be "cross-reactive" for two different antigens or antigenic determinants (such as e.g., MMP13 from different species of mammal, such as e.g., human MMP13, dog MMP13, bovine MMP13, rat MMP13, pig MMP13, mouse MMP13, rabbit MMP13, cynomolgus MMP13, and/or rhesus MMP13) if it is specific for (as defined herein) these different antigens or antigenic determinants. It will be appreciated that an ISVD or polypeptide may be considered to be cross-reactive although the binding affinity for the two different antigens can differ, such as by a factor, 2, 5, 10, 50, 100 or even more provided it is specific for (as defined herein) these different antigens or antigenic determinants.

MMP13 is also known as CLG3 or Collagenase 3, MANDP1, MMP-13, Matrix metallopeptidase 13, or MDST.

Relevant structural information for MMP13 may be found, for example, at UniProt Accession Numbers as depicted in the Table 1 below (cf. Table B).

TABLE 1

| Protein Acc. | Gene | Organism | SEQ ID NO: |
| --- | --- | --- | --- |
| NP 002418.1 | MMP13 | H. sapiens | 115 |
| XP 001154361.1 | MMP13 | P. troglodytes | 116 |
| XP 001098996.1 | MMP13 | M. mulatta | 117 |
| XP 536598.3 | MMP13 | C. lupus | 118 |
| NP 776814.1 | MMP13 | B. taurus | 119 |
| NP 032633.1 | Mmp13 | M. musculus | 120 |
| NP 598214.1 | Mmp13 | R. norvegicus | 121 |
| XP 003640635.1 | MMP13 | G. gallus | 122 |

"Human MMP13" refers to the MMP13 comprising the amino acid sequence of SEQ ID NO: 115. In an aspect the polypeptide of the invention specifically binds MMP13 from *Human sapiens, Mus musculus, Canis lupus, Bos taurus, Macaca mulatta, Rattus norvegicus, Gallus gallus*, and/or *P. troglodytes*, preferably human MMP13, preferably SEQ ID NO: 115.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, ISVD, polypeptide or other binding agent to interfere with the binding of other immunoglobulins, antibodies, ISVDs, polypeptides or binding agents to a given target. The extent to which an immunoglobulin, antibody, ISVD, polypeptide or other binding agent is able to interfere with the binding of another to the target, and therefore whether it may be said to cross-block according to the invention, may be determined using competition binding assays, which are common in the art, such as for instance by screening purified ISVDs against ISVDs displayed on phage in a competition ELISA as described in the examples. Methods for determining whether an immunoglobulin, antibody, immunoglobulin single variable domain, polypeptide or other binding agent directed against a target (cross)-blocks, is capable of (cross)-blocking, competitively binds or is (cross)-competitive as defined herein are described e.g. in Xiao-Chi Jia et al. (Journal of Immunological Methods 288: 91-98, 2004), Miller et al. (Journal of Immunological Methods 365: 118-125, 2011) and/or the methods described herein (see e.g. Example 7).

The present invention relates to a polypeptide as described herein, such as represented by SEQ ID NO:s 111, 11, 112, 12, 109, 9, 110, 10, 1, 13, 14, 15, 16, 17, 18, 19, 20, 21, 22, 2, 3, 4, 5, 6, 7 or 8, wherein said polypeptide competes with a polypeptide, for instance as determined by competition ELISA.

The present invention relates to a method for determining competitors, such as polypeptides, competing with a polypeptide as described herein, such as represented by any one of SEQ ID NO:s 111, 11, 112, 12, 109, 9, 110, 10, 1, 13, 14, 15, 16, 17, 18, 19, 20, 21, 22, 2, 3, 4, 5, 6, 7 or 8, wherein the polypeptide as described herein competes with or cross blocks the competitor, such as a polypeptide, for binding to MMP13, such as, for instance human MMP13 (SEQ ID NO: 115), wherein the binding to MMP13 of the competitor is reduced by at least 5%, such as 10%, 20%, 30%, 40%, 50% or even more, such as 80%, 90% or even 100% (i.e. virtually undetectable in a given assay) in the presence of a polypeptide of the invention, compared to the binding to MMP13 of the competitor in the absence of the polypeptide of the invention. Competition and cross blocking may be determined by any means known in the art, such as, for instance, competition ELISA. In an aspect the present invention relates to a polypeptide of the invention, wherein said polypeptide cross-blocks the binding to MMP13 of at least one of the polypeptides represented by SEQ ID NO:s 111, 11, 112, 12, 109, 9, 110, 10, 1, 13, 14, 15, 16, 17, 18, 19, 20, 21, 22, 2, 3, 4, 5, 6, 7 or 8 and/or is cross-blocked from binding to MMP13 by at least one of the polypeptides represented by SEQ ID NO:s 111, 11, 112, 12, 109, 9, 110, 10, 1, 13, 14, 15, 16, 17, 18, 19, 20, 21, 22, 2, 3, 4, 5, 6, 7 or 8.

The present invention also relates to competitors competing with a polypeptide as described herein, such as SEQ ID NO:s 111, 11, 112, 12, 109, 9, 110, 10, 1, 13, 14, 15, 16, 17, 18, 19, 20, 21, 22, 2, 3, 4, 5, 6, 7 or 8, wherein the competitor competes with or cross blocks the polypeptide as described herein for binding to MMP13, wherein the binding to MMP13 of the polypeptide of the invention is reduced by at least 5%, such as 10%, 20%, 30%, 40%, 50% or even more, such as 80%, or even more such as at least 90% or even 100% (i.e. virtually undetectable in a given assay) in the presence of said competitor, compared to the binding to MMP13 by the polypeptide of the invention in the absence of said competitor. In an aspect the present invention relates to a polypeptide cross-blocking binding to MMP13 by a polypeptide of the invention such as one of SEQ ID NO:s 111, 11, 112, 12, 109, 9, 110, 10, 1, 13, 14, 15, 16, 17, 18, 19, 20, 21, 22, 2, 3, 4, 5, 6, 7 or 8 and/or is cross-blocked from binding to MMP13 by at least one of SEQ ID NO:s 111, 11, 112, 12, 109, 9, 110, 10, 1, 13, 14, 15, 16, 17, 18, 19, 20, 21, 22, 2, 3, 4, 5, 6, 7 or 8, preferably wherein said polypeptide comprises at least one VH, VL, dAb, immunoglobulin single variable domain (ISVD) specifically binding to MMP13, wherein binding to MMP13 modulates an activity of MMP13.

"MMP13 activity" and "activity of MMP13" (these terms are used interchangeably herein) include, but are not limited to, proteolysis, such as protease activity (also called proteinase or peptidase activity), and endopeptidase activities, on the one hand, and binding the substrate, for instance by a Hemopexin-like domain and peptidoglycan binding domain. An MMP13 activity includes binding and/or proteolysis of substrates such as Aggrecan, Collagen II, Collagen I, Collagen III, Collagen IV, Collagen IX, Collagen X, Collagen XIV and gelatin. As used herein, proteolysis is the breakdown of proteins into smaller polypeptides or amino acids by hydrolysis of the peptide bonds that link amino acids together in a polypeptide chain.

In the context of the present invention, "modulating" or "to modulate" generally means altering an activity by MMP13, as measured using a suitable in vitro, cellular or in vivo assay (such as those mentioned herein). In particular, "modulating" or "to modulate" may mean either reducing or inhibiting an activity of, or alternatively increasing an activity of MMP13, as measured using a suitable in vitro, cellular or in vivo assay (for instance, such as those mentioned herein), by at least 1%, preferably at least 5%, such as at least 10% or at least 25%, for example by at least 50%, at least 60%, at least 70%, at least 80%, or 90% or more, compared to activity of MMP13 in the same assay under the same conditions but without the presence of the ISVD or polypeptide of the invention.

Accordingly, the present invention relates to a polypeptide as described herein, wherein said polypeptide modulates an activity of MMP13, preferably inhibiting an activity of MMP13.

Accordingly, the present invention relates to a polypeptide as described herein, wherein said polypeptide inhibits protease activity of MMP13, such as inhibits the proteolysis of a substrate, such as Aggrecan, Collagen II, Collagen I, Collagen III, Collagen IV, Collagen IX, Collagen X, Collagen XIV and/or gelatin.

Accordingly, the present invention relates to a polypeptide as described herein, wherein said polypeptide blocks the binding of MMP13 to a substrate, such as Aggrecan, Collagen II, Collagen I, Collagen III, Collagen IV, Collagen IX, Collagen X, Collagen XIV and/or gelatin, wherein said Collagen is preferably Collagen II.

In an aspect the invention relates to a polypeptide as described herein, wherein said polypeptide blocks the binding of MMP13 to Collagen and/or Aggrecan of at least 20%, such as at least 30%, 40%, 50%, 60%, 70%, 80%, 90%, 95% or even more, for instance as determined by ELISA-based competition assays (cf. Howes et al. 2014 J. Biol. Chem. 289:24091-24101).

In an aspect the invention relates to a polypeptide as described herein, wherein said polypeptide antagonizes or inhibits an activity of MMP13, such as (i) a protease activity, preferably cleavage of Aggrecan and/or Collagen, wherein said Collagen is preferably Collagen II; (ii) binding of Collagen to the hemopexin-like domain.

Accordingly, the present invention relates to a polypeptide as described herein, wherein said polypeptide inhibits protease activity of MMP13, preferably by at least 5%, such as 10%, 20%, 30%, 40%, 50% or even more, such as at least 60%, 70%, 80%, 90%, 95% or even more, as determined by any suitable method known in the art, such as for instance by competition assays or as described in the Examples section.

ISVD

Unless indicated otherwise, the terms "immunoglobulin" and "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain may be indicated as follows: FR1-CDR1-FR2-CDR2-FR3-CDR3FR4. It is the immunoglobulin variable domain(s) that confer specificity to an antibody for the antigen by carrying the antigen-binding site. In preferred embodiments of all aspects of the invention an immunoglobulin single variable domain (ISVD) according to the invention preferably consists of or essentially consists of 4 framework regions (FR1 to FR4, respectively) and 3 complementarity determining regions CDR1, CDR2 and CDR3 in said general structure as outlined above. Preferred framework sequences are outlined for example in the table A-2 below and can be used in an ISVD of the invention. Preferably, the CDRs depicted in Table A-2 are matched with the respective framework regions of the same ISVD construct.

The term "immunoglobulin single variable domain" (abbreviated herein as "ISVD" or "ISV"), and interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In the latter case, the complementarity determining regions (CDRs) of both $V_H$ and $V_L$ will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a $V_H$-$V_L$ pair of immunoglobulin domains, which jointly bind to an epitope of the respective antigen.

In contrast, ISVDs are capable of specifically binding to an epitope of the antigen without pairing with an additional immunoglobulin variable domain. The binding site of an ISVD is formed by a single $V_{HH}$, $V_H$ or $V_L$ domain. Hence, the antigen binding site of an ISVD is formed by no more than three CDRs.

As such, the single variable domain may be a light chain variable domain sequence (e.g., a $V_L$-sequence) or a suitable fragment thereof; or a heavy chain variable domain sequence (e.g., a $V_H$-sequence or $V_{HH}$ sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit).

In one embodiment of the invention, the ISVDs are heavy chain variable domain sequences (e.g., a $V_H$-sequence); more specifically, the ISVDs may be heavy chain variable domain sequences that are derived from a conventional four-chain antibody or heavy chain variable domain sequences that are derived from a heavy chain antibody.

For example, the ISVD may be a (single) domain antibody (or a peptide that is suitable for use as a (single) domain antibody), a "dAb" or dAb (or a peptide that is suitable for use as a dAb) or a Nanobody (as defined herein, and including but not limited to a VHH); other single variable domains, or any suitable fragment of any one thereof.

In particular, the ISVD may be a Nanobody® (as defined herein) or a suitable fragment thereof. [Note: Nanobody® and Nanobodies® are registered trademarks of Ablynx N.V.] For a general description of Nanobodies, reference is made to the further description below, as well as to the prior art cited herein, such as e.g. described in WO 08/020079 (page 16).

"$V_{HH}$ domains", also known as VHHs, $V_H$H domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. 1993 Nature 363: 446-448). The term "$V_{HH}$ domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHH's and Nanobodies, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations may be found e.g. in WO 08/101985 and WO 08/142164. For a further general description of Nanobodies, reference is made to the prior art cited herein, such as e.g. described in WO 08/020079 (page 16).

In particular, the framework sequences present in the MMP13 binders of the invention, such as the ISVDs and/or polypeptides of the invention, may contain one or more Hallmark residues (for instance as defined in WO 08/020079 (Tables A-3 to A-8)), such that the MMP13 binder of the invention is a Nanobody. Some preferred, but non-limiting examples of (suitable combinations of) such framework sequences will become clear from the further disclosure herein (see e.g., Table A-2). Generally, Nanobodies (in particular $V_{HH}$ sequences and partially humanized Nanobodies) can in particular be characterized by the presence of one or more "Hallmark residues" in one or more of the framework sequences (as e.g., further described in WO 08/020079, page 61, line 24 to page 98, line 3).

More in particular, the invention provides MMP13 binders comprising at least one immunoglobulin single variable domain that is an amino acid sequence with the (general) structure

FR1-CDR1-FR2-CDR2-FR3-CDR3FR4 in which FR1 to FR4 refer to framework regions 1 to 4, respectively, and in which CDR1 to CDR3 refer to the complementarity determining regions 1 to 3, respectively, and which said ISVD:
  i) have at least 80%, more preferably 90%, even more preferably 95% amino acid identity with at least one of the amino acid sequences of SEQ ID NO:s 111, 11, 112, 12, 109, 9, 110, 10, 1, 13, 14, 15, 16, 17, 18, 19, 20, 21, 22, 2, 3, 4, 5, 6, 7 or 8 (see Table A-1), in which for the purposes of determining the degree of amino acid identity, the amino acid residues that form the CDR sequences are disregarded. In this respect, reference is also made to Table A-2, which lists the framework 1 sequences (SEQ ID NOs: 67-79), framework 2 sequences (SEQ ID NOs: 80-87 and 108), framework 3 sequences (SEQ ID NOs: 88-99 and 113-114) and framework 4 sequences (SEQ ID NOs: 100-104) of the immunoglobulin single variable domains of SEQ ID NOs: 1-22 and 109-112; or
  ii) combinations of framework sequences as depicted in Table A-2; and in which:
  iii) preferably one or more of the amino acid residues at positions 11, 37, 44, 45, 47, 83, 84, 103, 104 and 108 according to the Kabat numbering are chosen from the Hallmark residues such as mentioned in Table A-3 to Table A-8 of WO 08/020079.

The MMP13 binders of the invention, such as the ISVDs and/or polypeptides of the invention, may also contain the specific mutations/amino acid residues described in the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.).

In particular, the MMP13 binders of the invention, such as the ISVDs and/or polypeptides of the invention, may suitably contain (i) a K or Q at position 112; or (ii) a K or Q at position 110 in combination with a V at position 11; or (iii) a T at position 89; or (iv) an L on position 89 with a K or Q at position 110; or (v) a V at position 11 and an L at position 89; or any suitable combination of (i) to (v).

As also described in said co-pending US provisional applications, when the MMP13 binder of the invention, such as the ISVD and/or polypeptide of the invention, contain the mutations according to one of (i) to (v) above (or a suitable combination thereof):
  the amino acid residue at position 11 is preferably chosen from L, V or K (and is most preferably V); and/or
  the amino acid residue at position 14 is preferably suitably chosen from A or P; and/or
  the amino acid residue at position 41 is preferably suitably chosen from A or P; and/or
  the amino acid residue at position 89 is preferably suitably chosen from T, V or L; and/or
  the amino acid residue at position 108 is preferably suitably chosen from Q or L; and/or
  the amino acid residue at position 110 is preferably suitably chosen from T, K or Q; and/or
  the amino acid residue at position 112 is preferably suitably chosen from S, K or Q.

As mentioned in said co-pending US provisional applications, said mutations are effective in preventing or reducing binding of so-called "pre-existing antibodies" to the immunoglobulins and compounds of the invention. For this purpose, the MMP13 binders of the invention, such as the ISVDs and/or polypeptides of the invention, may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), for which reference is again made to said US provisional applications as well as to WO 12/175741. In particular, an MMP13 binder of the invention, such as an ISVD and/or polypeptide of the invention, may contain such a C-terminal extension when it forms the C-terminal end of a protein, polypeptide or other compound or construct comprising the same (again, as further described in said US provisional applications as well as WO 12/175741).

An MMP13 binder of the invention may be an immunoglobulin, such as an immunoglobulin single variable domain, derived in any suitable manner and from any suitable source, and may for example be naturally occurring $V_{HH}$ sequences (i.e., from a suitable species of Camelid) or synthetic or semi-synthetic amino acid sequences, including but not limited to "humanized" (as defined herein) Nanobodies or VHH sequences, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when an immunoglobulin comprises a $V_{HH}$ sequence, said immunoglobulin may be suitably humanized, as further described herein, so as to provide one or more further (partially or fully) humanized immunoglobulins of the invention. Similarly, when an immunoglobulin comprises a synthetic or semi-synthetic sequence (such as a partially humanized sequence), said immunoglobulin may optionally be further suitably humanized, again as described herein, again so as to provide one or more further (partially or fully) humanized immunoglobulins of the invention.

"Domain antibodies", also known as "Dab"s, "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that, although less preferred in the context of the present invention because they are not of mammalian origin, single variable domains can be derived from certain species of shark (for example, the so-called "IgNAR domains", see for example WO 05/18629).

The present invention relates particularly to ISVDs, wherein said ISVDs are chosen from the group consisting of VHHs, humanized VHHs and camelized VHs.

The amino acid residues of a VHH domain are numbered according to the general numbering for $V_H$ domains given by Kabat et al. ("Sequence of proteins of immunological interest", US Public Health Services, NIH Bethesda, MD, Publication No. 91), as applied to VHH domains from Camelids, as shown e.g., in FIG. 2 of Riechmann and Muyldermans (J. Immunol. Methods 231: 25-38, 1999). Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of 110 to 120, often between 112 and 115. It should, however, be noted that smaller and longer sequences may also be suitable for the purposes described herein.

With regard to the CDRs, as is well-known in the art, there are multiple conventions to define and describe the CDRs of a VH or VHH fragment, such as the Kabat definition (which is based on sequence variability and is the most commonly used) and the Chothia definition (which is based on the location of the structural loop regions). Reference is for example made to the website http://www.bioinf.org.uk/abs/.

For the purposes of the present specification and claims the CDRs are most preferably defined on the basis of the Abm definition (which is based on Oxford Molecular's AbM antibody modelling software), as this is considered to be an optimal compromise between the Kabat and Chothia definitions (cf. http://www.bioinf.org.uk/abs/). As used herein, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

In the meaning of the present invention, the term "immunoglobulin single variable domain" or "single variable domain" comprises polypeptides which are derived from a non-human source, preferably a camelid, preferably a camelid heavy chain antibody. They may be humanized, as described herein. Moreover, the term comprises polypeptides derived from non-camelid sources, e.g. mouse or human, which have been "camelized", as described herein.

Accordingly, ISVDs such as Domain antibodies and Nanobodies (including VHH domains) may be subjected to humanization. In particular, humanized ISVDs, such as Nanobodies (including VHH domains) may be ISVDs that are as generally defined herein, but in which at least one amino acid residue is present (and in particular, in at least one of the framework residues) that is and/or that corresponds to a humanizing substitution (as defined herein). Potentially useful humanizing substitutions may be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined may be introduced into said $V_{HH}$ sequence (in any manner known per se, as further described herein) and the resulting humanized $V_{HH}$ sequences may be tested for affinity for the target, for stability, for ease and level of expression, and/or for other desired properties. In this way, by means of a limited degree of trial and error, other suitable humanizing substitutions (or suitable combinations thereof) may be determined by the skilled person based on the disclosure herein. Also, based on the foregoing, (the framework regions of) an ISVD, such as a Nanobody (including VHH domains) may be partially humanized or fully humanized.

Another particularly preferred class of ISVDs of the invention comprises ISVDs with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the $V_H$-$V_L$ interface, and/or at the so-called Camelidae hallmark residues, as defined herein (see also for example WO 94/04678 and Davies and Riechmann (1994 and 1996)). Preferably, the $V_H$ sequence that is used as a starting material or starting point for generating or designing the camelized immunoglobulin single variable domains is preferably a $V_H$ sequence from a mammal, more preferably the $V_H$ sequence of a human being, such as a V$_H$3 sequence. However, it should be noted that such camelized immunoglobulin single variable domains of the invention can be obtained in any suitable manner known per se and thus are not strictly limited to polypeptides that have been obtained using a polypeptide that comprises a naturally occurring V$_H$ domain as a starting material. Reference is for instance made to Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999)

For example, again as further described herein, both "humanization" and "camelization" can be performed by providing a nucleotide sequence that encodes a naturally occurring V$_{HH}$ domain or V$_H$ domain, respectively, and then changing, in a manner known per se, one or more codons in said nucleotide sequence in such a way that the new nucleotide sequence encodes a "humanized" or "camelized" ISVD of the invention, respectively. This nucleic acid can then be expressed in a manner known per se, so as to provide the desired ISVDs of the invention. Alternatively, based on the amino acid sequence of a naturally occurring V$_{HH}$ domain or V$_H$ domain, respectively, the amino acid sequence of the desired humanized or camelized ISVDs of the invention, respectively, can be designed and then synthesized de novo using techniques for peptide synthesis known per se. Also, based on the amino acid sequence or nucleotide sequence of a naturally occurring V$_{HH}$ domain or V$_H$ domain, respectively, a nucleotide sequence encoding the desired humanized or camelized ISVDs of the invention, respectively, can be designed and then synthesized de novo using techniques for nucleic acid synthesis known per se, after which the nucleic acid thus obtained can be expressed in a manner known per se, so as to provide the desired ISVDs of the invention.

ISVDs such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting ISVD for its respective antigen, as compared to the respective parent molecule. Affinity-matured ISVD molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an ISVD such as an, V$_H$, V$_L$, V$_{HH}$, Domain antibody or a Nanobody, is also referred to herein as "formatting" said ISVD; and an ISVD that is made part of a polypeptide is said to be "formatted" or to be "in the format of" said polypeptide. Examples of ways in which an ISVD may be formatted and examples of such formats will be clear to the skilled person based on the disclosure herein; and such formatted immunoglobulin single variable domain form a further aspect of the invention.

Preferred CDRs are depicted in Table A-2.

In particular, the present invention relates to an ISVD as described herein, wherein said ISVD specifically binds MMP13 and essentially consists of 4 framework regions (FR1 to FR4, respectively) and 3 complementarity determining regions (CDR1 to CDR3 respectively), in which (i) CDR1 is chosen from the group consisting of
  (a) SEQ ID NOs: 27, 28, 25, 26, 23, 29, 30, 31, 32, 33, 34, 35, 36 and 24; and
  (b) amino acid sequences that have 1, 2 or 3 amino acid difference(s) with SEQ ID NOs: 27, 28, 25, 26, 23, 29, 30, 31, 32, 33, 34, 35, 36 and 24;
(ii) CDR2 is chosen from the group consisting of
  (c) SEQ ID NOs: 42, 43, 40, 41, 37, 44, 45, 46, 47, 48, 49, 50, 51, 38 and 39; and
  (d) amino acid sequences that have 1, 2 or 3 amino acid difference(s) with SEQ ID NOs: 42, 43, 40, 41, 37, 44, 45, 46, 47, 48, 49, 50, 51, 38 and 39; and
(iii) CDR3 is chosen from the group consisting of
  (e) SEQ ID NO: SEQ ID NOs: 56, 107, 57, 54, 106, 55, 52, 58, 59, 60, 61, 62, 63, 64, 65, 66 and 53; and
  (f) amino acid sequences that have 1, 2, 3 or 4 amino acid difference(s) with SEQ ID NOs: 56, 107, 57, 54, 106, 55, 52, 58, 59, 60, 61, 62, 63, 64, 65, 66 and 53.

In particular, the present invention relates to an ISVD as described herein, wherein said ISVD specifically binds MMP13 and essentially consists of 4 framework regions (FR1 to FR4, respectively) and 3 complementarity determining regions (CDR1 to CDR3 respectively), in which (i) CDR1 is chosen from the group consisting of
  (a) SEQ ID NO: 23; and
  (b) amino acid sequence that has 1 amino acid difference with SEQ ID NO: 23, wherein at position 7 the Y has been changed into R;
(ii) CDR2 is chosen from the group consisting of
  (c) SEQ ID NO: 37; and
  (d) amino acid sequences that have 1, 2 or 3 amino acid difference(s) with SEQ ID NO: 37, wherein
    at position 4 the V has been changed into T;
    at position 5 the G has been changed into A; and/or
    at position 9 the N has been changed into H;
(iii) CDR3 is chosen from the group consisting of
  (e) SEQ ID NO: 52; and
  (f) amino acid sequence that has 1 amino acid difference with SEQ ID NO: 52, wherein at position 6 the Y has been changed into S.

In particular, the present invention relates to an ISVD as described herein, wherein said ISVD specifically binds MMP13 and essentially consists of 4 framework regions (FR1 to FR4, respectively) and 3 complementarity determining regions (CDR1 to CDR3 respectively), in which (i) CDR1 is SEQ ID NO: 26;
(ii) CDR2 is SEQ ID NO: 41; and
(iii) CDR3 is chosen from the group consisting of
  (e) SEQ ID NO: 55; and
  (f) amino acid sequence that has 1 or 2 amino acid difference(s) with SEQ ID NO: 55, wherein
    at position 8 the N has been changed into Q or 5; and/or
    at position 19 the N has been changed into V or Q.

In particular, the present invention relates to an ISVD as described herein, wherein said ISVD specifically binds MMP13 and essentially consists of 4 framework regions (FR1 to FR4, respectively) and 3 complementarity determining regions (CDR1 to CDR3 respectively), in which (i) CDR1 is SEQ ID NO: 28;
(ii) CDR2 is SEQ ID NO: 43; and
(iii) CDR3 is chosen from the group consisting of
  (e) SEQ ID NO: 57; and
  (f) amino acid sequence that has 1, 2, 3 or 4 amino acid difference(s) with SEQ ID NO: 57, wherein
    at position 10 the D has been changed into E, G, A, P, T, R, M, W or Y;

at position 16 the M has been changed into A, R, N, D, E, Q, Z, G, I, L, K, F, P, S, W, Y or V;

at position 17 the D has been changed into A, R, N, C, E, Q, Z, G, H, I, L, K, M, S, T, W, Y or V; and/or at position 18 the Y has been changed into A, R, N, D, C, E, Q, Z, G, H, I, L, K, M, F, P, S, T, W, or V.

In particular, the present invention relates to an ISVD as described herein, wherein said ISVD specifically binds MMP13 and essentially consists of 4 framework regions (FR1 to FR4, respectively) and 3 complementarity determining regions (CDR1 to CDR3 respectively), in which CDR1 is chosen from the group consisting of SEQ ID NOs: 27, 28, 25, 26, 23, 29, 30, 31, 32, 33, 34, 35, 36 and 24;

CDR2 is chosen from the group consisting of SEQ ID NOs: 42, 43, 40, 41, 37, 44, 45, 46, 47, 48, 49, 50, 51, 38 and 39; and CDR3 is chosen from the group consisting of SEQ ID NOs: 56, 107, 57, 54, 106, 55, 52, 58, 59, 60, 61, 62, 63, 64, 65, 66 and 53.

In particular, the present invention relates to an ISVD as described herein, wherein said ISVD specifically binds MMP13 and essentially consists of 4 framework regions (FR1 to FR4, respectively) and 3 complementarity determining regions (CDR1 to CDR3 respectively), in which said ISVD is chosen from the group of ISVDs, wherein:

CDR1 is SEQ ID NO: 27, CDR2 is SEQ ID NO: 42, and CDR3 is SEQ ID NO: 56;

CDR1 is SEQ ID NO: 28, CDR2 is SEQ ID NO: 43, and CDR3 is SEQ ID NO: 107;

CDR1 is SEQ ID NO: 28, CDR2 is SEQ ID NO: 43, and CDR3 is SEQ ID NO: 57;

CDR1 is SEQ ID NO: 25, CDR2 is SEQ ID NO: 40, and CDR3 is SEQ ID NO: 54;

CDR1 is SEQ ID NO: 26, CDR2 is SEQ ID NO: 41, and CDR3 is SEQ ID NO: 106;

CDR1 is SEQ ID NO: 26, CDR2 is SEQ ID NO: 41, and CDR3 is SEQ ID NO: 55;

CDR1 is SEQ ID NO: 23, CDR2 is SEQ ID NO: 37, and CDR3 is SEQ ID NO: 52;

CDR1 is SEQ ID NO: 26, CDR2 is SEQ ID NO: 48, and CDR3 is SEQ ID NO: 62;

CDR1 is SEQ ID NO: 26, CDR2 is SEQ ID NO: 41, and CDR3 is SEQ ID NO: 63;

CDR1 is SEQ ID NO: 29, CDR2 is SEQ ID NO: 44, and CDR3 is SEQ ID NO: 58;

CDR1 is SEQ ID NO: 30, CDR2 is SEQ ID NO: 45, and CDR3 is SEQ ID NO: 58;

CDR1 is SEQ ID NO: 31, CDR2 is SEQ ID NO: 46, and CDR3 is SEQ ID NO: 59;

CDR1 is SEQ ID NO: 32, CDR2 is SEQ ID NO: 47, and CDR3 is SEQ ID NO: 60;

CDR1 is SEQ ID NO: 33, CDR2 is SEQ ID NO: 41, and CDR3 is SEQ ID NO: 61;

CDR1 is SEQ ID NO: 34, CDR2 is SEQ ID NO: 49, and CDR3 is SEQ ID NO: 64;

CDR1 is SEQ ID NO: 35, CDR2 is SEQ ID NO: 50, and CDR3 is SEQ ID NO: 65;

CDR1 is SEQ ID NO: 36, CDR2 is SEQ ID NO: 51, and CDR3 is SEQ ID NO: 66;

CDR1 is SEQ ID NO: 23, CDR2 is SEQ ID NO: 39, and CDR3 is SEQ ID NO: 53; and

CDR1 is SEQ ID NO: 24, CDR2 is SEQ ID NO: 38, and CDR3 is SEQ ID NO: 52.

In particular, the present invention relates to an ISVD as described herein, wherein said ISVD specifically binds MMP13 and essentially consists of 4 framework regions (FR1 to FR4, respectively) and 3 complementarity determining regions (CDR1 to CDR3 respectively), in which CDR1 is SEQ ID NO: 27, CDR2 is SEQ ID NO: 42 and CDR3 is SEQ ID NO: 56.

In particular, the present invention relates to an ISVD as described herein, wherein said ISVD specifically binds MMP13 and essentially consists of 4 framework regions (FR1 to FR4, respectively) and 3 complementarity determining regions (CDR1 to CDR3 respectively), in which said ISVD is chosen from the group consisting of SEQ ID NO:s 111, 11, 112, 12, 109, 9, 110, 10, 1, 13, 14, 15, 16, 17, 18, 19, 20, 21, 22, 2, 3, 4, 5, 6, 7 and 8.

It will be appreciated that, without limitation, the immunoglobulin single variable domains of the present invention may be used as a "building block" for the preparation of a polypeptide, which may optionally contain one or more further immunoglobulin single variable domains that can serve as a building block (i.e., against the same or another epitope on MMP13 and/or against one or more other antigens, proteins or targets than MMP13).

Polypeptide

The polypeptide of the invention comprises at least one ISVD binding an MMP, preferably MMP13, such as two ISVDs binding MMP13, and preferably also at least on ISVD binding Aggrecan, more preferably two ISVDs binding Aggrecan. In a polypeptide of the invention, the ISVDs may be directly linked or linked via a linker. Even more preferably, the polypeptide of the invention comprises a C-terminal extension. As will be detailed below, the C-terminal extension essentially prevents/removes binding of pre-existing antibodies/factors in most samples of human subjects/patients. The C-terminal extension is present C-terminally of the last amino acid residue (usually a serine residue) of the last (most C-terminally located) ISVD.

As further elaborated herein, the ISVDs may be derived from a $V_{HH}$, $V_H$ or a $V_L$ domain, however, the ISVDs are chosen such that they do not form complementary pairs of $V_H$ and $V_L$ domains in the polypeptides of the invention. The Nanobody, $V_{HH}$, and humanized $V_{HH}$ are unusual in that they are derived from natural camelid antibodies which have no light chains, and indeed these domains are unable to associate with camelid light chains to form complementary $V_{HH}$ and $V_L$ pairs. Thus, the polypeptides of the present invention do not comprise complementary ISVDs and/or form complementary ISVD pairs, such as, for instance, complementary $V_H/V_L$ pairs.

Generally, polypeptides or constructs that comprise or essentially consist of a single building block, e.g. a single ISVD or single Nanobody, will be referred to herein as "monovalent" polypeptides and "monovalent constructs", respectively. Polypeptides or constructs that comprise two or more building blocks (such as e.g., ISVDs) will also be referred to herein as "multivalent" polypeptides or constructs, and the building blocks/ISVDs present in such polypeptides or constructs will also be referred to herein as being in a "multivalent format". For example, a "bivalent" polypeptide may comprise two ISVDs, optionally linked via a linker sequence, whereas a "trivalent" polypeptide may comprise three ISVDs, optionally linked via two linker sequences; whereas a "tetravalent" polypeptide may comprise four ISVDs, optionally linked via three linker sequences, etc.

In a multivalent polypeptide, the two or more ISVDs may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides and constructs that contain at least two building blocks (such as e.g., ISVDs) in which at least one building block is directed against a first antigen (i.e., MMP13) and at least one building block is directed against a second antigen (i.e., different from MMP13) will also be referred to as "multispecific" polypeptides and constructs, and the building blocks (such as e.g., ISVDs) present in such polypeptides and constructs will also be referred to herein as being in a "multispecific format". Thus, for example, a "bispecific" polypeptide of the invention is a polypeptide that comprises at least one ISVD directed against a first antigen (i.e., MMP13) and at least one further ISVD directed against a second antigen (i.e., different from MMP13), whereas a "trispecific" polypeptide of the invention is a polypeptide that comprises at least one ISVD directed against a first antigen (i.e., MMP13), at least one further ISVD directed against a second antigen (i.e., different from MMP13) and at least one further ISVD directed against a third antigen (i.e., different from both MMP13 and the second antigen); etc.

In an aspect, the present invention relates to a polypeptide comprising two or more ISVDs which specifically bind MMP13, wherein
 a) at least a "first" ISVD specifically binds a first antigenic determinant, epitope, part, domain, subunit or confirmation of MMP13; preferably said "first" ISVD specifically binding MMP13 is chosen from the group consisting of SEQ ID NO:s 111, 11, 110, 10, 112, 12, 109, 9, 13, 14, 15, 16, 17, 18, 19, 20, 21 and 22; and wherein,
 b) at least a "second" ISVD specifically binds a second antigenic determinant, epitope, part, domain, subunit or confirmation of MMP13, different from the first antigenic determinant epitope, part, domain, subunit or confirmation, respectively, preferably said "second" ISVD specifically binding MMP13 is chosen from the group consisting of SEQ ID NO:s 1, 2, 3, 4, 5, 6, 7 and 8.

In an aspect, the present invention relates to a polypeptide comprising two or more ISVDs which specifically bind MMP13, chosen from the group consisting of SEQ ID NO:s 160 to 165, preferably SEQ ID NO: 160 (cf. Table A-3).

"Multiparatopic" polypeptides and "multiparatopic" constructs, such as e.g., "biparatopic" polypeptides or constructs and "triparatopic" polypeptides or constructs, comprise or essentially consist of two or more building blocks that each have a different paratope.

Accordingly, the ISVDs of the invention that bind MMP13 can be in essentially isolated form (as defined herein), or they may form part of a construct or polypeptide, which may comprise or essentially consist of one or more ISVD(s) that bind MMP13 and which may optionally further comprise one or more further amino acid sequences (all optionally linked via one or more suitable linkers). The present invention relates to a polypeptide or construct that comprises or essentially consists of at least one ISVD according to the invention, such as one or more ISVDs of the invention (or suitable fragments thereof), binding MMP13.

The one or more ISVDs of the invention can be used as a building block in such a polypeptide or construct, so as to provide a monovalent, multivalent or multiparatopic polypeptide or construct of the invention, respectively, all as described herein. The present invention thus also relates to a polypeptide which is a monovalent construct comprising or essentially consisting of one monovalent polypeptide or ISVD of the invention.

The present invention thus also relates to a polypeptide or construct which is a multivalent polypeptide or multivalent construct, respectively, such as e.g., a bivalent or trivalent polypeptide or construct comprising or essentially consisting of two or more ISVDs of the invention (for multivalent and multispecific polypeptides containing one or more VHH domains and their preparation, reference is for instance also made to Conrath et al. (J. Biol. Chem. 276: 7346-7350, 2001), as well as to for example WO 96/34103, WO 99/23221 and WO 2010/115998).

In an aspect, in its simplest form, the multivalent polypeptide or construct of the invention is a bivalent polypeptide or construct of the invention comprising a first ISVD, such as a Nanobody, directed against MMP13, and an identical second ISVD, such as a Nanobody, directed against MMP13, wherein said first and said second ISVDs, such as Nanobodies, may optionally be linked via a linker sequence (as defined herein). In its simplest form a multivalent polypeptide or construct of the invention may be a trivalent polypeptide or construct of the invention, comprising a first ISVD, such as Nanobody, directed against MMP13, an identical second ISVD, such as Nanobody, directed against MMP13 and an identical third ISVD, such as a Nanobody, directed against MMP13, in which said first, second and third ISVDs, such as Nanobodies, may optionally be linked via one or more, and in particular two, linker sequences. In an aspect, the invention relates to a polypeptide or construct that comprises or essentially consists of at least two ISVDs according to the invention, such as 2, 3 or 4 ISVDs (or suitable fragments thereof), binding MMP13. The two or more ISVDs may optionally be linked via one or more peptidic linkers.

In another aspect, the multivalent polypeptide or construct of the invention may be a bispecific polypeptide or construct of the invention, comprising a first ISVD, such as a Nanobody, directed against MMP13, and a second ISVD, such as a Nanobody, directed against a second antigen, such as, for instance, Aggrecan, in which said first and second ISVDs, such as Nanobodies, may optionally be linked via a linker sequence (as defined herein); whereas a multivalent polypeptide or construct of the invention may also be a trispecific polypeptide or construct of the invention, comprising a first ISVD, such as a Nanobody, directed against MMP13, a second ISVD, such as a Nanobody, directed against a second antigen, such as for instance Aggrecan, and a third ISVD, such as a Nanobody, directed against a third antigen, in which said first, second and third ISVDs, such as Nanobodies, may optionally be linked via one or more, and in particular two, linker sequences.

The invention further relates to a multivalent polypeptide that comprises or (essentially) consists of at least one ISVD (or suitable fragments thereof) binding MMP13, preferably human MMP13, and at least one additional ISVD, such as an ISVD binding Aggrecan.

Particularly preferred trivalent, bispecific polypeptides or constructs in accordance with the invention are those shown in the Examples described herein and in Table A-3.

In a preferred aspect, the polypeptide or construct of the invention comprises or essentially consists of at least two ISVDs, wherein said at least two ISVDs can be the same or different, but of which at least one ISVD is directed against MMP13.

The two or more ISVDs present in the multivalent polypeptide or construct of the invention may consist of a light chain variable domain sequence (e.g., a $V_L$-sequence) or of a heavy chain variable domain sequence (e.g., a $V_H$-sequence); they may consist of a heavy chain variable domain sequence that is derived from a conventional four-chain antibody or of a heavy chain variable domain sequence that is derived from heavy chain antibody. In a preferred aspect, they consist of a Domain antibody (or a peptide that is suitable for use as a domain antibody), of a single domain antibody (or a peptide that is suitable for use as a single domain antibody), of a "dAb" (or a peptide that is suitable for use as a dAb), of a Nanobody® (including but not limited to $V_{HH}$), of a humanized $V_{HH}$ sequence, of a camelized $V_H$ sequence; or of a $V_{HH}$ sequence that has been obtained by affinity maturation. The two or more immunoglobulin single variable domains may consist of a partially or fully humanized Nanobody or a partially or fully humanized VHH.

In an aspect of the invention, the first ISVD and the second ISVD present in the multiparatopic (preferably biparatopic or triparatopic) polypeptide or construct of the invention do not (cross)-compete with each other for binding to MMP13 and, as such, belong to different families. Accordingly, the present invention relates to a multiparatopic (preferably biparatopic) polypeptide or construct comprising two or more ISVDs wherein each ISVD belongs to a different family. In an aspect, the first ISVD of this multiparatopic (preferably biparatopic) polypeptide or construct of the invention does not cross-block the binding to MMP13 of the second ISVD of this multiparatopic (preferably biparatopic) polypeptide or construct of the invention and/or the first ISVD is not cross-blocked from binding to MMP13 by the second ISVD. In another aspect, the first ISVD of a multiparatopic (preferably biparatopic) polypeptide or construct of the invention cross-blocks the binding to MMP13 of the second ISVD of this multiparatopic (preferably biparatopic) polypeptide or construct of the invention and/or the first ISVD is cross-blocked from binding to MMP13 by the second ISVD.

In a particularly preferred aspect, the polypeptide or construct of the invention comprises or essentially consists of three or more ISVDs, of which at least two ISVDs are directed against MMP13. It will be appreciated that said at least two ISVDs directed against MMP13 can be the same or different, can be directed against the same epitope or different epitopes of MMP13, can belong to the same epitope bin or to different epitope bins, and/or can bind to the same or different domains of MMP13.

In a preferred aspect, the polypeptide or construct of the invention comprises or essentially consists of at least two ISVDs binding MMP13, wherein said at least two ISVDs can be the same or different, which are independently chosen from the group consisting of SEQ ID NOs: SEQ ID NO:s 111, 11, 110, 10, 112, 12, 109, 9, 13, 14, 15, 16, 17, 18, 19, 20, 21 and 22 and SEQ ID NO:s 1, 2, 3, 4, 5, 6, 7 and 8, more preferably said at least two ISVDs are independently chosen from the group consisting of SEQ ID NOs: 111, 11, 110, 10, 112, 12, 109, 9 and 1 and/or at least one ISVDs is chosen from the group consisting of SEQ ID NO:s 111, 11, 110, 10, 112, 12, 109, 9, 13, 14, 15, 16, 17, 18, 19, 20, 21 and 22 and at least one ISVD is chosen from the group consisting of SEQ ID NOs: 1, 2, 3, 4, 5, 6, 7 and 8.

In a further aspect, the invention relates to a multiparatopic (preferably biparatopic) polypeptide or construct comprising two or more ISVDs directed against MMP13 that bind the same epitope(s) as is bound by any one of SEQ ID NOs: 111, 11, 110, 10, 112, 12, 109, 9, 13, 14, 15, 16, 17, 18, 19, 20, 21 and 22 or bound by any one of SEQ ID NOs: 1, 2, 3, 4, 5, 6, 7 and 8.

In a further aspect, the invention relates to a polypeptide as described herein, wherein said polypeptide has at least 80%, 90%, 95% or 100% (more preferably at least 95% and most preferably 100%) sequence identity with any one of SEQ ID NO:s 160-165 (i.e. 160, 161, 162, 163, 164 or 165) and 176-192 (i.e. 176, 177, 178, 179, 180, 181, 182, 183, 184, 185, 186, 187, 188, 189, 190, 191 or 192), preferably SEQ ID NO: 192.

Retention

The art is in need of more effective therapies for disorders affecting cartilage in joints, such as osteoarthritis. Even when administered intra-articularly, the residence time of most drugs for treating affected cartilage is insufficient. The present inventors hypothesized that the efficacy of a therapeutic drug, such as a construct, polypeptide and ISVD of the invention, could be increased significantly by coupling the therapeutic drug to a moiety which would "anchor" the drug in the joint and consequently increase retention of the drug, but which should not disrupt the efficacy of said therapeutic drug (this moiety is herein also indicated as "cartilage anchoring protein" or "CAP"). This anchoring concept not only increases the efficacy of the drug, but also the operational specificity for a diseased joint by decreasing toxicity and side-effects, thus widening the number of possible useful drugs.

It was anticipated that the final format of a molecule for clinical use comprises one or two building blocks, such as ISVDs, binding MMP13 and one or more building blocks, e.g. ISVDs, with such a retention mode of action, and possibly further moieties. In the Examples section it is demonstrated that such formats retain both MMP13 binding and therapeutic effect, e.g. inhibitory activity, as well as retention properties. The one or more building blocks, such as ISVDs, with a retention mode of action can be any building block having a retention effect ("CAP building block") in diseases in which MMP13 is involved, such as arthritic disease, osteoarthritis, spondyloepimetaphyseal dysplasia, lumbar disk degeneration disease, Degenerative joint disease, rheumatoid arthritis, osteochondritis dissecans, aggrecanopathies and metastases of malignancies.

A "CAP building block" is to be used for directing, anchoring and/or retaining other, e.g. therapeutic, building blocks, such as ISVDs binding MMP13 at a desired site, such as e.g. in a joint, in which said other, e.g. therapeutic, building block is to exert its effect, e.g. binding and/or inhibiting an activity of MMP13.

The present inventors further hypothesized that Aggrecan binders, such as ISVD(s) binding Aggrecan might potentially function as such an anchor, although Aggrecan is heavily glycosylated and degraded in various disorders affecting cartilage in joints. Moreover, in view of the costs and extensive testing in various animal models required before a drug can enter the clinic, such Aggrecan binders should preferentially have a broad species cross-reactivity, e.g. the Aggrecan binders should bind to Aggrecan of various species.

Using various ingenious immunization, screening and characterization methods, the present inventors were able to identify various Aggrecan binders with superior selectivity, stability and specificity features, which enabled prolonged retention and activity in the joint.

In an aspect the present invention relates to a method for reducing and/or inhibiting the efflux of a composition, a polypeptide or a construct from a joint, wherein said method comprises administering a pharmaceutically active amount of at least one polypeptide according to the invention, a construct according to the invention, or a composition according to the invention to a person in need thereof.

In the present invention the term "reducing and/or inhibiting the efflux" means reducing and/or inhibiting the outward flow of the composition, polypeptide or construct from within a joint to the outside. Preferably, the efflux is reduced and/or inhibited by at least 10% such as at least 20%, 30%, 40% or 50% or even more such as at least 60%, 70%, 80%, 90% or even 100%, compared to the efflux of the aforementioned composition, polypeptide or construct in a joint under the same conditions but without the presence of the Aggrecan binder of the invention, e.g. ISVD(s) binding Aggrecan.

Next to the diseases in which MMP13 is involved, such as arthritic disease, osteoarthritis, spondyloepimetaphyseal dysplasia, lumbar disk degeneration disease, Degenerative joint disease, rheumatoid arthritis, osteochondritis dissecans, aggrecanopathies and metastases of malignancies it is anticipated that the Aggrecan binders of the invention can also be used in various other diseases affecting cartilage, such as arthropathies and chondrodystrophies, arthritic disease (such as osteoarthritis, rheumatoid arthritis, gouty arthritis, psoriatic arthritis, traumatic rupture or detachment), achondroplasia, costochondritis, Spondyloepimetaphyseal dysplasia, spinal disc herniation, lumbar disk degeneration disease, degenerative joint disease, and relapsing polychondritis (commonly indicated herein as "Aggrecan associated diseases").

The CAP building block, e.g. ISVD(s) binding Aggrecan, preferably binds to cartilaginous tissue such as cartilage and/or meniscus. In a preferred aspect, the CAP building block is cross-reactive for other species and specifically binds one or more of human Aggrecan (SEQ ID NO: 105), dog Aggrecan, bovine Aggrecan, rat Aggrecan; pig Aggrecan; mouse Aggrecan, rabbit Aggrecan; cynomolgus Aggrecan and/or rhesus Aggrecan. Relevant structural information for Aggrecan may be found, for example, at (UniProt) Accession Numbers as depicted in the Table 2 below.

A preferred CAP building block is an ISVD binding Aggrecan, preferably human Aggrecan, preferably represented by SEQ ID NO: 105 as depicted in Table B.

TABLE 2

| name | accession number |
| --- | --- |
| human Aggrecan (SEQ ID NO: 105) | P16112 |
| dog Aggrecan | Q28343 |
| bovine Aggrecan | P13608 |
| rat Aggrecan | P07897 |
| pig Aggrecan (core) | Q29011 |
| mouse Aggrecan | Q61282 |
| rabbit Aggrecan | G1U677-1 |
| cynomolgus Aggrecan | XP_005560513.1 |
| rhesus Aggrecan | XP_002804990.1 |

The present invention thus pertains to a polypeptide or construct according to the invention, further comprising at least one CAP building block.

The present invention thus pertains to a polypeptide or construct according to the invention, further comprising at least one ISVD specifically binding Aggrecan, such as shown in Table E, and preferably chosen from the ISVDs represented by SEQ ID NO:s 166 to 168.

In particular, the present invention relates to an ISVD specifically binding Aggrecan, wherein said ISVD essentially consists of 4 framework regions (FR1 to FR4, respectively) and 3 complementarity determining regions (CDR1 to CDR3 respectively), in which said ISVD is chosen from the group of ISVDs, wherein (a) CDR1 is SEQ ID NO: 169, CDR2 is SEQ ID NO: 170 and CDR3 is SEQ ID NO: 171; and (b) CDR1 is SEQ ID NO: 172, CDR2 is SEQ ID NO: 173 and CDR3 is SEQ ID NO: 174.

In an aspect the present invention relates to a polypeptide as described herein, comprising at least 2 ISVDs specifically binding Aggrecan.

In an aspect the present invention relates to a polypeptide as described herein, comprising at least 2 ISVDs specifically binding Aggrecan, wherein said at least 2 ISVDs specifically binding Aggrecan can be the same or different.

In an aspect the present invention relates to a polypeptide as described herein, comprising at least 2 ISVDs specifically binding Aggrecan, wherein said at least 2 ISVDs specifically binding Aggrecan are independently chosen from the group consisting of SEQ ID NOs: 166 to 168.

In an aspect the present invention relates to a polypeptide as described herein, comprising at least 2 ISVDs specifically binding Aggrecan, wherein said at least 2 ISVDs specifically binding Aggrecan are represented by SEQ ID NO:s 166 to 168.

In an aspect the present invention relates to a polypeptide as described herein, comprising an ISVD specifically binding Aggrecan, wherein said ISVD specifically binding Aggrecan, specifically binds to human Aggrecan [SEQ ID NO: 105].

In an aspect the present invention relates to a polypeptide as described herein, wherein said ISVD specifically binding Aggrecan, specifically binds human Aggrecan (SEQ ID NO: 105), dog Aggrecan, bovine Aggrecan, rat Aggrecan; pig Aggrecan; mouse Aggrecan, rabbit Aggrecan; cynomolgus Aggrecan and/or rhesus Aggrecan.

In an aspect the present invention relates to a polypeptide as described herein, wherein said ISVD specifically binding Aggrecan preferably binds to cartilaginous tissue such as cartilage and/or meniscus.

It will be appreciated that the ISVD, polypeptide and construct of the invention is preferably stable. The stability of a polypeptide, construct or ISVD of the invention can be measured by routine assays known to the person skilled in the art. Typical assays include (without being limiting) assays in which the activity of said polypeptide, construct or ISVD is determined, followed by incubating in Synovial Fluid for a desired period of time, after which the activity is determined again, for instance as detailed in the Examples section.

In an aspect the present invention relates to an ISVD, polypeptide or construct of the invention having a stability of at least 7 days, such as at least 14 days, 21 days, 1 month, 2 months or even 3 months in synovial fluid (SF) at 37° C.

In an aspect the present invention relates to an ISVD, polypeptide or construct of the invention penetrating into the cartilage by at least 5 µm, such as at least 10 µm, 20 µm, 30 µm, 40 µm, 50 µm or even more.

The desired activity of the therapeutic building block, e.g. ISVD binding MMP13 in the multivalent polypeptide or construct of the invention can be measured by routine assays known to the person skilled in the art. Typical assays include (without being limiting) a GAG release assay as detailed in the Examples section.

The relative affinities may depend on the location of the ISVDs in the polypeptide. It will be appreciated that the order of the ISVDs in a polypeptide of the invention (orientation) may be chosen according to the needs of the person skilled in the art. The order of the individual ISVDs as well as whether the polypeptide comprises a linker is a matter of design choice. Some orientations, with or without linkers, may provide preferred binding characteristics in comparison to other orientations. For instance, the order of a first ISVD (e.g. ISVD 1) and a second ISVD (e.g. ISVD 2) in the polypeptide of the invention may be (from N-terminus to C-terminus): (i) ISVD 1 (e.g. Nanobody 1)-[linker]-ISVD 2 (e.g. Nanobody 2)-[C-terminal extension]; or (ii) ISVD 2 (e.g. Nanobody 2)-[linker]-ISVD 1 (e.g. Nanobody 1)-[C-terminal extension]; (wherein the moieties between the square brackets, i.e. linker and C-terminal extension, are optional). All orientations are encompassed by the invention. Polypeptides that contain an orientation of ISVDs that provides desired binding characteristics may be easily identified by routine screening, for instance as exemplified in the examples section. A preferred order is from N-terminus to C-terminus: ISVD binding MMP13-[linker]-ISVD binding Aggrecan-[C-terminal extension], wherein the moieties between the square brackets are optional. A further preferred order is from N-terminus to C-terminus: ISVD binding MMP13-[linker]-ISVD binding Aggrecan-[linker]-ISVD binding Aggrecan-[C-terminal extension], wherein the moieties between the square brackets are optional. See for instance Table F.

Half Life

In a specific aspect of the invention, a construct or polypeptide of the invention may have a moiety conferring an increased half-life, compared to the corresponding construct or polypeptide of the invention without said moiety. Some preferred, but non-limiting examples of such constructs and polypeptides of the invention will become clear to the skilled person based on the further disclosure herein, and for example comprise ISVDs or polypeptides of the invention that have been chemically modified to increase the half-life thereof (for example, by means of pegylation); MMP13 binders of the invention, such as ISVDs and/or polypeptides of the invention that comprise at least one additional binding site for binding to a serum protein (such as serum albumin); or polypeptides of the invention which comprise at least one ISVD of the invention that is linked to at least one moiety (and in particular at least one amino acid sequence) which increases the half-life of the amino acid sequence of the invention. Examples of constructs of the invention, such as polypeptides of the invention, which comprise such half-life extending moieties or ISVDs will become clear to the skilled person based on the further disclosure herein; and for example include, without limitation, polypeptides in which the one or more ISVDs of the invention are suitably linked to one or more serum proteins or fragments thereof (such as (human) serum albumin or suitable fragments thereof) or to one or more binding units that can bind to serum proteins (such as, for example, domain antibodies, immunoglobulin single variable domains that are suitable for use as a domain antibody, single domain antibodies, immunoglobulin single variable domains that are suitable for use as a single domain antibody, dAbs, immunoglobulin single variable domains that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more immunoglobulin single variable domains of the invention are suitably linked to one or more small proteins or peptides that can bind to serum proteins, such as, for instance, the proteins and peptides described in WO 91/01743, WO 01/45746, WO 02/076489, WO2008/068280, WO2009/127691 and PCT/EP2011/051559.

In an aspect the present invention provides a construct of the invention or a polypeptide, wherein said construct or said polypeptide further comprises a serum protein binding moiety or a serum protein. Preferably, said serum protein binding moiety binds serum albumin, such as human serum albumin.

In an aspect, the present invention relates to a polypeptide as described herein, comprising an ISVD binding serum albumin.

Generally, the constructs or polypeptides of the invention with increased half-life preferably have a half-life that is at least 1.5 times, preferably at least 2 times, such as at least 5 times, for example at least 10 times or more than 20 times, greater than the half-life of the corresponding constructs or polypeptides of the invention per se, i.e. without the moiety conferring the increased half-life. For example, the constructs or polypeptides of the invention with increased half-life may have a half-life e.g., in humans that is increased with more than 1 hour, preferably more than 2 hours, more preferably more than 6 hours, such as more than 12 hours, or even more than 24, 48 or 72 hours, compared to the corresponding constructs or polypeptides of the invention per se, i.e. without the moiety conferring the increased half-life.

In a preferred, but non-limiting aspect of the invention, the constructs of the invention and polypeptides of the invention, have a serum half-life e.g. in humans that is increased with more than 1 hour, preferably more than 2 hours, more preferably more than 6 hours, such as more than 12 hours, or even more than 24, 48 or 72 hours, compared to the corresponding constructs or polypeptides of the invention per se, i.e. without the moiety conferring the increased half-life.

In another preferred, but non-limiting aspect of the invention, such constructs of the invention, such as polypeptides of the invention, exhibit a serum half-life in human of at least about 12 hours, preferably at least 24 hours, more preferably at least 48 hours, even more preferably at least 72 hours or more. For example, constructs or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a particularly preferred but non-limiting aspect of the invention, the invention provides a construct of the invention and a polypeptide of the invention, comprising besides the one or more building blocks binding MMP13 and possibly the one or more CAP building blocks, e.g. (s) binding Aggrecan at least one building block binding serum albumin, such as an binding serum albumin, such as human serum albumin as described herein. Preferably, said binding serum albumin comprises or essentially consists of 4 framework regions (FR1 to FR4, respectively) and 3 complementarity determining regions (CDR1 to CDR3 respectively), in which CDR1 is SFGMS (SEQ ID NO: 157), CDR2 is SISGSGSDTLYADSVKG (SEQ ID NO: 158) and CDR3 is GGSLSR (SEQ ID NO: 159). Preferably, said binding human serum albumin is chosen from the group consisting of Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG, Alb92, Alb135 or Alb223 (cf. Table D).

In an embodiment, the present invention relates to constructs of the invention, such as a polypeptide comprising a serum protein binding moiety, wherein said serum protein binding moiety is a non-antibody based polypeptide.

Other Moieties

In an aspect, the present invention relates to a construct as described herein comprising one or more other groups, residues, moieties or binding units. The one or more other groups, residues, moieties or binding units are preferably chosen from the group consisting of a polyethylene glycol molecule, serum proteins or fragments thereof, binding units that can bind to serum proteins, an Fc portion, and small proteins or peptides that can bind to serum proteins, further amino acid residues, tags or other functional moieties, e.g., toxins, labels, radiochemicals, etc.

In an embodiment, as mentioned infra, the present invention relates to a construct of the invention, such as a polypeptide comprising a moiety conferring half-life extension, wherein said moiety is a PEG. Hence, the present invention relates also to a construct or polypeptide of the invention comprising PEG.

The further amino acid residues may or may not change, alter or otherwise influence other (biological) properties of the polypeptide of the invention and may or may not add further functionality to the polypeptide of the invention. For example, such amino acid residues:

a) can comprise an N-terminal Met residue, for example as result of expression in a heterologous host cell or host organism.

b) may form a signal sequence or leader sequence that directs secretion of the polypeptide from a host cell upon synthesis (for example to provide a pre-, pro- or prepro-form of the polypeptide of the invention, depending on the host cell used to express the polypeptide of the invention). Suitable secretory leader peptides will be clear to the skilled person, and may be as further described herein. Usually, such a leader sequence will be linked to the N-terminus of the polypeptide, although the invention in its broadest sense is not limited thereto;

c) may form a "tag", for example an amino acid sequence or residue that allows or facilitates the purification of the polypeptide, for example using affinity techniques directed against said sequence or residue. Thereafter, said sequence or residue may be removed (e.g. by chemical or enzymatic cleavage) to provide the polypeptide (for this purpose, the tag may optionally be linked to the amino acid sequence or polypeptide sequence via a cleavable linker sequence or contain a cleavable motif). Some preferred, but non-limiting examples of such residues are multiple histidine residues, glutathione residues, a myc-tag such as AAAEQKLISEEDLNGAA (SEQ ID NO:175), a MYC-HIS-tag (SEQ ID NO: 123) or a FLAG-HIS6-tag (SEQ ID NO: 124) (see Table B);

d) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the polypeptides of the invention.

Also encompassed in the present invention are constructs and/or polypeptides that comprise an ISVD of the invention and further comprise other functional moieties, e.g., toxins, labels, radiochemicals, etc.

The other groups, residues, moieties or binding units may for example be chemical groups, residues, moieties, which may or may not by themselves be biologically and/or pharmacologically active. For example, and without limitation, such groups may be linked to the one or more ISVDs or polypeptides of the invention so as to provide a "derivative" of the polypeptide or construct of the invention.

Accordingly, the invention in its broadest sense also comprises constructs and/or polypeptides that are derivatives of the constructs and/or polypeptides of the invention. Such derivatives can generally be obtained by modification, and in particular by chemical and/or biological (e.g., enzymatic) modification, of the constructs and/or polypeptides of the invention and/or of one or more of the amino acid residues that form a polypeptide of the invention.

Examples of such modifications, as well as examples of amino acid residues within the polypeptide sequences that can be modified in such a manner (i.e. either on the protein backbone but preferably on a side chain), methods and techniques that can be used to introduce such modifications and the potential uses and advantages of such modifications will be clear to the skilled person (see also Zangi et al., Nat Biotechnol 31(10):898-907, 2013).

For example, such a modification may involve the introduction (e.g., by covalent linking or in any other suitable manner) of one or more (functional) groups, residues or moieties into or onto the polypeptide of the invention, and in particular of one or more functional groups, residues or moieties that confer one or more desired properties or functionalities to the construct and/or polypeptide of the invention. Examples of such functional groups will be clear to the skilled person.

For example, such modification may comprise the introduction (e.g., by covalent binding or in any other suitable manner) of one or more functional moieties that increase the half-life, the solubility and/or the absorption of the construct or polypeptide of the invention, that reduce the immunogenicity and/or the toxicity of the construct or polypeptide of the invention, that eliminate or attenuate any undesirable side effects of the construct or polypeptide of the invention, and/or that confer other advantageous properties to and/or reduce the undesired properties of the construct or polypeptide of the invention; or any combination of two or more of the foregoing. Examples of such functional moieties and of techniques for introducing them will be clear to the skilled person, and can generally comprise all functional moieties and techniques mentioned in the general background art cited hereinabove as well as the functional moieties and techniques known per se for the modification of pharmaceutical proteins, and in particular for the modification of antibodies or antibody fragments (including ScFv's and single domain antibodies), for which reference is for example made to Remington (Pharmaceutical Sciences, 16th ed., Mack Publishing Co., Easton, PA, 1980). Such functional moieties may for example be linked directly (for example covalently) to a polypeptide of the invention, or optionally via a suitable linker or spacer, as will again be clear to the skilled person.

One specific example is a derivative polypeptide or construct of the invention wherein the polypeptide or construct of the invention has been chemically modified to increase the half-life thereof (for example, by means of pegylation). This is one of the most widely used techniques for increasing the half-life and/or reducing the immunogenicity of pharmaceutical proteins and comprises attachment of a suitable pharmacologically acceptable polymer, such as poly(ethyleneglycol) (PEG) or derivatives thereof (such as methoxy-poly(ethyleneglycol) or mPEG).

Generally, any suitable form of pegylation can be used, such as the pegylation used in the art for antibodies and antibody fragments (including but not limited to (single) domain antibodies and ScFv's); reference is made to for example Chapman (Nat. Biotechnol. 54: 531-545, 2002), Veronese and Harris (Adv. Drug Deliv. Rev. 54: 453-456, 2003), Harris and Chess (Nat. Rev. Drug. Discov. 2: 214-221, 2003) and WO 04/060965. Various reagents for pegylation of proteins are also commercially available, for example from Nektar Therapeutics, USA.

Preferably, site-directed pegylation is used, in particular via a cysteine-residue (see for example Yang et al. (Protein Engineering 16: 761-770, 2003). For example, for this purpose, PEG may be attached to a cysteine residue that naturally occurs in a polypeptide of the invention, a construct or polypeptide of the invention may be modified so as to suitably introduce one or more cysteine residues for attachment of PEG, or an amino acid sequence comprising one or more cysteine residues for attachment of PEG may be fused to the N- and/or C-terminus of a construct or polypeptide of the invention, all using techniques of protein engineering known per se to the skilled person.

Preferably, for the constructs or polypeptides of the invention, a PEG is used with a molecular weight of more than 5000, such as more than 10,000 and less than 200,000, such as less than 100,000; for example in the range of 20,000-80,000.

Another, usually less preferred modification comprises N-linked or 0-linked glycosylation, usually as part of co-translational and/or post-translational modification, depending on the host cell used for expressing the polypeptide of the invention.

Yet another modification may comprise the introduction of one or more detectable labels or other signal-generating groups or moieties, depending on the intended use of the polypeptide or construct of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radioisotopes (such as $^3$H $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metals chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe)), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled polypeptides and constructs of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional moiety that is one part of a specific binding pair, such as the biotin-(strept)avidin binding pair. Such a functional moiety may be used to link the polypeptide of the invention to another protein, polypeptide or chemical compound that is bound to the other half of the binding pair, i.e. through formation of the binding pair. For example, a construct or polypeptide of the invention may be conjugated to biotin, and linked to another protein, polypeptide, compound or carrier conjugated to avidin or streptavidin. For example, such a conjugated construct or polypeptide of the invention may be used as a reporter, for example in a diagnostic system where a detectable signal-producing agent is conjugated to avidin or streptavidin. Such binding pairs may for example also be used to bind the construct or polypeptide of the invention to a carrier, including carriers suitable for pharmaceutical purposes. One non-limiting example is the liposomal formulations described by Cao and Suresh (Journal of Drug Targeting 8: 257, 2000). Such binding pairs may also be used to link a therapeutically active agent to the polypeptide of the invention.

Other potential chemical and enzymatic modifications will be clear to the skilled person. Such modifications may also be introduced for research purposes (e.g. to study function-activity relationships). Reference is for example made to Lundblad and Bradshaw (Biotechnol. Appl. Biochem. 26: 143-151, 1997).

Preferably, the constructs, polypeptides and/or derivatives are such that they bind to MMP13, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein (i.e. as defined for the polypeptides of the invention).

Such constructs and/or polypeptides of the invention and derivatives thereof may also be in essentially isolated form (as defined herein).

In an aspect, the present invention relates to a construct of the invention, that comprises or essentially consists of an ISVD according to the invention or a polypeptide according to the invention, and which further comprises one or more other groups, residues, moieties or binding units, optionally linked via one or more peptidic linkers.

In an aspect, the present invention relates to a construct of the invention, in which one or more other groups, residues, moieties or binding units are chosen from the group consisting of a polyethylene glycol molecule, serum proteins or fragments thereof, binding units that can bind to serum proteins, an Fc portion, and small proteins or peptides that can bind to serum proteins.

Linkers

In the constructs of the invention, such as the polypeptides of the invention, the two or more building blocks, such as e.g. ISVDs, and the optionally one or more other groups, drugs, agents, residues, moieties or binding units may be directly linked to each other (as for example described in WO 99/23221) and/or may be linked to each other via one or more suitable spacers or linkers, or any combination thereof. Suitable spacers or linkers for use in multivalent and multispecific polypeptides will be clear to the skilled person, and may generally be any linker or spacer used in the art to link amino acid sequences. Preferably, said linker or spacer is suitable for use in constructing constructs, proteins or polypeptides that are intended for pharmaceutical use.

For instance, the polypeptide of the invention may, for example, be a trivalent, trispecific polypeptide, comprising one building block, such as an ISVD, binding MMP13, a CAP building block, such as an ISVD binding Aggrecan, and potentially another building block, such as a third ISVD, in which said first, second and third building blocks, such as ISVDs, may optionally be linked via one or more, and in particular 2, linker sequences. Also, the present invention provides a construct or polypeptide of the invention comprising a first ISVD binding MMP13 and possibly a second ISVD binding Aggrecan and/or possibly a third ISVD and/or possibly a fourth ISVD, wherein said first ISVD and/or said second ISVD and/or possibly said third ISVD and/or possibly said fourth ISVD are linked via linkers, in particular 3 linkers.

Some particularly preferred linkers include the linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each ISVD, such as Nanobodies, by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_xser_y)_z$, such as (for example $(gly_4ser)_3$ (SEQ ID NO: 131) or $(gly_3ser_2)_3$ (SEQ ID NO: 200), as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Preferred linkers are depicted in Table C.

Some other particularly preferred linkers are poly-alanine (such as AAA (SEQ ID NO: 125)), as well as the linkers GS30 (SEQ ID NO: 85 in WO 06/122825) and GS9 (SEQ ID NO: 84 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final construct of the invention, such as the polypeptide of the invention, including but not limited to the affinity, specificity or avidity for MMP13, or for one or more of the other antigens. Based on the disclosure herein, the skilled person will be able to determine the optimal linker(s) for use in a specific construct of the invention, such as the polypeptide of the invention, optionally after some limited routine experiments.

For example, in multivalent polypeptides of the invention that comprise building blocks, ISVDs or Nanobodies directed against MMP13 and another target, the length and flexibility of the linker are preferably such that it allows each building block, such as an ISVD, of the invention present in the polypeptide to bind to its cognate target, e.g. the antigenic determinant on each of the targets. Again, based on the disclosure herein, the skilled person will be able to determine the optimal linker(s) for use in a specific construct of the invention, such as a polypeptide of the invention, optionally after some limited routine experiments.

It is also within the scope of the invention that the linker(s) used confer one or more other favourable properties or functionality to the constructs of the invention, such as the polypeptides of the invention, and/or provide one or more sites for the formation of derivatives and/or for the attachment of functional groups (e.g. as described herein for the derivatives of the ISVDs of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the constructs such as polypeptides of the invention, these linkers may be the same or different. Again, based on the disclosure herein, the skilled person will be able to determine the optimal linkers for use in a specific construct or polypeptide of the invention, optionally after some limited routine experiments.

Usually, for ease of expression and production, a construct of the invention, such as a polypeptide of the invention, will be a linear polypeptide. However, the invention in its broadest sense is not limited thereto. For example, when a construct of the invention, such as a polypeptide of the invention, comprises three of more building blocks, ISVDs or Nanobodies, it is possible to link them by use of a linker with three or more "arms", with each "arm" being linked to a building block, ISVD or Nanobody, so as to provide a "star-shaped" construct. It is also possible, although usually less preferred, to use circular constructs.

Accordingly, the present invention relates to a construct of the invention, such as a polypeptide of the invention, wherein said ISVDs are directly linked to each other or are linked via a linker.

Accordingly, the present invention relates to a construct of the invention, such as a polypeptide of the invention, wherein a first ISVD and/or a second ISVD and/or possibly an ISVD binding serum albumin are linked via a linker.

Accordingly, the present invention relates to a construct of the invention, such as a polypeptide of the invention, wherein said linker is chosen from the group consisting of linkers of A3, 5GS, 7GS, 8GS, 9GS, 10GS, 15GS, 18GS, 20GS, 25GS, 30GS, 35GS, 40GS, G1 hinge, 9GS-G1 hinge, llama upper long hinge region, and G3 hinge, such as e.g. presented in Table C.

Accordingly, the present invention relates to a construct of the invention, such as a polypeptide of the invention, wherein said polypeptide is chosen from the group shown in Table A-3 and Table F, e.g. chosen from the group consisting of SEQ ID NOs: 164-165, 160, 161, 162, 163, and SEQ ID NO:s 176, 192 and 175-191 (i.e. 175, 176, 177, 178, 179, 180, 181, 182, 183, 184, 185, 186, 187, 188, 189, 190 or 191).

Preparation

The invention further relates to methods for preparing the constructs, polypeptides, ISVDs, nucleic acids, host cells, and compositions described herein.

The multivalent polypeptides of the invention can generally be prepared by a method which comprises at least the step of suitably linking the ISVD and/or monovalent polypeptide of the invention to one or more further ISVDs, optionally via one or more suitable linkers, so as to provide the multivalent polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multivalent polypeptides of the invention may comprise at least the steps of linking two or more ISVDs of the invention and for example one or more linkers together in a suitable manner. The ISVDs of the invention (and linkers) can be coupled by any method known in the art and as further described herein. Preferred techniques include the linking of the nucleic acid sequences that encode the ISVDs of the invention (and linkers) to prepare a genetic construct that expresses the multivalent polypeptide. Techniques for linking amino acids or nucleic acids will be clear to the skilled person, and reference is again made to the standard handbooks, such as Sambrook et al. and Ausubel et al., mentioned above, as well as the Examples below.

Accordingly, the present invention also relates to the use of an ISVD of the invention in preparing a multivalent polypeptide of the invention. The method for preparing a multivalent polypeptide will comprise the linking of an ISVD of the invention to at least one further ISVD of the invention, optionally via one or more linkers. The ISVD of the invention is then used as a binding domain or building block in providing and/or preparing the multivalent polypeptide comprising 2 (e.g., in a bivalent polypeptide), 3 (e.g., in a trivalent polypeptide), 4 (e.g., in a tetravalent) or more (e.g., in a multivalent polypeptide) building blocks. In this respect, the ISVD of the invention may be used as a binding domain or binding unit in providing and/or preparing a multivalent, such as bivalent, trivalent or tetravalent polypeptide of the invention comprising 2, 3, 4 or more building blocks.

Accordingly, the present invention also relates to the use of an ISVD polypeptide of the invention (as described herein) in preparing a multivalent polypeptide. The method for the preparation of the multivalent polypeptide will comprise the linking of the ISVD of the invention to at least one further ISVD of the invention, optionally via one or more linkers.

The polypeptides and nucleic acids of the invention can be prepared in a manner known per se, as will be clear to the skilled person from the further description herein. For example, the polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and nucleic acids include the methods and techniques described herein.

The method for producing a polypeptide of the invention may comprise the following steps:

the expression, in a suitable host cell or host organism (also referred to herein as a "host of the invention") or in another suitable expression system of a nucleic acid that encodes said polypeptide of the invention (also referred to herein as a "nucleic acid of the invention"), optionally followed by:

isolating and/or purifying the polypeptide of the invention thus obtained.

In particular, such a method may comprise the steps of:

cultivating and/or maintaining a host of the invention under conditions that are such that said host of the invention expresses and/or produces at least one polypeptide of the invention; optionally followed by:

isolating and/or purifying the polypeptide of the invention thus obtained.

Accordingly, the present invention also relates to a nucleic acid or nucleotide sequence that encodes a polypeptide, ISVD or construct of the invention (also referred to as "nucleic acid of the invention").

A nucleic acid of the invention can be in the form of single or double stranded DNA or RNA. According to one embodiment of the invention, the nucleic acid of the invention is in essentially isolated form, as defined herein. The nucleic acid of the invention may also be in the form of, be present in and/or be part of a vector, e.g. expression vector, such as for example a plasmid, cosmid or YAC, which again may be in essentially isolated form. Accordingly, the present invention also relates to an expression vector comprising a nucleic acid or nucleotide sequence of the invention.

The nucleic acids of the invention can be prepared or obtained in a manner known per se, based on the information on the polypeptides of the invention given herein, and/or can be isolated from a suitable natural source. Also, as will be clear to the skilled person, to prepare a nucleic acid of the invention, also several nucleotide sequences, such as at least two nucleic acids encoding ISVDs of the invention and for example nucleic acids encoding one or more linkers can be linked together in a suitable manner. Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as to the Examples below.

In a preferred but non-limiting embodiment, a genetic construct of the invention comprises a) at least one nucleic acid of the invention;
b) operably connected to one or more regulatory elements, such as a promoter and optionally a suitable terminator; and optionally also
c) one or more further elements of genetic constructs known per se; in which the terms "regulatory element", "promoter", "terminator" and "operably connected" have their usual meaning in the art.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

The nucleic acids of the invention and/or the genetic constructs of the invention may be used to transform a host cell or host organism, i.e., for expression and/or production of the polypeptide of the invention. Suitable hosts or host cells will be clear to the skilled person, and may for example be any suitable fungal, prokaryotic or eukaryotic cell or cell line or any suitable fungal, prokaryotic or (non-human) eukaryotic organism as well as all other host cells or (non-human) hosts known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. (Res Immunol. 149: 589-99, 1998); Riechmann and Muyldermans (1999), supra; van der Linden (J. Biotechnol. 80: 261-70, 2000); Joosten et al. (Microb. Cell Fact. 2: 1, 2003); Joosten et al. (Appl. Microbiol. Biotechnol. 66: 384-92, 2005); and the further references cited herein. Furthermore, the polypeptides of the invention can also be expressed and/or produced in cell-free expression systems, and suitable examples of such systems will be clear to the skilled person. Suitable techniques for transforming a host or host cell of the invention will be clear to the skilled person and may depend on the intended host cell/host organism and the genetic construct to be used. Reference is again made to the handbooks and patent applications mentioned above. The transformed host cell (which may be in the form of a stable cell line) or host organisms (which may be in the form of a stable mutant line or strain) form further aspects of the present invention. Accordingly, the present invention relates to a host or host cell comprising a nucleic acid according to the invention, or an expression vector according to the invention. Preferably, these host cells or host organisms are such that they express, or are (at least) capable of expressing (e.g., under suitable conditions), a polypeptide of the invention (and in case of a host organism: in at least one cell, part, tissue or organ thereof). The invention also includes further generations, progeny and/or offspring of the host cell or host organism of the invention that may for instance be obtained by cell division or by sexual or asexual reproduction.

To produce/obtain expression of the polypeptides of the invention, the transformed host cell or transformed host organism may generally be kept, maintained and/or cultured under conditions such that the (desired) polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g., using a specific, cleavable amino acid sequence fused with the polypeptide of the invention) and/or preparative immunological techniques (i.e. using antibodies against the polypeptide to be isolated).

In an aspect the invention relates to methods for producing a construct, polypeptide or ISVD according to the invention comprising at least the steps of: (a) expressing, in a suitable host cell or host organism or in another suitable expression system, a nucleic acid sequence according to the invention; optionally followed by (b) isolating and/or purifying the construct, polypeptide ISVD according to the invention.

In an aspect the invention relates to a composition comprising a construct, polypeptide, ISVD or nucleic acid according to the invention.

Medicaments (Uses of the ISVDs, Polypeptides, Constructs of the Invention)

As mentioned herein, there remains a need for safe and efficacious OA medicaments. Based on unconventional screening, characterization and combinatory strategies, the present inventors identified ISVDs binding and inhibiting MMP13. These MMP13 binders performed exceptionally well in in vitro and in vivo experiments. Moreover, the ISVDs of the invention were also demonstrated to be significantly more efficacious than the comparator molecules. The present invention thus provides ISVDs and polypeptides antagonizing MMPs, in particular MMP13, with improved prophylactic, therapeutic and/or pharmacological properties, including a safer profile, compared to the comparator molecules. In addition, these MMP13 binders when linked to CAP building blocks had an increased retention in the joint as well as retained activity on the other hand.

In an aspect the present invention relates to a composition according to the invention, an ISVD according to the invention, a polypeptide according to the invention, and/or a construct according to the invention for use as a medicament.

In another aspect, the invention relates to the use of an ISVD, polypeptide and/or construct of the invention in the preparation of a pharmaceutical composition for prevention and/or treatment of at least an MMP13 associated disease; and/or for use in one or more of the methods of treatment mentioned herein.

The invention also relates to the use of an ISVD, polypeptide, compound and/or construct of the invention in the preparation of a pharmaceutical composition for the prevention and/or treatment of at least one disease or disorder that can be prevented and/or treated by modulating an activity of an MMP, preferably MMP13 e.g. inhibiting Aggrecan and/or Collagen degradation.

The invention also relates to the use of an ISVD, polypeptide, compound and/or construct of the invention in the preparation of a pharmaceutical composition for the prevention and/or treatment of at least one disease, disorder or condition that can be prevented and/or treated by administering an ISVD, polypeptide, compound and/or construct of the invention to a patient.

The invention further relates to an ISVD, polypeptide, compound and/or construct of the invention or a pharmaceutical composition comprising the same for use in the prevention and/or treatment of at least one MMP13 associated disease.

It is anticipated that the MMP13 binders of the invention can be used in various diseases affecting cartilage, such as arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, and relapsing polychondritis, osteochondritis dissecans and aggrecanopathies (commonly indicated herein as "MMP13 associated diseases").

In an aspect the present invention relates to a composition, an ISVD, a polypeptide and/or a construct according to the invention for use in treating or preventing a symptom of an MMP13 associated disease, such as e.g. arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, and relapsing polychondritis, osteochondritis dissecans and aggrecanopathies. More preferably, said disease or disorder is an arthritic disease and most preferably osteoarthritis.

In an aspect the present invention relates to a method for preventing or treating arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis wherein said method comprises administering, to a subject in need thereof, a pharmaceutically active amount of at least a composition, immunoglobulin, polypeptide, or construct according to the invention to a person in need thereof. More preferably, said disease is an arthritic disease and most preferably osteoarthritis.

In an aspect the present invention relates to the use of an ISVD, polypeptide, composition or construct according to the invention, in the preparation of a pharmaceutical composition for treating or preventing a disease or disorder such as arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, and relapsing polychondritis, osteochondritis dissecans and aggrecanopathies. More preferably, said disease or disorder is an arthritic disease and most preferably osteoarthritis.

By binding to Aggrecan, the constructs and/or polypeptides of the invention may reduce or inhibit an activity of a member of the serine protease family, cathepsins, matrix metallo-proteinases (MMPs)/Matrixins or A Disintegrin and Metalloproteinase with Thrombospondin motifs (ADAMTS), MMP20, ADAMTS5 (Aggrecanase-2), ADAMTS4 (Aggrecanase-1) and/or ADAMTS11 in degrading Aggrecan.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The dosage regimen will be determined by the attending physician and clinical factors. As is well known in the medical arts, dosage for any one patient depends upon many factors, including the patient's size, weight, body surface area, age, the particular compound to be administered, the activity of the employed polypeptide (including antibodies), time and route of administration, general health, and combination with other therapies or treatments. Proteinaceous pharmaceutically active matter may be present in amounts between 1 g and 100 mg/kg body weight per dose; however, doses below or above this exemplary range are also envisioned. If the regimen is a continuous infusion, it may be in the range of 1 pg to 100 mg per kilogram of body weight per minute.

An ISVD, polypeptide or construct of the invention may be employed at a concentration of, e.g., 0.01, 0.1, 0.5, 1, 2, 5, 10, 20 or 50 pg/ml in order to inhibit and/or neutralize a biological function of MMP13 by at least about 50%, preferably 75%, more preferably 90%, 95% or up to 99%, and most preferably approximately 100% (essentially completely) as assayed by methods well known in the art.

An ISVD, polypeptide or construct of the invention may be employed at a concentration of, e.g., 1, 2, 5, 10, 20, 25, 30, 40, 50, 75, 100, 200, 250 or 500 ng/mg cartilage in order to inhibit and/or neutralize a biological function of MMP13 by at least about 50%, preferably 75%, more preferably 90%, 95% or up to 99%, and most preferably approximately 100% (essentially completely) as assayed by methods well known in the art.

Generally, the treatment regimen will comprise the administration of one or more ISVDs, polypeptides and/or constructs of the invention, or of one or more compositions comprising the same, in one or more pharmaceutically effective amounts or doses. The specific amount(s) or doses to be administered can be determined by the clinician, again based on the factors cited above. Useful dosages of the constructs, polypeptides, and/or ISVDs of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, depending on the specific disease, disorder or condition to be treated, the potency of the specific ISVD, polypeptide and/or construct of the invention to be used, the specific route of administration and the specific pharmaceutical formulation or composition used, the clinician will be able to determine a suitable daily dose.

The amount of the constructs, polypeptides, and/or ISVDs of the invention required for use in treatment will vary not only with the particular immunoglobulin, polypeptide, compound and/or construct selected but also with the route of administration, the nature of the condition being treated and the age and condition of the patient and will be ultimately at the discretion of the attendant physician or clinician. Also the dosage of the constructs, polypeptides, and/or ISVDs of the invention varies depending on the target cell, tissue, graft, joint or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. Preferably, the dose is administered once per week or even less frequent, such as once per two weeks, once per three weeks, once per month or even once per two months.

An administration regimen could include long-term treatment. By "long-term" is meant at least two weeks and preferably, several weeks, months, or years of duration.

Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, PA. The dosage can also be adjusted by the individual physician in the event of any complication.

Usually, in the above method, an ISVD, polypeptide and/or construct of the invention will be used. It is however within the scope of the invention to use two or more ISVDs, polypeptides and/or constructs of the invention in combination.

The ISVDs, polypeptides and/or constructs of the invention may be used in combination with one or more further pharmaceutically active compounds or principles, i.e., as a combined treatment regimen, which may or may not lead to a synergistic effect.

The pharmaceutical composition may also comprise at least one further active agent, e.g. one or more further antibodies or antigen-binding fragments thereof, peptides, proteins, nucleic acids, organic and inorganic molecules.

Again, the clinician will be able to select such further compounds or principles, as well as a suitable combined treatment regimen, based on the factors cited above and his expert judgment.

In particular, the ISVDs, polypeptides and/or constructs of the invention may be used in combination with other pharmaceutically active compounds or principles that are or can be used for the prevention and/or treatment of the diseases, disorders and conditions cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease, disorder or condition involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

Thus, in a further aspect, the invention relates to a pharmaceutical composition that contains at least one construct of the invention, at least one polypeptide of the invention, at least one ISVD of the invention, or at least one nucleic acid of the invention and at least one suitable carrier, diluent or excipient (i.e., suitable for pharmaceutical use), and optionally one or more further active substances. In a particular aspect, the invention relates to a pharmaceutical composition that comprises a construct, polypeptide, ISVD or nucleic acid according to the invention, preferably at least one of SEQ ID NOs: 111, 11, 112, 12, 109, 9, 110, 10, 1, 13, 14, 15, 16, 17, 18, 19, 20, 21, 22, 2, 3, 4, 5, 6, 7, 8, 160-165 (i.e. SEQ ID NO: 160, 161, 162, 163, 164 or 165) and 176-192 (i.e. SEQ ID NO: 176, 177, 178, 179, 180, 181, 182, 183, 184, 185, 186, 187, 188, 189, 190, 191 or 192) and at least one suitable carrier, diluent or excipient (i.e., suitable for pharmaceutical use), and optionally one or more further active substances.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases, disorders and conditions mentioned herein. Hence, in a preferred embodiment of the invention, the pharmaceutical compositions comprising a polypeptide of the invention are for use in medicine or diagnostics. Preferably, the pharmaceutical compositions are for use in human medicine, but they may also be used for veterinary purposes.

Again, in such a pharmaceutical composition, the one or more immunoglobulins, polypeptides, compounds and/or constructs of the invention, or nucleotide encoding the same, and/or a pharmaceutical composition comprising the same, may also be suitably combined with one or more other active principles, such as those mentioned herein.

The invention also relates to a composition (such as, without limitation, a pharmaceutical composition or preparation as further described herein) for use, either in vitro (e.g. in an in vitro or cellular assay) or in vivo (e.g. in a single cell or multi-cellular organism, and in particular in a mammal, and more in particular in a human being, such as in a human being that is at risk of or suffers from a disease, disorder or condition of the invention).

It is to be understood that reference to treatment includes both treatment of established symptoms and prophylactic treatment, unless explicitly stated otherwise.

Generally, for pharmaceutical use, the constructs, polypeptides and/or ISVDs of the invention may be formulated as a pharmaceutical preparation or composition comprising at least one construct, polypeptide and/or ISVD of the invention and at least one pharmaceutically acceptable carrier, diluent or excipient and/or adjuvant, and optionally one or more pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration (such as intra-articular administration), for administration by inhalation, by a skin patch, by an implant, by a suppository, etc., wherein the intra-articular administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition".

As exemplary excipients, disintegrators, binders, fillers, and lubricants may be mentioned. Examples of disintegrators include agar-agar, algins, calcium carbonate, cellulose, colloid silicon dioxide, gums, magnesium aluminium silicate, methylcellulose, and starch. Examples of binders include micro-crystalline cellulose, hydroxymethyl cellulose, hydroxypropylcellulose, and polyvinylpyrrolidone. Examples of fillers include calcium carbonate, calcium phosphate, tribasic calcium sulfate, calcium carboxymethylcellulose, cellulose, dextrin, dextrose, fructose, lactitol, lactose, magnesium carbonate, magnesium oxide, maltitol, maltodextrins, maltose, sorbitol, starch, sucrose, sugar, and xylitol. Examples of lubricants include agar, ethyl oleate, ethyl laureate, glycerin, glyceryl palmitostearate, hydrogenated vegetable oil, magnesium oxide, stearates, mannitol, poloxamer, glycols, sodium benzoate, sodium lauryl sulfate, sodium stearyl, sorbitol, and talc. Usual stabilizers, preservatives, wetting and emulsifying agents, consistency-improving agents, flavour-improving agents, salts for varying the osmotic pressure, buffer substances, solubilizers, diluents, emollients, colorants and masking agents and antioxidants come into consideration as pharmaceutical adjuvants.

Suitable carriers include but are not limited to magnesium carbonate, magnesium stearate, talc, sugar, lactose, pectin, dextrin, starch, gelatine, tragacanth, methylcellulose, sodium carboxymethyl-cellulose, a low melting-point wax, cocoa butter, water, alcohols, polyols, glycerol, vegetable oils and the like.

Generally, the constructs, polypeptides, and/or ISVDs of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

In a particular aspect, the invention relates to a pharmaceutical composition that comprises a construct, polypeptide, ISVD or nucleic acid according to the invention, and which further comprises at least one pharmaceutically acceptable carrier, diluent or excipient and/or adjuvant, and optionally comprises one or more further pharmaceutically active polypeptides and/or compounds.

The constructs, polypeptides, and/or ISVDs of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations preferable for suitable for parenteral administration (e.g. intravenous, intraperitoneal, subcutaneous, intramuscular, intraluminal, intra-arterial, intrathecal intranasal or intra bronchial administration) but also for topical (e.g. intra-articular, transdermal or intradermal) administration.

Preparations for topical or parenteral administration may for example be sterile solutions, suspensions, dispersions or emulsions that are suitable for infusion or injection. Suitable carriers or diluents for such preparations for example include those mentioned on page 143 of WO 08/020079. Usually, aqueous solutions or suspensions will be preferred.

The constructs, polypeptides, and/or ISVDs of the invention can also be administered using methods of delivery known from gene therapy, see, e.g., U.S. Pat. No. 5,399,346, which is incorporated by reference for its gene therapy delivery methods. Using a gene therapy method of delivery, primary cells transfected with the gene encoding a construct, polypeptide, and/or ISVD of the invention can additionally be transfected with tissue specific promoters to target specific organs, tissue, grafts, joints, or cells and can additionally be transfected with signal and stabilization sequences for subcellularly localized expression.

According to further aspects of the invention, the polypeptide of the invention may be used in additional applications in vivo and in vitro. For example, polypeptides of the invention may be employed for diagnostic purposes, e.g. in assays designed to detect and/or quantify the presence of MMP13 and/or to purify MMP13. Polypeptides may also be tested in animal models of particular diseases and for conducting toxicology, safety and dosage studies.

Finally, the invention relates to a kit comprising at least one polypeptide according to the invention, at least one nucleic acid sequence encoding said components, the vector or vector system of the invention, and/or a host cell according to the invention. It is contemplated that the kit may be offered in different forms, e.g. as a diagnostic kit.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

Sequences are disclosed in the main body of the description and in a separate sequence listing according to WIPO standard ST.25. A SEQ ID specified with a specific number should be the same in the main body of the description and in the separate sequence listing. By way of example SEQ ID no.: 1 should define the same sequence in both, the main body of the description and in the separate sequence listing. Should there be a discrepancy between a sequence definition in the main body of the description and the separate sequence listing (if e.g. SEQ ID no.: 1 in the main body of the description erroneously corresponds to SEQ ID no.: 2 in the separate sequence listing) then a reference to a specific sequence in the application, in particular of specific embodiments, is to be understood as a reference to the sequence in the main body of the application and not to the separate sequence listing. In other words a discrepancy between a sequence definition/designation in the main body of the description and the separate sequence listing is to be resolved by correcting the separate sequence listing to the sequences and their designation disclosed in the main body of the application which includes the description, examples, figures and claims.

EXAMPLES

The following examples illustrate the methods and products of the invention. Suitable modifications and adaptations of the described conditions and parameters normally encountered in the art of molecular and cellular biology that are apparent to those skilled in the art are within the spirit and scope of the present invention.

6.1 Methods

6.1.1 Llama Immunization

Immunization of llamas was performed according to standard procedures, with variations in the amount of antigen, type of adjuvant and injection method used. These variations are described in detail in the respective below sections. All immunization experiments were approved by the local ethical committee.

6.1.2 Library Construction cDNA was prepared using total RNA extracted from the blood samples of all llamas/alpacas immunized with MMP13. Nucleotide sequences encoding Nanobodies were amplified from the cDNA in a one-step RT-PCR reaction and ligated into the corresponding restriction sites of phagemid vector pAX212, followed by transformation of E. coli strain TG-1 with the ligation product via electroporation.

NNK libraries were generated via overlap extension PCR with a degenerated primer. PCR products were cloned in an expression vector (pAX129) and transformed into E. coli TG-1 competent cells. In frame with the Nanobody coding sequence, the vector codes for a C-terminal $FLAG_3$- and $His_6$-tag (SEQ ID NO: 201).

Clones of interest were sequence verified.

6.1.3 Selections

The phage display libraries were probed using recombinant MMP13. Different antigens were used in different rounds of selection as described in detail in the Results section, i.e. Example 6.2 and following.

Selections consisted of incubating antigen with the library phage particles for 2 hours (in PBS supplemented with 2% Marvel and 0.05% Tween 20). Biotinylated antigens were captured using streptavidin coated magnetic beads (Invitrogen, 112-05D). Non-biotinylated antigens were coated on MaxiSorp plates (Nunc, 430341). Unbound phage were washed away (with PBS supplemented with 0.05% Tween 20); bound phage were eluted by addition of trypsin (1 mg/mL in PBS) for 15 min. Eluted phage were used to infect exponentially growing E. coli TG-1 cells for phage rescue. Phage prepared from selected outputs was used as input in subsequent selection rounds.

6.1.4 ELISA Directly Coated Antigens

MaxiSorp plates (Nunc, 430341) were coated overnight with human proMMP13 at 4° C. followed by one hour blocking (PBS, 1% casein) at RT. After a washing step in PBS+0.05% Tween20, 10-fold dilutions of periplasmic extracts in PBS, 0.1% casein, 0.05% Tween 20 were added for one hour at RT. Bound Nanobodies were detected with mouse anti-FLAG-HRP (Sigma (A8592)).

Captured Antigens
  activated human MMP13 ELISA
  activated rat MMP13 ELISA
  activated dog MMP13 ELISA MaxiSorp plates (Nunc, 430341) were coated overnight with human MMP13 antibody mAb511 at 4° C. followed by one hour blocking (PBS, 1% casein) at RT. After a washing step in PBS+0.05% Tween20, 20 nM activated human, rat or dog MMP13 were added for one hour at RT. After a second washing step, 10-fold dilutions of periplasmic extracts or dilution series of purified Nanobodies in PBS, 0.1% casein, 0.05% Tween 20 were added for one hour at RT. Bound Nanobodies were detected with mouse anti-FLAG-HRP (Sigma (A8592)).

6.1.5 Fluorogenic Peptide Assay

The setup of human, cynomolgus, rat, dog and bovine MMP13 fluorogenic peptide assays, as well as human MMP1 and MMP14 fluorogenic peptide assays is in brief as follows: activated MMP was incubated with fluorogenic peptide substrate Mca-PLGL-Dpa-AR-NH2 (R&D Systems #ES001) and a ⅕ dilution of periplasmic extract or a dilution series of purified Nanobody/positive control (total volume=20 µl in assay buffer 50 mM Tris pH 7.5, 100 mM NaCl, 10 mM CaCl2, 0.01% Tween20), for 2 h at 37° C. The linear increase of fluorescence (v0-between 15 and 45 min incubation) was used as a measure for the enzymatic activity and % inhibition was calculated with the formula 100-100 (v0 in the presence of test Nanobody/v0 in the presence of negative control Nanobody (Cablys)).

6.1.6 Collagenolytic Assay

The setup of this assay is in brief as follows: 250 ng/ml immunization grade human Collagen II (Chondrex #20052) was incubated with 5 nM activated MMP13 in 100 µl assay buffer (50 mM Tris-Cl pH 7.5, 100 mM NaCl, 10 mM CaCl2, 0.01% Tween-20). After 1.5 h incubation at 35° C., the reaction was neutralized with EDTA (10 µl of 30 mM stock). MMP13 cleaved Collagen was further degraded with elastase for 20 min at 38° C. to avoid re-annealing of degraded Collagen II (10 µl of ⅓ diluted stock provided in Type II Collagen Detection kit (Chondrex #6009)). Remaining intact Collagen was detected via ELISA (reagents provided in Type II Collagen Detection kit (Chondrex #6009)).

6.1.7 Fluorogenic Collagen Assay

In brief, the setup of this assay is as follows: 100 µg/ml DQ™ Collagen, type I from Bovine skin (fluorescein conjugate; Molecular Probes #D-12060 lot 1149062) was incubated with 10 nM activated MMP13 and a dilution series of purified Nanobody/positive control, for 2 h at 37° C. in 40 µl assay buffer (50 mM Tris-Cl pH 7.5, 100 mM NaCl, 10 mM $CaCl_2$, 0.01% Tween-20). The linear increase of fluorescence (v0-between 15 and 45 min incubation) was used as a measure for the enzymatic activity and % inhibition was calculated with the formula 100-100 (v0 in the presence of test Nanobody/v0 in the presence of a negative control Nanobody (Cablys)).

6.1.8 TIMP-2 Competition Assay

50 µl TIMP-2 (0.63 nM; R&D Systems #971-TM) was captured (1 h at RT) on an anti-Human TIMP-2 Antibody (R&D Systems #MAB9711) coated plate (2 µg/ml in PBS; overnight). During this capturing, 1.26 nM activated MMP-13-biotin was pre-incubated with a dilution series of Nanobody/TIMP-3/MSC2392891A in 70 µl assay buffer (50 mM Tris-Cl pH 7.5, 100 mM NaCl, 10 mM $CaCl_2$, 0.01% Tween-20). 50 µl of this mixture were added to captured TIMP-2 and incubated for 1 h at room temperature. MMP13-biotin was detected with 50 µl Streptavidin-HRP (1:5000 Dako-Cytomation #P0397).

6.1.9 Thermal Shift Assay (TSA)

TSA was carried out with 5 µl of purified monovalent Nanobodies in essence according to Ericsson et al. (2006 Anals of Biochemistry, 357: 289-298).

6.1.10 Analytical Size Exclusion Chromatography (Analytical SEC)

Analytical SEC experiments were performed on an Ultimate 3000 machine (Dionex) in combination with a Biosep-SEC-3 (Agilent) column.

6.1.11 Forced Oxidation

Nanobody samples (1 mg/ml) were subjected for four hours at RT and in the dark to 10 mM $H_2O_2$ in PBS, in parallel with control samples without $H_2O_2$, followed by buffer switch to PBS using Zeba desalting spin columns (0.5 ml) (Thermo Scientific). Stressed and control samples were then analyzed by means of RPC on a Series 1200 or 1290 machine (Agilent Technologies) over a Zorbax 300SB-C3 column (Agilent Technologies) at 70° C. Oxidation of Nanobodies was quantified by determination of % peak area of pre-peaks occurring as a result of oxidative stress, compared to the main protein peak.

6.1.12 Temperature Stress

Nanobody samples (1-2 mg/ml) were stored in PBS for four weeks at −20° C. (negative control) 25 and 40° C. After this incubation period, Nanobodies were digested with Trypsin or LysC. Peptides of stressed and control samples were then analyzed by means of RPC on a Series 1290 machine (Agilent Technologies) over an Acquity UPLC BEH300-C18 column (Agilent Technologies) at 60° C. coupled to a Q-TOF mass spectrometer (6530 Accurate Mass Q-TOF (Agilent))

6.2 Immunizations

MMP13 is secreted as an inactive pro-form (proMMP13). It is activated once the pro-domain is cleaved, leaving an active enzyme composed of a catalytic domain, which forms the catalytic pocket, and a hemopexin-like domain (PDB: 1PEX), which is described to function as a docking/interaction domain of the substrate Collagen II (Col II).

It was hypothesized that the best region to inhibit the enzymatic activity of MMP13 would be the catalytic pocket. However, raising an immune response against the catalytic pocket poses various important problems.

First, in proMMP13 the pro-domain masks the catalytic pocket, because of which the pocket is not accessible for raising an immune response.

Second, activated MMP13 has a short half-life, which is mainly due to autoproteolysis. This short half-life impedes the development of a strong immune response.

Third, the sequence of the catalytic domain is highly conserved across species. Hence, the expected immune response would be weak, if raised at all.

6.2.1 Immunization Strategy

In order to handle these problems and to increase the chances of success in obtaining MMP13 inhibitors binding the catalytic pocket, sophisticated and elaborated immunization strategies were devised comprising various formats of MMP13. Eventually, the following immunizations were carried out:
(a) 3 llamas were immunized with a truncated MMP13 variant consisting of the catalytic domain and containing mutation F72D, which protects MMP13 from autoproteolysis;
(b) 3 llamas were immunized with the same truncated MMP13 variant as (a), which in addition to mutation F72D, contained mutation E120A that inactivates the enzymatic function;
(c) 3 more llamas were immunized with full length proMMP13 protein; and
(d) 3 llamas were immunized with a mixture of plasmids that encoded for either a secreted proMMP13 variant (V123A) or a GPI anchored proMMP13 variant (V123A). The V123A mutation is described for MMP13 to provoke a weak interaction of Cys104 with the catalytic zinc ion leading to spontaneous auto-activation.

6.2.2 Serum Titers

Serum titers were determined towards proMMP13 and the catalytic domain (F72D).

In general, animals immunized with the protein proMMP13 (c) or the DNA encoding proMMP13 V123A (d) showed a good immune response against proMMP13 but responded only weakly to the catalytic domain (F72D). Animals immunized with the catalytic domain (F72D) (a) or inactive catalytic domain (F72D, E120A) (b) showed no or only a weak immune response against the catalytic domain.

6.2.3 Library Construction

Despite the low serum titers against the catalytic domain, the inventors were convinced that extensive screening would enable identifying inhibitory binders to the catalytic pocket.

RNA was extracted from PBLs (primary blood lymphocytes) and used as template for RT-PCR to amplify Nanobody encoding gene fragments. These fragments were cloned into phagemid vector pAX212 enabling production of phage particles displaying Nanobodies fused with His6- (SEQ ID NO: 201) and FLAG3-tags. Phages were prepared and stored according to standard protocols (Phage Display of Peptides and Proteins: A Laboratory Manual 1st Edition, Brian K. Kay, Jill Winter, John McCafferty, Academic Press, 1996).

The average size of the 18 immune libraries eventually obtained, was about $5*10^8$ individual clones.

6.3 Primary Screening

Phage Display selections were performed with 18 immune libraries and two synthetic Nanobody libraries. The libraries were subjected to two to four rounds of enrichment against different combinations of human proMMP13, activated human, rat and dog MMP13 as well as human MMP13 catalytic domain (F72D) using different antigen presentation formats. Individual clones from the selection outputs were screened for binding in ELISA (using periplasmic extracts from E.coli cells expressing the Nanobodies) against human and rat MMP13 and for inhibitory activity in a fluorogenic peptide assay measuring an increase in fluorescence upon peptide hydrolysis using a broad-spectrum MMP fluorogenic peptide substrate. Nanobodies that showed binding in ELISA but did not show inhibitory activity in the fluorogenic peptide assay were further screened in a collagenolytic assay. The collagenolytic assay uses the natural substrate instead of a peptide surrogate. As Collagen has a much larger interaction surface with MMP13 than the fluorogenic peptide, it was hypothesized that the Nanobodies would interfere with Collagen degradation, but not with degradation of the peptide. The collagenolytic assay was, however, not compatible with periplasmic extracts and required the use of purified Nanobodies.

6.3.1 Campaign 1

In the first selection campaign, MMP13 was presented as directly coated antigen. This yielded high hit rates in the human and rat MMP13 ELISA (binding assay), including a good diversity of Nano bodies binding to human MMP13 with a broad range of binding signals in ELISA. The majority of Nanobodies was found to be cross-reactive to rat MMP13. However, extremely low hit rates in the fluorogenic peptide assay (inhibition assay) were obtained. Moreover, the observed inhibition was incomplete and some of these Nano bodies did not show rat cross-reactivity.

Since no monovalent fully inhibitory Nanobodies were obtained, the inventors hypothesized that the correct epitope was not being targeted and the conditions used during selections were not optimal. However, testing selection conditions was impeded by the absence of a positive control.

Eventually it was found that direct coating interferes with enzyme activity.

6.3.2 Campaign 2

In campaign 2, selections were performed in-solution with biotinylated MMP13. Using activated human and rat MMP13 captured via a non-neutralizing antibody instead of directly coated proMMP13, ELISA hit rates were however much lower than for campaign 1. Hit rates were also again very low in the fluorogenic peptide assay. However, one Nanobody fully inhibiting in the collagenolytic assay was found. As the pro-form of the enzyme was used for binder enrichment it was hypothesized that critical epitopes were masked by the pro-peptide.

6.3.3 Campaign 3

In view of the disappointing results of campaigns 1 and 2, the inventors opted to optimize the presentation of the critical epitopes in the catalytic domain by using activated MMP13 captured by a non-neutralizing antibody. The same capturing format was also used for the ELISA. This resulted in higher hit rates in ELISA for both human and rat MMP13. However, although the hit rates in the fluorogenic peptide assay were slightly higher compared to the previous campaigns, Nanobodies still gave only incomplete inhibition and did show weak or no rat cross-reactivity suggesting that the captured presentation of MMP13 was still suboptimal.

Three clones, including C0101040E09 ("40E09"), despite giving incomplete inhibition in the fluorogenic peptide assay were found positive in the collagenolytic assay. Family members of 40E09 were cloned and sequenced: C0101-PMP040E08, C0101PMP042A04, C0101PMP040805, C0-101PMP042D12, C0101PMP042A03, C0101PMP024A08 and C0101PMP040D01 (cf. Tables A-1 and A-2). The sequence variability of CDR regions is depicted in the Tables 6.3.3A, 6.3.3B and 6.3.3C below. The amino acid sequences of the CDRs of clone 40E09 were used as reference against which the CDRs of the family members were compared (CDR1 starts at Kabat position 26, CDR2 starts at Kabat position 50, and CDR3 starts at Kabat position 95).

TABLE 6.3.3A (40E09 CDR1)

| 40E09 | CDR1* | | | | | | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| wildtype sequence | G | S | T | F | S | R | Y | S | M | N |
| mutations | | | | | | | R | | | |

*Up to 1 CDR1 mutation in one clone (SEQ ID NO: 23) (Mutation encompassed in SEQ ID NO: 24)

TABLE 6.3.3B (40E09 CDR2)

| 40E09 | CDR2* | | | | | | | | |
|---|---|---|---|---|---|---|---|---|---|
| Kabat numbering | 50 | 51 | 52 | 53 | 54 | 55 | 56 | 57 | 58 |
| absolute numbering | 1 | 2 | 3 | 4 | 5 | 6 | 7 | 8 | 9 |
| wildtype sequence | G | I | S | V | G | R | I | T | N |
| mutations | | | | T | A | | | | H |

* Up to 3 CDR2 mutations in one clone (SEQ ID NO: 37) (Mutations encompassed in SEQ ID NOS: 38-39)

TABLE 6.3.3C (40E09 CDR3)

| 40E09 | CDR3* | | | | | |
|---|---|---|---|---|---|---|
| Kabat numbering | 95 | 96 | 97 | 98 | 99 | 100 |
| absolute numbering | 1 | 2 | 3 | 4 | 5 | 6 |
| wildtype sequence | G | G | L | Q | G | Y |
| mutations | | | | | | S |

*Up to 1 CDR mutation in one clone (SEQ ID NO: 52) (Mutation encompassed in SEQ ID NO: 53)

6.3.4 Campaign 4

In the 4$^{th}$ campaign, in addition to immune Nanobody phage display libraries derived from immunization strategies (a) and (c) also libraries derived from selection strategies (b) and (d) were explored (cf. Example 6.2.1). The selection strategy was focused on the MMP13 catalytic domain (F72D), which was used in solution. Hit rates in the fluorogenic peptide assay increased across libraries and many Nanobodies showed complete inhibition. The inhibitory Nanobodies showed only poor binding in ELISA confirming that also the captured presentation of MMP13 used in campaign 3 was suboptimal for accessibility of critical epitopes. Consequently, a rat fluorogenic peptide assay was used instead of the ELISA to assess rat cross reactivity. Family representatives of Nanobodies with confirmed inhibitory potential were all rat cross reactive suggesting that the epitopes recognized by this particular set of clones lie within the conserved MMP13 catalytic pocket.

In summary, it was found that any routine manipulation of MMP13 interfered with the enzyme's activity and with TIMP-2 binding (data not shown). After varying and evaluating various parameters, including different antigens (e.g. proMMP13, catalytic domain (F72D), activated human MMP13, activated rat MMP13, activated dog MMP13, different assays, including ELISA, human fluorogenic peptide assay, rat fluorogenic peptide assay and human collagenolytic assay, different assay set-ups, including variations in coating conditions, in-solution and capturing MMP13), it was found that the only successful strategies for the identification of fully inhibitory Nanobodies were selections using catalytic domain (F72D) or activated MMP13 species (campaign 4).

6.3.5 Lead Panel

Inhibitory Nanobodies identified in the fluorogenic peptide or collagenolytic assays were sequenced. Based on the sequence information, Nanobodies could be classified into various families. The 4 families derived from screening campaigns 2 and 3 showed full inhibition in the collagenolytic assay, but did not show activity in the fluorogenic peptide assay; indicated further herein as "profile 1" clones (cf. 40E09 and family members). The 10 families derived from screening campaign 4 showed inhibitory activity in both the collagenolytic assay and the fluorogenic peptide assay; indicated further herein as "profile 2" clones.

A representative clone per Nanobody family was chosen, totaling to 14 representatives. The sequences of the representative clones are depicted in Table A-1.

6.4 In Vitro Characterization of Monovalent Lead Panel

In order to further characterize the representative Nanobody clones functionally, they were recloned into pAX129, transformed into *E. coli* and expressed and purified according to standard protocols (e.g. Maussang et al. 2013 J Biol Chem 288(41): 29562-72). Subsequently, these clones were subjected to various functional in vitro assays.

6.4.1 Enzymatic Assays

The potency/efficacy of the Nanobodies was tested in the fluorogenic peptide assay, set up for different MMP13 orthologues and in the human collagenolytic assay (both assays were also used during screening, see Example 6.3). In addition, a second collagen-based assay (fluorogenic collagen assay) using higher Collagen concentrations in comparison with the collagenolytic assay was established to simulate the high Collagen concentration conditions in cartilage in which the MMP13 inhibitor is expected to be active. In this assay the fluorescence of the intact FITC-labelled Collagen substrate is low due to the reciprocal quenching effect of the fluorophores. Upon cleavage, quenching is lost and fluorescence increases.

An overview of the potencies in the enzymatic assays is given in Table 6.4.1.

TABLE 6.4.1

Potency of the lead panel in MMP13 enzymatic assays. Potencies are only reported when the efficacy is ~100%.

| | | IC50 [nM] | | | | | | |
|---|---|---|---|---|---|---|---|---|
| | clone | human fluorogenic peptide assay | rat fluorogenic peptide assay | dog fluorogenic peptide assay | bovine fluorogenic peptide assay | cyno fluorogenic peptide assay | human collagenolytic assay | human fluorogenic collagen assay |
| | TIMP-2 | 0.5 | 0.4 | 0.9 | 1.1 | 0.4 | 0.4 | 2.4 |
| profile 1 | 32B08 | No inhibition | No inhibition | No inhibition | No inhibition | No inhibition | 97.4 | partial inhibition |
| profile 1 | 40E09 | No inhibition | No inhibition | No inhibition | No inhibition | No inhibition | 10.2 | partial inhibition |
| profile 1 | 43E10 | No inhibition | No inhibition | No inhibition | No inhibition | No inhibition | 20.1 | partial inhibition |
| profile 1 | 43B05 | No inhibition | No inhibition | No inhibition | No inhibition | No inhibition | 72.6 | partial inhibition |
| profile 2 | 516G08 | 0.8 | 5.2 | 4.4 | 1.5 | 0.4 | 0.9 | 3.8 |
| profile 2 | 529C12 | 1.2 | 0.2 | 0.2 | 1.2 | 0.7 | | 4.9 |
| profile 2 | 62C02 | 1.4 | 1.1 | 1.0 | 3.1 | 1.4 | 1.4 | 8.3 |
| | MSC2392 891A | 3.7 | 0.7 | 0.7 | 8.5 | 3.0 | 4.7 | partial inhibition |
| profile 2 | 517A01 | 4.6 | 2.1 | 3.4 | 6.4 | 3.0 | 2.3 | 10.9 |
| profile 2 | 80A01 | 5.2 | 4.2 | 6.0 | 6.4 | 2.9 | | 10.8 |
| profile 2 | 521F02 | 7.2 | 2.1 | 5.5 | 16.1 | 7.0 | | 20.7 |
| profile 2 | 513C04 | 7.7 | 16.2 | 35.2 | 48.7 | 8.0 | | 18.1 |
| profile 2 | 519E04 | 9.5 | 3.0 | 7.0 | 17.1 | 7.2 | | 24.8 |
| profile 2 | 529G11 | 10.3 | 80.6 | 39.1 | 20.1 | 7.1 | | 17.9 |
| profile 2 | 520B06 | 13.4 | 7.8 | 17.3 | 27.7 | 9.5 | | 27.5 |
| profile 2 | 520C04 | 13.7 | 5.6 | 10.5 | 27.9 | 32.5 | | 31.5 |
| profile 2 | 59F06 | 56.3 | 38.9 | 82.6 | 108.1 | 48.5 | | 139.6 |
| profile 2 | 525C04 | 58.0 | 157.0 | 90.8 | 108.1 | 32.5 | | 90.5 |
| profile 2 | 63F01 | 82.4 | 20.2 | 73.9 | 191.2 | 107.5 | | 134.3 |

In FIG. 1 the dose response curves for inhibition of activated human MMP13 when using high concentrations of bovine Collagen I (fluorogenic Collagen assay) are depicted.

Although profile 1 Nanobodies showed full efficacy in the collagenolytic assay under low Collagen concentration conditions, their efficacy dropped in the fluorogenic Collagen assay under high Collagen concentration conditions (FIG. 1, left panel).

Also the comparator drug MSC2392891A showed weaker efficacy in the fluorogenic Collagen assay (FIG. 1).

Profile 2 representative Nanobodies were potent and fully efficacious in both the collagenolytic assay and the fluorogenic collagen assay. Most Nanobodies were more active than the comparator drug in this assay. These profile 2 representatives showed comparable potencies (cf. Table 6.4.1) and efficacies (FIG. 1, right panel) in human, cynomolgus, rat, dog and bovine fluorogenic peptide assays.

6.4.2 Binding Assays

An ELISA setup was used in order to assess binding affinity. However, it was found that this assay was only suitable for assessing the affinity of profile 1 Nanobodies, but not profile 2 Nanobodies (cf. Example 6.3).

The results are depicted in Table 6.4.2A.

TABLE 6.4.2A

Binding affinities (EC50) assessed by ELISA for profile 1 Nanobodies EC50 [nM]

| clone | human MMP13 ELISA (EC50) | rat MMP13 ELISA (EC50) | dog MMP13 ELISA (EC50) |
|---|---|---|---|
| 32B08 | 3.85 | 0.52 | 4.1 |
| 40E09 | 0.66 | 0.44 | 0.38 |
| 43E10 | 0.35 | 2.39 | 0.62 |
| 43B05 | 1.64 | 4.21 | 7.19 |

In conclusion, the binding affinity of the profile 1 Nanobodies is comparable for the three species tested (i.e. less than 10 fold difference). Although clone 40E09 has only the second best binding affinity for human MMP13, it shows the best affinity across species.

As it was found that profile 2 Nanobodies competed with TIMP-2 for binding to MMP13, a TIMP-2 competition ELISA was set up and used to assess the affinities of profile 2 Nanobodies. Notably, profile 1 Nanobodies do not compete with TIMP-2.

The results are depicted in Table 6.4.23.

TABLE 6.4.2B

Potencies (IC50) assessed by TIMP-2 competition ELISA for profile 2 Nanobodies

| clone | IC50 [nM] TIMP-2 competition ELISA | clone | IC50 [nM] TIMP-2 competition ELISA |
|---|---|---|---|
| 516G08 | 0.5 | 519E04 | 5.5 |
| 529C12 | 0.4 | 529G11 | 7.9 |
| 62C02 | 0.9 | 520B06 | 9.3 |
| 517A01 | 2.6 | 520C04 | 8.0 |
| 80A01 | 2.7 | 59F06 | 51.8 |
| 521F02 | 8.5 | 525C04 | 36.2 |
| 513C04 | 7.7 | 63F01 | 177.1 |

In conclusion, the rating was similar to the potencies obtained in the enzymatic assays, with Nanobodies 516G08, 529C12 and 62C02 showing the best inhibitory potential, while Nanobodies 59F06, 525C04 and 63F01 were secondary thereto.

6.4.3 Selectivity Assays

In order to determine the selectivity of the Nanobodies for MMP13 over MMP1 and MMP14, fluorogenic peptide assays were used. MMP1 and MMP14 are two closely related MMP family members. Since profile 1 Nanobodies did not show inhibition in the MMP13 fluorogenic peptide assay, only profile 2 Nanobodies could be tested. TIMP-2, a non-selective MMP inhibitor, was used as positive control in these assays.

The results are depicted in FIG. 2.

All Nanobodies were highly selective. They did not show MMP1 inhibition and only very minor inhibition was observed at high concentrations of MMP14 for some Nanobodies.

6.4.4 Epitope Binning

For epitope-binning a panel of monovalent Nanobodies derived from profile 1 and profile 2 were tested in a competition ELISA against the purified Nanobody 40E09 (profile 1).

The results of the competition ELISA are shown in FIG. 3.

The profile 1 Nanobodies 32B08, 43B05, 43E10 and 40E09 (positive control), all compete with 40E09. On the other hand, neither the profile 2 Nanobodies 59F06, 62C02, 63F01, 513C04, 516G08 and 517A01 nor the negative control cAbLys compete with 40E09.

Hence, the profile 1 Nanobodies appear to belong to a different epitope bin (tentatively called "bin 1") than the profile 2 Nanobodies (tentatively called "bin 2"), which would also reflect the immunization and selection strategies.

6.5 Bivalent Constructs

As demonstrated in Example 6.4.1 above, profile 1 Nanobodies showed no inhibition in the fluorogenic peptide assays (cf. Table 6.4.1). The inventors set out to investigate the effect of a combination of profile 1 Nanobodies and profile 2 Nanobodies.

As best species cross-reactive binder (cf. Example 6.4.2) Nanobody 40E09 was selected as representative of profile 1 Nanobodies. For profile 2, three Nanobodies were selected: 516G08, 62C02 and 517A01. Profile 1 and profile 2 Nanobodies were combined in a bivalent format with a 35GS linker (see Table 6.5; Nb(A)-35GS-Nb(B)). The bivalent Nanobodies were cloned into pAX205, transformed into *P. pastoris*, expressed and purified according to standard procedures. To assess the potency of these bivalent constructs, the rat fluorogenic peptide assay was used, but with a lower MMP13 concentration compared to the screening setup (0.15 nM instead of 1.33 nM) to improve the sensitivity of the assay. Bivalent constructs were tested in this adapted fluorogenic peptide assay as well as in the human fluorogenic collagen assay.

The resulting data are summarized in Table 6.5.

TABLE 6.5

Potency of bivalent Nanobodies in the rat fluorogenic peptide assay (adapted to be more sensitive) and the human fluorogenic collagen assay IC50 [nM]

| clone | description | (adapted) rat fluorogenic peptide assay | human fluorogenic collagen assay |
|---|---|---|---|
| TIMP-2 | | 0.18 | 2.402 |
| 40E09 | | neutral | partial |
| 516G08 | | 4.98 | 3.777 |
| 62C02 | | 2.88 | 8.317 |
| MSC2392891A | | 4.86 | partial |
| 517A01 | | 2.64 | 10.85 |
| 80 | 517A01-40E09 | 0.13 | 4.06 |
| 76 | 516G08-40E09 | 0.16 | 3.55 |
| 72 | 62C02-40E09 | 0.1 | 2.4 |
| 71 | 40E09-517A01 | 0.11 | 6.5 |

TABLE 6.5-continued

Potency of bivalent Nanobodies in the rat fluorogenic
peptide assay (adapted to be more sensitive)
and the human fluorogenic collagen assay
IC50 [nM]

| clone | description | (adapted) rat fluorogenic peptide assay | human fluorogenic collagen assay |
|---|---|---|---|
| 70 | 40E09-516G08 | 0.12 | 2.9 |
| 69 | 40E09-62C02 | 1.12/partial | low efficacy |

The results indicate that bivalent constructs consisting of a profile 1 Nanobody combined with a profile 2 Nanobody are more potent than their monovalent building blocks in the adapted rat fluorogenic peptide assay with potency improvements of up to 40 fold. Also in the human fluorogenic collagen assay potency improvements were observed (up to 4 fold). In both assays the bivalent constructs were equally potent to the positive, non-selective control TIMP-2.

Hence, although profile 1 Nanobodies are not particularly inhibitory on their own, they improved potency of profile 2 Nanobodies when combined in a bivalent construct.

6.6 Biophysical Characterization

To facilitate patient's convenience, a low administration frequency and high retention of the therapeutic compound is favored. Therefore, it is preferred that the Nanobodies have a high stability.

In order to test the stability, 5 representative profile 2 Nanobodies and one representative profile 1 Nanobody were subjected to biophysical characterization.

6.6.1 Thermal Shift Assay

The thermal stability of the wildtype anti-MMP13 Nanobodies was investigated in a thermal shift assay (TSA).

The results are depicted in Table 6.6.1.

TABLE 6.6.1

Tm at pH 7 for monovalent Nanobodies

| Nanobody | Tm at pH 7 (° C.) |
|---|---|
| C0101516G08 | 65.2 |
| C0101040E09 | 68.6 |
| C0101080A01 | 68.6 |
| C0101062C02 | 76.4 |
| C0101517A01 | 77.8 |
| C0101529C12 | 82.7 |

Tm values at pH 7 range from 65° C. to 83° C., indicative of good to very good stability characteristics.

6.6.2 Analytical SEC

The tendency for multimerisation and aggregation of a selected panel of 5 representative anti-MMP13 Nanobodies was investigated by analytical size exclusion chromatography (aSEC).

A summary of the results is shown in Table 6.6.2.

TABLE 6.6.2

Analytical SEC parameters for MMP13 lead Nanobodies

| Nanobody | Retention time [min] | relative area [%] | % recovery | Overall aSEC behavior | SDS-Page results |
|---|---|---|---|---|---|
| C0101040E09 | 7.6 | 100 | 90 | OK | 1 band |
| C0101062C02 | 7.6 | 100 | 98 | OK | 1 band |
| C0101517A01 | 8.1 | 100 | 105 | OK | 1 band |
| C0101529C12 | 8.2 | 100 | 91 | OK | 1 band |
| C0101080A01 | 7.66 | 95 | 92 | OK | minor mono/dimers |

The 5 representative Nanobodies had retention times within the expected range for monovalent Nanobodies (7.6-8.2 min) and the relative area of the main peak and overall recovery was above 90% for all Nanobodies.

Biophysical properties based on TSA and aSEC were considered suitable for further development for all Nanobodies tested.

6.7 Selection of Clones for Further Development and Sequence Optimization

Based on the functional and biophysical characteristics of the representative Nanobodies and bivalent constructs, 4 exemplary lead Nanobodies: 62C02, 529C12, 80A01 and bivalent construct C01010080 ("0080", consisting of profile 2 Nanobody 517A01 and profile 1 Nanobody 40E09) were selected for further development.

The present inventors set out to optimize the amino acid sequence ("Sequence Optimization" or "SO") of the lead panel. In the process of sequence optimisation it is attempted to (1) knock out sites for post-translational modifications (PTM); (2) humanize the parental Nanobody; as well as (3) knock out epitopes for potential pre-existing antibodies. At the same time the functional and biophysical characteristics of the Nanobodies should preferably be maintained or even ameliorated.

6.7.1 Post-Translational Modifications (PTM)

Post-translational modifications (PTM) which were assessed are: Met-oxidation, Asn-deamidation, Asp-isomerisation, Asn-glycosylation and pyroglutamate formation.

Although the E1D mutation (usually incorporated to prevent pyroglutamate formation) was not analyzed during sequence optimization, it was included in the formatted Nanobodies. The mutation was accepted for all MMP13 lead Nano bodies, except 62C02, for which a 12-fold potency drop was observed. Therefore, it was decided not to incorporate the E1D mutation in the 62C02 building block.

In order to assess potential PTM, forced oxidation and temperature stress was applied on the lead panel. With the exception of C0101517A01 ("517A01") and C0101080A01 ("80A01") no modifications were observed for the lead panel.

Under the forced oxidation and temperature stress conditions, C0101080A01 was prone to Asp-isomerization, and Met-oxidation. However, the degree of isomerization and oxidation differed at the assessed conditions and were just below or above the applied threshold in each case. Eventually, amino acid residues 54-55, 100d-100e, M100j and 101-102 were identified as the residues responsible for the PTM. Notably, all of these residues are located in either the CDR2 or CDR3 regions, and therefore potentially involved in target binding. In order to attempt accommodating the different requirements, NKK libraries were constructed in which these residues were mutated, and subsequently screened in the fluorogenic peptide assay to evaluate possible potency losses as well as screened for biophysical properties (Tm). It was found—unexpectedly—that various positions could be mutated in these CDRs without any significant loss of potency, i.e. retaining more than 80% inhibition.

For the D100dX library, 9 amino acid ("AA") substitutions showed >80% inhibition (E, G, A, P, T, R, M, W and Y).

For the M100jX library, 16 AA substitutions showed >85% inhibition (all except T, C and H).

For the D101X library, 16 AA substitutions showed >90% inhibition (all except for D, F and P).

For the Y102X library, most clones showed >90% inhibition. Hence, it was believed that amino acid position 102 could be mutated into any residue.

The following conserved mutations were particularly preferred: D100dE and M100jL.

An overview of preferred mutations in the CDR regions is provided in the Tables 6.7.1A, 6.7.1B and 6.7.1C below. The amino acid sequences of the CDRs of clone 80A01 were used as reference against which the CDRs of the family members were compared. CDR1 starts at amino acid residue 26, CDR2 starts at amino acid residue 50, CDR3 starts at amino acid residue 95 according to Kabat numbering.

TABLE 6.7.1A (80A01SO CDR1)

| 80A01 SO | CDR1* | | | | | | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| wildtype sequence | G | F | T | L | A | Y | Y | S | I | G |
| mutations | | | | | | | | | | |

*Up to 0 CDR1 mutations in one clone SEQ ID NO: 28

TABLE 6.7.1B (80A01SO CDR2)

| 80A01 SO | CDR2* | | | | | | | | | | |
|---|---|---|---|---|---|---|---|---|---|---|---|
| Kabat numbering | 50 | 51 | 52 | 53 | 54 | 55 | 56 | 57 | 58 | 59 | 60 |
| absolute numbering | 1 | 2 | 3 | 4 | 5 | 6 | 7 | 8 | 9 | 10 | 11 |
| wildtype sequence | C | I | S | S | G | I | D | G | S | T | Y |
| mutations | | | | | | | | | | | |

*Up to 0 CDR2 mutations in one clone SEQ ID NO: 43

TABLE 6.7.1C (80A01SO CDR3)

| 80A01 | CDR3* | | | | | | | | | | | | | | | | | |
|---|---|---|---|---|---|---|---|---|---|---|---|---|---|---|---|---|---|---|
| Kabat numbering | 95 | 96 | 97 | 98 | 99 | 100 | 100a | 100b | 100c | 100d | 100e | 100f | 100g | 100h | 100i | 100j | 101 | 102 |
| absolute numbering | 1 | 2 | 3 | 4 | 5 | 6 | 7 | 8 | 9 | 10 | 11 | 12 | 13 | 14 | 15 | 16 | 17 | 18 |
| wildtype sequence | D | P | S | H | Y | Y | S | E | Y | D | C | G | Y | Y | G | M | D | Y |
| mutations | | | | | | | | | | X1 | | | | | | X2 | X3 | X4 |

*Up to 4 CDR mutations in one clone (SEQ ID NO: 57) (Mutations encompassed in SEQ ID NO: 198)
X1 = E, G, A, P, T, R, M, W, Y
X2 = A, R, N, D, E, Q, Z, G, I, L, K, F, P, S, W, Y and V
X3 = A, R, N, C, E, Q, Z, G, H, I, L, K, M, S, T, W, Y and V
X4 = A, R, N, D, C, E, Q, Z, G, H, I, L, K, M, F, P, S, T, W, and V Under the forced oxidation and temperature stress conditions, C0101517A01 was prone to deamidation. Eventually, amino acid residues N100b and N101 were identified as residues sensitive to deamidation via temperature stress experiments. However, these residues are located in the CDR3 region, and potentially involved in target binding. Thus, knocking out the deamidation sites could have an impact on binding. Also in this case NKK libraries were constructed in which the residues prone to deamidation were mutated, and subsequently screened in the fluorogenic peptide assay to evaluate possible potency losses as well as screened for biophysical properties (Tm).

It was wholly unexpectedly shown that mutating N100b to Q or S or mutating N101 to Q or V abrogated deamidation, but at the same time resulted in a 1-3° C. increased Tm compared to parental Nanobody C0101517A01, while potency was comparable. 4 preferred variants are shown in Table 6.7.1D, which also summarizes the results of the TSA and fluorogenic peptide assay. An overview of preferred mutations in the CDRs is depicted in the tables below.

TABLE 6.7.1D

Data summary 2nd round C0101517A01 sequence optimization variants

| Nanobase ID | mutations | TSA Tm (° C.)@ pH 7 | Fluorogenic peptide assay IC50 (nM) |
|---|---|---|---|
| C010100087 | parental | 78 | 2.5 |
| C010100647 | N100bQ, N101V | 81 | 2.1 |
| C010100648 | N100bQ, N101Q | 81 | 2.8 |
| C010100649 | N100bS, N101Q | 79 | 2 |
| C010100650 | N100bS, N101V | 81 | 2.1 |

An overview of preferred mutations in the CDR regions is provided in the Tables 6.7.1E, 6.7.1F and 6.7.1G below.

The amino acid sequences of the CDRs of clone 517A01 were used as reference against which the CDRs of the other clones were compared. CDR1 starts at amino acid residue 26, CDR2 starts at amino acid residue 50, CDR3 starts at amino acid residue 95 according to Kabat numbering.

TABLE 6.7.1E (517A01SO CDR1)

| 517A01SO | CDR1* | | | | | | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| wildtype sequence | G | R | T | F | S | S | Y | A | M | G |
| mutations | | | | | | | | | | |

*Up to 0 CDR1 mutations in one clone (SEQ ID NO: 26)

TABLE 6.7.1F (517A01SO CDR2)

| 517A01SO | CDR2* | | | | | | | | | |
|---|---|---|---|---|---|---|---|---|---|---|
| Kabat numbering | 50 | 51 | 52 | 53 | 54 | 55 | 56 | 57 | 58 | 59 |
| absolute numbering | 1 | 2 | 3 | 4 | 5 | 6 | 7 | 8 | 9 | 10 |
| wildtype sequence | A | I | S | W | S | G | G | S | T | Y |
| mutations | | | | | | | | | | |

*Up to 0 CDR2 mutations in one clone (SEQ ID NO: 41)

TABLE 6.7.1G (517A01SO CDR3)

| 517A01SO | CDR3* | | | | | | | | | | | | | | | | | | | |
|---|---|---|---|---|---|---|---|---|---|---|---|---|---|---|---|---|---|---|---|---|
| Kabat numbering | 95 | 96 | 97 | 98 | 99 | 100 | 100a | 100b | 100c | 100d | 100e | 100f | 100g | 100h | 100i | 100j | 100k | 100l | 101 | 102 |
| absolute numbering | 1 | 2 | 3 | 4 | 5 | 6 | 7 | 8 | 9 | 10 | 11 | 12 | 13 | 14 | 15 | 16 | 17 | 18 | 19 | 20 |
| wildtype sequence | A | L | A | V | Y | G | P | N | R | Y | R | Y | G | P | V | G | E | Y | N | Y |
| mutations | | | | | | | | Q | | | | | | | | | | | V | |
| | | | | | | | | S | | | | | | | | | | | Q | |

*Up to 2 CDR mutations in one clone (SEQ ID NO: 55) (Mutations encompassed in SEQ ID NOS: 199 and 106)

6.7.2 Humanisation

For humanisation, the Nanobody sequence is made more homologous to the human IGHV3-IGHJ germline consensus sequence. With the exception of the Nanobody "hallmark" residues, specific amino acids in the framework regions that differ between the Nanobody and the human IGHV3-IGHJ germline consensus sequence were altered to the human counterpart in such a way that the protein structure, activity and stability were kept intact.

6.7.3 Pre-Existing Antibodies and Anti-Drug Antibodies

The inventors made an early risk assessment for immunogenicity-related clinical consequences guiding the sequence optimisation strategy. The assessment included both the immunogenic potential of the drug candidate as well as the possible impact of anti-drug antibodies based on the mode of action and the nature of the eventual biotherapeutic molecule. To this, the sequence of the Nanobody was assessed in order to potentially (i) minimise binding of any naturally occurring pre-existing antibodies and (ii) reduce the potential to evoke a treatment-emergent immunogenicity response.

Mutations L11V and V89L were introduced into all MMP13 Nano bodies.

6.7.4 Preferred SO-Clones

In Tables A-1 and A-2, the sequences are depicted based on the Sequence Optimization of the lead panel, in which the sequences were elaborated in view of PTM, humanization and epitopes for potential pre-existing antibodies and anti-drug antibodies.

6.8 Bispecific Constructs

The anti-MMP13 Nanobodies should preferentially be active at the sites of interest, such as the joints, in order to inhibit the cartilage-degrading function of MMP13. Aggrecan is abundantly present in the joints and the main proteoglycan in the extracellular matrix (ECM) accounting for ca. 50% of total protein content. Hence, at least in theory, anchoring the anti-MMP13 Nanobodies to an Aggrecan binder would allow to direct the anti-MMP13 Nanobody to the relevant tissue and improve its retention.

It was set out to combine the anti-MMP13 binders of the present invention with these Aggrecan binders, and test the potency of the resulting bispecific constructs in a human fluorogenic peptide assay and a competition ELISA assay. A variety of bispecific constructs, comprising Aggrecan binder(s) and MMP13 inhibitor(s) were generated and tested as indicated in the tables.

The format and the potency of typical results are depicted in Table 6.8A and Table 6.8B.

TABLE 6.8A

Bispecific MMP13-CAP Nanobodies were tested in the human fluorogenic peptide assay. The potencies were compared with their respective monospecific counterpart. TIMP-2 and MSC2392891A served as internal references in each individual assay. SO: Sequence optimized, excluding pre-Ab mutations. SOvar: Non-final SO variant.

Human fluorogenic peptide assay (MMP13)

| ID | Format | potency |
|---|---|---|
| Bispecific Nano bodies formatted with 62C02 | | |
| C010100689 | 62C02$^{SO}$-114F08$^{SO}$ | 1.91E−09 |
| C010100683 | 62C02$^{SO}$-114F08$^{SO}$-114F08$^{SO}$ | 9.53E−10 |
| C010100692 | 62C02$^{SO}$-604F02$^{SO}$ | 8.28E−10 |

TABLE 6.8A-continued

Bispecific MMP13-CAP Nanobodies were tested in the human fluorogenic peptide assay. The potencies were compared with their respective monospecific counterpart. TIMP-2 and MSC2392891A served as internal references in each individual assay. SO: Sequence optimized, excluding pre-Ab mutations. SOvar: Non-final SO variant.
Human fluorogenic peptide assay (MMP13)

| ID | Format | potency |
|---|---|---|
| | Monospecific reference | |
| C010100280 | 62C02-FLAGHis | 1.01E−09 |
| | Bispecific Nanobodies formatted with 80A01 | |
| C010100687 | 80A01-114F08$^{SO}$ | 1.57E−09 |
| C010100681 | 80A01-114F08$^{SO}$-114F08$^{SO}$ | 1.08E−09 |
| C010100690 | 80A01-604F02$^{SO}$ | 2.42E−09 |
| | Monospecific reference | |
| C010100101 | 80A01-FLAGHis | 3.92E−09 |
| | Bispecific Nanobodies formatted with 517A01-40E09 | |
| C010100729 | 517A01$^{SO}$-40E09$^{SO}$-604F02$^{SO}$-A | 5.41E−10 |
| C010100700 | 517A01$^{SO}$-40E09$^{SOvar}$-114F08$^{SO}$ | 3.18E−11 |
| C010100702 | 517A01$^{SO}$-40E09$^{SOvar}$-114F08$^{SO}$-114F08$^{SO}$ | 7.71E−11 |
| C010100696 | 517A01$^{SO}$-40E09$^{SOvar}$-604F02$^{SO}$ | 1.07E−10 |
| C010100726 | 517A01$^{SO}$-40E09$^{SOvar}$ | 6.71E−11 |
| C010100727 | 517A01$^{SO}$-40E09$^{SO}$ | 1.34E−10 |
| | Monospecific reference | |
| C010100080 | 517A01-40E09-FLAGHis | 4.88E−10 |
| | Bispecific Nanobodies formatted with 529C12 | |
| C010100724 | 529C12$^{SO}$-604F02$^{SO}$-A | 6.97E−10 |
| C010100688 | 529C12$^{SO}$-114F08$^{SO}$ | 9.27E−10 |
| C010100682 | 529C12$^{SO}$-114F08$^{SO}$-114F08$^{SO}$ | 5.51E−10 |
| C010100691 | 529C12$^{SO}$-604F02$^{SO}$ | 4.84E−10 |
| | Monospecific reference | |
| C010100170 | 529C12$^{SO}$-FLAGHis | 6.08E−10 |
| | Internal references | |
| MSC2392891A | | 5.80E−09 |
| hTIMP-2 | | 2.09E−10 |

TABLE 6.8B

Bispecific MMP13-CAP Nanobodies were tested in a competition ELISA assay. The potencies were compared with their respective monospecific counterpart (ALB26 fusion). SO: Sequence optimized (excluding pre-Ab mutations). SOvar: Non-final SO variant.
IC$_{50}$ Competition ELISA (CAP)

| ID | Format | Aggrecan |
|---|---|---|
| | Bispecific Nanobodies formatted with 114F08 | |
| C010100683 | 62C02$^{SO}$-114F08$^{SO}$-114F08$^{SO}$ | 2.3E−10 |
| C010100682 | 529C12$^{SO}$-114F08$^{SO}$-114F08$^{SO}$ | 4.5E−10 |
| C010100702 | 517A01$^{SO}$-40E09$^{SOvar}$-114F08$^{SO}$-114F08$^{SO}$ | 1.2E−10 |
| C010100681 | 80A01-114F08$^{SO}$-114F08$^{SO}$ | 9.9E−10 |
| | Monospecific reference | |
| C010100626 | ALB26-114F08$^{SO}$-114F08$^{SO}$ | 8.7E−10 |
| | Bispecific Nanobodies formatted with 604F02 | |
| C010100725 | 62C02$^{SO}$-604F02$^{SO}$-A | 1.4E−08 |
| C010100724 | 529C12$^{SO}$-604F02$^{SO}$-A | 3.2E−08 |
| C010100729 | 517A01$^{SO}$-40E09$^{SO}$-604F02$^{SO}$-A | 2.1E−08 |
| C010100690 | 80A01-604F02$^{SO}$ | 2.4E−08 |
| | Monospecific reference | |
| C010100637 | ALB26-604F02$^{SO}$ | 1.5E−08 |

The results shown in Table 6.8A and 6.8B demonstrate that combining an Aggrecan binder(s) to MMP13 inhibitor(s) has no negative effect on the potency of the MMP13 inhibitor. Notably, in most instances the lead panel MMP13 inhibitors have the same potency as the non-selective MMP inhibitor TIMP-2.

Example 6.9 In Vivo Rat MMT Model DMOAD Study

In order to further demonstrate the in vivo efficacy of the MMP13 inhibitors fused to a CAP binder of the invention, a surgically induced Medial Meniscal Tear (MMT) model in rats was used. In short, an anti-MMP13 Nanobody was coupled to a CAP binder ("754" or C010100754). Rats were operated in one knee to induce OA-like symptoms. Treatment started 3 days post-surgery by IA injection. Histopathology was performed at day 42 post surgery. Interim and terminal serum samples were taken for exploratory biomarker analysis. The medial and total substantial cartilage degeneration width were determined, as well as the percentage reduction of cartilage degeneration. 20 animals were used per group.

The inhibition of the cartilage degradation in the medial tibia is shown in FIG. 4.

The results demonstrate that the cartilage width was substantially reduced by the MMP13-CAP construct after 42 days compared to the vehicle. These results suggest that
(a) the CAP-moiety has no negative impact on the activity of the anti-MMP13 Nanobody (754) consistent with the results of Example 6.8;
(b) the CAP-moiety enables the retention of the anti-MMP13 Nanobody; and
(c) the anti-MMP13 Nanobody has a positive effect on the cartilage width.

The entire contents of all of the references (including literature references, issued patents, published patent applications, and co-pending patent applications) cited throughout this application are hereby expressly incorporated by reference, in particular for the teaching that is referenced hereinabove.

TABLE A-1

Amino acid sequences of anti-MMP13 inhibitors ("ID" refers to the SEQ ID NO as used herein)

| Name | ID | Sequence |
|---|---|---|
| C0101PMP040E09 | 1 | EVQLVESGGGSVQAGGSLRLSCAASGSTFSRYSMNWYRQAPGKQREFVAGISVGRITNYAVSVRGRFTISRDNAEGTGYLQMNSLKPEDTAVYYCNAGGLQGYWGLGTQVTVSS |
| C0101PMP040E08 | 2 | KVQLVESGGGSVQAGGSLRLSCAASGSTFSRRSMNWYRQAPGKQREFVAGISTGRITNYAVSVKGRFTISRDNAEGTGYLQMNSLKPEDTAVYYCNAGGLQGYWGLGTQVTVSS |
| C0101PMP042A04 | 3 | EVQLVESGRGGSVQAGGSLRLSCAASGSTFSRRSMNWYRQAPGKQREFVAGISTGRITNYAVSVKGRFTISRDNAEGTGYLQMNSLKPEDTAVYYCNAGGLQGYWGLGTQVTVSS |
| C0101PMP040B05 | 4 | EVQLVESGGGSVQTGGSLRLSCAASGSTFSRRSMNWYRQAPGKQREFVAGISTGRITNYAVSVKGRFTISRDNAEGTGYLQMNSLKPEDTAVYYCNAGGLQGYWGLGTQVTVSS |
| C0101PMP042D12 | 5 | EVQLVESGGGSVQAGGSLRLSCAASGSTFSRYSMNWYRQAPGKQREFVAGISVGRITNYAVSVKGRFTISRDNAEGTGYLQMNSLKPEDTAVYYCNAGGLQGYWGLGTQVTVSS |
| C0101PMP042A03 | 6 | EVQLVESRGGSVQAGGSLRLSCAASGSTFSRYSMNWYRQAPGKQREFVAGISVGRITNYAVSVKGRFTISRDNAEGTGYLQMNSLKPEDTAVYYCNAGGLQGYWGLGTQVTVSS |
| C0101PMP024A08 | 7 | EVQLVESGGGSVQAGGSLRLSCAASGSTFSRYSMNWYRQAPGKQREFVAGISVGRITNYAVSVKGRFTISRDNAEGTGFLQMNGLKPEDTAVYYCNAGGLQGYWGLGTQVTVSS |
| C0101PMP040D01 | 8 | EVQLVESGGGSVQAGGSLRLSCAASGSTFSRYSMNWYRQAPRKQREFVAGISTARITHYAVSVKGRFTISRDNAEGTGYLQMNSLKPEDTAVYYCNAGGLQGSWGLGTLVTVSS |
| C0101PMP529C12 | 9 | DVQLVESGGGLVQPGGSLRLSCVASGSIFSINAMGWYRQAPGKQRELVAAISSGGSTYYADSVKGRFTISRDNSKNTVYLQMNSLRPEDTAVYYCNAAVDASRGLPYELYYYWGQGTLVTVSS |
| 529C12SO | 109 | EVQLVESGGGLVQPGGSLRLSCAASGSIFSINAMGWYRQAPGKQRELVAAISSGGSTYYADSVKGRFTISRDNSKNTVYLQMNSLRPEDTAVYYCNAAVDASRGLPYELYYYWGQGTLVTVSS |
| C0101PMP517A01 | 10 | DVQLVESGGGLVQPGGSLRLSCAASGRTFSSYAMGWFRQAPGKEREFVAAISWSGSTYYADSVKGRFTISRDNSKNTVYLQMNSLRPEDTAVYYCTAALAVYGPNRYRYGPVGEYNYWGQGTLVTVSS |
| 517A01SO | 110 | DVQLVESGGGLVQPGGSLRLSCAASGRTFSSYAMGWFRQAPGKEREFVAAISWSGSTYYADSVKGRFTISRDNSKNTVYLQMNSLRPEDTAVYYCTAALAVYGPSRYRYGPVGEYQYWGQGTLVTVSS |
| C0101PMP062C02 | 11 | EVQLVESGGALVRPGGSLRLSCAASGFAFSAAYMSWVRQAPGRGLEMVSSISDDGSKTYYADSVKGRFTISRDNAKNTVYLQMNNLKPDDTAVYYCNTGYGATTTRPGRYWGQGTQVTVSS |
| 62C02SO | 111 | EVQLVESGGGLVQPGGSLRLSCAASGFAFSAAYMSWVRQAPGKGLEMVSSISDDGSKTYYADSVKGRFTISRDNSKNTVYLQMNSLRPEDTAVYYCNTGYGATTTRPGRYWGQGTLVTVSS |
| C0101PMP080A01 | 12 | EVQLVESGGGLVQPGGSLRLSCAASGFTLAYYSIGWFRQAPGKEREGVSCISSGIDGSTYYADSVKGRFTISRDNAKNTMYLQMNNLKPEDTGVYYCAADPSHYYSEYDCGYYGMDYWGKGTLVTVSS |
| 80A01SO | 112 | EVQLVESGGGLVQPGGSLRLSCAASGFTLAYYSIGWFRQAPGKEREGVSCISSGIDGSTYYADSVKGRFTISRDNAKNTLYLQMNSLRPEDTAVYYCAADPSHYSEYECGYYGMDYWGQGTLVTVSS |

TABLE A-1-continued

Amino acid sequences of anti-MMP13 inhibitors ("ID" refers to the SEQ ID NO as used herein)

| Name | ID | Sequence |
|---|---|---|
| C0101PMP516G08 | 13 | DVQLVESGGGLVQPGGSLRLSCAGSGSIFRINVMAWYRQAPGKQRELVAAITSGGTNYADSVKGRFTISRDNSKNTVYLQMNSLRPEDTAVYYCYADIGWPYVLDYDFWGQGTLVTVSS |
| C0101PMP529G11 | 14 | DVQLVESGGGLVQPGGSLRLSCAASGSIFRINAMGWYRQAPGKQRELVAAIISGGTTYYADSVKGRFTISRDNSKNTVYLQMNSLRPEDTAVYYCYADIGWPYVLDYDFWGQGTLVTVSS |
| C0101PMP513C04 | 15 | DVQLVESGGGLVQPGGSLRLSCAASGRTFSRYVMGWFRQAPGKEREFVAAINWSSGSTYYADSVKGRFTISRDNSKNTVYLQMNSLRPEDTAVYYCAADRRVYDTYPNLRGYDYWGQGTLVTVSS |
| C0101PMP521F02 | 16 | DVQLVESGGGLVQPGGSLRLSCVASGLTFSSYAMGWFRQAPGKEREFVAAISWSGGRTYYADSVKGRFTISRDNSKNTVYLQMNSLRPEDTAVYYCTAARGPGSVGPSEEYNYWGQGTLVTVSS |
| C0101PMP519E04 | 17 | DVQLVESGGGLVQPGGSLRLSCVASGPTFSDYAMGWFRQAPGKEREFVAAISWSGGSTYYADSVKGRFTISRDNSKNTVYLQMNSLRPEDTAVYYCTAARGGGYRASGPLSEYNYWGQGTLVTVSS |
| C0101PMP520B06 | 18 | DVQLVESGGGLVQPGGSLRLSCAASGRTFSSYAMGWFRQAPGKEREFVAAISWGGGSTYYSDSVKGRFTISRDNSKNTVYLQMNSLRPEDTAVYYCTAALGSTGSGSTPVPEYRYWGQGTLVTVSS |
| C0101PMP520C04 | 19 | DVQLVESGGGLVQPGGSLRLSCAASGRTFSSYAMGWFRQAPGKEREFVAAISWSGGSTYYSDSVKGRFTISRDNSKNTVYLQMNSLRPEDTAVYYCTAARGGVAGTDGPLGDYNYWGQGTLVTVSS |
| C0101PMP525C04 | 20 | DVQLVESGGGLVQPGGSLRLSCAGSGSIFSGNAMGWYRQAPGKQRELVAAITSGGVTNYADSVKGRFTISRDNSKNTVYLQMNSLRPEDTAVYYCAADIRYPTGLVGDYWGQGTLVTVSS |
| C0101PMP063F01 | 21 | EVQLVESEGGTVEPGSGLVQPGGSLRLSCCSASTGIFRINTMGWHRQAPGKQRDLVATFTSDDNTKYADSVKGRFTISRDNAENTVYLQMNDLKPEDTAVYYCHATTVMYDSNSPDYWGQGTQVTVSS |
| C0101PMP059F06 | 22 | EVQLVESEGGTVEPGSLRLACAAPGPGIRTNFMAWYRQAPEKEREMVASISRDGSTHYADSVKGRFTISSDNATSTFYLQMNSLQVEDTAVYYCATDPHILHNDRAGAFLVEDYDHWGQGTQVTVSS |
| C0101002S0 80(62C02S0-FLAGHis) | 194 | EVQLVESGGGLVQPGGSLRLSCAASGFAFSAAYMSWVRQAPGKGLEMVSSISDDGSKTYYADSVKGRFTISRDNAKNTMYLQMNNLKPEDTGVYYCAADPSHYSEYDCGYYGMDYWGKGTLVTVSSSAAADYKDHDGDYKDHDIDYKDDDDKGAAHHHHHH |
| C0101001S01 80A01-FLAGHis | 195 | EVQLVESGGGLVQPGGSLRLSCAASGPTLAYYSIGWFRQAPGKEREGVSCISSGIDGSTYYADSVKGRFTISRDNSKNTVYLQMNSLRPEDTAVYYCAADPSHYSEYDCGYYGMDYWGKGTLVTVSSSAAADYKDHDGDYKDHDIDYKDDDDKGAAHHHHHH |
| C0101000080 517A01-40E09-FLAGHis | 196 | EVQLVESGGGLVQPGGSLRLSCAASGRTFSSYAMGWFRQAPGKEREFVAAISWSGGSTYYADSVKGRFTISRDNSKNTVYLQMNSLRPEDTAVYYCTAALAVYGPNRYRYGPVGEYNYWGKGTLVTVSSGGGGSGGGGSGGGGSEVQLVESGGSVQAGGSLRLSCAASGSTPSRYSMNWYRQAPGKQREFVAGISVGRITNYAVSVRGRFTISRDNAEGTGYLQMNSLKPEDTAVYYCNAGGLQGYWGLGTLVTVSSGAADYKDHDGDYKDHDIDYKDDDDKGAAHHHHHH |
| C0101000170 529C12S0-FLAGHis | 197 | EVQLVESGGGLVQPGGSLRLSCAASGSIFSINAMGWYRQAPGKQRELVAAISSGGSTYYADSVKGRFTISRDNSKNTVYLQMNSLRPEDTAVYYCNAAVDASRGLPYELYYYWGQGTLVTVSSSAAADYKDHDGDYKDHDIDYKDDDDKGAAHHHHHH |

TABLE A-2

Sequences for CDRs and frameworks, plus preferred combinations as provided in formula I, namely FR1-CDR1-FR2-CDR2-FR3-CDR3-FR4 (the following terms: "ID" refers to the given SEQ ID NO; the first column refers to ID of the whole SVD)

| ID | Construct | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 1 | 40E09 | 67 | EVQLVESGGGSVQAGGSLRLSCAAS | 23 | GSTFSRYSMN | 80 | WYRQAPGKQREFVA | 37 | GISVGRITN | 88 | YAVSVRGRFTISRDNAEGTGYLQMNSLKPEDTAVYYCNA | 52 | GGLQGY | 100 | WGLGTQVTVSS |
| 2 | 40E08 | 68 | KVQLVESGGGSVQAGGSLRLSCAAS | 24 | GSTFSRRSMN | 80 | WYRQAPGKQREFVA | 38 | GISTGRITN | 89 | YAVSVKGRFTISRDNAEGTGYLQMNSLKPEDTAVYYCNA | 52 | GGLQGY | 100 | WGLGTQVTVSS |
| 3 | 42A04 | 69 | EVQLVESGRGGSVQAGGSLRLSCAAS | 24 | GSTFSRRSMN | 80 | WYRQAPGKQREFVA | 38 | GISTGRITN | 89 | YAVSVKGRFTISRDNAEGTGYLQMNSLKPEDTAVYYCNA | 52 | GGLQGY | 100 | WGLGTQVTVSS |
| 4 | 40B05 | 70 | EVQLVESGGGSVTGGSLRLSCAAS | 24 | GSTFSRRSMN | 80 | WYRQAPGKQREFVA | 38 | GISTGRITN | 89 | YAVSVKGRFTISRDNAEGTGYLQMNSLKPEDTAVYYCNA | 52 | GGLQGY | 100 | WGLGTQVTVSS |
| 5 | 42D12 | 71 | EVQLVESEGGSVQAGGSLRLSCAAS | 23 | GSTFSRYSMN | 80 | WYRQAPGKQREFVA | 37 | GISVGRITN | 88 | YAVSVRGRFTISRDNAEGTGYLQMNSLKPEDTAVYYCNA | 52 | GGLQGY | 100 | WGLGTQVTVSS |
| 6 | 42A03 | 72 | EVQLVESRGGSVQAGGSLRLSCAAS | 23 | GSTFSRYSMN | 80 | WYRQAPGKQREFVA | 37 | GISVGRITN | 89 | YAVSVKGRFTISRDNAEGTGYLQMNSLKPEDTAVYYCNA | 52 | GGLQGY | 100 | WGLGTQVTVSS |
| 7 | 24A08 | 67 | EVQLVESGGGSVQAGGSLRLSCAAS | 23 | GSTFSRYSMN | 80 | WYRQAPGKQREFVA | 37 | GISVGRITN | 90 | YAVSVKGRFTISRDNAEGTGFLQMNGLKPEDTAVYYCNA | 52 | GGLQGY | 100 | WGLGTQVTVSS |
| 8 | 40D01 | 67 | EVQLVESGGGSVQAGGSLRLSCAAS | 23 | GSTFSRYSMN | 81 | WYRQAPRKQREFVA | 39 | GISTARTTH | 89 | YAVSVKGRFTISRDNAEGTGYLQMNSLKPEDTAVYYCNA | 53 | GGLQGS | 100 | WGLGTQVTVSS |
| 9 | 529C12 | 73 | DVQLVESGGGLVQPGGSLRLSCVAS | 25 | GSIFSINAMG | 82 | WYRQAPGKQRELVA | 40 | AISSGGSTY | 91 | YADSVKGRFTISRDETSKITTVYLQMNSLRPEDTAVYYCNA | 54 | AVDASRGLPYELYYY | 102 | WGQGTLVTVSS |
| 109 | 529C12 SO | 76 | EVQLVESGGGLVQPGGSLRLSCAAS | 25 | GSIESINAMG | 82 | WYRQAPGKQRELVA | 40 | AISSGGSTY | 91 | YADSVKGRFTISRDITSKETTVYLQMNSLRPEDTAVYYCNA | 54 | AVDASRGLPYELYYY | 102 | WGQGTLVTVSS |
| 10 | 517A01 | 74 | DVQLVESGGGLVQPGGSLRLSCAAS | 26 | GRTFSSYAMG | 83 | WFRQAPGKEREFVA | 41 | AISWGGSTY | 92 | YADSVKGRFTISRDNSKNTVYLQMNSLRPEDTAVYYCTA | 55 | ALAVYGPNRYRYGPVGEYNY | 102 | WGQGTLVTVSS |
| 110 | 517A01 SO | 74 | DVQLVESGGGLVQPGGSLRLSCAAS | 26 | GRTFSSYAMG | 83 | WFRQAPGKEREFVA | 41 | AISWGGSTY | 92 | YADSVKGRFTISRDNSKNTVYLQMNSLRPEDTAVYYCTA | 106 | ALAVYGPSRYRYGPVGEYQY | 102 | WGQGTLVTVSS |
| 11 | 62C02 | 75 | EVQLVESGGALVRPGGSLRLSCAAS | 27 | GFAFSAAYMS | 84 | WVRQAPGRGLEWVS | 42 | SISDDGSKTY | 93 | YADSVKGRFTISRDNAKNTVYLQMNLKFDDTAVYYCNT | 56 | GYGATTTRPGRY | 103 | WGQGTQVTVSS |
| 111 | 62C02 SO | 76 | EVQLVESGGGLVQPGGSLRLSCAAS | 27 | GFAFSAAYMS | 108 | WVRQAPGKGLEWVS | 42 | SISDDGSKTY | 113 | YADSVKGRFTISRDNSKNTVYLQMNSLRPEDTAVYYCNT | 56 | GYGATTTRPGRY | 102 | WGQGTLVTVSS |
| 12 | 80A01 | 76 | EVQLVESGGGLVQPGGSLRLSCAAS | 28 | GFTLAYYSIG | 85 | WFRQAPGKEREGVS | 43 | CISSGIDGSTY | 94 | YADSVKGRFTISRDNAKNTMYLQMNNLKPEDTGVYYCAA | 57 | DPSHYYSEYDCGYYGMDY | 104 | WGKGTLVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO; the first column refers to ID of the whole SVD)

| ID | Con-struct | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 112 | 80A01SO | 76 | EVQLVESGGGLVQPGGSLRLSCAAS | 28 | GFTLAYYSIG | 85 | WFRQAPGKEREGVS | 43 | CISSGIDGSTY | 114 | YADSVKGRFTISRDNSKNTLYLQMNSLRPEDTAVYYCAA | 107 | DPSHYSEYECGYYGMDY | 102 | WGQGTLVTVSS |
| 13 | 516G08 | 77 | DVQLVESGGGLVQPGGSLRLSCAGS | 29 | GSIFRINVMA | 82 | WYRQAPGKQRELVA | 44 | AITSGGTTN | 95 | YADSVKGRFTISRDNSKNTVYLQMNSLRPEDTAVYYCYA | 58 | DIGWPYVLDYDF | 102 | WGQGTLVTVSS |
| 14 | 529G11 | 74 | DVQLVESGGGLVQPGGSLRLSCAAS | 30 | GSIFRINAMG | 82 | WYRQAPGKQRELVA | 45 | AIISGGTTY | 95 | YADSVKGRFTISRDNSKNTVYLQMNSLRPEDTAVYYCYA | 58 | DIGWPYVLDYDF | 102 | WGQGTLVTVSS |
| 15 | 513C04 | 74 | DVQLVESGGGLVQPGGSLRLSCAAS | 31 | GRTFSRYVMG | 83 | WFRQAPGKEREFVA | 46 | AINWSSGSTY | 96 | YADSVKGRFTISRDNSKNTVYLQMNSLRPEDTAVYYCAA | 59 | DRRVYYDTYPNLRGYDY | 102 | WGQGTLVTVSS |
| 16 | 521F02 | 73 | DVQLVESGGGLVQPGGSLRLSCVAS | 32 | GLTFSSYAMG | 83 | WFRQAPGKEREFVA | 47 | AISWSGGRTY | 92 | YADSVKGRFTISRDNSKNTVYLQMNSLRPEDTAVYYCTA | 60 | ARGPGSVGPSEEYNY | 102 | WGQGTLVTVSS |
| 17 | 519E04 | 73 | DVQLVESGGGLVQPGGSLRLSCVAS | 33 | GPTFSDYAMG | 83 | WFRQAPGKEREFVA | 41 | AISWGGSTY | 92 | YADSVKGRFTISRDNSKNTVYLQMNSLRPEDTAVYYCTA | 61 | ARGGYRASGGPLSEYNY | 102 | WGQGTLVTVSS |
| 18 | 520B06 | 74 | DVQLVESGGGLVQPGGSLRLSCAAS | 26 | GRTFSSYAMG | 83 | WFRQAPGKEREFVA | 48 | AISWGGGSTY | 97 | YSDSVKGRFTISRDNSKNTVYLQMNSLRPEDTAVYYCTA | 62 | ALGSTGSGSTPVPEYRY | 102 | WGQGTLVTVSS |
| 19 | 520C04 | 74 | DVQLVESGGGLVQPGGSLRLSCAAS | 26 | GRTFSSYAMG | 83 | WFRQAPGKEREFVA | 41 | AISWSGGSTY | 97 | YSDSVKGRFTISRDNSKNTVYLQMNSLRPEDTAVYYCTA | 63 | ARGGVAGTDGPLGDYETY | 102 | WGQGTLVTVSS |
| 20 | 525C04 | 77 | DVQLVESGGGLVQPGGSLRLSCAGS | 34 | GSIFSGNAMG | 82 | WYRQAPGKQRELVA | 49 | AITSGGVTN | 96 | YADSVKGRFTISRDNSKNTVYLQMNSLRPEDTAVYYCAA | 64 | DIRYPTGLVGDY | 102 | WGQGTLVTVSS |
| 21 | 63F01 | 78 | EVQLVESGGGLVQPGGSLRLSCSAS | 35 | TGIFRINTMG | 86 | WHRQAPGKQRDLVA | 50 | TFTSDDNTK | 98 | YADSVKGRFTISRDNAENTVYLQMNDLKPEDTAVYYCHA | 65 | TTVMYDSNSPDY | 103 | WGQGTQVTVSS |
| 22 | 59F06 | 79 | EVQLVESEGGTVEFGESLRLACAAP | 36 | GPGIRTNFMA | 87 | WYRQAPEKEREMVA | 51 | SISRDGSTH | 99 | YADSVKGRFTISSDNATSTFYLQMNSLQVEDTAVYYCAT | 66 | DPHILHNDRAGAFLVEDYDH | 103 | WGQGTQVTVSS |

TABLE A-3

Amino acid sequences of anti-MMP13 constructs ("ID" refers to the SEQ ID NO as used herein)

| Name | ID | Sequence |
|---|---|---|
| 517A01-40E09 clone 80 | 160 | EVQLVESGGGLVQPGGSLRLSCAASGTFSSYAMGWFRQAPGKEREFVAAISWSGGSTYYADSVKGRFTISRDNAEGTGYLQMNSLRPEDTAVYYCTAALAVYGPNRY RYGPVGEYNYWGQGTLVTVSSGGGGSGGGGSGGGGSGGGGSEVQLVESGGGSVQAGGSLRLSCAASGSTFSRYSMNWYRQAPGKQREFVAGIS VGRITNYAVSVRGRFTISRDNSKNTVYLQMNSLRPEDTAVYYCNAAPGKQREFVAGISVGRITNYAV |
| 516G08-40E09 clone 76 | 161 | EVQLVESGGGLVQPGGSLRLSCAGSGSIFRINVMAWYRQAPGKQRELVAAITSGGTTNYADSVKGRFTISRDNSKNTVYLQMNSLRPEDTAVYYCYADIGWPYVLDYD FWGQGTLVTVSSGGGGSGGGGSGGGGSGGGGSEVQLVESGGGSVQAGGSLRLSCAASGSTFSRYSMNWYRQAPGKQREFVAGISVGRITNYAV SVRGRFTISRDNAEGTGYLQMNSLRPEDTAVYYCNAGGLQGYWGLGTLVTVSS |
| 62C02-40E09 clone 72 | 162 | EVQLVESGGALVRPGGSLRLSCAASGFAFSAAYMSWVRQAPGRGLEWVSSISDDGSKTYYADSVKGRFTISRDNAKNTVVLQMNNLKPDDTAVYYCNTGYGATTIRPG RYWGQGTLVTVSSGGGGSGGGGSGGGGSGGGGSEVQLVESGGGSVQAGGSLRLSCAASGSTFSRYSMNWYRQAPGKQREFVAGISVGRITNYA VSVRGRFTISRDNAEGTGYLQMNSLRPEDTAVYYCNAGGLQGYWGLGTLVTVSS |
| 40E09-517A01 clone 71 | 163 | EVQLVESGGGSVQAGGSLRLSCAASGSTFSRYSMNWYRQAPGKQREFVAGISVGRITNYAVSVRGRFTISRDNAEGTGYLQMNSLKPEDTAVYYCNAGGLQGYWGLGT LVTVSSGGGGSGGGGSGGGGSGGGGSEVQLVESGGGLVQPGGSLRLSCAASGRTFSSYAMGWFRQAPGKEREFVAAISWSGGSTYYADSVKGR FTISRDNSKNTVYLQMNSLRPEDTAVYYCTAALAVYGPNRYRYGPVGEYNYWGQGTLVTVSS |
| 40E09-516G08 clone 70 | 164 | EVQLVESGGGSVQAGGSLRLSCAASGSTFSRYSMNWYRQAPGKQREFVAGISVGRITNYAVSVRGRFTISRDNAEGTGYLQMNSLKPEDTAVYYCNAGGLQGYWGLGT LVTVSSGGGGSGGGGSGGGGSGGGGSEVQLVESGGGLVQPGGSLRLSCAGSGSIFRINVMAWYRQAPGKQRELVAAITSGGTTNYADSVKGRF TISRDNSKNTVYLQMNSLRPEDTAVYYCYADIGWPYVLDYDFWGQGTLVTVSS |
| 40E09-62C02 clone 69 | 165 | EVQLVESGGGSVQAGGSLRLSCAASGSTFSRYSMNWYRQAPGKQREFVAGISVGRITNYAVSVRGRFTISRDNAEGTGYLQMNSLKPEDTAVYYCNAGGLQGYWGLGT LVTVSSGGGGSGGGGSGGGGSGGGGSEVQLVESGGALVRPGGSLRLSCAASGFAFSAAYMSWVRQAPGRGLEWVSSISDDGSKTYYADSVKGR FTISRDNAKNTVVLQMNNLKPDDTAVYYCNTGYGATTTRPGRYWGQGTLVTVSS |

TABLE B

| ID | Amino acid sequences |
|---|---|
| Human Aggrecan | 105 | MTTLLWVFVTLRVITAAVTVETSDHDNSLSVSIPQPSPLRVLLGTSLITPCYFIDPMHPVTTAPSTAPLAPRIKWSRVSKEKEVVLLVATEGRVRV NSAYQDKVSLPNYPAIPSDATLEVQSLRSNDSGVVRCEVMHGIEDSEATLEVVVKGIVPHYRAISTRYTLDFDRAQRACLQNSAIIATPEQLQAAY EDGFHQCDAGWLADQTVRYPIHTPREGCYGKDEFPGVRTYGIRDTNETYDVYCFAEEMEGEVFYATSPEKFTFQEAANECRRLGARLATTGHVYL AWQAGMDMCSAGWLADRSVRYPISKARPNCGGNLLGVRTYVYHANQTGYPDPSSRYDAICYTGEDFVDIPENFFGVGGEDITVQTVTWPDMELPL PRNITEGEARGSVILITVKPIFEVSPSPLEPEEPFTFAPEIGATAPAEVENETGEATRPWGFPTPGLGPATAFTSEDLVQVTAVPGQPHLPGGVVF HYRPGPTRYSLTFEEAQQACPGTGAVIASPEQLQAAYEAGYEQCDAGWLRDQTVRYPIVSPRTPCVGDKDSSPGVRTYGVRPSTETYDVYCFVDRL EGEVFFATRLEQFTFQEALEFCESHNATATTGQLYAAWSRGLDKCYAGWLADGSLRYPITVPPRACGDKPGVRTVYLYPNQTGLPDPLSRHHAFC FRGISAVPSPGEEGGTPTSPSGEVNETTAILEFTTEPENQTEWEPAYTPVGTSPLPGLLPTWPPTGAETE ESTEGPSATEVPSASEEPSPSEVPPSEEPSPSEEPPSVRPFPSVELFPSEEPPSKEPSPSEEPSASEEPYTPSPPEPSWTELPSSGEESGAPD VSGDFTGSGDVSGHLDFSQQLSGDRASGLPSGDLDSSGLTSTVGSGLTVESGLPSGEVLETTAPGVEDISGLPSGEVLETTAAPGVEDISGLPSGEVL VLETSASGVDLSGLPSGEVLETTAAPGVEDISGLPSGEVLETAAPGVEDISLPSGDERIEWPSTPTVGELPSGAELLEGSASGVGDLSGLPSGEV LETTAPGVEDISGLPSGEVLETAAPGVEDISGLPSGEVLETTAAPGVEDISGLPSGEVLETAAPGVEDISGLPSGEVLETAAPGVEDISGLPSGEVL ETAAPGVEDISGLPSGLPSGGEVLETAAPGVEDISGLPSGEVLETTAPGVEDISGLPSGEVLETTAPGVEEISGLPSGEVLET TAAPGVEDISGLPSGLPSGEVLETAAPGVEDISGLPSGEVLETTAPGVEDISASGFDLSASGFGDLSGVPSGGEGL STSAVGDLSGLPSGGEVLEISVSGVEDISGLPSGEVVETSASGIEDVSELPSGEGLETSASGVEDISLRLPSGEVLEISASGFGDLSGVPSGGEGL ETSASEVGTDLSGLPSGREGLETSASGAEDLSGLPSGEVLETAPGVEDISLPSGQAPETSGLSGQPPSGVDLGSGQAPETSGLSGQPPSGLPDFSG LPSGFPTVSLVDSTVLVEVVTASTASELEGRGTIGISGAGEISGLPSSELDISGRASGLPSGTELSGQASGSPDVSGEIPGLFGVSGQPSGFPDTSG ETSGVTELSLSSGQPGVSGEASGVLYGTSQPFGITDLSGETSGVPDLSGQPSGLPGFSGATSGVPDLVSGTTSGSGESSGITFVDTSLVEVAPTT FKEEBGLGSVELSGLPSGEADLSGKSGMVDVSGQPSGTVDSSGFTSQTPEFSGLPSGIAEVSGESSRAEIGSSLLPSGAYYGSGTPSSFPTVSLVDR TLVESVTQAPTAQEAGEGPSGIILELSGAHSGAPDMSGEHSGFLDSGLQSGLIEPSGEPPGTPYFSGDFASTNVSGESSVAMGTSGEASGLPEVT LITSEFVEGVTEPTISQELGQRPPVTHTPQLFESSGKVSTAGDISGATPVLPGSGVEVSVPESSSETSAYPEAGFGASAAPEASREDSGSPDLSE TTSAFHEANLERSSGLGVSGSTLFTPQEGEASAAPEVSGESTTTSDVGTEAPGLPSATPTASGDRTEISGDLSGHTSQLGVVISTSIPESEMTQQTQ RPAETHLEIESSSLLYSGEETHTVETATSPTDASIPASPEWKRESESTAAAPARSCAEEPCGAGTCKETEGHVICLCPPGYTGEHCNIDQEVCEEG WNKYQGHCYRHFPDRETWDAERRCREQQSHLSSIVTPEEQEFVNNAQDYQWIGLNDRTIEGDFRWSDGHPMQFENWRPNQPDNFFAAGEDCVVM IWHEKGEWNDVPCNYHLPFTCKKGTVACGEPPVVEHARTFGQKDRYEINSLVRYQCTEGFVQRHMPTIRCQPSGHWEEPRITCTDATTYKRRLQK RSSRHPRRSRPSTAH |
| MMP13 human NP_002418.1 | 115 | MHPGVLAAFLFLSWTHCRALPLPSGGDEDDLSEEDLQFAERYLRSYYHPTNLAGILKENAASSMTERLREMQSFFGLEVTGKLDDNTLDVMKKPRC GVPDVGEYNVFPRTLKWSKMNLTYRIVNYTPDMTHSEVEKAFKKAFKVWSDVTPLNFTRLHDGIADIMISFGIKEHGDFYPFDGPSGLLAHAFPPG PNYGGDAHFDDDETWTSSSKGYNLFLVAAHEFGHSLGLDHSKDPGALMFPIYTYTGKSHFMLPDDDVQGIQSLYGPGDEDPNPKHPKTPDKCDPSL SLDAITSLRGETMIFKDRFFWRLHPQQVDAELFLTKSFWPELPNRIDAAYEHPSHDLIFIFRGRKFWALNGYDILEGYPKKISELGLPKEVKKISA AVHFEDTGKTLLFSGNQVWRYDDTNHIMDKYDYPRLIEEDPPGIGDKVDAVYEKNGYIYFFNGPIQFEYSIWSNRIVRVMPANSILWC |
| MMP13 P. troglodytes | 116 | MHPGVLAAFLFLSWAHCRALPLPSGGDEDDLSEEDLQFAERYLRSYYHPTNLAGILKENAASSMTERLREMQSFFGLEVTGKLDDNTLDVMKKPRC GVPDVGEYNVFPRTLKWSKMNLTYRIVNYTPDMTHSEVEKAFKKAFKVWSDVTPLNFTRLHDGIADIMSFGIKEHGDFYPFDGPSGLLAHAFPPG PNYGGDAHFDDDETWTSSSKGYNLFLVAAHEFGHSLGLDHSKDPGALMFPIYTYTGKSHFMLPDDDVQGIQSLYGPGDEDPNPKHPKTPDKCDPSL SLDAITSLRGETMIFKDRFFWRLHPQQVDAELFLTKSFWPELPNRIDAAYEHPSHDLIFIFRGRKFWALNGYDILEGYPKKISELGLPKEVKKISA TVHFEDTGKTLLFSGNQVWRYDDTNHIMDKYDYPRLIEEFPGIGDKVDAVYEKNGYIYFFNGPIQFEYSIWSNRIVRVMPANSILWC |
| MMP13 M. mulatta | 117 | MHPGVLAAFLFLSWTHCRALPLPSGGDEDDLSEEDLQFAERYLRSYYYPTNLAGILKENAASSMTDRLREMQSFFGLEVTGKLDDNTLDVMKKPRC GVPDVGEYNVFPRTLKWSKMNLTYRIVNYTPDMTHSEVEKAFKKAFKVWSDVTPLNFTRLHDGIADIMLSFGTKEHGDFYPFDGPSGLLAHAFPPG PNYGGDAHFDDDETWTSSSKGYNLFLVAAHEFGHSLGLDHSKDPGALMFPIYTYTGKSHFMLPDDDVQGIQSLYGPGDEDPNPKHPKTPDKCDPSL SLDAITSLRGETMIFKDRFFWRLHPQQVDAELFLTKSFWPELPNRIDAAYEHPSHDLIFIFRGRKFWALNGYDILEGYPKKISELGFPKEVKKISA AVHFEDTGKTLLFSGNQVWRYDDTNHIMDKYDYPRLIEEDPPGIGDKVDAVYEKNGYIYFFNGPIQFEYSIWSNRIVRVMPANSILWC |
| MMP13 C. lupus | 118 | MSHHCRSIKVKLVWERQQAPGTTKMLPGILAAFLCLSWTQCWSLPLPSGDGDDLSEEDFQLAERYLKSYYYPLNPAGILKKSAAGSVADRLREM QSFFGLEVTGKLDDNTLDIMKKPRCGVPDVGEYNVFPRTLKWSKTNLTYRIVNYTPDLTHSEVEKAFKVWSDVTPLNFTRLHDGTADIMLSF GTKEHGDFYPFDGPSGLLAHAFPPGPNYGGDAHFDDETWTSSSKGYNLFLVAAHEFGHSLGLDHSKDPGALMFPIYTYTGKSHFMLPDDDVQGIQ SLYGPGDEDPNPRHFPKTPDKCDPSLSLDAITSLRGETMIFKDRFFWRLHPQQVDAELFLTKSFWPELPNRIDAAYEHPSRDLIFIFRGRKYWALNG |

TABLE B-continued

| | ID | Amino acid sequences |
|---|---|---|
| | | YDILEGYPQKISELGFPKEVKKISAAVHFEDTGKTLFFSGNQVWSYDDTNQIMDKYPRLIEEDFPGIGDKVDAVYEKNGYIYFFNGPIQFEYNIW SKRIVRVMPANSLLWC |
| MMP13 B. taurus | 119 | MHPRVLAGFLFFSWTACWSLPLPSDGDSEDLSEEDFQFAESYLKSYYPQNPAGILKKTAASSVIDRLREMQSFFGLEVTGRLDDNTLDIMKKPRC GVPDVGEYNVFPRTLKWSKMNLTYRIVNYTPDLTHSEVEKAFRKAFKVWSDVTPLNFTRIHNGTADIMISFGTKEHGDFYPDGPSLLAHAFPPG PNYGGDAHFDDDETWTSSSKGYNLFLVAAHEFGHSLGLDHSKDPGALMPPIYTYTGKSHFMLPDDDVQGIQSLYGPGDEDPYSKHPKTPDKCDPSL SLDAITSLRGETLIFKDRFFWRLHPQQVEAELFLTKSFGPELPNRIDAAYEHPSHDLIFIFRGRKFWALSGYDILEDYPKKISELGFPKHVKKISA ALHFEDSGKTLFFSENQVWSYDDTNHVMDKYPRLIEEVFPGIGDKVDAVYQKNGYIYFFNGPIQFEYSIWSNRIVRVMTTNSLLWC |
| MMP13 M. musculus | 120 | MHSAILATFLLSWTPCWSLPLPYGDDDDDLSEEDLVFAEHYLKSYYHPATLAGILKKSTVTSTVDRLREMQSFFGLEVTGKLDDPTLDIMRKPR CGVPDVGEYNVFPRTLKWSQTNLTYRIVNYTPDMSHSEVEKAFRKAFKVWSDVTPLNFTRIYDGTADIMISFGTKEHGDFYPFDGPSGLLAHAFPP GPNYGGDAHFDDDETWTSSSKGYNLFIVAAHELGHSLGLDHSKDPGALMPPIYTYTGKSHFMLPDDDVQGIQFLYGPGDEDPNPKHPKTPEKCDPA LSLDAITSLRGETMIFRDRFFWRLHPQQVEAELFLTKSFWPELPNHVDAAYEHPSRDLMFIFRGRKFWALNGYDILEGYPRKILGFPKEVKRLS AAVHFENTGKTLFFSENHVWSYDDVNQTMDKDYPRLIEEEFPGIGNKVDAVYEKNGYIYFFNGPIQFEYSIWSNRIVRVMPTNSILLWC |
| MMP13 R. norvegicus | 121 | MHSAILATFLLSWTHCWSLPLPYGDDDDDLSEEDLEFAEHYLKSYYHPVTLAGILKKSTVTSTVDRLREMQSFFGLDVTGKLDDPTLDIMRKPR CGVPDVGEYNVFPRTLKWSQTNLTYRIVNYTPDISHSEVEKAFRKAFKVWSDVTPLNFTRIHDGTADIMISFGTKEHGDFYPFDGPSGLLAHAFPP GPNLGGDAHFDDDETWTSSSKGYNLFIVAAHELGHSLGLDHSKDPGALMPPIYTYTGKSHFMLPDDDVQGIQSLYGPGDEDPNPKHPKTPEKCDPA LSLDAITSLRGETMIFKDRFFWRLHPQQVEPELFLTKSFWPELPNHVDAAYEHPSRDLMFIFRGRKFWALNGYDIMEGYPRKISDLGFPKEVKRLS AAVHFEDTGKTLFFSGNHVWSYDDANQTMDKDYPRLIEEEFPGIGDKVDAVYEKNGYIYFFNGPIQFEYSIWSNRIVRVMPTNSLLWC |
| MMP13 G. gallus | 122 | MQPRLSAVFFLLGLSFCLTVPIPLDDSHEFTEEDLRFABRYLRTHYDLRPNPTGIMKKSANTMASKLREMQAFFGLEVTGKLDEETYELMQKPRC GVPDVGEYNFFPRKLKWSNTNLTYRIMSYTSDLRRAEVERAFKRAFKVWSDVTPLNFTRIRSGTADIMISFGTKEHGDFYPFDGPSGLLAHAFPPG PDYGGDAHFDDDETWSDDSRGYNLFLVAAHEFGHSLGLEHSRDPGALMPPIYTYTGKSGFVLPDDDVQGIQELYGAGDRDPNPKHPKTPEKCAADL SIDAITKLRGEMLVFKDRFFWRLHPQMVEAELVLIKSFWPELPNKIDAAYENPIKDLVFMFGKKVWAMNGYDIVEGFPKKIYEMGFPKEMKRIDA VVHIDDTGKTLFFTGNKYWSYDEETEVMDTGYPKFIEDEFAGIGDRVDAVYHRNGYLYFFNGPIQFEYSIWSKRIVRILHTNSLFWC |
| MYC-HIS tag | 123 | AAAEQKLISEEDLNGAAHHHHHH |
| FLAG3-HIS6 tag | 124 | AAADYKDHDGDYKDHDIDYKDDDDKGAAHHHHHH |
| myc-tag | 175 | AAAEQKLISEEDLNGAA |

TABLE C

Various Linker sequences ("ID" refers to the SEQ ID NO as used herein)

| Name | ID | Amino acid sequence |
|---|---|---|
| A3 | 125 | AAA |
| 5GS linker | 126 | GGGGS |
| 7GS linker | 127 | SGGSGGS |
| 8GS linker | 128 | GGGGGGGS |
| 9GS linker | 129 | GGGSGGGS |
| 10GS linker | 130 | GGGGSGGGGS |
| 15GS linker | 131 | GGGGSGGGGSGGGGS |
| 18GS linker | 132 | GGGGSGGGGSGGGGGGGS |
| 20GS linker | 133 | GGGGSGGGGSGGGGSGGGGS |
| 25GS linker | 134 | GGGGSGGGGSGGGGSGGGGSGGGGS |
| 30GS linker | 135 | GGGGSGGGGSGGGGSGGGGSGGGGSGGGGS |
| 35GS linker | 136 | GGGGSGGGGSGGGGSGGGGSGGGGSGGGGSGGGGS |
| 40GS linker | 137 | GGGGSGGGGSGGGGSGGGGSGGGGSGGGGSGGGGSGGGGS |
| G1 hinge | 138 | EPKSCDKTHTCPPCP |
| 9GS-G1 hinge | 139 | GGGGSGGGSEPKSCDKTHTCPPCP |
| Llama upper long hinge region | 140 | EPKTPKPQPAAA |
| G3 hinge | 141 | ELKTPLGDTTHTCPRCPEPKSCDTPPPCPRCPEPKSCDTPPPCPRCPEPKSCDTPPPCPRCP |

TABLE D

Serum albumin binding ISVD sequences ("ID" refers to the SEQ ID NO as used herein), including the CDR sequences

| Name | ID | Amino acid sequence |
|---|---|---|
| Alb8 | 142 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| Alb23 | 143 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| Alb129 | 144 | EVQLVESGGGVVQPGNSLRLSCAASGFTFSSFGMSWVRQAPGKGLEWVSSISGSGSDTLYADSVKGRFTISRDNAKTTLYLQMNSLRPEDTATYYCTIGGSLSRSSQGTLVTVSSA |
| Alb132 | 145 | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVTVSSA |
| Alb135 | 193 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVKSA |
| Alb11 | 146 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| Alb11 (S112K)-A | 147 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVKVSSA |

TABLE D-continued

Serum albumin binding ISVD sequences ("ID" refers to the SEQ ID NO as used herein), including the CDR sequences

| Name | ID | Amino acid sequence |
|---|---|---|
| Alb82 | 148 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSS |
| Alb82-A | 149 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| Alb82-AA | 150 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAA |
| Alb82-AAA | 151 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAAA |
| Alb82-G | 152 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSG |
| Alb82-GG | 153 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSGG |
| Alb82-GGG | 154 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSGGG |
| Alb92 | 155 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSS |
| Alb223 | 156 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |
| ALB CDR1 | 157 | SFGMS |
| ALB CDR2 | 158 | SISGSGSDTLYADSVKG |
| ALB CDR3 | 159 | GGSLSR |

TABLE E

Aggrecan binding ISVD sequences ("ID" refers to the SEQ ID NO as used herein), including the CDR sequences

| Name | ID | Amino acid sequence |
|---|---|---|
| 00269 114F08SO | 166 | EVQLVESGGGLVQPGGSLRLSCAASGSTFIINVRWYRRAPGKQRELVATISSGGNANYVDSVRGRFTISRDNSKNTVYLQMNSLRPEDTAVYYCNVPTTHYGGVYYGPYWGQGTLVTVSS |
| 00745 114F08PEA | 167 | EVQLVESGGGVVQPGGSLRLSCAASGSTFIINVRWYRRAPGKQRELVATISSGGNANYVDSVRGRFTISRDNSKNTVYLQMNSLRPEDTALYYCNVPTTHYGGVYYGPYWGQGTLVTVSSA |
| 00747 604F02PEA | 168 | EVQLVESGGGVVQPGGSLRLSCAASGRTFSSYTMGWFRQAPGKEREFVAAISWSGGRTYYADSVKGRFTISRDNSKNTVYLQMNSLRPEDTALYYCAAYRRRASSNRGLWDYWGQGTLVTVSSA |
| CDR1 114F08 | 169 | GSTFIINVVR |
| CDR2 114F08 | 170 | TISSGGNAN |
| CDR3 114F08 | 171 | PTTHYGGVYYGPY |
| CDR1 604F02 | 172 | GRTFSSYTMG |

TABLE E-continued

Aggrecan binding ISVD sequences ("ID" refers to the SEQ ID NO as used herein), including the CDR sequences

| Name | ID | Amino acid sequence |
|---|---|---|
| CDR2 604F02 | 173 | AISWSGGRTY |
| CDR3 604F02 | 174 | YRRRRASSNRGLWDY |

TABLE F

Multivalent constructs ("ID" refers to the SEQ ID NO as used herein), including the CDR sequences

| Name | ID | Amino acid sequence |
|---|---|---|
| C010100689<br>62C02S0-114F08S0 | 176 | EVQLVESGGGLVQPGGSLRLSCAASGFAFSAAYMSWVRQAPGKGLEWVSSISDDGSKTYYADSVKGRFTISRDNSK NTVYLQMNSLRPEDTAVYYCNTGYGATTTRPGRYWGQGTLVTVSSGGGSGGGGSGGGGSGGGGSGGGGSGGGGSG GGGSEVQLVESGGGLVQPGGSLRLSCAASGSTFIINVRWYRRAPGKQRELVATISSGGNANYVDSVRGRFTISRD NSKNTVYLQMNSLRPEDTAVYYCNVPTTHYGGVYYGPYWGQGTLVTVSS |
| C010100683<br>62C02S0-114F08S0-<br>114F08S0 | 177 | EVQLVESGGGLVQPGGSLRLSCAASGFAFSAAYMSWVRQAPGKGLEWVSSISDDGSKTYYADSVKGRFTISRDNSK NTVYLQMNSLRPEDTAVYYCNTGYGATTTRPGRYWGQGTLVTVSSGGGSGGGGSGGGGSGGGGSGGGGSGGGGSG GGGSEVQLVESGGGLVQPGGSLRLSCAASGSTFIINVRWYRRAPGKQRELVATISSGGNANYVDSVRGRFTISRD NSKNTVYLQMNSLRPEDTAVYYCNVPTTHYGGVYYGPYWGQGTLVTVSSGGGSGGGGSGGGGSGGGGSGGGGSGG GGSGGGGSEVQLVESGGGLVQPGGSLRLSCAASGSTFIINVRWYRRAPGKQRELVATISSGGNANYVDSVRGRFT ISRDNSKNTVYLQMNSLRPEDTAVYYCNVPTTHYGGVYYGPYWGQGTLVTVSS |
| C010100692<br>62C02S0-604F02S0 | 178 | EVQLVESGGGLVQPGGSLRLSCAASGFAFSAAYMSWVRQAPGKGLEWVSSISDDGSKTYYADSVKGRFTISRDNSK NTVYLQMNSLRPEDTAVYYCNTGYGATTTRPGRYWGQGTLVTVSSGGGSGGGGSGGGGSGGGGSGGGGSGGGGSG GGGSEVQLVESGGGLVQPGGSLRLSCAASGRTFSSSYTMGWFRQAPGKEREFVAAISWSGGRTYYADSVKGRFTISR DNSKNTVYLQMNSLRPEDTAVYYCAAYRRRASSNRGLWDYWGQGTLVTVSS |
| C010100687<br>80A01-114F08S0 | 179 | EVQLVESGGGLVQPGGSLRLSCAASGFTLAYYSIGWFRQAPGKEREGVSCISSGIDGSTYYADSVKGRFTISRDNA KNTMYLQMNNLKPEDTGVYYCAADPSHYYSEYDCGYYGMDYWGKGTLVTVSSGGGSGGGGSGGGGSGGGGSGGGG SGGGGSGGGGSEVQLVESGGGLVQPGGSLRLSCAASGSTFIINVRWYRRAPGKQRELVATISSGGNANYVDSVRG RFTISRDNSKNTVYLQMNSLRPEDTAVYYCNVPTTHYGGVYYGPYWGQGTLVTVSS |
| C010100681<br>80A01-114F08S0-<br>114F08S0 | 180 | EVQLVESGGGLVQPGGSLRLSCAASGFTLAYYSIGWFRQAPGKEREGVSCISSGIDGSTYYADSVKGRFTISRDNA KNTMYLQMNNLKPEDTGVYYCAADPSHYYSEYDCGYYGMDYWGKGTLVTVSSGGGSGGGGSGGGGSGGGGSGGGG SGGGGSGGGGSEVQLVESGGGLVQPGGSLRLSCAASGSTFIINVRWYRRAPGKQRELVATISSGGNANYVDSVRG RFTISRDNSKNTVYLQMNSLRPEDTAVYYCNVPTTHYGGVYYGPYWGQGTLVTVSSGGGSGGGGSGGGGSGGGGS GGGGSGGGGSGGGGSEVQLVESGGGLVQPGGSLRLSCAASGSTFIINVRWYRRAPGKQRELVATISSGGNANYVD SVRGRFTISRDNSKNTVYLQMNSLRPEDTAVYYCNVPTTHYGGVYYGPYWGQGTLVTVSS |
| C010100690<br>80A01-604F02S0 | 181 | EVQLVESGGGLVQPGGSLRLSCAASGFTLAYYSIGWFRQAPGKEREGVSCISSGIDGSTYYADSVKGRFTISRDNA KNTMYLQMNNLKPEDTGVYYCAADPSHYYSEYDCGYYGMDYWGKGTLVTVSSGGGSGGGGSGGGGSGGGGSGGGG SGGGGSGGGGSEVQLVESGGGLVQPGGSLRLSCAASGRTFSSSYTMGWFRQAPGKEREFVAAISWSGGGRTYYADSVK GRFTISRDNSKNTVYLQMNSLRPEDTAVYYCAAYRRRASSNRGLWDYWGQGTLVTVSS |
| C010100729<br>517A01S0-40E09S0-<br>604F02S0-A | 182 | DVQLVESGGGLVQPGGSLRLSCAASGRTFSSYAMGWFRQAPGKEREFVAAISWSGGSTYYADSVKGRFTISRDNSK NTVYLQMNSLRPEDTAVYYCTAALAVYGPSRYRYGPVGEYQYWGQGTLVTVSSGGGSGGGGSGGGGSGGGGSGGG GSGGGGSGGGGSEVQLVESGGGLVQPGGSLRLSCAASGSTFSRYSMNWYRQAPGKQREFVAGISVGRITNYAVSVK GRFTISRDNSKNTGYLQMNSLRPEDTAVYYCNAGGLQGYWGQGTLVTVSSGGGSGGGGSGGGGSGGGGSGGGGSG GGGSGGGGSEVQLVESGGGLVQPGGSLRLSCAASGRTFSSYTMGWFRQAPGKEREFVAAISWSGGRTYYADSVKGR FTISRDNSKNTVYLQMNSLRPEDTAVYYCAAYRRRASSNRGLWDYWGQGTLVTVSSA |
| C010100700<br>517A01S0-40E09S0var-<br>114F08S0 | 183 | EVQLVESGGGLVQPGGSLRLSCAASGRTFSSYAMGWFRQAPGKEREFVAAISWSGGSTYYADSVKGRFTISRDNSK NTVYLQMNSLRPEDTAVYYCTAALAVYGPSRYRYGPVGEYQYWGQGTLVTVSSGGGSGGGGSGGGGSGGGGSGGG GSGGGGSGGGGSEVQLVESGGGLVQPGGSLRLSCAASGSTFSRYSMNWYRQAPGKQREFVAGLSVGRITNYAVSVR GRFTISRDNSEGTGYLQMNSLRPEDTAVYYCNAGGLQGYWGLGTLVTVSSGGGSGGGGSGGGGSGGGGSGGGGSG GGGSGGGGSEVQLVESGGGLVQPGGSLRLSCAASGSTFIINVRWYRRAPGKQRELVATISSGGNANYVDSVRGRF TISRDNSKNTVYLQMNSLRPEDTAVYYCNVPTTHYGGVYYGPYWGQGTLVTVSS |

TABLE F-continued

Multivalent constructs ("ID" refers to the SEQ ID NO as used herein), including the CDR sequences

| Name | | ID | Amino acid sequence |
|---|---|---|---|
| C010100702 | 517A01SO-40E09SOvar-114F08SO-114F08SO | 184 | EVQLVESGGGLVQPGGSLRLSCAASGRTFSSYAMGWFRQAPGKEREFVAAISWSGGSTYYADSVKGRFTISRDNSKNTVYLQMNSLRPEDTAVYYCTAALAVYGPSRYRYGPVGEYQYWGQGTLVTVSSGGGGSGGGGSGGGGSGGGGSGGGGSGGGGSEVQLVESGGGSEVQLVESGGGLVQPGGSLRLSCAASGSTFSRYSMNWYRQAPGKQREFVAGISVGRITNYAVSVRGRFTISRDNSEGTGYLQMNSLRPEDTAVYYCNAGGLQGYWGLGTLVTVSSGGGGSGGGGSGGGGSGGGGSGGGSGGGSGGGGSEVQLVESGGGLVQPGGSLRLSCAASGTFIINVRWYRRAPGKQRELVATISSGGNANYVDSVRGRFTISRDNSKNTVYLQMNSLRPEDTAVYYCNVPTTHYGGVYYGPYWGQGTLVTVSSGGGGSGGGGSGGGGSGGGGSGGGGSEVQLVESGGGLVQPGGSLVQPGGSLRLSCAASGTFIINVRWYRRAPGKQRELVATISSGGNANYVDSVRGRFTISRDNSKNTVYLQMNSLRPEDTAVYYCNVPTTHYGGVYYGPYWGQGTLVTVSS |
| C010100696 | 517A01SO-40E09SOvar-604F02SO | 185 | EVQLVESGGGLVQPGGSLRLSCAASGRTFSSYAMGWFRQAPGKEREFVAAISWSGGSTYYADSVKGRFTISRDNSKNTVYLQMNSLRPEDTAVYYCTAALAVYGPSRYRYGPVGEYQYWGQGTLVTVSSGGGGSGGGGSGGGGSGGGGSGGGGSGGGGSEVQLVESGGGSEVQLVESGGGLVQPGGSLRLSCAASGSTFSRYSMNWYRQAPGKQREFVAGISVGRITNYAVSVRGRFTISRDNSEGTGYLQMNSLRPEDTAVYYCNAGGLQGYWGLGTLVTVSSGGGGSGGGGSGGGGSGGGGSGGGSGGGSGGGGSEVQLVESGGGLVQPGGSLRLSCAASGRTFSSYTMGWFRQAPGKEREFVAAISWSGGRTYYADSVKGRFTISRDNSKNTVYLQMNSLRPEDTAVYYCAAYRRRASSNRGLWDYWGQGTLVTVSS |
| C010100726 | 517A01SO-40E09SOvar | 186 | EVQLVESGGGLVQPGGSLRLSCAASGRTFSSYAMGWFRQAPGKEREFVAAISWSGGSTYYADSVKGRFTISRDNSKNTVYLQMNSLRPEDTAVYYCTAALAVYGPSRYRYGPVGEYQYWGQGTLVTVSSGGGGSGGGGSGGGGSGGGGSGGGGSGGGGSEVQLVESGGGSGGGGSEVQLVESGGGLVQPGGSLRLSCAASGSTFSRYSMNWYRQAPGKQREFVAGISVGRITNYAVSVKGRFTISRDNSKNTVYLQMNSLRPEDTAVYYCNAGGLQGYWGQGTLVTVSS |
| C010100727 | 517A01SO-40E09SO | 187 | EVQLVESGGGLVQPGGSLRLSCAASGRTFSSYAMGWFRQAPGKEREFVAAISWSGGSTYYADSVKGRFTISRDNSKNTVYLQMNSLRPEDTAVYYCTAALAVYGPSRYRYGPVGEYQYWGQGTLVTVSSGGGGSGGGGSGGGGSGGGGSGGGGSGGGGSEVQLVESGGGSGGGGSEVQLVESGGGLVQPGGSLRLSCAASGSTFSRYSMNWYRQAPGKQREFVAGISVGRITNYAVSVKGRFTISRDNSKNTGYLQMNSLRPEDTAVYYCNAGGLQGYWGQGTLVTVSS |
| C010100724 | 529C12SO-604F02SO-A | 188 | DVQLVESGGGLVQPGGSLRLSCAASGSIFSINAMGWYRQAPGKQRELVAAISSGGSTYYADSVKGRFTISRDNSKNTVYLQMNSLRPEDTAVYYCNAAVDASRGLPYELYYWGQGTLVTVSSGGGGSGGGGSGGGGSGGGGSGGGGSGGGGSEVQLVESGGGLVQPGGSLRLSCAASGRTFSSYTMGWFRQAPGKEREFVAAISWSGGRTYYADSVKGRFTISRDNSKNTVYLQMNSLRPEDTAVYYCAAYRRRASSNRGLWDYWGQGTLVTVSSA |
| C010100688 | 529C12SO-114F08SO | 189 | EVQLVESGGGLVQPGGSLRLSCAASGSIFSINAMGWYRQAPGKQRELVAAISSGGSTYYADSVKGRFTISRDNSKNTVYLQMNSLRPEDTAVYYCNAAVDASRGLPYELYYWGQGTLVTVSSGGGGSGGGGSGGGGSGGGGSGGGGSGGGGSEVQLVESGGGSEVQLVESGGGLVQPGGSLRLSCAASGTFIINVRWYRRAPGKQRELVATISSGGNANYVDSVRGRFTISRDNSKNTVYLQMNSLRPEDTAVYYCNVPTTHYGGVYYGPYWGQGTLVTVSS |

TABLE F-continued

Multivalent constructs ("ID" refers to the SEQ ID NO as used herein), including the CDR sequences

| Name | ID | Amino acid sequence |
|---|---|---|
| C010100682<br>529C12SO-114F08SO-<br>114F08SO | 190 | EVQLVESGGGLVQPGGSLRLSCAASGSIFSINAMGWYRQAPGKQRELVAAISSGGSTYYADSVKGRFTISRDNSKN<br>TVYLQMNSLRPEDTAVYYCNAAVDASRGLPYELYYWGQGTLVTVSSGGGSGGGGSGGGGSGGGGSGGGGS<br>SGGGGSEVQLVESGGGLVQPGGSLRLSCAASGSTFIINVRWYRRAPGKQRELVATISSGGNANYVDSVRGRFTIS<br>RDNSKNTVYLQMNSLRPEDTAVYYCNVPTTHYGGVYYGPYWGQGTLVTVSSGGGGSGGGGSGGGGSGGGGSGGGGS<br>GGGGSGGGGSEVQLVESGGGLVQPGGSLRLSCAASGSTFIINVRWYRRAPGKQRELVATISSGGNANYVDSVRGR<br>FTISRDNSKNTVYLQMNSLRPEDTAVYYCNVPTTHYGGVYYGPYWGQGTLVTVSS |
| C010100691<br>529C12SO-604F02SO | 191 | EVQLVESGGGLVQPGGSLRLSCAASGSIFSINAMGWYRQAPGKQRELVAAISSGGSTYYADSVKGRFTISRDNSKN<br>TVYLQMNSLRPEDTAVYYCNAAVDASRGLPYELYYWGQGTLVTVSSGGGSGGGGSGGGGSGGGGSGGGGSGGGG<br>SGGGGSEVQLVESGGGLVQPGGSLRLSCAASGRTFSSYTMGWFRQAPGKEREFVAAISWSGGRTYYADSVKGRFTI<br>SRDNSKNTVYLQMNSLRPEDTAVYYCAAYRRRRASSNRGLWDYWGQGTLVTVSS |
| 00754<br>MMP13-CAP | 192 | EVQLVESGGGLVQPGGSLRLSCAASGFAFSAAYMSWVRQAPGKGLEWVSSISDDGSKTYYADSVKGRFTISRDNSK<br>NTVYLQMNSLRPEDTALYYCNTGYGATTTRPGRYWGQGTLVTVSSGGGGSGGGGSGGGGSGGGGSGGGGSGGGGSG<br>GGGSEVQLVESGGGVVQPGGSLRLSCAASGSTFIINVRWYRRAPGKQRELVATISSGGNANYVDSVRGRFTISRD<br>NSKNTVYLQMNSLRPEDTALYYCNVPTTHYGGVYYGPYWGQGTLVTVSSGGGGSGGGGSGGGGSGGGGSGGGGSGG<br>GGSGGGGSEVQLVESGGGVVQPGGSLRLSCAASGSTFIINVRWYRRAPGKQRELVATISSGGNANYVDSVRGRFT<br>ISRDNSKNTVYLQMNSLRPEDTALYYCNVPTTHYGGVYYGPYWGQGTLVTVSSA |

The invention claimed is:

1. A polypeptide comprising at least 1 immunoglobulin single variable domain (ISVD) binding matrix metalloproteinase 13 (MMP13); wherein the polypeptide comprises a first ISVD binding MMP13 comprising
   3 complementarity determining regions, wherein the complementarity determining regions are CDR1, CDR2, and CDR3, in which
      (i) CDR1 is SEQ ID NO: 27;
      (ii) CDR2 is SEQ ID NO: 42; and
      (iii) CDR3 is SEQ ID NOs: 56, wherein said polypeptide comprises an amino acid sequence selected from the group consisting of SEQ ID NO: 11 and 111, or comprises a polypeptide which has at least 95% sequence identity to SEQ ID NO: 11.

2. The polypeptide according to claim 1, wherein said first ISVD binding MMP13 does not inhibit activated human MMP1.

3. The polypeptide according to claim 1, wherein said polypeptide antagonizes a protease activity of MMP13.

4. The polypeptide according to claim 3, wherein said polypeptide inhibits bovine collagen I degradation by human MMP13 by at least 20%.

5. The polypeptide according to claim 1, further comprising a second ISVD.

6. The polypeptide according to claim 5, wherein the second ISVD specifically binds MMP13.

7. The polypeptide according to claim 6, wherein the second ISVD specifically binding MMP13 comprises an amino acid sequence selected from the group consisting of SEQ ID NOs: 1, 2, 3, 4, 5, 6, 7 and 8.

8. The polypeptide according to claim 6, wherein the polypeptide is SEQ ID NO: 162 or SEQ ID NO: 165.

9. The polypeptide according to claim 1, further comprising one or two ISVDs that specifically bind Aggrecan.

10. A method of reducing cartilage degeneration in an individual, the method comprising administering the polypeptide according to claim 9 to said individual in an effective amount.

11. The method of claim 10, wherein said individual has osteoarthritis or rheumatoid arthritis.

12. The polypeptide according to claim 9, wherein the polypeptide is selected from the group consisting of SEQ ID NO: 176, SEQ ID NO: 177, SEQ ID NO: 178, and SEQ ID NO: 192.

13. The polypeptide according to claim 1, further comprising an ISVD binding serum albumin.

14. The polypeptide according to claim 1, further comprising a C-terminal extension, wherein said C-terminal extension is a C-terminal extension (X)n, in which n is 1 to 10; and each X is an amino acid residue that is independently selected the group consisting of alanine (A), glycine (G), valine (V), leucine (L) and isoleucine (I).

15. The polypeptide according to claim 14, wherein the polypeptide is SEQ ID NO: 192.

16. The polypeptide according to claim 1, wherein the polypeptide is SEQ ID NO: 194.

* * * * *

UNITED STATES PATENT AND TRADEMARK OFFICE
CERTIFICATE OF CORRECTION

| | | |
|---|---|---|
| PATENT NO. | : 12,129,308 B2 | Page 1 of 1 |
| APPLICATION NO. | : 16/617869 | |
| DATED | : October 29, 2024 | |
| INVENTOR(S) | : Francis Descamps et al. | |

It is certified that error appears in the above-identified patent and that said Letters Patent is hereby corrected as shown below:

On the Title Page

Item (72) Inventors, the second inventor's residence information should be listed as follows:
Gerald Beste, Gent (BE)

Signed and Sealed this
Fourth Day of February, 2025

Coke Morgan Stewart
*Acting Director of the United States Patent and Trademark Office*